US011174253B2

(12) United States Patent
Chung et al.

(10) Patent No.: US 11,174,253 B2
(45) Date of Patent: Nov. 16, 2021

(54) COMPOUND AND PHARMACEUTICAL COMPOSITION CONTAINING THE SAME

(71) Applicant: ALPHALA CO., LTD., Taipei (TW)

(72) Inventors: Cheng-Ho Chung, Taipei (TW); Shi-Liang Tseng, Taipei (TW); Yen-Fu Chen, Taipei (TW); Jian-Bin Lee, Taipei (TW)

(73) Assignee: ALPHALA CO., LTD., Taipei (TW)

( * ) Notice: Subject to any disclaimer, the term of this patent is extended or adjusted under 35 U.S.C. 154(b) by 0 days.

(21) Appl. No.: 16/622,053

(22) PCT Filed: Aug. 1, 2018

(86) PCT No.: PCT/US2018/044747
§ 371 (c)(1),
(2) Date: Dec. 12, 2019

(87) PCT Pub. No.: WO2019/028104
PCT Pub. Date: Feb. 7, 2019

(65) Prior Publication Data
US 2020/0172531 A1   Jun. 4, 2020

Related U.S. Application Data

(60) Provisional application No. 62/540,114, filed on Aug. 2, 2017.

(51) Int. Cl.
C07D 417/14 (2006.01)
A61P 35/00 (2006.01)
C07D 417/12 (2006.01)

(52) U.S. Cl.
CPC ............ *C07D 417/14* (2013.01); *A61P 35/00* (2018.01); *C07D 417/12* (2013.01)

(58) Field of Classification Search
CPC .................................................. C07D 417/14
See application file for complete search history.

(56) References Cited

U.S. PATENT DOCUMENTS

| | | | |
|---|---|---|---|
| 4,490,393 | A | 12/1984 | Sakano et al. |
| 2004/0157827 | A1 | 8/2004 | Pevarello et al. |
| 2006/0135782 | A1 | 6/2006 | Herz et al. |
| 2010/0179121 | A1 | 7/2010 | Chen et al. |
| 2012/0028918 | A1 | 2/2012 | Gupta |
| 2016/0101096 | A1 | 4/2016 | Schmidt et al. |

FOREIGN PATENT DOCUMENTS

| | | |
|---|---|---|
| EP | 1558607 B | 5/2010 |
| WO | 2009158118 A | 12/2009 |

OTHER PUBLICATIONS

Bellenghi, et al. Document No. 48:11036, retrieved from STN; (1952).*
Makino, et al. Document No. 58:66503, retrieved from STN (1962).*
Mohamed, et al. Document No. 167:393953, retrieved from STN (2016).*
Nenitzescu, et al. Document No. 52:65795, retrieved from STN (1956).*
Novitskii, et al. Document No. 58:81476, retrieved from STN; (1963).*
Ran, et al. Document No. 165:137258, retrieved from STN (2016).*
Saikachi, et al. Document No. 70:47189, retrieved from STN (1968).*
Simithy, et al. Document No. 161:166693, retrieved from STN (2014).*
Turner, et al. Document No. 131:243271, retrieved from STN, (1999).*
Chen, et al. Document No. 63:31511, retrieved from STN, (1965).*
Cancer and Metastasis Reviews (1998), 17(1), 91-106.*
Science (1999), vol. 286, 531-537.*
Cancer [online], [retrieved on Jul. 6, 2007], Retrieved from the internet, URL http://www.nlm.nih.gov/medlineplus/cancer.html>.*
Binh An Diep, Liana Chan, Pierre Tattevin, Osamu Kajikawa, Thomas R. Martin, Li Basuino, Thuy T. Mai,Helene Marbach, Kevin R. Braughton, Adeline R. Whitney, Donald J. Gardner, Xuemo-Fan, Ching W. Tseng,George Y. Liu, Cedric Badiou, Jerome Etienne, Gerard Lina, Michael A. Matthay, Frank R. Deleo,and Henry F. Chambers, Polymorphonuclear leukocytes mediate *Staphylococcus aureus* Panton-Valentine leukocidininduced lung inflammation and injury, PNAS | Mar. 23, 2010.
International Search Report cited in International Appln. No. PCT/US18/44747 dated Aug. 1, 2018.

* cited by examiner

*Primary Examiner* — Shawquia Jackson
(74) *Attorney, Agent, or Firm* — Bacon & Thomas, PLLC

(57) ABSTRACT

Disclosed are compounds of formula (I) below and pharmaceutically acceptable salts thereof: Formula (I), in which each of variables L, $R_3$, $R_4$, Y, $Z_1$, $Z_2$ and $Z_3$ is defined herein. Also disclosed is a method for treating a cancer with a compound of formula (I) or a salt thereof and a pharmaceutical composition containing same.

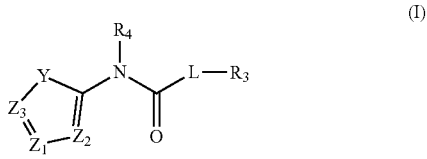

(I)

23 Claims, No Drawings

COMPOUND AND PHARMACEUTICAL COMPOSITION CONTAINING THE SAME

This application claims the benefit of filing date of U.S. Provisional Application Ser. No. 62/540,114, filed Aug. 2, 2017, which is hereby incorporated by reference.

FIELD OF THE DISCLOSURE

The present disclosure relates to compounds that can inhibit the growth of tumor cells, pharmaceutical compositions comprising the compounds, and the uses of the compounds or compositions.

BACKGROUND

Foods or food additives, and environmental pollutions have been a source of contention as a cause or catalyst for promoting cancer in recent years. Not coincidentally, the same event is happening as well in the developed countries and around the world, positing as an alarming sign that the incidence rates of cancers are quite high. According to the data published by the American Cancer Society, cancer is being proved to be the most significant threat to public health.

The general methods for treating cancer include surgery, radiotherapy, chemotherapy and immune therapy. In recent years, the development of several therapeutic agents has lead to cancer treatments through new anti-cancer mechanisms, and it has been proven that the survival rate of patients can be increased by treating them with these therapeutic agents. Generally, the therapeutic agents can treat cancers through inhibition of cell cycle progression, angiogenesis, farnesyl transferase, and tyrosine kinases.

Although it is known that certain agents exhibit therapeutic effects on cancer, these agents do have their limitations. For example, "Gefitinib" is a drug for inhibiting non-small cell lung cancer, but it fails to cure in most cases. Also, it has no effects on blocking the progression of breast and colorectal cancers. In addition, the therapeutic effects of the anti-cancer drugs also depend on the locations of tumor cells, genetic variations of patients, and the side effects of drugs. Furthermore, cancer cells may become malignant and spread from its original sites to target organs via the lymphatic system or bloodstream, thereby establishing metastatic cancers.

Since the risk of developing cancer generally increases with age, the occurrence rates of cancer go up as more people live to an old age and as mass lifestyle changes. Hence, there is a long unfulfilled need to provide new agents for cancer treatment and prevention.

SUMMARY

The present disclosure relates to certain compounds that can inhibit the growth of tumor cells.

An aspect of this disclosure is drawn to the compounds of formula (I) below and pharmaceutically acceptable salts thereof:

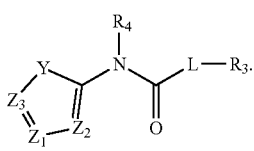

(I)

In this formula, $Z_1$ is N or C—$R_2$; $Z_2$ is C or N; and $Z_3$ is N or C—X—$R_1$, with the proviso that no more than two of $Z_1$, $Z_2$ and $Z_3$ are N. X is a direct bond, —(CH$_2$)$_n$—, —O—, —(C=O)NH— or —(C=O)—, in which n is 1, 2 or 3, and $R_a$ is hydrogen or alkyl. Y is —CH—, O or S, in which $R_b$ is hydrogen or alkyl. L is a direct bond, —(CH$_2$)$_m$— or —NH—, in which m is 1, 2 or 3. $R_1$ is hydrogen, halogen, cyano, alkyl, alkyloxy, cycloalkyl, heterocycloalkyl, aryl or heteroaryl, wherein each of alkyloxy, cycloalkyl, heterocycloalkyl, aryl and heteroaryl is optionally substituted with one to three moieties selected from the group consisting of halogen, hydroxyl, nitro, cyano, —NR$_c$R$_d$, lower alkyl carbamoyl, heterocycloalkyl, alkyl optionally substituted with one to three halo or aryl, and alkyloxy optionally substituted with one to three halo, alkyloxy, cycloalkyl, heterocycloalkyl, —NR$_e$R$_f$ or aryl, in which each of R$_c$, R$_d$, R$_e$ and R$_f$ independently is hydrogen or alkyl. $R_2$ is hydrogen, halogen, alkyl, alkyloxy, cycloalkyl, heterocycloalkyl, aryl or heteroaryl, wherein each of alkyloxy, cycloalkyl, heterocycloalkyl, aryl and heteroaryl is optionally substituted with one to three moieties selected from the group consisting of halogen, hydroxyl, nitro, cyano, —NR$_g$R$_h$, lower alkyl carbamoyl, alkynyl, alkyl optionally substituted with one to three halo, and alkyloxy optionally substituted with one to three halo or alkyloxy, in which each of R$_g$ and R$_h$ independently is hydrogen or alkyl. $R_3$ is

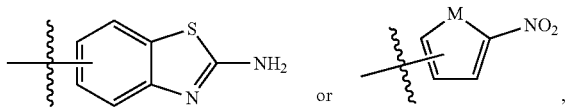

in which M is O or S. And, $R_4$ is H or alkyl.

The term "alkyl" herein refers to a straight or branched hydrocarbon group, containing 1-12 carbon atoms (e.g., $C_1$-$C_{10}$, $C_1$-$C_8$ and $C_1$-$C_6$). Examples include methyl, ethyl, n-propyl, i-propyl, n-butyl, i-butyl, and t-butyl.

The term "alkynyl" herein refers to a straight or branched monovalent or bivalent hydrocarbon containing 2-20 carbon atoms (e.g., $C_2$-$C_{16}$, $C_2$-$C_{12}$, $C_2$-$C_8$, $C_2$-$C_6$ and $C_2$-$C_4$) and one or more triple bonds. Examples of alkynyl include, but are not limited to, ethynyl, ethynylene, 1-propynyl, 1- and 2-butynyl, and 1-methyl-2-butynyl.

The term "cycloalkyl" refers to a saturated and partially unsaturated monocyclic, bicyclic, tricyclic, or tetracyclic hydrocarbon group having 3-12 (e.g., 3-10 and 3-7) carbon atoms. Examples include cyclopropyl, cyclobutyl, cyclopentyl, cyclopentenyl, cyclohexyl, cyclohexenyl, cycloheptyl, and cyclooctyl.

The term "heterocycloalkyl" refers to a nonaromatic 5-8 membered monocyclic, 8-12 membered bicyclic, or 11-14 membered tricyclic ring system having one or more heteroatoms (e.g., 0, N, P, and S). Examples include piperazinyl, imidazolidinyl, azepanyl, pyrrolidinyl, dihydrothiadiazolyl, dioxanyl, morpholinyl, tetrahydropuranyl, and tetrahydrofuranyl.

The term "alkoxy" or "alkyloxy" refers to an —O-alkyl group. Examples include methoxy, ethoxy, propoxy, and isopropoxy.

The term "halogen" refers to a fluoro, chloro, bromo, or iodo radical.

The term "amino" refers to a radical derived from amine, which is unsubstituted or mono-/di-substituted with alkyl, aryl, cycloalkyl, heterocycloalkyl, or heteroaryl.

The term "aryl" refers to a 6-carbon monocyclic, 10-carbon bicyclic, 14-carbon tricyclic aromatic ring system. Examples of aryl groups include phenyl, naphthyl, and anthracenyl.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include thiophenyl, triazolyl, oxazolyl, thiadiazolyl, tetrazolyl, pyrazolyl, pyridyl, furyl, imidazolyl, benzimidazolyl, pyrimidinyl, thienyl, quinolinyl, indolyl, thiazolyl, and benzothiazolyl.

The term "lower alkyl carbamoyl" refers to a —N(alkyl)$_2$-C(=O)—O-group, wherein the alkyl refers to a straight or branched hydrocarbon group containing 1-4 carbon atoms, such as methyl or ethyl.

Alkyl, cycloalkyl, heterocycloalkyl, alkyloxy, aryl, and heteroaryl mentioned herein include both substituted and unsubstituted moieties. Possible substituents on cycloalkyl, heterocycloalkyl, alkoxy, aryl, and heteroaryl include, but are not limited to, $C_{1-6}$ alkyl, $C_{2-6}$ alkenyl, $C_{2-6}$ alkynyl, $C_{3-12}$ cycloalkyl, $C_{3-12}$ cycloalkenyl, $C_{1-12}$ heterocycloalkyl, $C_{1-12}$ heterocycloalkenyl, $C_{1-6}$ alkoxy, aryl, aryloxy, heteroaryl, heteroaryloxy, amino, $C_{1-6}$ alkylamino, $C_{1-20}$ dialkylamino, arylamino, diarylamino, $C_{1-6}$ alkylsulfonamino, arylsulfonamino, $C_{1-6}$ alkylimino, arylimino, $C_{1-6}$ alkylsulfonimino, arylsulfonimino, hydroxyl, halo, thio, $C_{1-6}$ alkylthio, arylthio, $C_{1-6}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl include all of the above-recited substituents except $C_{1-6}$ alkyl. Cycloalkyl, heterocycloalkyl, aryl, and heteroaryl can also be fused with each other.

In addition to the compounds of formula (I) described above, their pharmaceutically acceptable salts and solvates, where applicable, are also covered by this disclosure. A salt can be formed between an anion and a positively charged group (e.g., amino) on a compound. Examples of a suitable anion include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. A salt can also be formed between a cation and a negatively charged group. Examples of a suitable cation include sodium ion, potassium ion, magnesium ion, calcium ion, and an ammonium cation such as tetramethylammonium ion. A salt further includes those containing quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine.

Another aspect of this disclosure is a pharmaceutical composition for treating a cancer.

The pharmaceutical composition contains one of the compounds of formula (I) described above or its pharmaceutically acceptable salt and a pharmaceutically acceptable carrier, excipient or diluent.

This disclosure also covers use of such a composition for the manufacture of a medicament for treating treating a cancer.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Oral solid dosage forms can be prepared by spray dried techniques; hot melt extrusion strategy, micronization, and nano milling technologies.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters, fluorocarbons, and/or other solubilizing or dispersing agents known in the art. A composition having an active compound can also be administered in the form of suppositories for rectal administration.

The carrier, the excipient and the diluent in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

Still within the scope of the present disclosure is a method of treating treating a cancer.

The method includes administering to a subject in need thereof an effective amount of a compound of formula (I) or a pharmaceutically acceptable salt thereof.

The above-described compounds or a pharmaceutical composition containing one or more of them can be administered to a subject orally, parenterally, by inhalation spray, topically, rectally, nasally, buccally, or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

The term "treating", "treat" or "treatment" refers to application or administration of the compound to a subject with the purpose to cure, alleviate, relieve, alter, remedy, improve, or affect the disease, the symptom, or the predisposition. "An effective amount" refers to the amount of the compound which is required to confer the desired effect on the subject. Effective amounts vary, as recognized by those skilled in the art, depending on route of administration, excipient usage, and the possibility of co-usage with other therapeutic treatments such as use of other active agents.

The details of one or more embodiments of the disclosure are set forth in the description below. Other features, objects, and advantages of the disclosure will be apparent from the description and from the claims.

DETAILED DESCRIPTION

A first embodiment of the present disclosure is the compounds of formula (I) or pharmaceutically acceptable salts thereof:

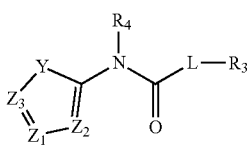

in which each of variables each of variables L, R$_3$, R$_4$, Y, Z$_1$, Z$_2$ and Z$_3$ is defined as in the SUMMARY section.

A second embodiment of the present disclosure is the compound of the first embodiment or a pharmaceutically acceptable salt thereof,

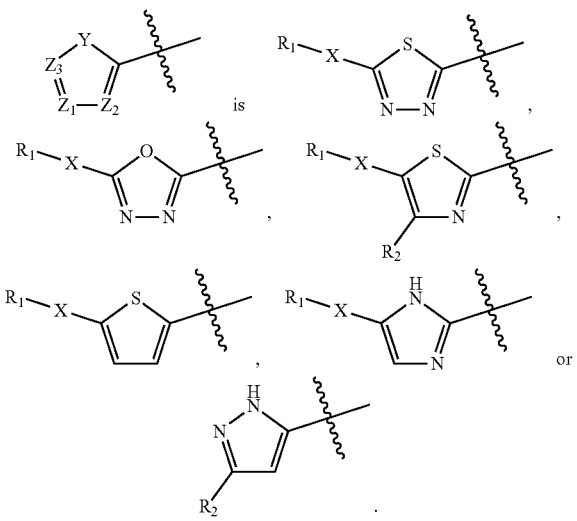

A third embodiment of the present disclosure is the compound of the first or second embodiments or a pharmaceutically acceptable salt thereof, wherein

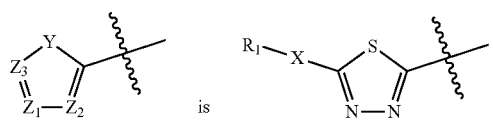

A fourth embodiment of the present disclosure is the compound of any one of the first to third embodiments or a pharmaceutically acceptable salt thereof, wherein X is a direct bond.

A fifth embodiment of the present disclosure is the compound of any one of the first to fourth embodiments or a pharmaceutically acceptable salt thereof, wherein L is a —CH$_2$—, and R$_3$ is

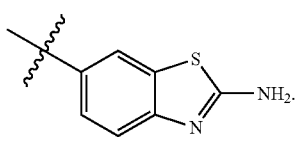 [SMILES: *c1ccc2nc(N)sc2c1]

A sixth embodiment of the present disclosure is the compound of any one of the first to fifth embodiments or a pharmaceutically acceptable salt thereof, wherein R$_1$ is aryl or heteroaryl, wherein each of aryl and heteroaryl is optionally substituted with one to three moieties selected from the group consisting of halogen, hydroxyl, nitro, cyano, —NR$_c$R$_d$, lower alkyl carbamoyl, heterocycloalkyl, alkyl optionally substituted with one to three halo or aryl, and alkyloxy optionally substituted with one to three halo, alkyloxy, cycloalkyl, heterocycloalkyl, —NR$_e$R$_f$ or aryl, in which each of R$_c$, R$_d$, R$_e$ and R$_f$ independently is hydrogen, methyl or ethyl.

A seventh embodiment of the present disclosure is the compound of any one of the first to sixth embodiments or a pharmaceutically acceptable salt thereof, wherein R$_1$ is phenyl or pyridinyl, wherein each of phenyl or pyridinyl is optionally substituted with one to three alkyloxy optionally substituted with one to three halo, alkyloxy, cycloalkyl, heterocycloalkyl, —NR$_e$R$_f$ or aryl, in which each of R$_c$, R$_d$, R$_e$ and R$_f$ independently is hydrogen, methyl or ethyl.

An eighth embodiment of the present disclosure is the compound of any one of the first to seventh embodiments or a pharmaceutically acceptable salt thereof, wherein R$_4$ is H or methyl.

A ninth embodiment of the present disclosure is the compound of any one of the first to eighth embodiments or a pharmaceutically acceptable salt thereof, wherein L is a —CH$_2$—; R$_3$ is

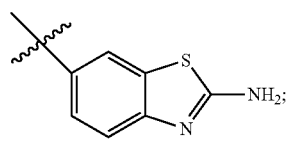 [SMILES: *c1ccc2nc(N)sc2c1]

R$_4$ is H or methyl; and R$_1$ is phenyl or pyridinyl, wherein each of phenyl or pyridinyl is optionally substituted with one or two ethoxy, butoxy, methoxy substituted with ethoxy, or ethoxy substituted with dimethylamino.

A tenth embodiment of the present disclosure is the compound of the first or second embodiments or a pharmaceutically acceptable salt thereof, wherein

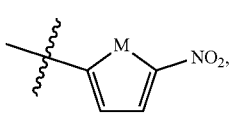

A eleventh embodiment of the present disclosure is the compound of any one of the first, second and tenth embodiments or a pharmaceutically acceptable salt thereof, wherein X is a direct bond, —CH$_2$—, —O—, —N(CH$_3$)—, —(C=O)NH— or —(C=O)—.

An twelfth embodiment of the present disclosure is the compound of any one of the first, second, tenth and eleventh embodiments or a pharmaceutically acceptable salt thereof, wherein L is a direct bond, and R$_3$ is in which M is O or S.

A thirteenth embodiment of the present disclosure is the compound of any one of the first, second, tenth to twelfth embodiments or a pharmaceutically acceptable salt thereof, wherein L is a —CH$_2$—, and R$_3$ is

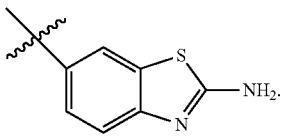 [SMILES: *c1ccc2nc(N)sc2c1]

A fourteenth embodiment of the present disclosure is the compound of any one of the first, second, tenth to thirteenth embodiments or a pharmaceutically acceptable salt thereof, wherein R$_1$ is hydrogen, halogen, cyano, alkoxy, aryl or heteroaryl, wherein each of aryl and heteroaryl is optionally substituted with one to three moieties selected from the group consisting of halogen, hydroxyl, nitro, cyano, —NR$_c$R$_d$, lower alkyl carbamoyl, heterocycloalkyl, alkyl optionally substituted with one to three halo or aryl, and alkyloxy optionally substituted with one to three halo, alkyloxy, cycloalkyl, heterocycloalkyl, —NR$_e$R$_f$ or aryl, in which each of R$_c$, R$_d$, R$_e$ and R$_f$ independently is hydrogen, methyl or ethyl.

A fifteenth embodiment of the present disclosure is the compound of any one of the first, second, tenth to fourteenth embodiments or a pharmaceutically acceptable salt thereof, wherein R$_1$ is phenyl, which is optionally substituted with one to three moieties selected from the group consisting of halogen and alkyl optionally substituted with one to three halo.

A sixteenth embodiment of the present disclosure is the compound of any one of the first, second, tenth to fifteenth embodiments or a pharmaceutically acceptable salt thereof, wherein R$_2$ is aryl or heteroaryl, wherein each of aryl and heteroaryl is optionally substituted with one to three moieties selected from the group consisting of halogen, nitro, cyano, lower alkyl carbamoyl, alkynyl, alkyl optionally substituted with one to three halo, and alkyloxy optionally substituted with one to three halo or alkyloxy.

A seventeenth embodiment of the present disclosure is the compound of any one of the first, second, tenth to sixteenth embodiments or a pharmaceutically acceptable salt thereof, wherein R$_2$ is phenyl, which is optionally substituted with one to three moieties selected from the group consisting of halogen, alkyl optionally substituted with one to three halo, and alkyloxy.

An eighteenth embodiment of the present disclosure is the compound of any one of the first, second, tenth to seventeenth embodiments or a pharmaceutically acceptable salt thereof, wherein R$_4$ is H or methyl.

A nineteenth embodiment of the present disclosure is the compound of any one of the first, second, tenth to eighteenth embodiments or a pharmaceutically acceptable salt thereof, wherein X is —O—; L is a direct bond; R$_3$ is

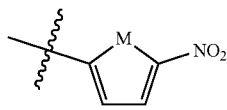

in which M is S; R$_4$ is H; R$_1$ is phenyl optionally substituted with fluoro, tert-pentyl or trifluoromethyl; and R$_2$ is phenyl substituted with ethoxy, butoxy, fluoro, tert-butyl, tert-pentyl or trifluoromethyl.

A twentieth embodiment of the present disclosure is the compound of any one of the first, second, tenth to eighteenth embodiments or a pharmaceutically acceptable salt thereof, wherein X is a direct bond; L is a direct bond; R$_3$ is

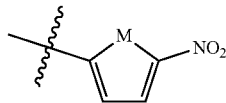

in which M is S; R$_4$ is H; R$_1$ is phenyl optionally substituted with one or two fluoro; and R$_2$ is phenyl substituted with tert-butyl or tert-pentyl.

A twenty first embodiment of the present disclosure is a compound selected from the group consisting of Compounds 1-1 to 1-37, Compounds 2-1 to 2-4, Compounds 3-1 to 3-14, Compounds 4-1 to 4-4, Compounds 5-1 to 5-108, and Compounds 6-1 to 6-61, which are listed in the following Tables 1 to 6.

The compounds of the present disclosure may contain asymmetric or chiral centers, and exist in different stereoisomeric forms. Unless specified otherwise, all stereoisomeric forms of the compounds of the present disclosure as well as mixtures thereof, including racemic mixtures are within the scope of the present disclosure. In addition, the compounds of the present disclosure may also exist in different geometric and positional isomers. For example, both the cis- and trans-forms, as well as mixtures of the compound with a double bond or a fused ring, are also within the scope of the present disclosure.

Diastereomeric mixtures can be separated into their individual diastereoisomers by any methods, such as by chromatography and/or fractional crystallization. Enantiomers can be separated by use of a chiral HPLC column or by converting the enantiomeric mixture into a diastereomeric mixture by reaction with an appropriate optically active compound to separate the diastereoisomers and convert the individual diastereoisomers into pure enantiomers. The specific stereoisomers may be synthesized by converting one stereoisomer into the other by asymmetric transformation, by using an optically active starting material or by asymmetric synthesis using optically active reagents, catalysts, substrates or solvents.

Also within the present disclosure is a pharmaceutical composition, comprising: (1) the compound of the present disclosure or the pharmaceutically acceptable salt thereof; and (2) a pharmaceutically acceptable carrier, excipient or diluent. The composition may also comprise at least one additional pharmaceutical agent such as anti-cancer agents. The compound or the pharmaceutically acceptable salt thereof or the composition of the present disclosure may be used in the manufacture of a medicament of inhibiting the growth of tumor cells or treating cancer.

Also within the present disclosure is a method for treating a cancer, which includes the step of administering to the subject in need thereof an effective amount of the compound of the present disclosure or the pharmaceutically acceptable salt thereof.

Further covered by the present disclosure a method of inhibiting a growth of tumor cells, which includes the step of administering to a subject in need thereof an effective amount of the compound of the present disclosure or the pharmaceutically acceptable salt thereof.

In the present disclosure, the aforesaid subject can be mammal, for example, human.

In the present disclosure, the compound of the present disclosure or the pharmaceutically acceptable salt thereof can inhibit the growth of tumor cells to achieve the purpose of treating a cancer. Examples of the cancer include, but are not limited to, gastric cancer, colon cancer, colorectal cancer, breast cancer, lung cancer, prostate cancer, bladder cancer, pancreatic cancer, liver cancer, uterine cancer, cervical caner, endometrial cancer, esophageal cancer, leukemia, lymphoma, kidney cancer, osteosarcoma, ovarian cancer, skin cancer, small intestine cancer, thymus cancer, thyroid cancer, nervous system cancers, bone cancer, brain cancer, or head and neck cancer.

The compounds or the pharmaceutically acceptable salt thereof of the present disclosure may be administered in combination with at least one additional pharmaceutical agent such as anti-cancer agent. The administration formulation can be, for example, (a) a single formulation comprising the compound of the present disclosure or the pharmaceutically acceptable salt thereof, a pharmaceutically acceptable carrier, excipient or diluent and at least one additional pharmaceutical agent; or (b) two formulations administered simultaneously or sequentially and in any order, wherein one comprises the compound of the present disclosure or the pharmaceutically acceptable salt thereof, a pharmaceutically acceptable carrier, excipient or diluent and the other one comprises at least one additional pharmaceutical agent.

Suitable anti-cancer agents may include Herceptin, Rituximab, Docetaxel, Capecitabine, Cetuximab, Gefitinib, PD-1, Sorafenib tosylate or Imatinib, but the present disclosure is not limited thereto. Any other anti-cancer agents known in the art can also be used in the present disclosure.

Methods for synthesizing the compounds of formula (I) are well known in the art. See, for example, R. Larock, Comprehensive Organic Transformations ($2^{nd}$ Ed., VCH Publishers 1999); P. G. M. Wuts and T. W. Greene, Greene's Protective Groups in Organic Synthesis ($4^{th}$ Ed., John Wiley and Sons 2007); L. Fieser and M. Fieser, Fieser and Fieser's Reagents for Organic Synthesis (John Wiley and Sons 1994); L. Paquette, ed., Encyclopedia of Reagents for Organic Synthesis ($2^{nd}$ ed., John Wiley and Sons 2009); P. Roszkowski, J. K. Maurin, Z. Czarnocki "Enantioselective synthesis of (R)-(–)-praziquantel (PZQ)" Tetrahedron: Asymmetry 17 (2006) 1415-1419; and L. Hu, S. Magesh, L. Chen, T. Lewis, B. Munoz, L. Wang "Direct inhibitors of keap1-nrf2 interaction as antioxidant inflammation modulators," WO2013/067036.

The compounds of formula (I) thus prepared can be initially screened using in vitro assays, e.g., NCI-60 screening platform or MTS method. They can be subsequently evaluated using in vivo assays known in the field. The selected compounds can be further tested to verify their efficacy in disease related efficacy and adverse effects models. Based on the results, an appropriate dosage range and administration route can be determined.

The following embodiments are made to clearly exhibit the above-mentioned and other technical contents, features and/or effects of the present disclosure. Through the exposition by means of the specific embodiments, people would further understand the technical means and effects the present disclosure adopts to achieve the above-indicated objectives. Moreover, as the contents disclosed herein should be readily understood and can be implemented by a person skilled in the art, all equivalent changes or modifications which do not depart from the concept of the present disclosure should be encompassed by the appended claims.

EXAMPLE

Without further elaboration, it is believed that one skilled in the art can, based on the above description, utilize the present disclosure to its fullest extent. The following specific examples, i.e., EXAMPLES 1-6, are therefore to be construed as merely illustrative, and not limitative of the remainder of the disclosure in any way whatsoever. All publications cited herein are incorporated by reference in their entirety.

Among the specific examples, EXAMPLES 1-6 set forth the procedures for preparing certain intermediates and 228 exemplary compounds of formula (I), as well as the analytical data for the compounds thus prepared; and EXAMPLE 7 and EXAMPLE 8 set forth the protocols for testing these compounds.

Described below are the procedures used to synthesize the exemplary compounds of the present disclosure.

Unless otherwise stated, all starting materials used were commercially available and used as supplied. Reactions requiring anhydrous conditions were performed in flame-dried glassware and cooled under an argon or nitrogen atmosphere. Unless otherwise stated, reactions were carried out under argon or nitrogen and monitored by analytical thin-layer chromatography performed on glass-backed plates (5 cm_10 cm) precoated with silica gel 60 F254 as supplied by Merck. Visualization of the resulting chromatograms was done by looking under an ultraviolet lamp ($\lambda$=254 nm), followed by dipping in an nBuOH solution of Ninhydrin (0.3% w/v) containing acetic acid (3% v/v) or ethanol solution of phosphomolybdic acid (2.5% w/v) and caning by heat gun. Solvents for reactions were dried under an argon or nitrogen atmosphere prior to use as follows. THF, Toluene, and DCM were dried by the column of Dried molecular Sieve 5A (LC technology solution Inc). DMF dried by calcium hydride or anhydrous is commercial available. Flash chromatography was used routinely for purification and separation of product mixtures using RediSep Rf Silica Gel Disposable Flash Columns, Gold® 20-40/40-60 microns silica gel and Reusable Redi Sep Rf Gold® C18 Reversed Phase columns, 20-40 microns supplied by RediSep. Eluent systems are given in volume/volume concentrations. $^{13}$C and $^1$H NMR spectra were recorded on Bruker AVIII (400 MHz). Chloroform-d or dimethyl sulfoxide-d6 and $CD_3OD$ was used as the solvent and TMS ($\delta$ 0.00 ppm) as an internal standard. Chemical shift values are reported in ppm relative to the TMS in delta ($\delta$) units. Multiplicities are recorded as s (singlet), br s (broad singlet), d (doublet), t (triplet), q (quartet), dd (doublet of doublet), dt (doublet of triplet), m (multiplet). Coupling constants (J) are expressed in Hz. Electrospray mass spectra (ESMS) were recorded using a Thermo LTQ XL mass spectrometer. Spectral data were recorded as m/z values.

In the preparation of compounds of the present invention, protection of remote functionality (e.g., primary or secondary amine) of intermediates may be necessary. The need for such protection may vary depending on the nature of the remote functionality and the conditions of the preparation methods. Suitable amino protecting groups (NHPg) include, for example, acetyl, trifluoroacetyl, tbutoxycarbonyl (BOC), 9-fluorenylmethyleneoxycarbonyl (Fmoc) and benzyloxycarbonyl (CBz). Similarly, a "hydroxyl protecting group" refers to a substituent of a hydroxy group that blocks or protects the hydroxyl functionality. Suitable hydroxyl protecting groups (OPg) include, for example, allyl, acetyl, silyl, benzyl, paramethoxy benzyl, trityl, and the like. The need for such protection is readily determined by one skilled in the art.

Typical synthesis procedure of Compounds of EXAMPLE 1

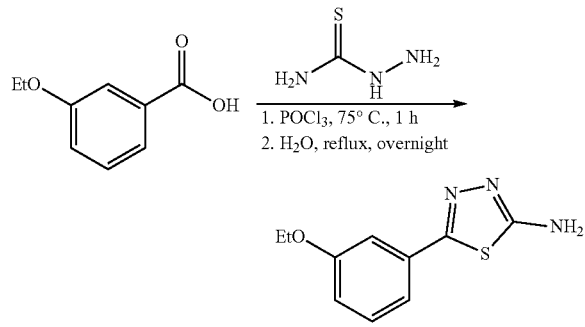

Synthesis of 5-(3-ethoxyphenyl)-1,3,4-thiadiazol-2-amine

To a mixture of 3-ethoxybenzoic acid (2.38 g, 10 mmol) and thiosemicarbazide (1.37 g, 15 mmol) with 5 mL of phosphorus oxychloride was refluxed gently for 2 hours. After cooling, 50 mL of water was added, and the mixture was refluxed for 7 hours and filtered, neutralized with 50% potassium hydroxide. The precipitate was washed with water and recrystallized from ethanol to give titled compound (1.22 g, 55%).

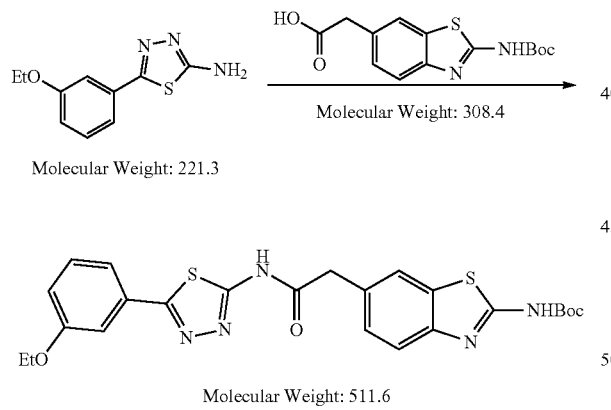

Synthesis of tert-butyl (6-(2-((5-(3-ethoxyphenyl)-1,3,4-thiadiazol-2-yl)amino)-2-oxoethyl)benzo[d]thiazol-2-yl)carbamate To a mixture of 5-(3-ethoxyphenyl)-1,3,4-thiadiazol-2-amine (0.44 g, 2 mmol) and HOBt (0.27 g, 2 mmol), EDCI (0.46 g, 2.4 mmol), 2-(2-((tert-butoxycarbonyl)amino)benzo[d]thiazol-6-yl)acetic acid (0.74 g, 2.4 mmol) in dry 12 mL DMF. The reaction was stirred overnight at room temperature then added water. The precipitate was washed with water and recrystallized from methanol to give titled compound (0.75 g, 73%).

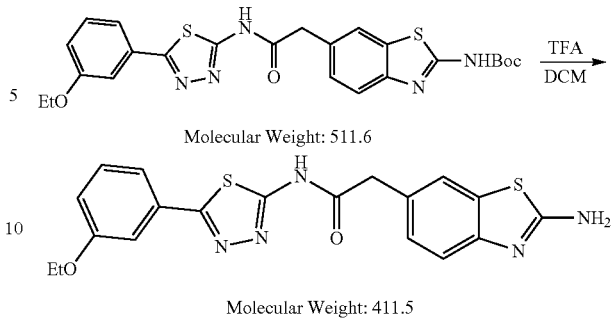

Synthesis of 2-(2-aminobenzo[d]thiazol-6-yl)-N-(5-(3-ethoxyphenyl)-1,3,4-thiadiazol-2-yl)acetamide To a vigorous stirred solution of 2-(2-aminobenzo[d]thiazol-6-yl)-N-(5-(3-ethoxyphenyl)-1,3,4-thiadiazol-2-yl)acetamide (0.75 g, 1.46 mmol) in anhydrous dichloromethane (15 mL) at room temperature, added trifluoroacetic acid (1.5 mL, 20 mmol) and stirred for overnight. Excess trifluoroacetic acid was neutralized by added dropwised of $Na_2CO_3$(aq) until pH=10. The precipitate was washed with water and MeOH then further purified by silica gel flash column chromatography using dichloromethane and methanol as eluent and concentrated to give white solid (0.95 g, 65%).

Example 1: Compounds 1-1 to 1-37

Compound 1-1

2-(2-aminobenzo[d]thiazol-6-yl)-N-(5-(3-ethoxyphenyl)-1,3,4-thiadiazol-2-yl)acetamide

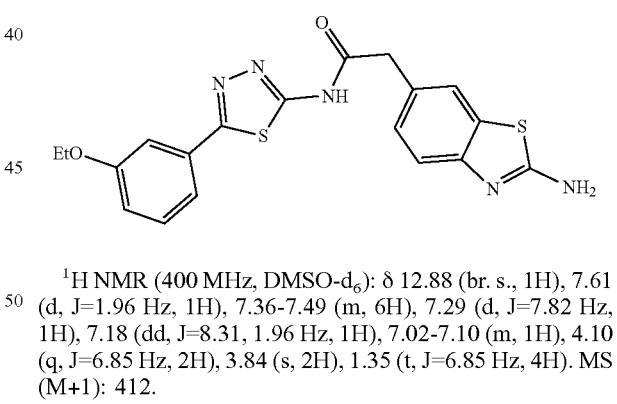

$^1$H NMR (400 MHz, DMSO-$d_6$): δ 12.88 (br. s., 1H), 7.61 (d, J=1.96 Hz, 1H), 7.36-7.49 (m, 6H), 7.29 (d, J=7.82 Hz, 1H), 7.18 (dd, J=8.31, 1.96 Hz, 1H), 7.02-7.10 (m, 1H), 4.10 (q, J=6.85 Hz, 2H), 3.84 (s, 2H), 1.35 (t, J=6.85 Hz, 4H). MS (M+1): 412.

Compound 1-2

2-(2-aminobenzo[d]thiazol-6-yl)-N-(5-(4-ethoxyphenyl)-1,3,4-thiadiazol-2-yl)acetamide

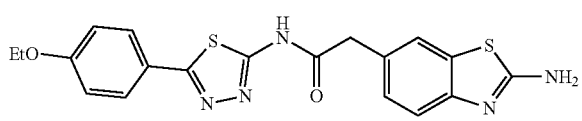

¹H NMR (400 MHz, DMSO-d₆): δ 12.76 (s, 1H), 7.80-7.87 (m, 2H), 7.60 (d, J=1.96 Hz, 1H), 7.41 (s, 2H), 7.28 (d, J=8.31 Hz, 1H), 7.17 (dd, J=8.31, 1.96 Hz, 1H), 7.02-7.10 (m, 2H), 4.09 (q, J=7.01 Hz, 2H), 3.83 (s, 2H), 1.34 (t, J=7.09 Hz, 3H). MS (M+1): 412

Compound 1-3

2-(2-aminobenzo[d]thiazol-6-yl)-N-(5-(2-hydroxyphenyl)-1,3,4-thiadiazol-2-yl)acetamide

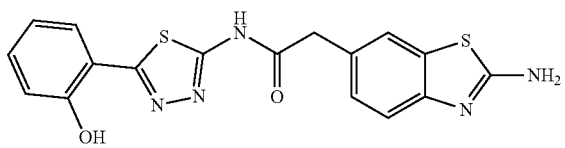 [SMILES: Nc1nc2ccc(CC(=O)Nc3nnc(-c4ccccc4O)s3)cc2s1]

¹H NMR (400 MHz, DMSO-d₆): δ 12.61 (br. s., 1H), 8.26 (dd, J=8.1, 1.2 Hz, 1H), 7.44-7.52 (m, 1H), 7.22 (d, J=8.3 Hz, 1H), 7.10 (t, J=7.6 Hz, 1H), 6.92 (s, 1H), 6.87 (d, J=7.8 Hz, 1H), 6.80 (d, J=7.8 Hz, 1H), 5.98 (s, 2H), 4.26 (q, J=6.8 Hz, 2H), 3.74 (s, 2H), 1.45 (t, J=6.8 Hz, 3H). MS (M+1): 384.

Compound 1-4

2-(2-aminobenzo[d]thiazol-6-yl)-N-(5-(2-nitrophenyl)-1,3,4-thiadiazol-2-yl)acetamide

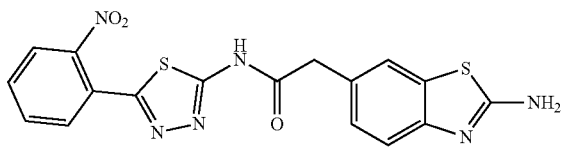

¹H NMR (400 MHz, DMSO-d₆): δ 13.01 (s, 1H), 8.04-8.08 (m, 1H), 7.82-7.89 (m, 2H), 7.59-7.63 (m, 2H), 7.29 (d, J=8.3 Hz, 2H), 7.15-7.21 (m, 2H), 3.86 (s, 2H). MS (M+1): 413

Compound 1-5

2-(2-aminobenzo[d]thiazol-6-yl)-N-(5-(4-(trifluoromethyl)phenyl)-1,3,4-thiadiazol-2-yl)acetamide

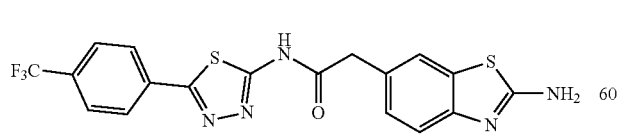

¹H NMR (400 MHz, DMSO-d₆): δ 13.02 (s, 1H), 8.14 (d, J=7.8 Hz, 2H), 7.87 (d, J=8.3 Hz, 3H), 7.65 (d, J=2.0 Hz, 1H), 7.60 (br. s., 2H), 7.32 (d, J=7.8 Hz, 1H), 3.88 (s, 2H). MS (M+1): 436.

Compound 1-6

2-(2-aminobenzo[d]thiazol-6-yl)-N-(5-(2-methoxyphenyl)-1,3,4-thiadiazol-2-yl)acetamide

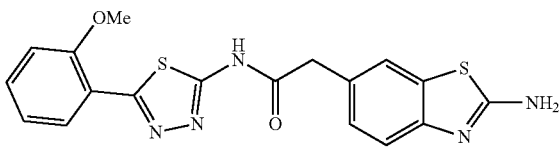 [SMILES: COc1ccccc1-c1nnc(NC(=O)Cc2ccc3nc(N)sc3c2)s1]

¹H NMR (400 MHz, DMSO-d₆): δ 12.69 (s, 1H), 8.26 (dd, J=7.8, 1.5 Hz, 1H), 7.41 (td, J=7.6, 1.0 Hz, 2H), 7.22-7.33 (m, 2H), 7.07-7.22 (m, 2H), 3.94-4.01 (m, 4H), 3.83 (s, 2H). MS (M+1): 398.

Compound 1-7

2-(2-aminobenzo[d]thiazol-6-yl)-N-(5-(4-bromophenyl)-1,3,4-thiadiazol-2-yl)acetamide

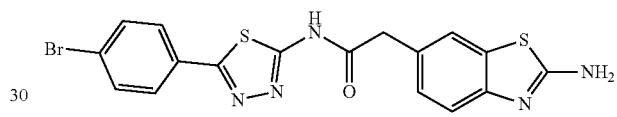

¹H NMR (400 MHz, DMSO-d₆): δ 12.91 (s, 1H), 7.87 (d, J=8.3 Hz, 2H), 7.68-7.76 (m, 2H), 7.60 (s, 1H), 7.42 (s, 2H), 7.28 (d, J=8.3 Hz, 1H), 7.17 (d, J=7.8 Hz, 1H), 3.84 (s, 2H). MS (M+1): 446

Compound 1-8

2-(2-aminobenzo[d]thiazol-6-yl)-N-(5-(4-nitrophenyl)-1,3,4-thiadiazol-2-yl)acetamide

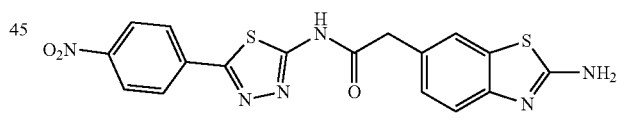

¹H NMR (400 MHz, DMSO-d₆): δ 13.06 (br. s., 1H), 8.31-8.41 (m, 2H), 8.18-8.27 (m, 2H), 7.61 (d, J=1.5 Hz, 1H), 7.42 (s, 2H), 7.29 (d, J=8.3 Hz, 1H), 7.18 (dd, J=8.3, 1.5 Hz, 1H), 3.86 (s, 2H). MS (M+1): 413.

Compound 1-9

2-(2-aminobenzo[d]thiazol-6-yl)-N-(5-(4-(dimethylamino)phenyl)-1,3,4-thiadiazol-2-yl)acetamide

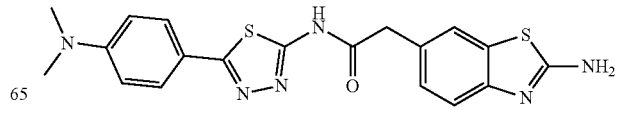

¹H NMR (400 MHz, DMSO-d₆): δ 12.67 (s, 1H), 7.68-7.74 (m, 2H), 7.60 (d, J=1.5 Hz, 1H), 7.42 (s, 2H), 7.28 (d, J=8.3 Hz, 1H), 7.17 (dd, J=8.1, 1.7 Hz, 1H), 6.75-6.81 (m, J=8.8 Hz, 2H), 3.81 (s, 2H), 2.98 (s, 6H). MS (M+1):411

Compound 1-10

2-(2-aminobenzo[d]thiazol-6-yl)-N-(5-(2-propoxyphenyl)-1,3,4-thiadiazol-2-yl)acetamide

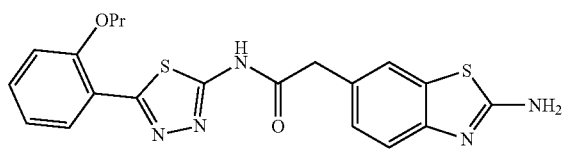

¹H NMR (400 MHz, DMSO-d₆): δ 12.66 (s, 1H), 8.28 (dd, J=7.8, 2.0 Hz, 1H), 7.61 (d, J=1.5 Hz, 1H), 7.48 (td, J=7.8, 2.0 Hz, 1H), 7.43 (s, 2H), 7.29 (d, J=8.3 Hz, 1H), 7.15-7.26 (m, 2H), 7.10 (t, J=7.6 Hz, 1H), 4.17 (t, J=6.6 Hz, 2H), 3.83 (s, 2H), 1.79-1.92 (m, 2H), 1.06 (t, J=7.6 Hz, 3H). MS (M+1):426.

Compound 1-11

2-(2-aminobenzo[d]thiazol-6-yl)-N-(5-(2-(trifluoromethoxy)phenyl)-1,3,4-thiadiazol-2-yl)acetamide

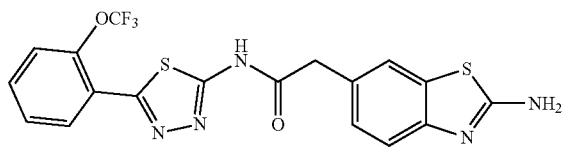 [SMILES: Nc1nc2ccc(CC(=O)Nc3nnc(-c4ccccc4OC(F)(F)F)s3)cc2s1]

¹H NMR (400 MHz, DMSO-d₆): δ 12.95 (s, 1H), 8.27-8.33 (m, 1H), 7.67 (d, J=6.8 Hz, 1H), 7.56-7.64 (m, 3H), 7.42 (s, 2H), 7.26-7.32 (m, 1H), 7.19 (d, J=2.0 Hz, 1H), 3.86 (s, 2H). MS (M+1): 452.

Compound 1-12

2-(2-aminobenzo[d]thiazol-6-yl)-N-(5-(4-iodophenyl)-1,3,4-thiadiazol-2-yl)acetamide

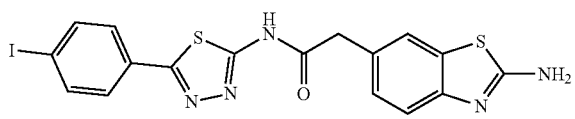 [SMILES: Nc1nc2ccc(CC(=O)Nc3nnc(-c4ccc(I)cc4)s3)cc2s1]

¹H NMR (400 MHz, DMSO-d₆): δ 12.92 (br. s., 1H), 7.86-7.91 (m, 2H), 7.69-7.73 (m, 2H), 7.60 (d, J=2.0 Hz, 1H), 7.43 (s, 2H), 7.28 (d, J=8.3 Hz, 1H), 7.17 (dd, J=8.3, 1.5 Hz, 1H), 3.80-3.87 (m, 2H). MS (M+1):494

Compound 1-13

2-(2-aminobenzo[d]thiazol-6-yl)-N-(5-(4-bromo-3-nitrophenyl)-1,3,4-thiadiazol-2-yl)acetamide

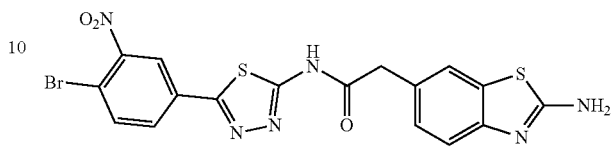

¹H NMR (400 MHz, DMSO-d₆): δ 13.04 (s, 1H), 8.55 (d, J=2.0 Hz, 1H), 8.12 (dd, J=8.3, 2.0 Hz, 1H), 8.05 (d, J=8.3 Hz, 1H), 7.61 (d, J=1.5 Hz, 1H), 7.46 (s, 2H), 7.29 (d, J=8.3 Hz, 1H), 7.18 (dd, J=8.3, 2.0 Hz, 1H), 3.86 (s, 2H). MS (M+1): 491.

Compound 1-14

2-(2-aminobenzo[d]thiazol-6-yl)-N-(5-(4-isopropoxyphenyl)-1,3,4-thiadiazol-2-yl)acetamide

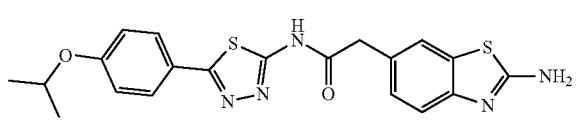 [SMILES: CC(C)Oc1ccc(-c2nnc(NC(=O)Cc3ccc4nc(N)sc4c3)s2)cc1]

¹H NMR (400 MHz, DMSO-d₆): δ 12.80 (s, 2H), 7.86 (br. s., 2H), 7.76-7.85 (m, 2H), 7.65 (d, J=1.5 Hz, 1H), 7.31 (dd, J=8.6, 4.6 Hz, 1H), 7.22 (dd, J=8.3, 1.5 Hz, 1H), 6.99-7.08 (m, 2H), 4.69 (spt, J=6.0 Hz, 1H), 3.84 (s, 2H), 1.35 (s, 3H), 1.22 (s, 3H). MS (M+1):460

Compound 1-15

2-(2-aminobenzo[d]thiazol-6-yl)-N-(5-(2-isopropoxyphenyl)-1,3,4-thiadiazol-2-yl)acetamide

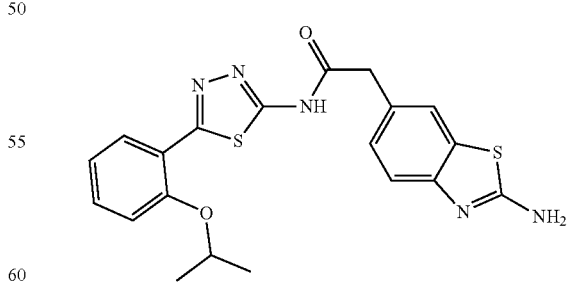

¹H NMR (400 MHz, DMSO-d₆): δ 12.67 (s, 1H), 8.28 (dd, J=8.0, 1.6 Hz, 1H), 7.86 (br, 2H), 7.66 (d, J=1.6 Hz, 1H), 7.49-7.44 (m, 1H), 7.32 (d, J=8.4 Hz, 1H), 7.26-7.21 (m, 2H), 7.10-7.06 (m, 1H), 4.90 (quin, J=6.0 Hz, 1H), 3.85 (s, 2H), 1.37 (d, J=6.0 Hz, 6H). MS (M+1): 426.

Compound 1-16

2-(2-aminobenzo[d]thiazol-6-yl)-N-(5-(4-(pentan-3-yloxy)phenyl)-1,3,4-thiadiazol-2-yl)acetamide

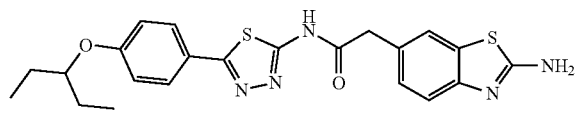 [SMILES: CCC(CC)Oc1ccc(-c2nnc(NC(=O)Cc3ccc4nc(N)sc4c3)s2)cc1]

¹H NMR (400 MHz, DMSO-d₆): δ 12.80 (s, 1H), 7.81 (d, J=8.8 Hz, 2H), 7.80 (br. s., 2H), 7.64 (d, J=1.5 Hz, 1H), 7.31 (d, J=8.3 Hz, 1H), 7.21 (dd, J=8.3, 1.5 Hz, 1H), 7.05 (d, J=8.8 Hz, 2H), 4.32 (quin, J=5.7 Hz, 1H), 3.84 (s, 2H), 1.56-1.72 (m, 2H), 0.90 (t, J=7.6 Hz, 3H). MS (M+1):454.

Compound 1-17

2-(2-aminobenzo[d]thiazol-6-yl)-N-(5-(4-propoxyphenyl)-1,3,4-thiadiazol-2-yl)acetamide

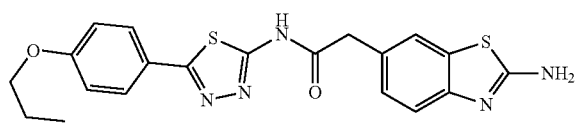 [SMILES: CCCOc1ccc(-c2nnc(NC(=O)Cc3ccc4nc(N)sc4c3)s2)cc1]

¹H NMR (400 MHz, DMSO-d₆): δ 12.78 (br. s., 1H), 7.80-7.86 (m, J=8.8 Hz, 2H), 7.64-7.68 (m, 1H), 7.33 (d, J=7.8 Hz, 1H), 7.23 (dd, J=8.1, 1.2 Hz, 1H), 7.02-7.08 (m, J=8.8 Hz, 2H), 3.99 (t, J=6.6 Hz, 2H), 1.69-1.79 (m, 2H), 1.51 (s, 2H), 0.98 (t, J=7.3 Hz, 3H). MS (M+1):440.

Compound 1-18

2-(2-aminobenzo[d]thiazol-6-yl)-N-(5-(2,4-diethoxyphenyl)-1,3,4-thiadiazol-2-yl)acetamide

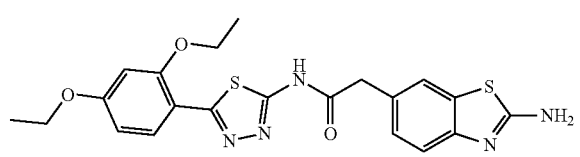 [SMILES: CCOc1ccc(-c2nnc(NC(=O)Cc3ccc4nc(N)sc4c3)s2)c(OCC)c1]

¹H NMR (400 MHz, DMSO-d₆): δ 12.61 (s, 1H), 8.32 (br. s., 2H), 8.16 (d, J=8.8 Hz, 1H), 7.70 (d, J=1.5 Hz, 1H), 7.35 (d, J=8.3 Hz, 1H), 7.27 (dd, J=8.1, 1.7 Hz, 1H), 6.65-6.75 (m, 2H), 4.24 (q, J=6.8 Hz, 2H), 4.11 (q, J=7.2 Hz, 2H), 3.85 (s, 2H), 1.43 (t, J=6.8 Hz, 3H), 1.34 (t, J=6.8 Hz, 3H). MS (M+1): 456.

Compound 1-19

2-(2-aminobenzo[d]thiazol-6-yl)-N-(5-(4-hydroxyphenyl)-1,3,4-thiadiazol-2-yl)acetamide

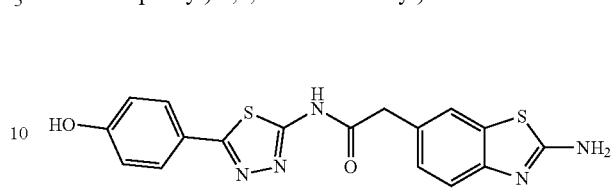

¹H NMR (400 MHz, DMSO-d₆): δ 12.77 (s, 1H), 8.19 (br. s., 2H), 7.73 (d, J=8.8 Hz, 2H), 7.68 (s, 1H), 7.30-7.40 (m, 1H), 7.21-7.30 (m, 1H), 6.68 (d, J=8.8 Hz, 2H), 3.85 (s, 2H). MS (M+1):384.

Compound 1-20

2-(2-aminobenzo[d]thiazol-6-yl)-N-(5-(2-butoxyphenyl)-1,3,4-thiadiazol-2-yl)acetamide

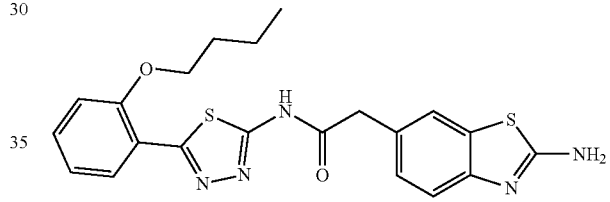

¹H NMR (400 MHz, DMSO-d₆): δ 12.71 (s, 1H), 8.42 (br. s., 2H), 8.27 (dd, J=7.8, 2.0 Hz, 1H), 7.72 (s, 1H), 7.44-7.53 (m, 1H), 7.34-7.40 (m, 1H), 7.27-7.34 (m, 1H), 7.23 (d, J=8.3 Hz, 1H), 7.10 (t, J=7.6 Hz, 1H), 4.21 (t, J=6.4 Hz, 2H), 3.87 (s, 2H), 1.77-1.88 (m, 2H), 1.52 (sxt, J=7.4 Hz, 2H), 0.94 (t, J=7.6 Hz, 3H). MS (M+1):440.

Compound 1-21

2-(2-aminobenzo[d]thiazol-6-yl)-N-(5-(4-butoxyphenyl)-1,3,4-thiadiazol-2-yl)acetamide

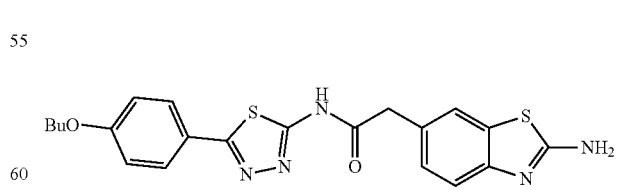

¹H NMR (400 MHz, DMSO-d₆): δ 12.81 (br. s., 1H), 11.71 (br. s., 1H), 7.88 (s, 1H), 7.80-7.85 (m, J=8.8 Hz, 2H), 7.63 (d, J=8.3 Hz, 1H), 7.36 (dd, J=8.3, 1.5 Hz, 1H), 7.01-7.07 (m, J=8.8 Hz, 2H), 4.02 (t, J=6.6 Hz, 2H), 3.93 (s, 1H), 1.51 (s, 7H), 0.93 (t, J=7.3 Hz, 3H). MS (M+1):440.

Compound 1-22

2-(2-aminobenzo[d]thiazol-6-yl)-N-(5-(2-(pentan-3-yloxy)phenyl)-1,3,4-thiadiazol-2-yl)acetamide

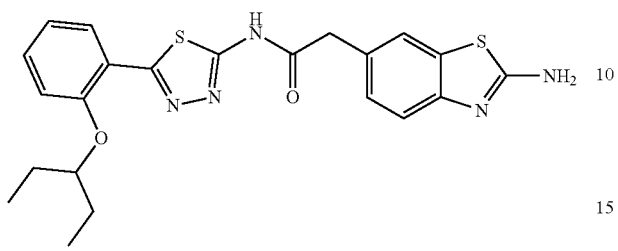

$^1$H NMR (400 MHz, DMSO-d$_6$): δ 12.71 (br. s., 1H), 9.15 (br. s., 2H), 8.29 (dd, J=7.8, 1.5 Hz, 1H), 7.79 (s, 1H), 7.41-7.48 (m, 2H), 7.33-7.39 (m, 1H), 7.24 (d, J=8.3 Hz, 1H), 7.06 (t, J=7.6 Hz, 1H), 4.58 (t, J=5.6 Hz, 1H), 3.90 (s, 2H), 1.67-1.76 (m, 4H), 0.89 (t, J=7.3 Hz, 6H). MS (M+1): 454

Compound 1-23

2-(2-aminobenzo[d]thiazol-6-yl)-N-(5-(2-butoxy-4-ethoxyphenyl)-1,3,4-thiadiazol-2-yl)acetamide

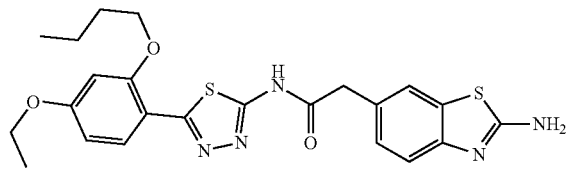 [SMILES: CCCCOc1cc(OCC)ccc1-c1nnc(NC(=O)Cc2ccc3nc(N)sc3c2)s1]

$^1$H NMR (400 MHz, DMSO-d$_6$): δ 12.57 (s, 1H), 8.16 (d, J=8.8 Hz, 1H), 7.79 (br. s., 2H), 7.65 (d, J=1.5 Hz, 1H), 7.31 (d, J=7.8 Hz, 1H), 7.22 (dd, J=8.3, 1.5 Hz, 1H), 6.72 (d, J=2.0 Hz, 1H), 6.68 (dd, J=8.6, 2.2 Hz, 1H), 4.19 (t, J=6.6 Hz, 2H), 4.11 (q, J=6.8 Hz, 2H), 3.83 (s, 2H), 1.75-1.88 (m, 2H), 1.47-1.56 (m, 2H), 1.34 (t, J=7.1 Hz, 3H), 0.94 (t, J=7.6 Hz, 3H). MS (M+1):484.

Compound 1-24

2-(2-aminobenzo[d]thiazol-6-yl)-N-(5-(2,4,6-triethoxyphenyl)-1,3,4-thiadiazol-2-yl)acetamide

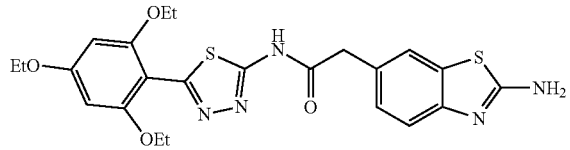 [SMILES: CCOc1cc(OCC)c(-c2nnc(NC(=O)Cc3ccc4nc(N)sc4c3)s2)c(OCC)c1]

$^1$H NMR (400 MHz, DMSO-d$_6$): δ 7.59 (d, J=1.5 Hz, 1H), 7.38 (s, 2H), 7.27 (d, J=8.3 Hz, 1H), 7.16 (dd, J=8.3, 1.5 Hz, 1H), 6.28 (s, 2H), 4.08 (q, J=1.0 Hz, 2H), 3.99 (q, J=1.0 Hz, 4H), 3.75 (s, 2H), 1.33 (t, J=1.0 Hz, 4H), 1.17 (t, J=1.0 Hz, 6H).

MS (M+1): 500.

Compound 1-25

2-(2-aminobenzo[d]thiazol-6-yl)-N-(5-(3-ethoxypyridin-4-yl)-1,3,4-thiadiazol-2-yl)acetamide

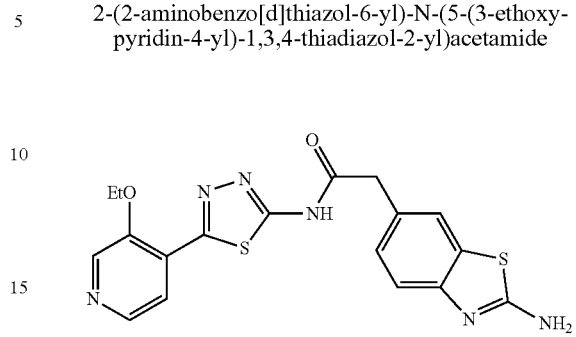

$^1$H NMR (400 MHz, DMSO-d$_6$): δ 12.87 (br s, 1H), 8.60 (s, 1H), 8.34 (d, J=4.8 Hz, 1H), 8.16 (d, J=4.8 Hz, 1H), 7.60 (d, J=2.0 Hz, 1H), 7.42 (s, 2H), 7.29 (d, J=8.4 Hz, 1H), 7.17 (dd, J=8.4, 1.6 Hz, 1H), 4.40 (q, J=6.8 Hz, 2H), 3.84 (s, 2H), 1.46 (t, J=6.8 Hz, 3H). MS (M+1):413.

Compound 1-26

2-(2-aminobenzo[d]thiazol-6-yl)-N-(5-(4-ethoxy-2-(ethoxymethoxy)phenyl)-1,3,4-thiadiazol-2-yl)acetamide

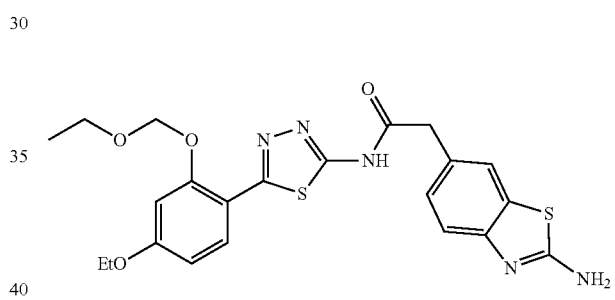

$^1$H NMR (400 MHz, DMSO-d$_6$): δ 12.61 (br s, 1H), 8.17 (d, J=9.2 Hz, 1H), 7.60 (d, J=1.2 Hz, 1H), 7.42 (s, 2H), 7.28 (d, J=8.4 Hz, 1H), 7.17 (dd, J=9.2, 1.6 Hz, 1H), 6.81 (d, J=2.4 Hz, 1H), 6.74 (dd, J=8.8, 2.8 Hz, 1H), 5.45 (s, 2H), 4.09 (q, J=6.8 Hz, 2H), 3.81 (s, 2H), 3.68 (q, J=6.8 Hz, 2H), 1.35 (t, J=7.2 Hz, 3H), 1.11 (t, J=7.2 Hz, 3H). MS (M+1): 486.

Compound 1-27

2-(2-aminobenzo[d]thiazol-6-yl)-N-(5-(4-ethoxy-2-(2-(4-methylpiperazin-1-yl)ethoxy)phenyl)-1,3,4-thiadiazol-2-yl)acetamide

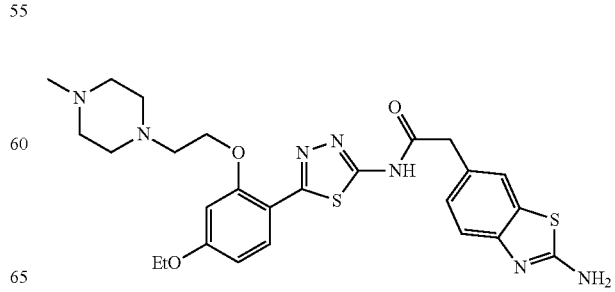

¹H NMR (400 MHz, DMSO-d₆): δ 12.53 (br s, 1H), 8.15 (d, J=8.8 Hz, 1H), 7.60 (d, J=1.6 Hz, 1H), 7.40 (s, 2H), 7.28 (d, J=8.4 Hz, 1H), 7.17 (dd, J=8.4, 2.0 Hz, 1H), 6.75 (d, J=2.4 Hz, 1H), 6.68 (dd, J=8.8, 2.4 Hz, 1H), 4.25 (t, J=5.6 Hz, 2H), 4.12 (q, J=6.8 Hz, 2H), 3.80 (s, 2H), 2.77 (t, J=5.6 Hz, 2H), 2.24-2.20 (m, 4H), 2.06 (s, 3H), 1.35 (t, J=6.8 Hz, 3H). MS (M+1):554.

Compound 1-28

2-(2-aminobenzo[d]thiazol-6-yl)-N-(5-(2-(3-(dimethylamino)propoxy)-4-ethoxyphenyl)-1,3,4-thiadiazol-2-yl)acetamide

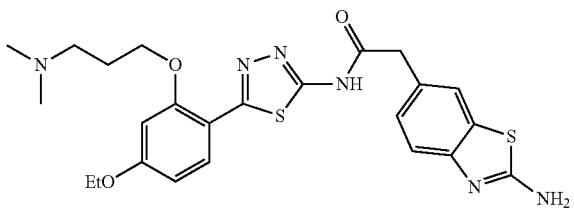 [SMILES: CCOc1ccc(-c2nnc(NC(=O)Cc3ccc4nc(N)sc4c3)s2)c(OCCCN(C)C)c1]

¹H NMR (400 MHz, DMSO-d₆): δ 12.57 (br s, 1H), 8.15 (d, J=8.8 Hz, 1H), 7.60 (d, J=1.6 Hz, 1H), 7.42 (s, 2H), 7.28 (d, J=8.4 Hz, 1H), 7.17 (dd, J=8.0, 1.6 Hz, 1H), 6.71 (d, J=2.0 Hz, 1H), 6.68 (dd, J=8.8, 2.4 Hz, 1H), 4.21 (t, J=6.4 Hz, 2H), 4.11 (q, J=6.8 Hz, 2H), 3.81 (s, 2H), 2.46 (t, J=6.8 Hz, 2H), 2.13 (s, 6H), 1.95 (quin, J=6.8 Hz, 2H), 1.34 (t, J=6.8 Hz, 3H). MS (M+1):513.

Compound 1-29

2-(2-aminobenzo[d]thiazol-6-yl)-N-(5-(2-(2-(dimethylamino)ethoxy)-4-ethoxyphenyl)-1,3,4-thiadiazol-2-yl)acetamide

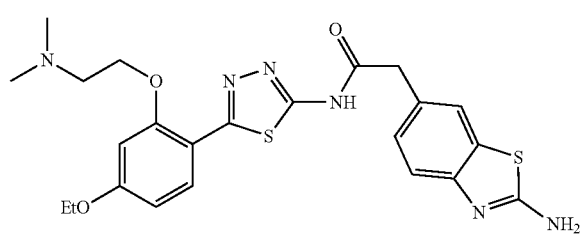 [SMILES: CCOc1ccc(-c2nnc(NC(=O)Cc3ccc4nc(N)sc4c3)s2)c(OCCN(C)C)c1]

¹H NMR (400 MHz, DMSO-d₆): δ 12.55 (br s, 1H), 8.16 (d, J=8.4 Hz, 1H), 7.60 (d, J=1.6 Hz, 1H), 7.42 (s, 2H), 7.28 (d, J=8.4 Hz, 1H), 7.18 (dd, J=8.4, 1.2 Hz, 1H), 6.76 (d, J=2.0 Hz, 1H), 6.68 (dd, J=8.8, 2.4 Hz, 1H), 4.26 (t, J=6.0 Hz, 2H), 4.12 (q, J=6.8 Hz, 2H), 3.81 (s, 2H), 2.76 (t, J=6.0 Hz, 2H), 2.25 (s, 6H), 1.35 (t, J=6.0 Hz, 3H). MS (M+1): 499.

Compound 1-30

2-(2-aminobenzo[d]thiazol-6-yl)-N-(5-(5-ethoxypyridin-2-yl)-1,3,4-thiadiazol-2-yl)acetamide

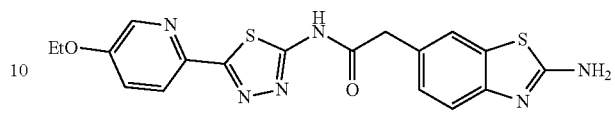

¹H NMR (400 MHz, DMSO-d₆): δ 12.79 (br s, 1H), 8.16 (d, J=8.4 Hz, 1H), 7.60 (d, J=1.6 Hz, 1H), 7.42 (s, 2H), 7.28 (d, J=8.4 Hz, 1H), 7.18 (dd, J=8.4, 1.2 Hz, 1H), 6.76 (d, J=2.0 Hz, 1H), 6.68 (dd, J=8.8, 2.4 Hz, 1H), 4.26 (t, J=6.0 Hz, 2H), 4.12 (q, J=6.8 Hz, 2H), 3.81 (s, 2H), 2.76 (t, J=6.0 Hz, 2H), 2.25 (s, 6H), 1.35 (t, J=6.0 Hz, 3H). MS (M+1): 413.

Compound 1-31

2-(2-aminobenzo[d]thiazol-6-yl)-N-(5-(3-(2-(dimethylamino)ethoxy)pyridin-4-yl)-1,3,4-thiadiazol-2-yl)acetamide

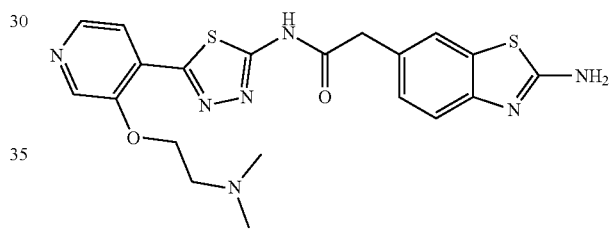

¹H NMR (400 MHz, DMSO-d₆): δ 12.84 (br s, 1H), 8.65 (s, 1H), 8.35 (d, J=5.2 Hz, 1H), 8.16 (d, J=4.8 Hz, 1H), 7.60 (d, J=1.6 Hz, 1H), 7.43 (s, 2H), 7.29 (d, J=8.4 Hz, 1H), 7.18 (dd, J=8.4, 1.6 Hz, 1H), 4.42 (t, J=5.6 Hz, 2H), 3.85 (s, 2H), 2.77 (t, J=6.0 Hz, 2H), 2.24 (s, 6H). MS (M+1):456.

Compound 1-32

2-(2-aminobenzo[d]thiazol-6-yl)-N-(5-(4-ethoxy-2-(2-methoxyethoxy)phenyl)-1,3,4-thiadiazol-2-yl)acetamide

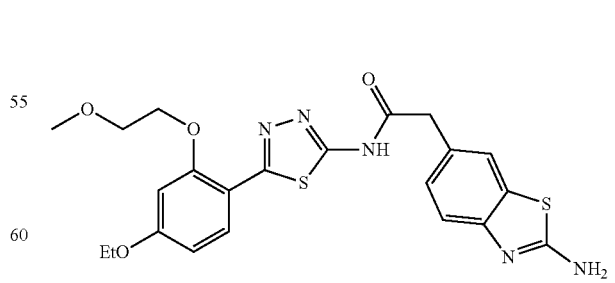

¹H NMR (400 MHz, DMSO-d₆): δ 12.54 (br s, 1H), 8.16 (d, J=8.8 Hz, 1H), 7.60 (d, J=1.6 Hz, 1H), 7.41 (br s, 2H), 7.28 (d, J=8.0 Hz, 1H), 7.18 (dd, J=8.0, 1.6 Hz, 1H), 6.74 (d, J=2.0 Hz, 1H), 6.69 (dd, J=8.8, 2.4 Hz, 1H), 4.30-4.32 (m,

2H), 4.11 (q, J=7.2 Hz, 2H), 3.81 (s, 2H), 3.77-3.75 (m, 2H), 3.34 (s, 3H), 1.35 (t, J=7.4 Hz, 3H). MS (M+1):486.

Compound 1-33

2-(2-aminobenzo[d]thiazol-6-yl)-N-(5-(4-propylphenyl)-1,3,4-thiadiazol-2-yl)acetamide

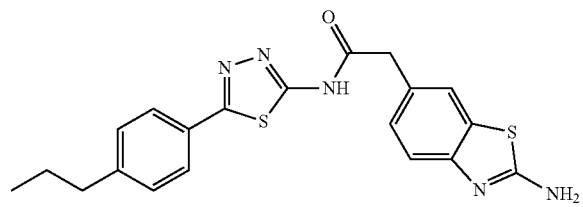 [SMILES: CCCc1ccc(-c2nnc(NC(=O)Cc3ccc4nc(N)sc4c3)s2)cc1]

¹H NMR (400 MHz, DMSO-d₆): δ 12.82 (s, 1H), 7.78-7.86 (m, 2H), 7.60 (d, J=1.5 Hz, 1H), 7.42 (s, 2H), 7.32-7.38 (m, J=8.3 Hz, 2H), 7.28 (d, J=7.8 Hz, 1H), 7.17 (dd, J=8.1, 1.7 Hz, 1H), 3.83 (s, 2H), 2.61 (t, J=7.6 Hz, 2H), 1.57-1.70 (m, 2H), 0.90 (t, J=7.3 Hz, 3H). MS (M+1):410.

Compound 1-34

2-(2-aminobenzo[d]thiazol-6-yl)-N-(5-(4-ethoxypyridin-3-yl)-1,3,4-thiadiazol-2-yl)acetamide

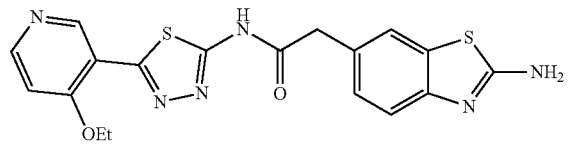

¹H NMR (400 MHz, DMSO-d₆): δ 12.77 (br, 1H), 9.19 (s, 1H), 8.49 (d, J=6.0 Hz, 1H), 7.59 (d, J=2.0 Hz, 1H), 7.40 (br, 2H), 7.29 (d, J=8.4 Hz, 1H), 7.24 (d, J=6.0 Hz, 1H), 7.17 (dd, J=8.4, 2.0 Hz, 1H), 4.32 (q, J=6.8 Hz, 2H), 3.83 (s, 2H), 1.42 (t, J=6.8 Hz, 3H). MS (M+1):413.

Compound 1-35

2-(2-aminobenzo[d]thiazol-6-yl)-N-(5-(4,6-diethoxypyridin-3-yl)-1,3,4-thiadiazol-2-yl)acetamide

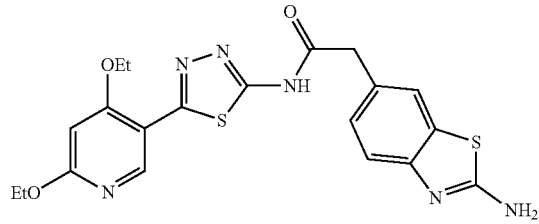

¹H NMR (400 MHz, DMSO-d₆): δ 12.71 (br, 1H), 8.84 (s, 1H), 7.60 (d, J=1.2 Hz, 1H), 7.42 (s, 2H), 7.28 (d, J=8.4 Hz, 1H), 7.17 (dd, J=8.4, 1.6 Hz, 1H), 6.57 (s, 1H), 4.36 (q, J=6.8 Hz, 2H), 4.29 (q, J=6.8 Hz, 2H), 3.82 (s, 2H), 1.42 (t, J=6.8 Hz, 3H), 1.32 (t, J=6.8 Hz, 3H). MS (M+1): 457.

Compound 1-36

2-(2-aminobenzo[d]thiazol-6-yl)-N-(5-(2,4-diethoxyphenyl)-1,3,4-thiadiazol-2-yl)-N-methylacetamide

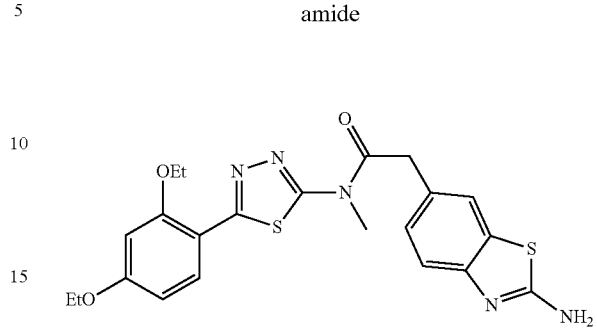

¹H NMR (400 MHz, DMSO-d₆): δ 12.79 (br s, 1H), 8.16 (d, J=8.4 Hz, 1H), 7.60 (d, J=1.6 Hz, 1H), 7.42 (s, 2H), 7.28 (d, J=8.4 Hz, 1H), 7.18 (dd, J=8.4, 1.2 Hz, 1H), 6.76 (d, J=2.0 Hz, 1H), 6.68 (dd, J=8.8, 2.4 Hz, 1H), 4.26 (t, J=6.0 Hz, 2H), 4.12 (q, J=6.8 Hz, 2H), 3.81 (s, 2H), 2.76 (t, J=6.0 Hz, 2H), 2.25 (s, 6H), 1.35 (t, J=6.0 Hz, 3H). MS (M+1): 470.

Compound 1-37

2-(2-aminobenzo[d]thiazol-6-yl)-N-(5-(4,6-diethoxypyridin-3-yl)-1,3,4-thiadiazol-2-yl)-N-methylacetamide

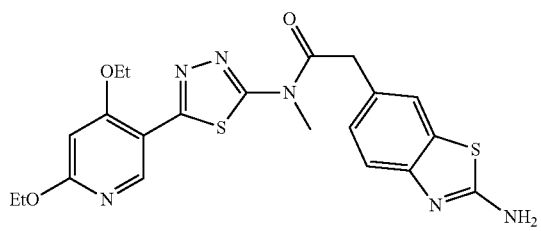 [SMILES: CCOc1cc(OCC)c(-c2nnc(N(C)C(=O)Cc3ccc4nc(N)sc4c3)s2)cn1]

¹H NMR (400 MHz, DMSO-d₆): δ 8.83 (s, 1H), 7.55 (s, 1H), 7.43 (s, 2H), 7.30 (d, J=8.0 Hz, 1H), 7.12 (dd, J=8.4, 1.6 Hz, 1H), 6.56 (s, 1H), 4.36 (q, J=6.8 Hz, 2H), 4.28 (q, J=6.8 Hz, 2H), 4.16 (s, 2H), 3.81 (s, 3H), 1.40 (t, J=6.8 Hz, 3H), 1.32 (t, J=6.8 Hz, 3H). MS (M+1): 471.

Typical synthesis procedure of Compounds of EXAMPLE 2

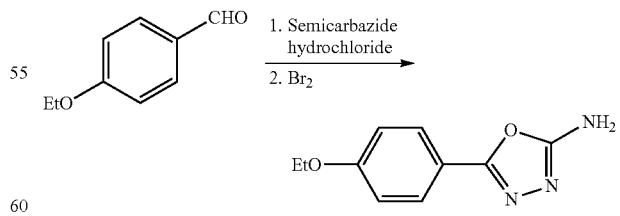

Step 1: Synthesis of 4-ethoxybenzylidene hydrazinecarboxamides

Semicarbazide hydrochloride (1.11 g, 10 mmol) and sodium acetate (1.64 g, 20 mmol) were dissolved in 15-20 ml of distilled water in a flat-bottomed flask. 4-ethoxybenzaldehyde (1.5 g, 10 mmol) was dissolved in ethanol. This solution was added slowly to the solution of semicarbazide hydrochloride. The precipitate was filtered, dried, and recrystallized from hot ethanol (95%) to obtain 4-ethoxybenzylidene hydrazinecarboxamide.

Step 2: Synthesis of 4-ethoxyphenyl-1,3,4-Oxadiazol-2-amines

Sodium acetate (20 mmol) and 4-ethoxybenzylidene hydrazinecarboxamide (2.1 g, 10 mmol) were dissolved in 30-40 ml of glacial acetic acid with continuous stirring. Bromine (0.7 ml in 5 ml of glacial acetic acid) was added slowly. Solution was stirred for 1 h and poured on crushed ice. The resulting solid was separated, dried, and recrystallized from hot ethanol (95%) to afford 4-ethoxyphenyl-1,3,4-oxadiazol-2-amines.

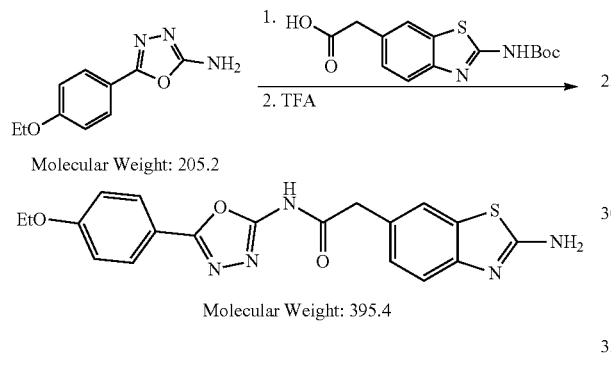

Synthesis of tert-butyl (6-(2-((5-(4-ethoxyphenyl)-1,3,4-oxadiazol-2-yl)amino)-2-oxoethyl)benzo[d]thiazol-2-yl)carbamate To a mixture of 4-ethoxyphenyl-1,3,4-oxadiazol-2-amines (0.41 g, 2 mmol) and HOBt (0.27 g, 2 mmol), EDCI (0.46 g, 2.4 mmol), 2-(2-((tert-butoxycarbonyl)amino)benzo[d]thiazol-6-yl)acetic acid (0.74 g, 2.4 mmol) in dry 12 mL DMF. The reaction was stirred overnight at room temperature then added water. The precipitate was washed with water and recrystallized from methanol to give tert-butyl (6-(2-((5-(4-ethoxyphenyl)-1,3,4-oxadiazol-2-yl)amino)-2-oxoethyl)benzo[d]thiazol-2-yl)carbamate (0.74 g, 75%).

Synthesis of 2-(2-aminobenzo[d]thiazol-6-yl)-N-(5-(4-ethoxyphenyl)-1,3,4-oxadiazol-2-yl)acetamide To a vigorous stirred solution of tert-butyl (6-(2-((5-(4-ethoxyphenyl)-1,3,4-oxadiazol-2-yl)amino)-2-oxoethyl)benzo[d]thiazol-2-yl)carbamate (0.74 g, 1.50 mmol) in anhydrous dichloromethane (15 mL) at room temperature, added trifluoroacetic acid (1.5 mL, 20 mmol) and stirred for overnight. Excess trifluoroacetic acid was neutralized by added dropwised of Na$_2$CO$_3$(aq) until pH=10. The precipitate was washed with water and MeOH then further purified by silica gel flash column chromatography using dichloromethane and methanol as eluent and concentrated to give white solid. (0.35 g, 60%)

Example 2: Compounds 2-1 to 2-4

Compound 2-1

2-(2-aminobenzo[d]thiazol-6-yl)-N-(5-(4-ethoxyphenyl)-1,3,4-oxadiazol-2-yl)acetamide

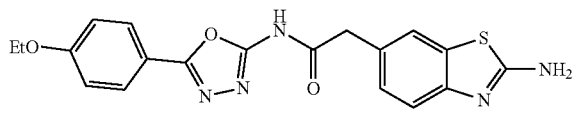

$^1$H NMR (400 MHz, DMSO-d$_6$): δ 11.87 (br. s., 1H), 7.99-8.07 (m, 1H), 7.79-7.86 (m, 2H), 7.67-7.74 (m, 5H), 7.59 (d, J=1.0 Hz, 1H), 7.42 (s, 2H), 7.28 (d, J=8.3 Hz, 1H), 7.12-7.20 (m, 3H), 4.09 (q, J=7.01 Hz, 2H), 3.76 (s, 2H), 1.34 (t, J=7.09 Hz, 4H). MS (M+1): 356.

Compound 2-2

2-(2-aminobenzo[d]thiazol-6-yl)-N-(5-(2-ethoxyphenyl)-1,3,4-oxadiazol-2-yl)acetamide

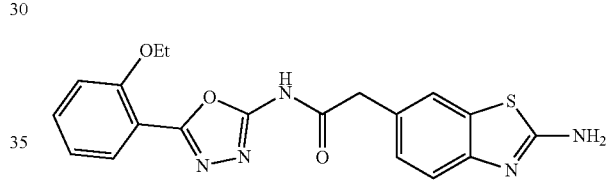

$^1$H NMR (400 MHz, DMSO-d$_6$): δ 11.89 (br. s., 1H), 8.04 (br. s., 1H), 7.71-7.74 (m, 1H), 7.55 (ddd, J=8.6, 7.3, 1.7 Hz, 1H), 7.33 (d, J=7.8 Hz, 1H), 7.23 (dd, J=8.3, 2.0 Hz, 2H), 7.06-7.11 (m, 2H), 4.14 (q, J=1.0 Hz, 2H), 3.80 (s, 2H), 1.33 (t, J=1.0 Hz, 3H). MS (M+1): 396.

Compound 2-3

2-(2-aminobenzo[d]thiazol-6-yl)-N-(5-(2-propoxyphenyl)-1,3,4-oxadiazol-2-yl)acetamide

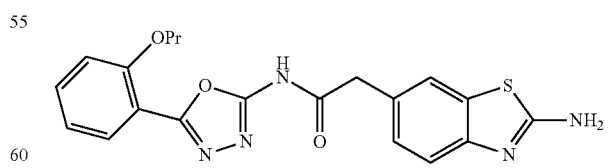

$^1$H NMR (400 MHz, DMSO-d$_6$): δ 11.82 (br. s., 1H), 7.73 (dd, J=7.8, 2.0 Hz, 1H), 7.50-7.62 (m, 1H), 7.40 (s, 2H), 7.18-7.32 (m, 2H), 7.16 (dd, J=8.1, 1.7 Hz, 1H), 7.05-7.12 (m, 2H), 4.03 (t, J=6.4 Hz, 2H), 3.76 (s, 2H), 1.65-1.77 (m, 2H), 0.94 (t, J=7.3 Hz, 3H). MS (M+1): 410.

Compound 2-4

2-(2-aminobenzo[d]thiazol-6-yl)-N-(5-(2-(trifluoromethoxy)phenyl)-1,3,4-oxadiazol-2-yl)acetamide

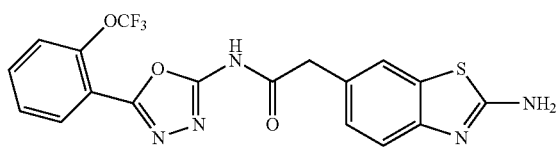 [SMILES: Nc1nc2ccc(CC(=O)Nc3nnc(-c4ccccc4OC(F)(F)F)o3)cc2s1]

$^1$H NMR (400 MHz, DMSO-d$_6$): δ 10.55 (s, 1H), 7.61-7.71 (m, 2H), 7.49-7.55 (m, 2H), 7.40 (s, 2H), 7.25 (d, J=8.3 Hz, 1H), 7.08 (dd, J=8.3, 2.0 Hz, 1H), 3.54 (s, 2H). MS (M+1): 436.

Typical synthesis procedure of Compounds of EXAMPLE 3 and EXAMPLE 4

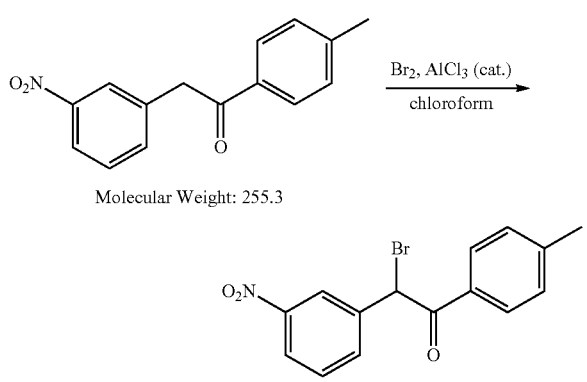

Synthesis of 2-bromo-2-(3-nitrophenyl)-1-(p-tolyl)ethan-1-one 2-(3-nitrophenyl)-1-(p-tolyl)ethan-1-one (25.5 g, 100 mmol) and AlCl$_3$ (30 mg, 0.23 mmol) were dissolved in 20 mL CHCl$_3$. Bromine (22 g, 120 mmol) in 100 mL CHCl$_3$ was then added dropwise by addition funnel at 0° C. by ice bath. The reaction was stirred at rt for 2 h and then extraction dried with Na$_2$SO$_4$ and concentrated under reduced pressure. The crude reaction mixture was directly purified by flash chromatography on silica gel (DCM/hexanes to 5:1). The title compound was isolated to obtain white solid (30.0 g, 89%).

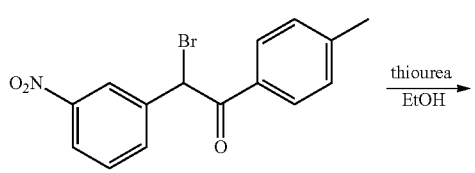

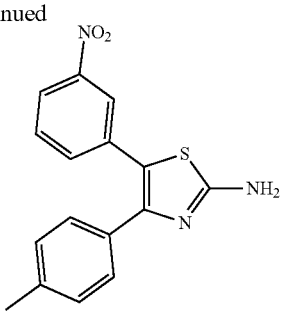

Synthesis of 5-(3-nitrophenyl)-4-(p-tolyl)thiazol-2-amine

This compound was prepared from refluxing of a solution of 2-bromo-2-(3-nitrophenyl)-1-(p-tolyl)ethan-1-one (16.7 g, 50 mmol) in ethanol (30 ml) and thiourea (4.28 g, 55 mmol) for 1 h. The reaction was work up by 100 mL of Na$_2$CO$_{3(sat)}$. The crude product was filtered and washed with water to neutrality and then was recrystallized from ethanol to obtain pale yellow crystals (7.78 g, 80%).

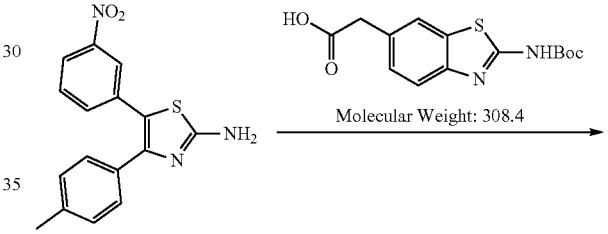

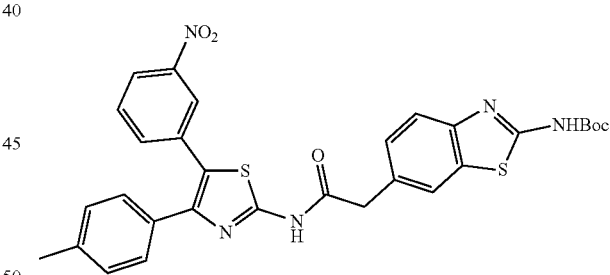

Synthesis of tert-butyl (6-(2-((5-(3-nitrophenyl)-4-(p-tolyl)thiazol-2-yl)amino)-2-oxoethyl) benzo[d]thiazol-2-yl)carbamate To a mixture of 5-(3-nitrophenyl)-4-(p-tolyl)thiazol-2-amine (0.62 g, 2 mmol), 2-(2-((tert-butoxycarbonyl)amino)benzo[d]thiazol-6-yl) acetic acid (0.62 g, 2 mmol), EDCI (0.76 g, 4 mmol), and HOBt (0.54 g, 4 mmol) in dry 20 mL DCM. The reaction was stirred at room temperature overnight then added water and extracted with DCM and concentrated got a crude residue. Purification of the crude residue by column chromatography with EtOAc/hexane (0:100-30:70) as the eluent and concentrated to afford orange solid (0.84 g, 70%).

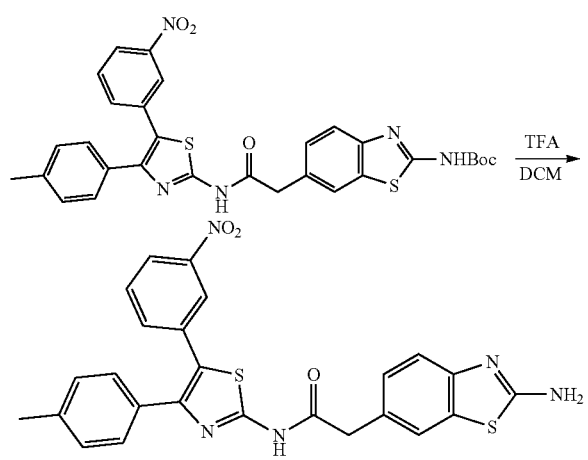

Synthesis of 2-(2-aminobenzo[d]thiazol-6-yl)-N-(5-(3-nitrophenyl)-4-(p-tolyl)thiazol-2-yl)acetamide To a vigorous stirred solution of tert-butyl(6-(2-((5-(3-nitrophenyl)-4-(p-tolyl)thiazol-2-yl)amino)-2-oxoethyl)benzo[d]thiazol-2-yl)carbamate (0.84 g, 1.40 mmol) in anhydrous dichloromethane (15 mL) at room temperature, added trifluoroacetic acid (1.5 mL, 20 mmol) and stirred overnight. Excess trifluoroacetic acid was neutralized by dropwised addition of Na$_2$CO$_3$(aq) until pH=10. The precipitate was washed with water and MeOH then further purified by silica gel flash column chromatography using dichloromethane and methanol as eluent and concentrated to give white solid (0.45 g, 64%).

Example 3: Compounds 3-1 to 3-14

Compound 3-1

2-(2-aminobenzo[d]thiazol-6-yl)-N-(5-(3-nitrophenyl)-4-(p-tolyl)thiazol-2-yl)acetamide

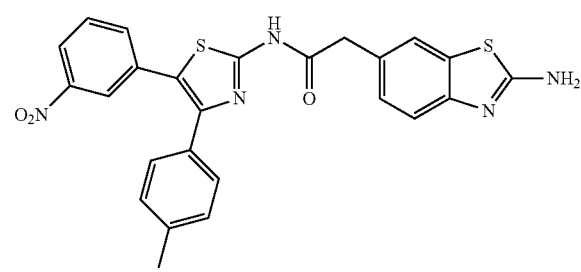 [SMILES: Cc1ccc(-c2nc(NC(=O)Cc3ccc4nc(N)sc4c3)sc2-c2cccc([N+](=O)[O-])c2)cc1]

$^1$H NMR (400 MHz, DMSO-d$_6$): δ 12.68 (s, 1H), 8.16 (dt, J=7.1, 1.3 Hz, 1H), 8.06 (t, J=2.0 Hz, 1H), 7.61-7.75 (m, 4H), 7.31 (t, J=7.8 Hz, 3H), 7.20 (dd, J=8.3, 1.5 Hz, 1H), 7.15 (d, J=8.3 Hz, 2H), 3.81 (s, 2H), 2.30 (s, 3H). MS (M+1):440.

Compound 3-2

2-(2-aminobenzo[d]thiazol-6-yl)-N-(4-(4-bromophenyl)-5-phenylthiazol-2-yl)acetamide

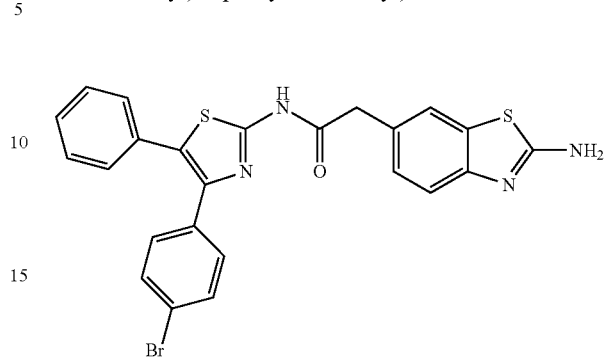

$^1$H NMR (400 MHz, CDCl$_3$): δ 9.09 (br. s., 1H), 7.49-7.57 (m, 2H), 7.32-7.39 (m, 2H), 7.25-7.32 (m, 7H), 7.20 (d, J=7.8 Hz, 1H), 5.29 (br. s., 2H), 3.81 (s, 2H). MS (M+1): 521.

Compound 3-3

2-(2-aminobenzo[d]thiazol-6-yl)-N-(5-(4-bromophenyl)-4-(p-tolyl)thiazol-2-yl)acetamide

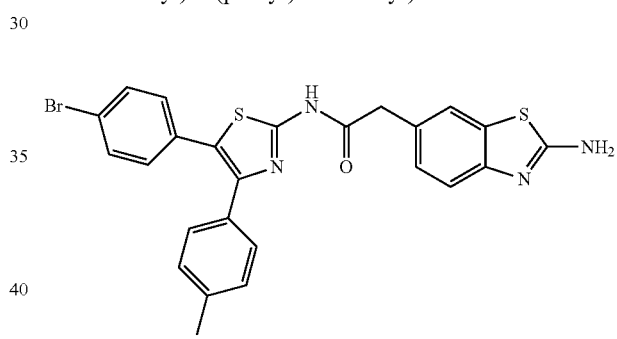

$^1$H NMR (400 MHz, DMSO-d$_6$): δ 12.61 (s, 1H), 8.16 (br. s., 2H), 7.68 (d, J=1.5 Hz, 1H), 7.53-7.59 (m, 2H), 7.28-7.38 (m, 3H), 7.19-7.28 (m, 3H), 7.14 (d, J=8.3 Hz, 2H), 3.81 (s, 2H), 2.29 (s, 3H). MS (M+1): 535.

Compound 3-4

2-(2-aminobenzo[d]thiazol-6-yl)-N-(5-(4-fluorophenyl)-4-(p-tolyl)thiazol-2-yl)acetamide

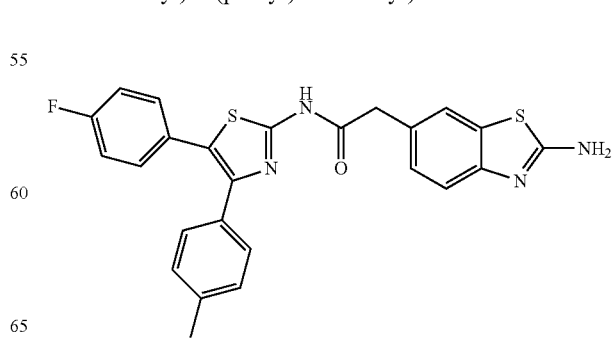

¹H NMR (400 MHz, DMSO-d₆): δ 12.57 (s, 1H), 8.18 (br. s., 2H), 7.26-7.41 (m, 6H), 7.15-7.26 (m, 3H), 7.06-7.15 (m, 2H), 3.81 (s, 2H), 2.28 (s, 3H). MS (M+1):475.

Compound 3-5

2-(2-aminobenzo[d]thiazol-6-yl)-N-(5-(3,4-dimethoxyphenyl)-4-(p-tolyl)thiazol-2-yl)acetamide

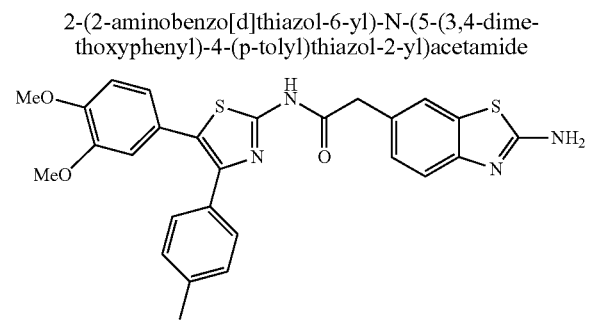

¹H NMR (400 MHz, DMSO-d₆): δ 12.49 (s, 1H), 8.39 (br. s., 2H), 7.71 (d, J=1.0 Hz, 1H), 7.31-7.41 (m, 3H), 7.25-7.31 (m, 1H), 7.09-7.16 (m, 2H), 6.91-6.99 (m, 1H), 6.78-6.87 (m, 2H), 3.82 (s, 2H), 3.76 (s, 3H), 3.58 (s, 3H), 2.28 (s, 3H). MS (M+1): 517.

Compound 3-6

2-(2-aminobenzo[d]thiazol-6-yl)-N-(5-(4-fluorophenyl)-4-(4-propoxyphenyl)thiazol-2-yl)acetamide

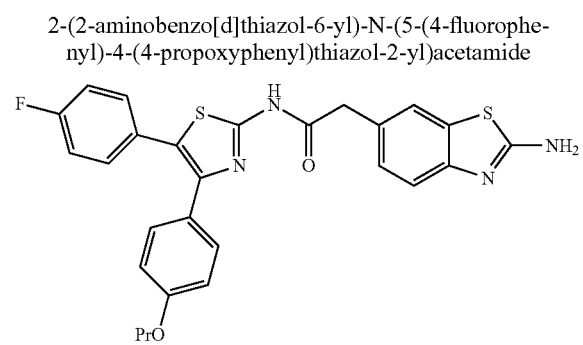

¹H NMR (400 MHz, DMSO-d₆): δ 12.53 (s, 1H), 7.92 (br. s., 2H), 7.66 (s, 1H), 7.29-7.38 (m, 5H), 7.14-7.29 (m, 3H), 6.81-6.91 (m, 2H), 3.91 (t, J=6.6 Hz, 3H), 3.80 (s, 2H), 1.65-1.76 (m, 2H), 0.96 (t, J=7.3 Hz, 3H). MS (M+1): 519.

Compound 3-7

2-(2-aminobenzo[d]thiazol-6-yl)-N-(5-(3,5-bis(trifluoromethyl)phenyl)-4-(p-tolyl)thiazol-2-yl)acetamide

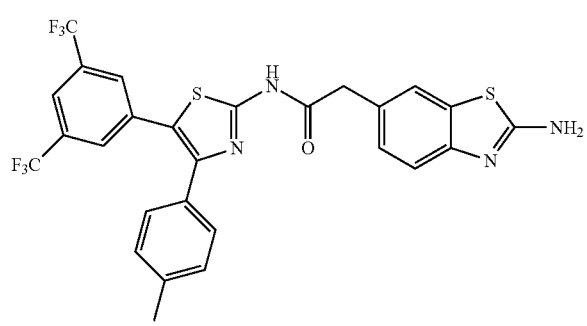 [SMILES: Cc1ccc(-c2nc(NC(=O)Cc3ccc4nc(N)sc4c3)sc2-c2cc(C(F)(F)F)cc(C(F)(F)F)c2)cc1]

¹H NMR (400 MHz, CDCl₃): δ 9.39 (br. s., 1H), 7.71 (s, 3H), 7.50-7.54 (m, 2H), 7.17-7.23 (m, 3H), 7.08 (d, J=7.8 Hz, 2H), 5.28 (d, J=10.8 Hz, 2H), 3.80 (s, 2H), 2.31 (s, 3H). MS (M+1): 593.

Compound 3-8

2-(2-aminobenzo[d]thiazol-6-yl)-N-(5-bromo-4-(3-methoxyphenyl)thiazol-2-yl)acetamide

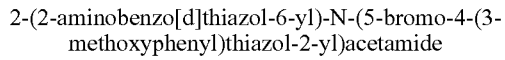

¹H NMR (400 MHz, CDCl₃): δ 9.14 (br. s., 1H), 7.49-7.56 (m, 2H), 7.34-7.38 (m, 1H), 7.30-7.34 (m, 1H), 7.26-7.30 (m, 1H), 7.20 (dd, J=8.3, 2.0 Hz, 1H), 6.88 (ddd, J=8.2, 2.6, 1.0 Hz, 1H), 5.28 (br. s., 2H), 3.81 (s, 2H), 3.80 (s, 3H). MS (M+1): 475.

Compound 3-9

2-(2-aminobenzo[d]thiazol-6-yl)-N-(4-(4-ethoxyphenyl)-5-(4-fluorophenyl)thiazol-2-yl)acetamide

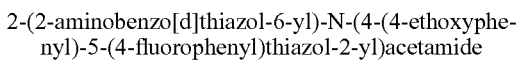

¹H NMR (400 MHz, DMSO-d₆): δ 12.51 (s, 1H), 7.98 (br. s., 2H), 7.63-7.69 (m, 1H), 7.28-7.37 (m, 5H), 7.16-7.28 (m, 3H), 6.80-6.90 (m, 2H), 4.01 (q, J=7.2 Hz, 2H), 3.80 (s, 2H), 1.31 (t, J=7.1 Hz, 3H). MS (M+1):505.

Compound 3-10

2-(2-aminobenzo[d]thiazol-6-yl)-N-(4,5-bis(4-bromophenyl)thiazol-2-yl)acetamide

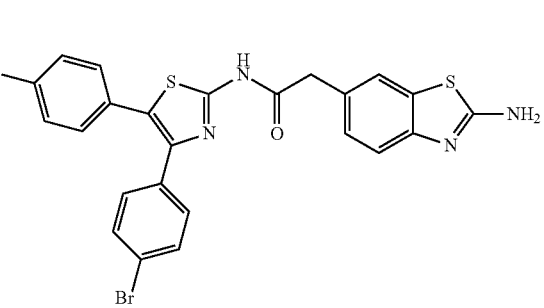

¹H NMR (400 MHz, DMSO-d₆): δ 12.59 (s, 1H), 7.52-7.61 (m, 5H), 7.40 (s, 2H), 7.33-7.38 (m, 2H), 7.21-7.32 (m, 3H), 7.17 (dd, J=8.1, 1.7 Hz, 1H), 3.79 (s, 2H). MS (M+1): 599.

Compound 3-11

2-(2-aminobenzo[d]thiazol-6-yl)-N-(5-(4-ethoxyphenyl)thiazol-2-yl)acetamide

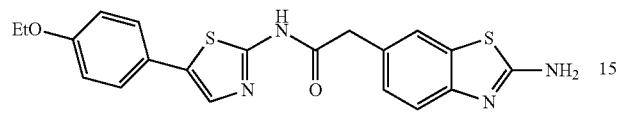

¹H NMR (400 MHz, DMSO-d₆): δ 7.68 (s, 1H), 7.58 (d, J=1.5 Hz, 1H), 7.44-7.49 (m, 2H), 7.40 (s, 2H), 7.27 (d, J=7.8 Hz, 1H), 7.16 (dd, J=8.3, 2.0 Hz, 1H), 6.92-6.98 (m, 3H), 6.86-6.90 (m, 1H), 4.03 (q, J=6.8 Hz, 2H), 3.74 (s, 2H), 1.32 (t, J=6.8 Hz, 3H). MS (M+1):411.

Compound 3-12

2-(2-aminobenzo[d]thiazol-6-yl)-N-(4-(2,4-diethoxyphenyl)thiazol-2-yl)acetamide

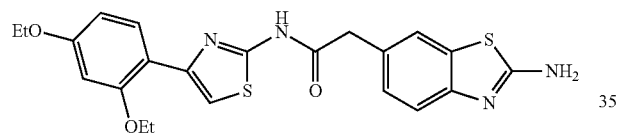

¹H NMR (400 MHz, DMSO-d₆): δ 12.30 (s, 1H), 7.99 (d, J=8.0 Hz, 1H), 7.60 (m, 1H), 7.48 (s, 1H), 7.41 (br s, 2H), 7.29 (d, J=7.6 Hz, 1H), 7.17 (dd, J=8.4, 1.6 Hz, 1H), 6.61-6.58 (m, 2H), 4.13 (q, J=6.8 Hz, 2H), 4.06 (q, J=6.8 Hz, 2H), 3.76 (s, 2H), 1.43 (t, J=6.8 Hz, 3H), 1.33 (t, J=6.8 Hz, 3H). MS (M+1):455

Compound 3-13

2-(2-aminobenzo[d]thiazol-6-yl)-N-(4-(4-ethoxyphenyl)-5-phenoxythiazol-2-yl)acetamide

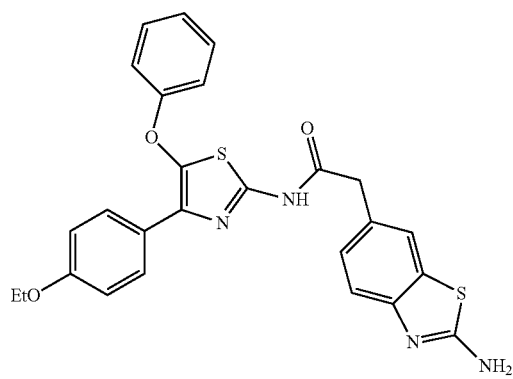 [SMILES: CCOc1ccc(-c2nc(NC(=O)Cc3ccc4nc(N)sc4c3)sc2Oc2ccccc2)cc1]

¹H NMR (400 MHz, DMSO-d₆): δ 12.44 (s, 1H), 7.77-7.74 (m, 2H), 7.59 (d, J=2.0 Hz, 1H), 7.43 (s, 2H), 7.38-7.34 (m, 2H), 7.28 (d, J=2.0 Hz, 1H), 7.18-7.08 (m, 4H), 6.95-6.92 (m, 2H), 4.01 (q, J=6.8 Hz, 2H), 3.75 (s, 2H), 1.30 (t, J=6.8 Hz, 3H).
LCMS, [M+1]⁺: 503.

Compound 3-14

2-(2-aminobenzo[d]thiazol-6-yl)-N-(5-benzyl-4-(4-ethoxyphenyl)thiazol-2-yl)acetamide

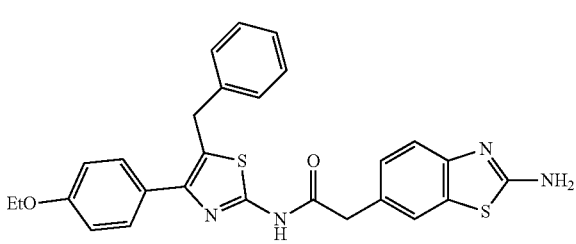 [SMILES: CCOc1ccc(-c2nc(NC(=O)Cc3ccc4nc(N)sc4c3)sc2Cc2ccccc2)cc1]

¹H NMR (400 MHz, DMSO-d₆): δ 12.29 (s, 1H), 7.47-7.59 (m, 3H), 7.41 (s, 2H), 7.23-7.34 (m, 3H), 7.10-7.23 (m, 5H), 6.93-7.01 (m, 2H), 4.17 (s, 2H), 4.04 (q, J=7.0 Hz, 2H), 3.71 (s, 2H), 1.32 (t, J=7.1 Hz, 3H). LCMS [M+1]⁺:501.

Example 4: Compounds 4-1 to 4-4

Compound 4-1 (1-(2-aminobenzo[d]thiazol-6-yl)-3-(5-(4-ethoxyphenyl)-1,3,4-thiadiazol-2-yl)urea)

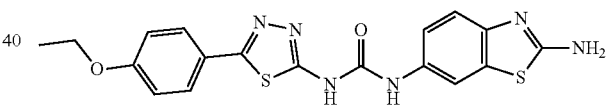

¹H NMR (400 MHz, DMSO-d₆): δ 10.96 (br. s., 1H), 8.97 (br. s., 1H), 7.88 (br. s., 1H), 7.75-7.84 (m, J=8.8 Hz, 2H), 7.37 (br. s., 2H), 7.26 (q, J=8.3 Hz, 2H), 7.00-7.10 (m, J=8.8 Hz, 2H), 4.09 (q, J=7.2 Hz, 2H), 1.34 (t, J=6.8 Hz, 3H). MS (M+1): 413.

Compound 4-2 (2-(2-aminobenzo[d]thiazol-6-yl)-N-(5-(4-ethoxyphenyl)thiophen-2-yl)acetamide)

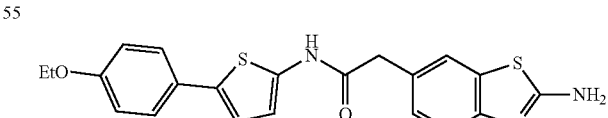

¹H NMR (400 MHz, DMSO-d₆): δ 11.36 (s, 1H), 7.92 (br. s., 2H), 7.64 (d, J=1.5 Hz, 1H), 7.42-7.48 (m, 2H), 7.32 (d, J=8.3 Hz, 1H), 7.21 (dd, J=8.3, 2.0 Hz, 1H), 7.07 (d, J=3.9 Hz, 2H), 6.90-6.93 (m, 2H), 6.64 (d, J=3.9 Hz, 1H), 4.02 (q, J=6.8 Hz, 2H), 3.68 (s, 2H), 1.31 (t, J=6.8 Hz, 3H). MS (M+1):410.

Compound 4-3 (2-(2-aminobenzo[d]thiazol-6-yl)-N-(5-(4-ethoxy-2-(2-methoxyethoxy)phenyl)-1H-imidazol-2-yl)acetamide)

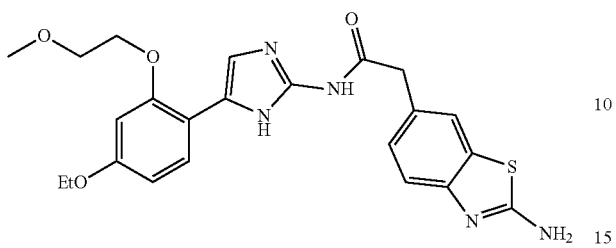

¹H NMR (400 MHz, DMSO-d₆): δ 11.53 (br s, 1H), 7.74 (d, J=8.0 Hz, 1H), 7.62 (d, J=2.0 Hz, 1H), 7.53 (br s, 2H), 7.27-7.30 (m, 2H), 7.19 (dd, J=8.0, 1.6 Hz, 1H), 6.61 (d, J=2.4 Hz, 1H), 6.57 (dd, J=8.0, 2.0 Hz, 1H), 4.19-4.17 (m, 2H), 4.04 (q, J=6.8 Hz, 2H), 3.75-7.32 (m, 2H), 3.71 (s, 2H), 3.31 (s, 3H), 1.32 (t, J=6.8 Hz, 3H). MS (M+1): 468.

Compound 4-4 (2-(2-aminobenzo[d]thiazol-6-yl)-N-(5-(2,4-diethoxyphenyl)-1H-imidazol-2-yl)acetamide)

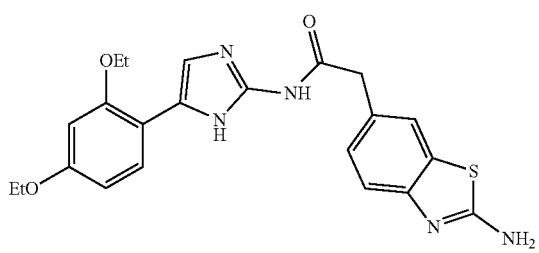 [SMILES: CCOc1ccc(-c2cnc(NC(=O)Cc3ccc4nc(N)sc4c3)[nH]2)c(OCC)c1]

¹H NMR (400 MHz, DMSO-d₆): δ 11.41 (s, 1H), 11.35 (s, 1H), 7.84 (d, J=8.4 Hz, 1H), 7.59 (d, J=1.2 Hz, 1H), 7.40 (br s, 2H), 7.27 (d, J=8.4 Hz, 1H), 7.19-7.15 (m, 2H), 6.54 (s, 1H), 4.09 (q, J=6.8 Hz, 2H), 4.02 (q, J=6.8 Hz, 2H), 3.66 (s, 2H), 1.41 (t, J=6.8 Hz, 3H), 1.32 (t, J=6.8 Hz, 3H). MS (M+1):438.

Typical synthesis procedure of Compounds of EXAMPLE 5

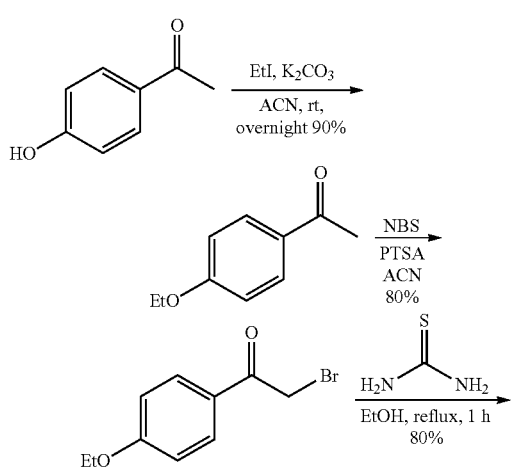

-continued

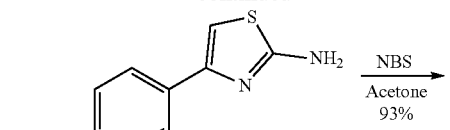

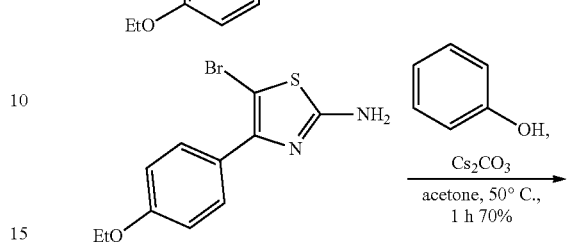

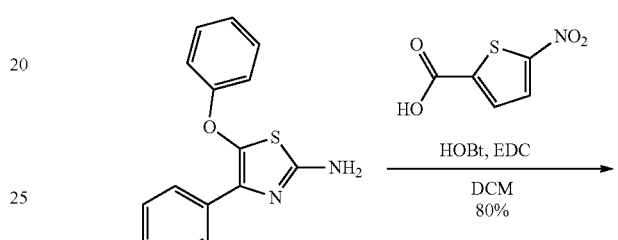

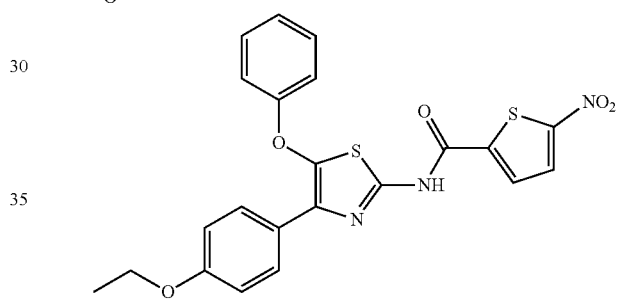

Synthesis of 1-(4-Ethoxy-phenyl)-ethanone

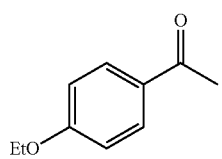

1-(4-ethoxyphenyl)ethan-1-one

K₂CO₃ (20.73 g, 150 mmol) was added to a solution of 1-(4-hydroxy-phenyl)-ethanone (13.62 g, 100 mmol) in MeCN (200 ml) under constant stirring. Ethyl bromide (23.4 g, 150 mmol) was added and the reaction mixture is heated at 80° C. for 20 hours. Water (100 ml) is added and the reaction mixture is extracted with EtOAc. The organic phase is washed with brine, dried (Na₂SO₄) and concentrated in vacuum. The crude residues was purified by column chromatography with EtOAc/hexane (0:100-5:95) as the eluent. Yield (14.43 g, 88%). LCMS:MH⁺ 165.

Synthesis of 2-Bromo-1-(4-ethoxyphenyl)ethanone

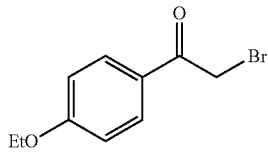

2-bromo-1-(4-ethoxyphenyl)ethan-1-one

To a solution of NBS (16.5 g, 91 mmol), PTSA:hydrate (27 g, 142 mmole), 1-(4-ethoxy-phenyl)-ethanone (11.6 g, 71 mmol) in ACN (348 ml) and the resulting mixture are stirred at 82° C. reflux room temperature for 2 hours. Then removed ACN and added Water (400 ml) extracted with EtOAc (450 ml). The organic phase is washed with brine, dried (Na$_2$SO$_4$) and concentrated in vacuum, and the obtained crude product (17.5 g, yield 99%) could be employed in further process steps without further purification.

Synthesis of 4-(4-ethoxyphenyl)thiazol-2-amine

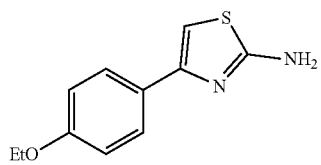 [SMILES: CCOc1ccc(-c2csc(N)n2)cc1]

4-(4-ethoxyphenyl)thiazol-2-amine

To a mixture of thiourea (6.58 g) and 2-bromo-1-(4-ethoxyphenyl)ethan-1-one (17.50 g) was added ethanol (90 mL). The reaction mixture was heated up to reflux for 2.5 hours. The reaction was cooled down to RT. Ethanol was removed under vacuum to afford the residue as a brown solid. The mixture was obtained by washed with 100 ml water and 50 ml saturated sodium bicarbonate until yellow color was observed in the aqueous phase. The mixture was suction to removed water then washed cake by 50 ml water. The crude product was slurry by 75 ml hot EtOH for 2 h then removed 40 ml EtOH by distilled and solution cooled to RT then suction to afford the solid powder 4-(4-ethoxyphenyl)thiazol-2-amine 15.84 g. MS (ES$^+$) m/z 221 (MH$^+$).

Synthesis of 5-bromo-4-(4-ethoxyphenyl)thiazol-2-amine

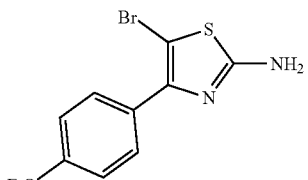

To a solution of N-bromosuccinimide (4.84 g, 27.2 mmol) in Acetone (200 mL) was added over 30 min to a solution of 4-(4-ethoxyphenyl)thiazol-2-amine (5.00 g, 22.7 mmol) in Acetone (200 mL) at 0° C. by ice bath. After 1 h, the reaction was concentrated in vacuo, then the residue was extraction with EA (100 mL) and sodium thiosulfate aqueous two times. The combination of organic solvent were washed with brine, dried and evaporated, which was sufficiently pure to use directly. 5-bromo-4-(4-ethoxyphenyl)thiazol-2-amine (6.31 g, 93%). MS (ES$^+$) m/z 299 (MH$^+$)

Synthesis of 4-(4-ethoxyphenyl)-5-phenoxythiazol-2-amine

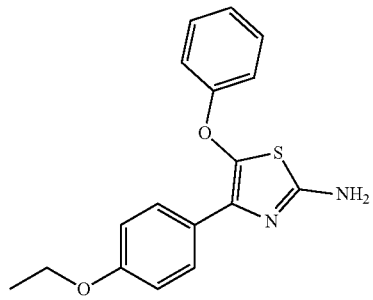 [SMILES: CCOc1ccc(-c2nc(N)sc2Oc2ccccc2)cc1]

4-(4-ethoxyphenyl)-5-phenoxythiazol-2-amine

To a mixture of 5-bromo-4-(4-ethoxyphenyl)thiazol-2-amine (3.1 g, 10.4 mmol), phenol (1.27 g, 13.5 mmol) and cesium carbonate (4.40 g, 13.5 mmol) was added acetone (100 mL). The reaction mixture was heated to 50° C. and stirred for 10 hours. Solvent was removed. The crude product was purified by flash chromatography (EtOAc:PE=0:1 to 1:4) to afford 4-(4-ethoxyphenyl)-5-phenoxythiazol-2-amine. 2.23 g. MS (ES$^+$) m/z 313 (MH$^+$).

Synthesis of N-(4-(4-ethoxyphenyl)-5-phenoxythiazol-2-yl)-5-nitrothiophene-2-carboxamide

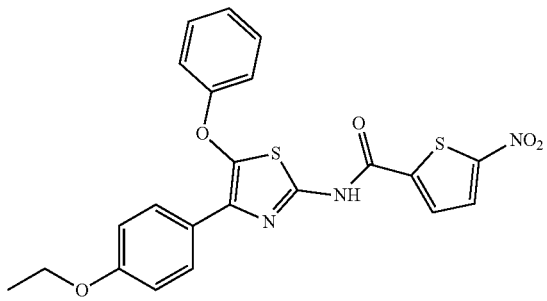 [SMILES: CCOc1ccc(-c2nc(NC(=O)c3ccc([N+](=O)[O-])s3)sc2Oc2ccccc2)cc1]

N-(4-(4-ethoxyphenyl)-5-phenoxythiazol-2-yl)-5-nitrothiophene-2-carboxamide

To a solution of 5-nitrothiophene-2-carboxylic acid (1.71 g, 10 mmol), 4-(4-ethoxyphenyl)-5-phenoxythiazol-2-amine (3.12 g, 10 mmol), EDCl (3.83 g, 20 mmol) and HOBt (2.70 g, 20 mmol) in DCM (50 mL) were stirred at room temperature for overnight. Extraction and remove solvent. The crude product was purified by flash chromatography (DCM: EtOAc=1:0 to 4:1) to afford N-(4-(4-ethoxyphenyl)-5-phenoxythiazol-2-yl)-5-nitrothiophene-2-carboxamide as red solid. Yield: 4.22 g, 90%.

Example 5: Compounds 5-1 to 5-108

Compound 5-1

N-(4-(4-bromophenyl)-5-phenoxythiazol-2-yl)-5-nitrothiophene-2-carboxamide

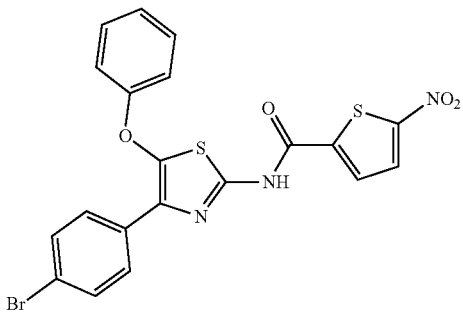 [SMILES: O=C(Nc1nc(-c2ccc(Br)cc2)c(Oc2ccccc2)s1)c1ccc([N+](=O)[O-])s1]

¹H NMR (400 MHz, DMSO-d₆): δ 9.69 (br, 1H), 7.85 (d, J=4.4 Hz, 1H), 7.75-7.72 (m, 2H), 7.51 (d, J=4.4 Hz, 1H), 7.48-7.44 (m, 2H), 7.36-7.31 (m, 2H), 7.16-7.09 (m, 3H). MS (M+1): 502.

Compound 5-2

N-(4-(4-bromophenyl)-5-(4-(trifluoromethoxy)phenoxy)thiazol-2-yl)-5-nitrothiophene-2-carboxamide

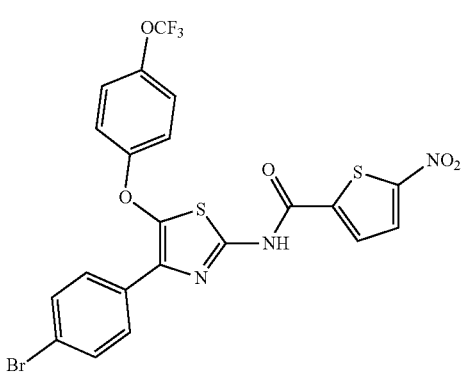 [SMILES: O=C(Nc1nc(-c2ccc(Br)cc2)c(Oc2ccc(OC(F)(F)F)cc2)s1)c1ccc([N+](=O)[O-])s1]

¹H NMR (400 MHz, CDCl₃): δ 9.57 (br, 1H), 7.89 (d, J=4.4 Hz, 1H), 7.74-7.71 (m, 2H), 7.58 (d, J=4.4 Hz, 1H), 7.50-7.47 (m, 2H), 7.22-7.17 (m, 2H), 7.12-7.09 (m, 2H). MS (M+1): 586.

Compound 5-3

5-nitro-N-(4-(3-nitrophenyl)-5-phenoxythiazol-2-yl)thiophene-2-carboxamide

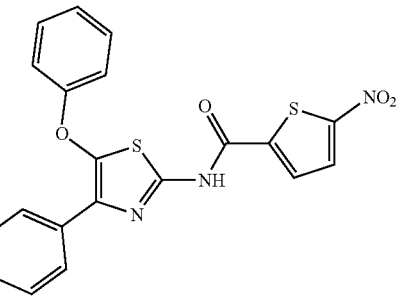

¹H NMR (400 MHz, CDCl₃): δ 9.63 (br, 1H), 8.82 (s, 1H), 8.25 (d, J=8.0 Hz, 1H), 8.11 (d, J=7.6 Hz, 1H), 7.93 (d, J=4.4 Hz, 1H), 7.66 (d, J=4.4 Hz, 1H), 7.52 (t, J=8.0 Hz, 1H), 7.38-7.34 (m, 2H), 7.19-7.14 (m, 3H). MS (M+1): 469.

Compound 5-4

N-(4-(3-methoxyphenyl)-5-phenoxythiazol-2-yl)-5-nitrothiophene-2-carboxamide

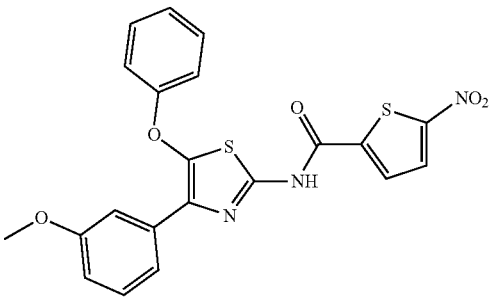 [SMILES: COc1cccc(-c2nc(NC(=O)c3ccc([N+](=O)[O-])s3)sc2Oc2ccccc2)c1]

¹H NMR (400 MHz, CDCl₃): δ 10.85 (br, 1H), 7.72 (d, J=4.4 Hz, 1H), 7.45 (d, J=4.4 Hz, 1H), 7.38-7.31 (m, 4H), 7.23-7.19 (m, 1H), 7.14-7.11 (m, 3H), 6.77-6.74 (m, 1H), 3.71 (s, 3H). MS (M+1): 454.

Compound 5-5

N-(4-(2-ethoxyphenyl)-5-phenoxythiazol-2-yl)-5-nitrothiophene-2-carboxamide

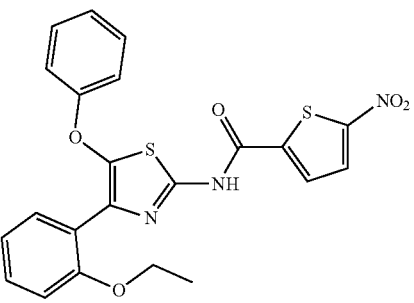 [SMILES: CCOc1ccccc1-c1nc(NC(=O)c2ccc([N+](=O)[O-])s2)sc1Oc1ccccc1]

<sup>1</sup>H NMR (400 MHz, CDCl₃): δ 11.44 (br s, 1H), 7.72 (d, J=4.4 Hz, 1H), 7.62 (dd, J=8.0, 1.6 Hz, 1H), 7.53 (d, J=4.4 Hz, 1H), 7.34-7.29 (m, 2H), 7.25-7.21 (m, 1H), 7.13-7.08 (m, 3H), 6.92-6.86 (m, 2H), 4.08 (q, J=6.8 Hz, 2H), 1.40 (t, J=6.8 Hz, 3H). MS (M+1): 468.

Compound 5-6

N-(4-(4-ethoxyphenyl)-5-phenoxythiazol-2-yl)-5-nitrothiophene-2-carboxamide

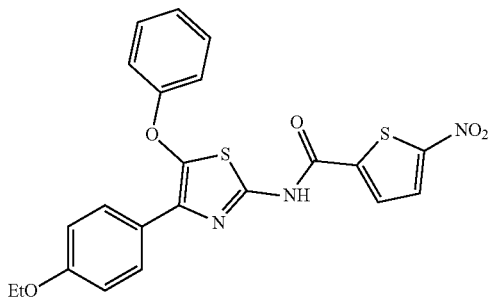 [SMILES: CCOc1ccc(-c2nc(NC(=O)c3ccc([N+](=O)[O-])s3)sc2Oc2ccccc2)cc1]

¹H NMR (400 MHz, CDCl₃): δ 11.03 (br. s, 1H), 7.71 (d, J=4.4 Hz, 1H), 7.68-7.65 (m, 2H), 7.49 (d, J=4.4 Hz, 1H), 7.35-7.30 (m, 2H), 7.13-7.09 (m, 3H), 6.82-6.78 (m, 2H), 3.97 (q, J=6.8 Hz, 2H), 1.37 (t, J=6.8 Hz, 3H). MS (M+1): 468.

Compound 5-7

N-(4-(4-bromophenyl)-5-(4-(trifluoromethyl)phenoxy)thiazol-2-yl)-5-nitrothiophene-2-carboxamide

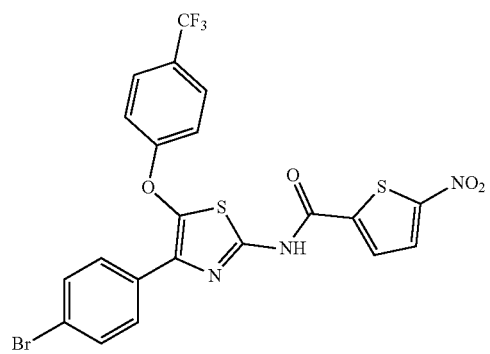

¹H NMR (400 MHz, CDCl₃): δ 9.87 (br. s, 1H), 7.86 (d, J=4.4 Hz, 1H), 7.69-7.66 (m, 2H), 7.59 (d, J=8.8 Hz, 2H), 7.57 (d, J=4.4 Hz, 1H), 7.48-7.45 (m, 2H), 7.17 (d, J=8.4 Hz, 2H), 1.22 (s, 9H). MS (M+1):570.

Compound 5-8

5-nitro-N-(4-(4-propoxyphenyl)-5-(4-(trifluoromethoxy)phenoxy)thiazol-2-yl)thiophene-2-carboxamide

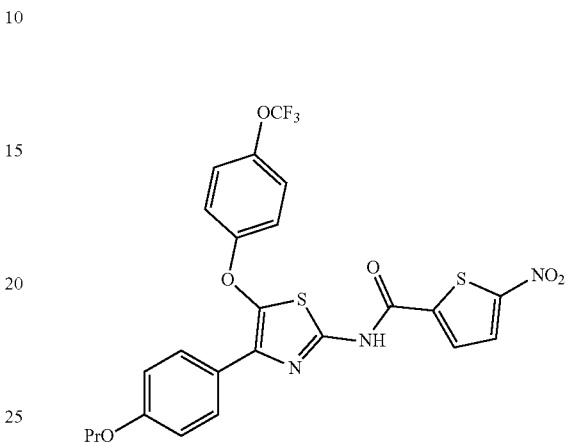

¹H NMR (400 MHz, CDCl₃): δ 10.59 (br. s, 1H), 7.70 (d, J=4.4 Hz, 1H), 7.67-7.63 (m, 2H), 7.39 (d, J=4.0 Hz, 1H), 7.17 (d, J=8.0 Hz, 2H), 7.12-7.08 (m, 2H), 6.83-6.79 (m, 2H), 3.86 (q, J=6.8 Hz, 2H), 1.77 (sex, J=7.2 Hz, 2H), 1.00 (t, J=7.2 Hz, 3H). MS (M+1): 570.

Compound 5-9

5-nitro-N-(5-phenoxy-4-(4-propoxyphenyl)thiazol-2-yl)thiophene-2-carboxamide

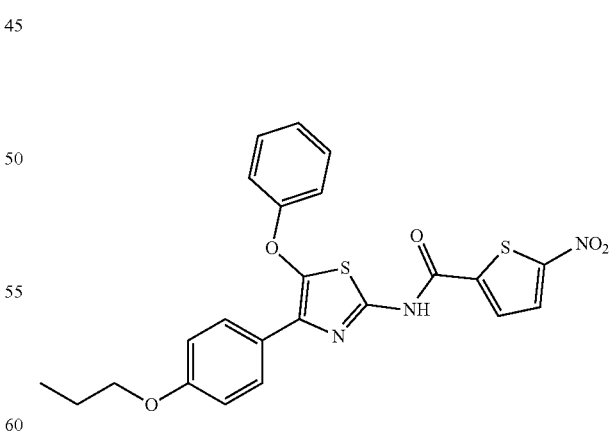

¹H NMR (400 MHz, DMSO-d₆): δ 13.32 (br. s., 1H), 8.17-8.27 (m, 2H), 7.77-7.83 (m, J=8.8 Hz, 2H), 7.37-7.43 (m, 2H), 7.13-7.19 (m, 3H), 6.94-6.99 (m, 2H), 3.92 (t, J=6.6 Hz, 2H), 1.66-1.76 (m, 2H), 0.96 (t, J=7.3 Hz, 3H). MS (M+1):482.

Compound 5-10

N-(4-(4-isopropoxyphenyl)-5-phenoxythiazol-2-yl)-5-nitrothiophene-2-carboxamide

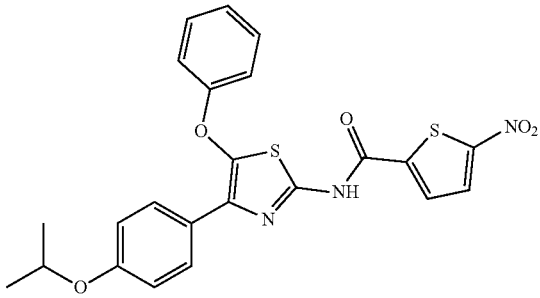 [SMILES: CC(C)Oc1ccc(-c2nc(NC(=O)c3ccc([N+](=O)[O-])s3)sc2Oc2ccccc2)cc1]

$^1$H NMR (400 MHz, DMSO-d$_6$): δ 13.33 (br. s., 1H), 8.18-8.26 (m, 2H), 7.80 (d, J=8.8 Hz, 2H), 7.37-7.44 (m, 2H), 7.14-7.19 (m, 3H), 6.95 (d, J=9.3 Hz, 2H), 4.61 (spt, J=6.0 Hz, 1H), 1.25 (d, J=5.9 Hz, 6H). MS (M+1): 482

Compound 5-11

N-(4-(4-bromophenyl)-5-(3-(trifluoromethyl)phenoxy)thiazol-2-yl)-5-nitrothiophene-2-carboxamide

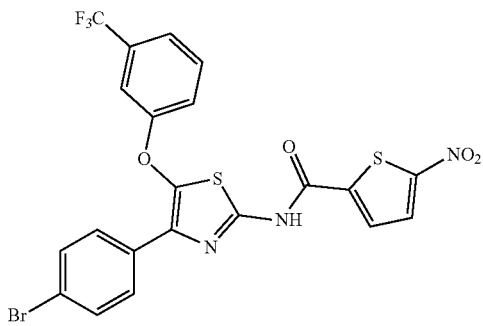 [SMILES: O=C(Nc1nc(-c2ccc(Br)cc2)c(Oc2cccc(C(F)(F)F)c2)s1)c1ccc([N+](=O)[O-])s1]

$^1$H NMR (400 MHz, DMSO-d$_6$): δ 13.45 (br. s., 1H), 8.22-8.25 (m, 1H), 8.19-8.22 (m, 1H), 7.82 (d, J=8.3 Hz, 2H), 7.63 (d, J=8.3 Hz, 4H), 7.53-7.58 (m, 2H), 7.47-7.51 (m, 1H). MS (M+1): 570

Compound 5-12

N-(4-(2,4-diethoxyphenyl)-5-phenoxythiazol-2-yl)-5-nitrothiophene-2-carboxamide

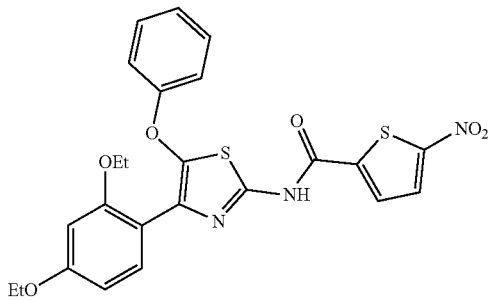 [SMILES: CCOc1ccc(-c2nc(NC(=O)c3ccc([N+](=O)[O-])s3)sc2Oc2ccccc2)c(OCC)c1]

$^1$H NMR (400 MHz, CDCl$_3$): δ 11.68 (br, 1H), 7.67 (d, J=4.4 Hz, 1H), 7.48-7.45 (m, 2H), 7.33-7.28 (m, 2H), 7.12-7.06 (m, 3H), 6.38-6.34 (m, 2H), 4.00 (q, J=7.2 Hz, 2H), 3.95 (q, J=7.2 Hz, 2H), 1.39-1.34 (m, 6H). MS (M+1): 512.

Compound 5-13

5-nitro-N-(4-(4-propoxyphenyl)-5-(pyridin-3-yloxy)thiazol-2-yl)thiophene-2-carboxamide

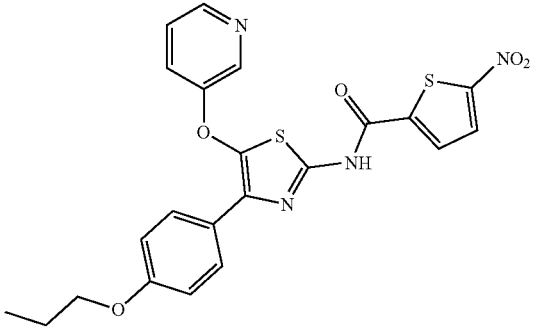 [SMILES: CCCOc1ccc(-c2nc(NC(=O)c3ccc([N+](=O)[O-])s3)sc2Oc2cccnc2)cc1]

$^1$H NMR (400 MHz, DMSO-d$_6$): δ 13.38 (br. s., 1H), 8.53 (d, J=2.9 Hz, 1H), 8.35-8.40 (m, 1H), 8.18-8.25 (m, 2H), 7.78 (d, J=8.8 Hz, 2H), 7.56 (ddd, J=8.6, 2.9, 1.2 Hz, 1H), 7.42 (dd, J=8.6, 4.6 Hz, 1H), 6.97 (d, J=8.8 Hz, 2H), 3.92 (t, J=6.6 Hz, 2H), 1.66-1.76 (m, 2H), 0.96 (t, J=7.3 Hz, 3H). MS (M+1):483

Compound 5-14

N-(4-(4-(tert-butyl)phenyl)-5-phenoxythiazol-2-yl)-5-nitrothiophene-2-carboxamide

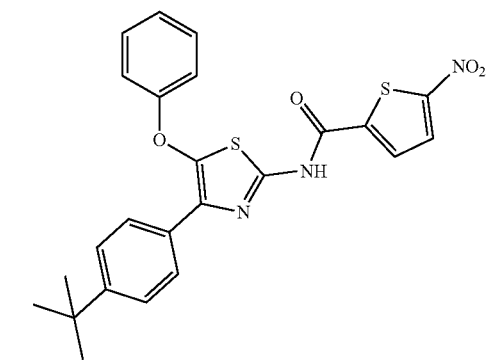 [SMILES: CC(C)(C)c1ccc(-c2nc(NC(=O)c3ccc([N+](=O)[O-])s3)sc2Oc2ccccc2)cc1]

$^1$H NMR (400 MHz, DMSO-d$_6$): δ 13.37 (br. s., 1H), 8.22 (br. s., 2H), 7.84 (d, J=8.3 Hz, 2H), 7.38-7.48 (m, 4H), 7.19 (br. s., 3H), 1.27 (br. s., 9H). MS (M+1): 480.

Compound 5-15

N-(4-(4-(2-methoxyethoxy)phenyl)-5-(pyridin-3-yloxy)thiazol-2-yl)-5-nitrothiophene-2-carboxamide

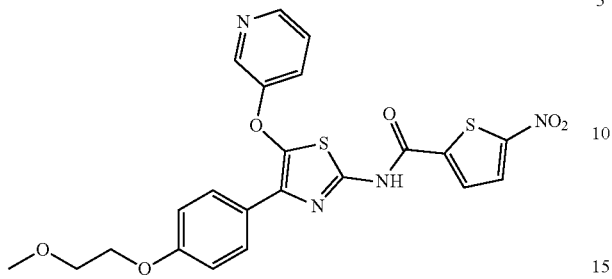

$^1$H NMR (400 MHz, DMSO-d$_6$): δ 13.39 (br, 1H), 8.54 (d, J=2.8 Hz, 1H), 8.39-8.37 (m, 1H), 8.23-8.20 (m, 2H), 7.79 (d, J=8.8 Hz, 2H), 7.59-7.55 (m, 1H), 7.44-7.41 (m, 1H), 7.02-6.98 (m, 2H), 4.11-4.08 (m, 2H), 3.65-3.63 (m, 2H), 3.29 (s, 3H). MS (M+1): 499.

Compound 5-16

N-(4-(4-(2-methoxyethoxy)phenyl)-5-phenoxythiazol-2-yl)-5-nitrothiophene-2-carboxamide

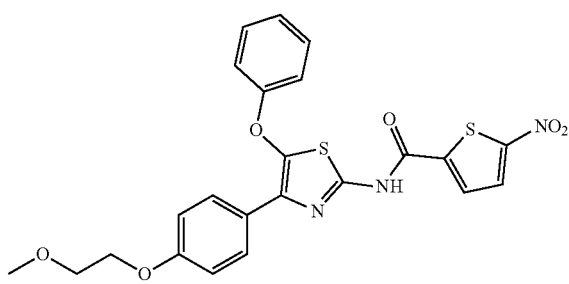 [SMILES: COCCOc1ccc(-c2nc(NC(=O)c3ccc([N+](=O)[O-])s3)sc2Oc2ccccc2)cc1]

$^1$H NMR (400 MHz, CDCl$_3$): δ 10.35 (br, 1H), 7.74 (d, J=4.0 Hz, 1H), 7.72-7.69 (m, 2H), 7.43 (d, J=4.4 Hz, 1H), 7.34-7.30 (m, 2H), 7.13-7.10 (m, 3H), 6.87-6.84 (m, 2H), 4.08-4.06 (m, 2H), 3.73-3.70 (m, 2H), 3.42 (s, 3H). MS (M+1): 498.

Compound 5-17

5-nitro-N-(4-(4-propoxyphenyl)-5-(3-(trifluoromethyl)phenoxy)thiazol-2-yl)thiophene-2-carboxamide

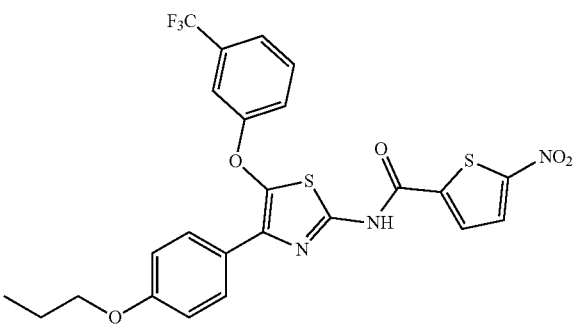 [SMILES: CCCOc1ccc(-c2nc(NC(=O)c3ccc([N+](=O)[O-])s3)sc2Oc2cccc(C(F)(F)F)c2)cc1]

$^1$H NMR (400 MHz, DMSO-d$_6$): δ 13.39 (br. s., 1H), 8.18-8.26 (m, 2H), 7.75-7.81 (m, J=8.8 Hz, 2H), 7.60-7.66 (m, 1H), 7.48-7.55 (m, 2H), 7.45 (dd, J=8.3, 2.0 Hz, 1H), 6.93-6.99 (m, J=9.3 Hz, 2H), 3.92 (t, J=6.6 Hz, 2H), 1.70 (sxt, J=7.1 Hz, 2H), 0.95 (t, J=7.3 Hz, 3H). MS (M+1):550

Compound 5-18

N-(4-(4-bromophenyl)-5-(4-(trifluoromethoxy)phenoxy)thiazol-2-yl)-5-nitrothiophene-2-carboxamide

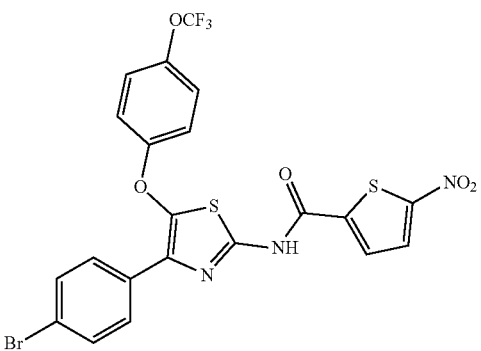 [SMILES: O=C(Nc1nc(-c2ccc(Br)cc2)c(Oc2ccc(OC(F)(F)F)cc2)s1)c1ccc([N+](=O)[O-])s1]

$^1$H NMR (400 MHz, DMSO-d$_6$): δ 13.42 (br. s., 1H), 8.23 (s, 1H), 8.18-8.21 (m, 1H), 7.79-7.84 (m, 2H), 7.61-7.66 (m, 2H), 7.38-7.44 (m, 2H), 7.29-7.33 (m, 2H). MS (M+1): 585

Compound 5-19

N-(4-(4-bromophenyl)-5-(2-(trifluoromethyl)phenoxy)thiazol-2-yl)-5-nitrothiophene-2-carboxamide

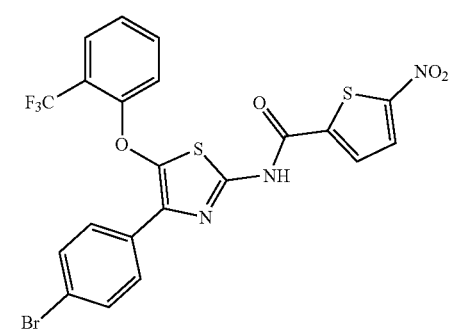 [SMILES: O=C(Nc1nc(-c2ccc(Br)cc2)c(Oc2ccccc2C(F)(F)F)s1)c1ccc([N+](=O)[O-])s1]

$^1$H NMR (400 MHz, DMSO-d$_6$): δ 13.50 (br. s., 1H), 8.19-8.26 (m, 2H), 7.77-7.86 (m, 3H), 7.63-7.69 (m, 3H), 7.38 (t, J=7.6 Hz, 1H), 7.30 (d, J=8.3 Hz, 1H). MS (M+1): 569. 571

Compound 5-20

N-(4-(4-(tert-butyl)phenyl)-5-(4-fluorophenoxy)thiazol-2-yl)-5-nitrothiophene-2-carboxamide

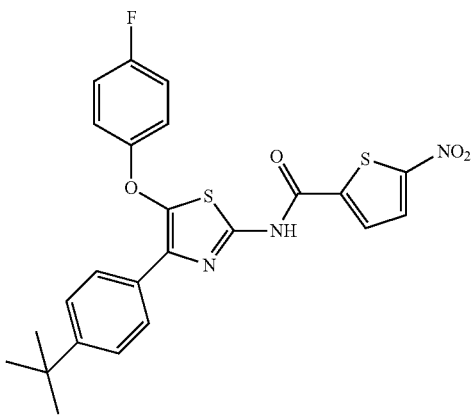 [SMILES: CC(C)(C)c1ccc(-c2nc(NC(=O)c3ccc([N+](=O)[O-])s3)sc2Oc2ccc(F)cc2)cc1]

$^1$H NMR (400 MHz, DMSO-d$_6$): δ 13.36 (br. s., 1H), 8.16-8.29 (m, 2H), 7.79-7.86 (m, J=8.3 Hz, 2H), 7.41-7.48 (m, J=8.8 Hz, 2H), 7.18-7.27 (m, 4H), 1.27 (s, 9H). MS (M+1): 498

Compound 5-21

N-(5-(2-ethoxyphenoxy)-4-(4-propoxyphenyl)thiazol-2-yl)-5-nitrothiophene-2-carboxamide

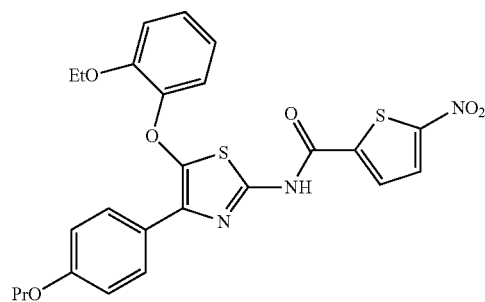

$^1$H NMR (400 MHz, CDCl$_3$): δ 7.73 (d, J=8.8 Hz, 2H), 7.63 (d, J=4.4 Hz, 1H), 7.33 (d, J=4.0 Hz, 1H), 7.12-7.05 (m, 2H), 6.98 (dd, J=8.4, 1.6 Hz, 1H), 6.88-6.83 (m, 1H), 6.81-6.78 (m, 2H), 4.12 (t, J=6.8 Hz, 2H), 3.85 (t, J=6.8 Hz, 2H), 1.75 (sex, J=7.2 Hz, 2H), 1.39 (t, J=6.8 Hz, 3H), 1.00 (t, J=7.2 Hz, 3H). MS (M+1): 526.

Compound 5-22

N-(4-(4-(tert-butyl)phenyl)-5-(3-fluorophenoxy)thiazol-2-yl)-5-nitrothiophene-2-carboxamide

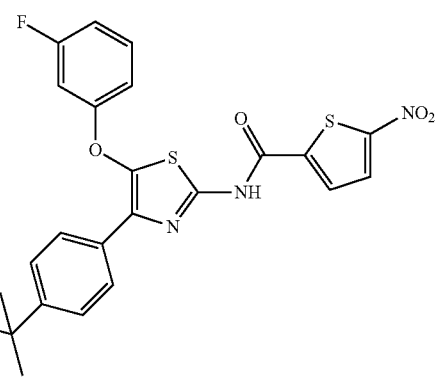

$^1$H NMR (400 MHz, DMSO-d$_6$): δ 13.42 (br. s., 1H), 8.18-8.32 (m, 2H), 7.81 (d, J=8.8 Hz, 2H), 7.39-7.48 (m, 3H), 7.06-7.13 (m, 1H), 6.97-7.05 (m, 2H), 1.27 (s, 9H) MS (M+1):498

Compound 5-23

N-(4-(4-ethoxyphenyl)-5-(3-(trifluoromethyl)phenoxy)thiazol-2-yl)-5-nitrothiophene-2-carboxamide

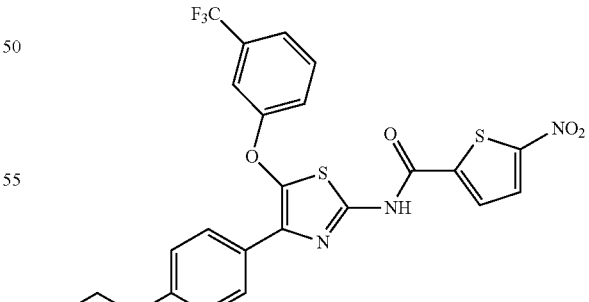

$^1$H NMR (400 MHz, DMSO-d$_6$): δ 13.39 (br. s., 1H), 8.18-8.28 (m, 2H), 7.75-7.81 (m, J=8.8 Hz, 2H), 7.60-7.67 (m, 1H), 7.49-7.56 (m, 2H), 7.43-7.48 (m, 1H), 6.93-6.99 (m, J=8.8 Hz, 2H), 4.02 (q, J=6.8 Hz, 2H), 1.31 (t, J=6.8 Hz, 3H). MS (M+1):536

Compound 5-24

N-(5-(3-fluorophenoxy)-4-(4-propoxyphenyl)thiazol-2-yl)-5-nitrothiophene-2-carboxamide

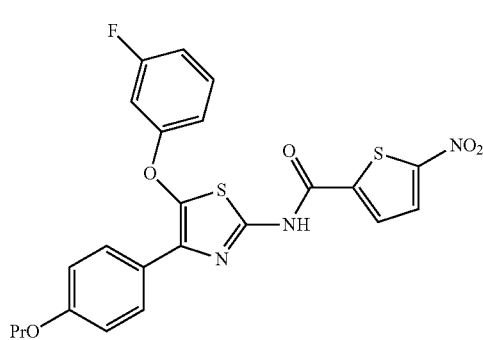

$^1$H NMR (400 MHz, DMSO-d$_6$): δ 13.39 (s, 1H), 8.25-8.21 (m, 2H), 7.78 (d, J=8.8 Hz, 2H), 7.46-7.40 (m, 1H), 7.08 (td, J=10.4, 2.4 Hz, 1H), 7.03-6.97 (m, 4H), 3.93 (t, J=6.8 Hz, 2H), 1.71 (sex, J=6.8 Hz, 2H), 0.96 (t, J=7.2 Hz, 3H). MS (M+1):500.

Compound 5-25

N-(4-(4-ethoxyphenyl)-5-(4-(trifluoromethyl)phenoxy)thiazol-2-yl)-5-nitrothiophene-2-carboxamide

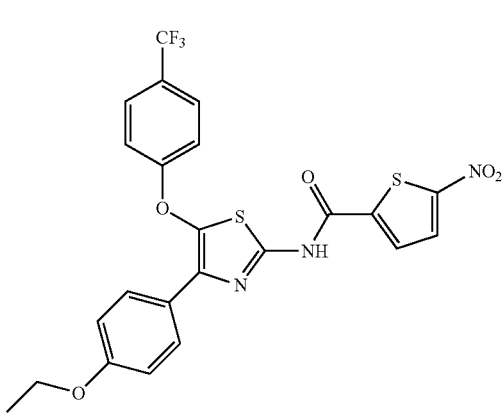 [SMILES: CCOc1ccc(-c2nc(NC(=O)c3ccc([N+](=O)[O-])s3)sc2Oc2ccc(C(F)(F)F)cc2)cc1]

$^1$H NMR (400 MHz, DMSO-d$_6$): δ 13.42 (br. s., 1H), 8.18-8.29 (m, 2H), 7.72-7.80 (m, 4H), 7.34 (d, J=8.8 Hz, 2H), 6.92-6.99 (m, 2H), 4.01 (q, J=6.8 Hz, 2H), 1.30 (t, J=6.8 Hz, 3H). MS (M+1): 536

Compound 5-26

5-nitro-N-(4-(4-propoxyphenyl)-5-(4-(trifluoromethyl)phenoxy)thiazol-2-yl)thiophene-2-carboxamide

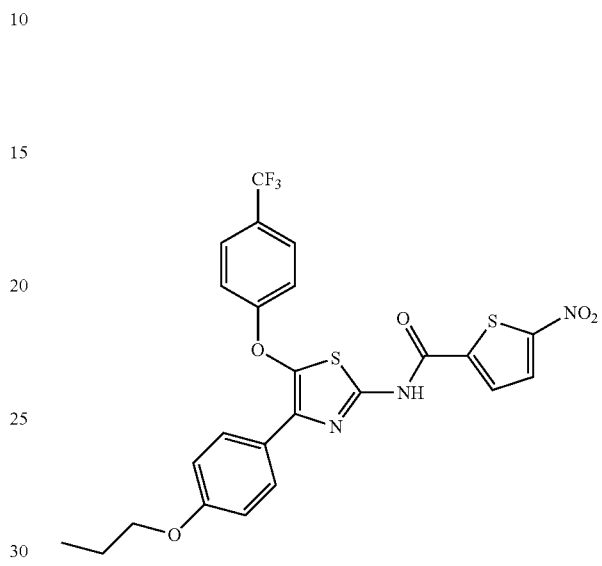

$^1$H NMR (400 MHz, DMSO-d$_6$): δ 13.42 (br. s., 1H), 8.18-8.29 (m, 2H), 7.76 (d, J=8.8 Hz, 4H), 7.34 (d, J=8.3 Hz, 2H), 6.93-7.00 (m, 2H), 3.91 (t, J=6.6 Hz, 2H), 1.65-1.75 (m, 2H), 0.95 (t, J=7.6 Hz, 3H). MS (M+1):550

Compound 5-27

N-(5-(4-bromophenoxy)-4-(4-propoxyphenyl)thiazol-2-yl)-5-nitrothiophene-2-carboxamide

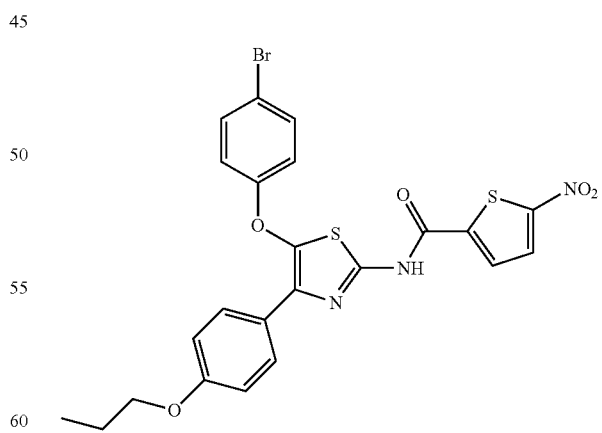

$^1$H NMR (400 MHz, DMSO-d$_6$): δ 13.37 (br. s., 1H), 8.16-8.29 (m, 2H), 7.76 (d, J=9.3 Hz, 2H), 7.52-7.60 (m, 2H), 7.07-7.16 (m, 2H), 6.92-7.01 (m, 2H), 3.92 (t, J=6.6 Hz, 2H), 1.65-1.76 (m, 2H), 0.95 (t, J=7.6 Hz, 3H). MS (M+1): 559,561

Compound 5-28

N-(5-(4-bromo-3,5-dimethylphenoxy)-4-(4-propoxyphenyl)thiazol-2-yl)-5-nitrothiophene-2-carboxamide

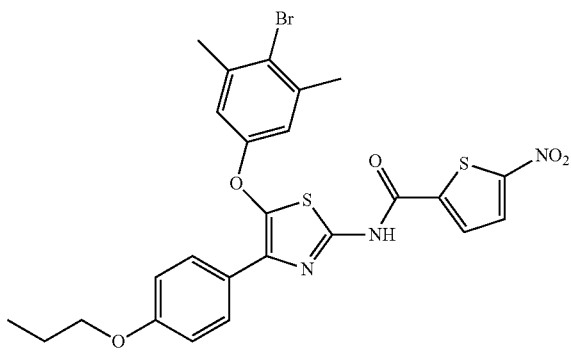 [SMILES: CCCOc1ccc(-c2nc(NC(=O)c3ccc([N+](=O)[O-])s3)sc2Oc2cc(C)c(Br)c(C)c2)cc1]

$^1$H NMR (400 MHz, DMSO-$d_6$): δ 13.34 (br. s., 1H), 8.21 (br. s., 2H), 7.78 (d, J=6.8 Hz, 2H), 6.91-7.09 (m, 4H), 3.93 (br. s., 2H), 2.34 (br. s., 6H), 1.71 (d, J=6.4 Hz, 2H), 0.92-1.00 (m, 3H). MS (M+1):588.

Compound 5-29

N-(5-(4-(tert-butyl)phenoxy)-4-(4-ethoxyphenyl)thiazol-2-yl)-5-nitrothiophene-2-carboxamide

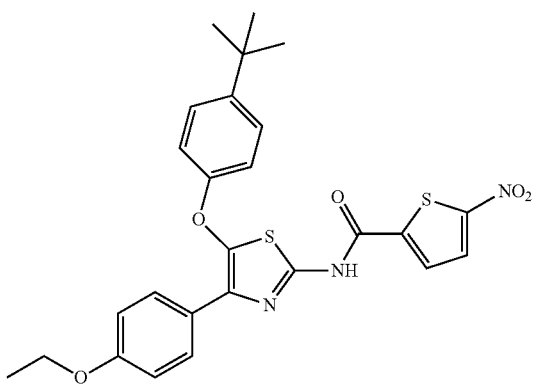 [SMILES: CCOc1ccc(-c2nc(NC(=O)c3ccc([N+](=O)[O-])s3)sc2Oc2ccc(C(C)(C)C)cc2)cc1]

$^1$H NMR (400 MHz, DMSO-$d_6$): δ 13.31 (br. s., 1H), 8.21 (br. s., 2H), 7.82 (d, J=7.8 Hz, 2H), 7.36-7.46 (m, J=8.3 Hz, 2H), 7.04-7.13 (m, J=8.3 Hz, 2H), 6.97 (d, J=8.3 Hz, 2H), 4.03 (q, J=6.7 Hz, 2H), 1.31 (t, J=6.8 Hz, 3H), 1.26 (s, 9H). MS (M+1):524

Compound 5-30

N-(5-(4-fluorophenoxy)-4-(4-propoxyphenyl)thiazol-2-yl)-5-nitrothiophene-2-carboxamide $^1$H NMR (400 MHz, CDCl$_3$): δ 11.27 (br, 1H), 7.62-7.58 (m, 3H), 7.28 (d, J=4.4 Hz, 1H), 7.09-6.98 (m, 4H), 6.78-6.74 (m, 2H), 7.04-6.98 (m, 2H), 6.84-6.80 (m, 2H), 3.83 (t, J=6.8 Hz, 2H), 1.75 (sex, J=7.2 Hz, 2H), 1.00 (t, J=7.2 Hz, 3H). MS (M+1): 500.

Compound 5-31

N-(4-(4-fluorophenyl)-5-(2-(trifluoromethyl)phenoxy)thiazol-2-yl)-5-nitrothiophene-2-carboxamide

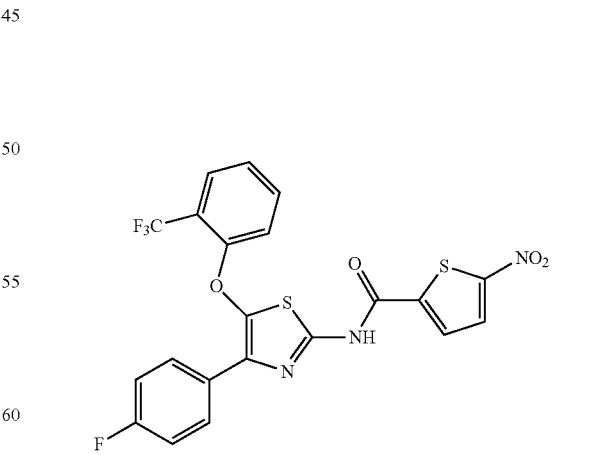

$^1$H NMR (400 MHz, CDCl$_3$): δ 7.88 (d, J=3.9 Hz, 1H), 7.80-7.87 (m, 2H), 7.65-7.71 (m, 1H), 7.61 (d, J=4.4 Hz, 1H), 7.41-7.48 (m, 1H), 7.17-7.23 (m, 1H), 7.01-7.08 (m, 3H). MS (M+1): 510.

Compound 5-32

N-(4-(4-fluorophenyl)-5-(2-(trifluoromethoxy)phenoxy)thiazol-2-yl)-5-nitrothiophene-2-carboxamide

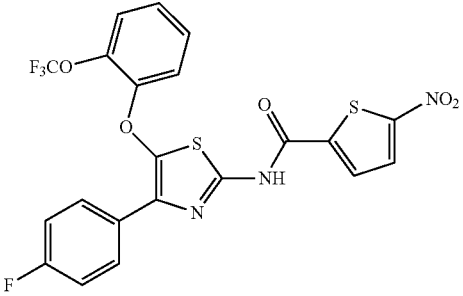 [SMILES: O=C(Nc1nc(-c2ccc(F)cc2)c(Oc2ccccc2OC(F)(F)F)s1)c1ccc([N+](=O)[O-])s1]

$^1$H NMR (400 MHz, CDCl$_3$): δ 10.02 (br. s., 1H), 7.79-7.87 (m, 3H), 7.54 (d, J=4.4 Hz, 1H), 7.35 (dt, J=7.9, 1.4 Hz, 1H), 7.18-7.23 (m, 1H), 7.11-7.18 (m, 1H), 7.00-7.10 (m, 3H). MS (M+1):526.

Compound 5-33

N-(4-(4-fluorophenyl)-5-(4-(trifluoromethoxy)phenoxy)thiazol-2-yl)-5-nitrothiophene-2-carboxamide

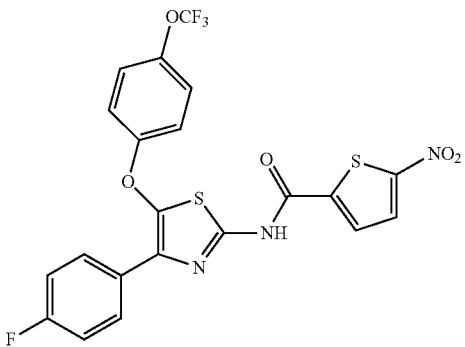 [SMILES: O=C(Nc1nc(-c2ccc(F)cc2)c(Oc2ccc(OC(F)(F)F)cc2)s1)c1ccc([N+](=O)[O-])s1]

$^1$H NMR (400 MHz, CDCl$_3$): δ 10.05 (br. s., 1H), 7.84 (d, J=3.9 Hz, 1H), 7.77-7.83 (m, 2H), 7.53-7.56 (m, 1H), 7.15-7.22 (m, 2H), 7.07-7.14 (m, 2H), 7.00-7.07 (m, 2H). MS (M+1): 526.

Compound 5-34

N-(4-(4-methoxyphenyl)-5-phenoxythiazol-2-yl)-5-nitrothiophene-2-carboxamide

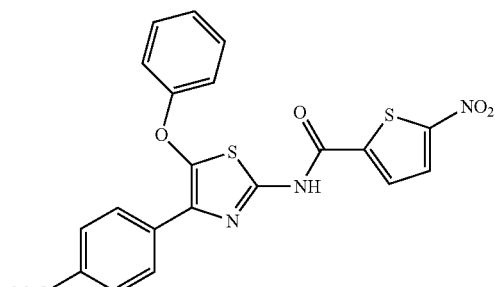

$^1$H NMR (400 MHz, CDCl$_3$): δ 7.79 (d, J=4.4 Hz, 1H), 7.73 (d, J=8.8 Hz, 2H), 7.49 (d, J=4.4 Hz, 1H), 7.28-7.37 (m, 2H), 7.06-7.16 (m, 3H), 6.85 (d, J=8.8 Hz, 2H), 3.77 (s, 3H). MS (M+1):454.

Compound 5-35

N-(5-(4-fluorophenoxy)-4-(4-(methylcarbamoyl)phenyl)thiazol-2-yl)-5-nitrothiophene-2-carboxamide

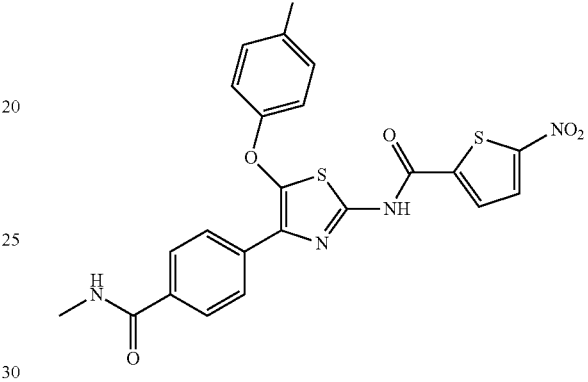

$^1$H NMR (400 MHz, DMSO-d$_6$): δ 13.40 (s, 1H), 8.41 (q, 1H), 8.24 (d, J=4.4 Hz, 1H), 8.21 (d, J=4.4 Hz, 1H), 7.97 (d, J=8.8 Hz, 2H), 7.88 (d, J=8.4 Hz, 2H), 7.30-7.23 (m, 4H), 2.78 (d, J=4.4 Hz, 3H). MS (M+1):499.

Compound 5-36

N-(4-(3,5-diethoxyphenyl)-5-phenoxythiazol-2-yl)-5-nitrothiophene-2-carboxamide

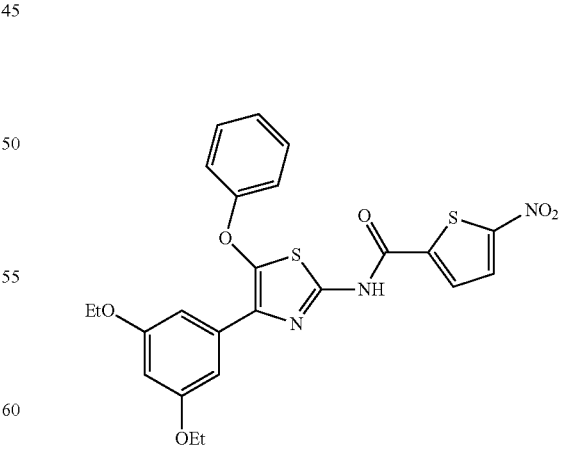

$^1$H NMR (400 MHz, DMSO-d$_6$): δ 13.28 (s, 1H), 8.24 (br, 1H), 8.20 (d, J=4.4 Hz, 1H), 7.45-7.39 (m, 2H), 7.20-7.16 (m, 3H), 7.03 (d, J=2.4 Hz, 2H), 6.41 (t, J=2.4 Hz, 2H), 3.94 (q, J=6.8 Hz, 4H), 1.27 (t, J=6.8 Hz, 6H). MS (M+1): 512.

Compound 5-37

N-(5-(2,4-difluorophenoxy)-4-(4-propoxyphenyl)thiazol-2-yl)-5-nitrothiophene-2-carboxamide

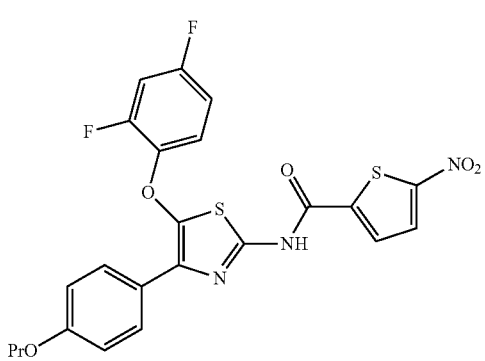

$^1$H NMR (400 MHz, DMSO-d$_6$): δ 13.37 (s, 1H), 8.22-8.20 (m, 2H), 7.81 (d, J=8.8 Hz, 2H), 7.55-7.50 (m, 1H), 7.32-7.26 (m, 1H), 7.10-7.06 (m, 1H), 7.03-6.99 (m, 2H), 3.94 (t, J=6.8 Hz, 2H), 1.72 (sex, J=7.2 Hz, 2H), 0.97 (t, J=7.2 Hz, 3H). MS (M+1): 512.

Compound 5-38

N-(5-(2-chloro-4-(trifluoromethyl)phenoxy)-4-(4-propoxyphenyl)thiazol-2-yl)-5-nitrothiophene-2-carboxamide

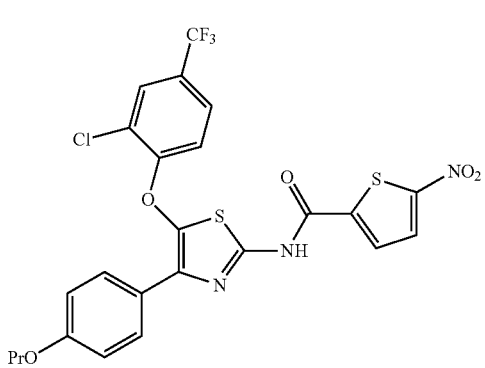

$^1$H NMR (400 MHz, DMSO-d$_6$): δ 13.48 (s, 1H), 8.25-8.21 (m, 2H), 8.07 (d, J=2.0 Hz, 1H), 7.75 (d, J=8.8 Hz, 2H), 7.68 (dd, J=8.8, 1.6 Hz, 1H), 7.30 (d, J=8.4 Hz, 1H), 7.00-6.96 (m, 2H), 3.93 (t, J=6.8 Hz, 2H), 1.70 (sex, J=7.2 Hz, 2H), 0.95 (t, J=7.2 Hz, 3H). MS (M+1): 584.

Compound 5-39

N-(5-(4-cyanophenoxy)-4-(4-propoxyphenyl)thiazol-2-yl)-5-nitrothiophene-2-carboxamide

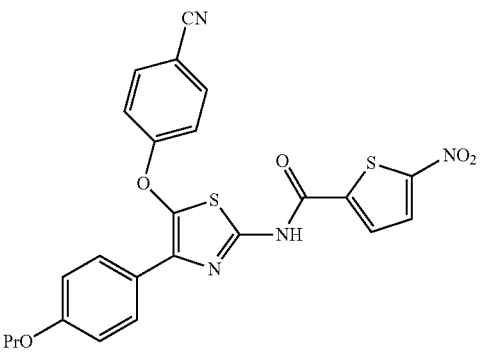

$^1$H NMR (400 MHz, DMSO-d$_6$): δ 13.44 (s, 1H), 8.25-8.21 (m, 2H), 7.90-7.86 (m, 2H), 7.74 (d, J=8.8 Hz, 2H), 7.35-7.31 (m, 2H), 6.98-6.95 (m, 2H), 3.92 (t, J=6.8 Hz, 2H), 1.71 (sex, J=7.2 Hz, 2H), 0.95 (t, J=7.2 Hz, 3H). MS (M+1):507.

Compound 5-40

N-(5-(4-cyano-2-methoxyphenoxy)-4-(4-propoxyphenyl)thiazol-2-yl)-5-nitrothiophene-2-carboxamide

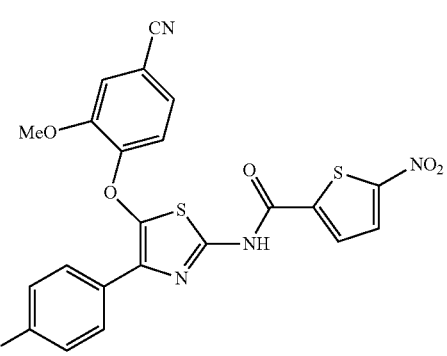

$^1$H NMR (400 MHz, DMSO-d$_6$): δ 13.39 (s, 1H), 8.23-8.20 (m, 2H), 7.76 (d, J=8.8 Hz, 2H), 7.68 (d, J=2.0 Hz, 1H), 7.39 (dd, J=8.4, 2.0 Hz, 1H), 7.15 (d, J=8.4 Hz, 1H), 6.99-6.96 (m, 2H), 3.95 (s, 3H), 3.93 (t, J=6.8 Hz, 2H), 1.71 (sex, J=7.2 Hz, 2H), 0.96 (t, J=7.2 Hz, 3H). MS (M+1): 537.

Compound 5-41

N-(4-(5-(3,3-dimethylbut-1-yn-1-yl)thiophen-2-yl)-5-phenoxythiazol-2-yl)-5-nitrothiophene-2-carboxamide

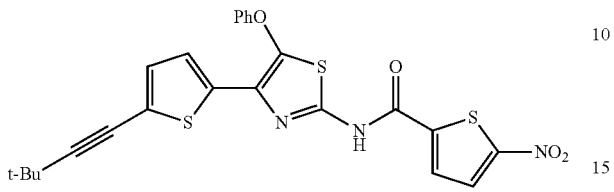

¹H NMR (400 MHz, CDCl₃): δ 9.77-10.06 (m, 2H), 7.85 (d, J=4.4 Hz, 2H), 7.54 (d, J=4.4 Hz, 2H), 7.31-7.37 (m, 4H), 7.24 (s, 1H), 7.23 (s, 1H), 7.10-7.17 (m, 6H), 6.96 (d, J=3.9 Hz, 2H), 1.28 (s, 9H). MS (M+1): 510

Compound 5-42

N-(4-(5-bromothiophen-2-yl)-5-phenoxythiazol-2-yl)-5-nitrothiophene-2-carboxamide

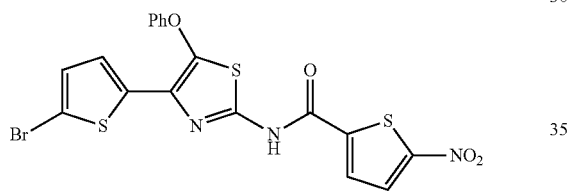

¹H NMR (400 MHz, CDCl₃): δ 9.90 (br. s., 1H), 7.85-7.88 (m, 1H), 7.56 (d, J=4.4 Hz, 1H), 7.32-7.38 (m, 2H), 7.10-7.18 (m, 4H), 6.92-6.95 (m, 1H). MS (M+1): 509.

Compound 5-43 (5-nitro-N-(4-(4-propoxyphenyl)-5-(pyridin-4-yloxy)thiazol-2-yl)thiophene-2-carboxamide)

N-(4-(5-(3-(dimethylamino)prop-1-yn-1-yl)thiophen-2-yl)-5-phenoxythiazol-2-yl)-5-nitrothiophene-2-carboxamide

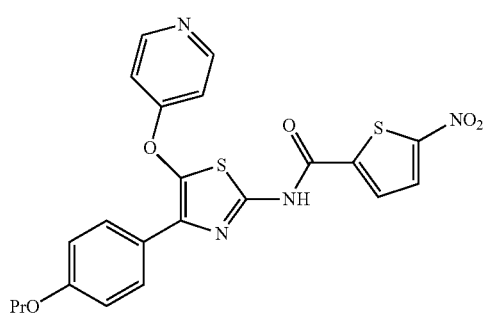

¹H NMR (400 MHz, DMSO-d₆): δ 8.14 (d, J=4.4 Hz, 2H), 7.98 (d, J=4.4 Hz, 1H), 7.39-7.45 (m, 2H), 7.26-7.30 (m, 2H), 7.15-7.21 (m, 3H), 3.74 (s, 2H), 2.41 (s, 6H). MS (M+1): 511.

Compound 5-44

N-(5-(3,4-dichlorophenoxy)-4-(4-propoxyphenyl)thiazol-2-yl)-5-nitrothiophene-2-carboxamide

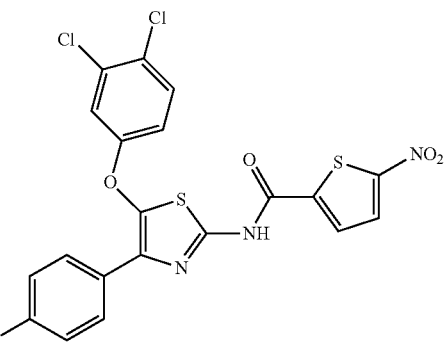

¹H NMR (400 MHz, CDCl₃): δ 11.03 (br, 1H), 7.65 (d, J=4.4 Hz, 1H), 7.61-7.57 (m, 2H), 7.37-7.35 (m, 2H), 7.18 (d, J=2.8 Hz, 1H), 6.95 (dd, J=8.8, 2.8 Hz, 1H), 6.80-6.77 (m, 2H), 3.85 (t, J=6.4 Hz, 2H), 1.76 (sex, J=7.2 Hz, 2H), 1.00 (t, J=7.2 Hz, 3H). MS (M+1): 550.

Compound 5-45

N-(5-(2-chloro-4-fluorophenoxy)-4-(4-propoxyphenyl)thiazol-2-yl)-5-nitrothiophene-2-carboxamide

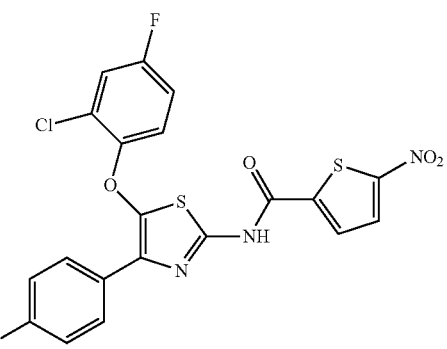

¹H NMR (400 MHz, CDCl₃): δ 11.05 (br, 1H), 7.68-7.65 (m, 2H), 7.63 (d, J=4.0 Hz, 1H), 7.32 (d, J=4.4 Hz, 1H), 7.20 (dd, J=7.6, 2.8 Hz, 1H), 7.02 (dd, J=8.8, 4.8 Hz, 1H), 6.91-6.86 (m, 1H), 6.81-6.77 (m, 2H), 3.85 (t, J=6.8 Hz, 2H), 1.76 (sex, J=7.2 Hz, 2H), 1.00 (t, J=7.2 Hz, 3H). MS (M+1): 534.

Compound 5-46

N-(4-(5-(3-(dimethylamino)prop-1-yn-1-yl)thiophen-2-yl)-5-phenoxythiazol-2-yl)-5-nitrothiophene-2-carboxamide

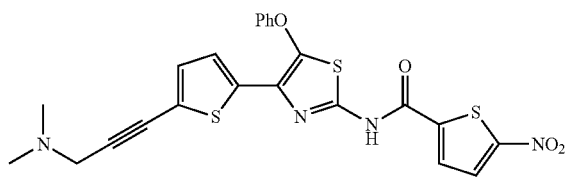 [SMILES: CN(C)CC#Cc1ccc(-c2nc(NC(=O)c3ccc([N+](=O)[O-])s3)sc2Oc2ccccc2)s1]

¹H NMR (400 MHz, DMSO-d₆): □8.14 (d, J=4.4 Hz, 2H), 7.98 (d, J=4.4 Hz, 1H), 7.39-7.45 (m, 2H), 7.26-7.30 (m, 2H), 7.15-7.21 (m, 3H), 3.74 (s, 2H), 2.41 (s, 6H). MS (M+1): 511

Compound 5-47

N-(4-(4-ethoxyphenyl)-5-phenoxythiazol-2-yl)-5-nitrofuran-2-carboxamide

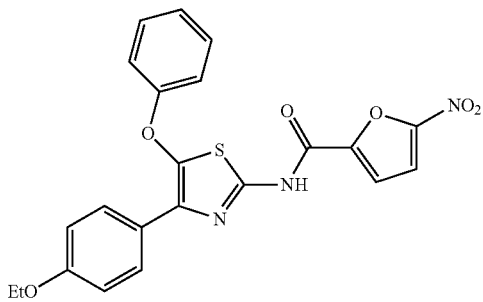

¹H NMR (400 MHz, DMSO-d₆): δ 12.94 (br, 1H), 7.82-7.80 (m, 4H), 7.42-7.38 (m, 2H), 7.17-7.14 (m, 3H), 6.97-6.94 (m, 2H), 4.03 (q, J=6.8 Hz, 2H), 1.31 (t, J=7.2 Hz, 3H). LCMS, [M+1]⁺: 452.

Compound 5-48

5-nitro-N-(5-phenoxy-4-(4-propoxyphenyl)thiazol-2-yl)furan-2-carboxamide

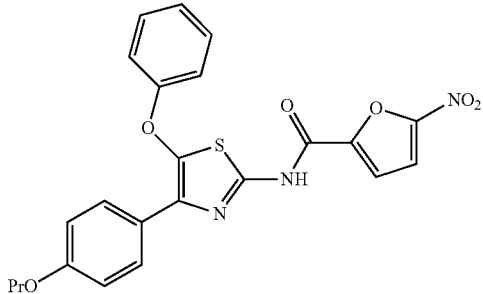

¹H NMR (400 MHz, DMSO-d₆): δ 7.82-7.77 (m, 4H), 7.42-7.37 (m, 2H), 7.17-7.14 (m, 3H), 6.98-6.94 (m, 2H), 3.92 (t, J=6.8 Hz, 2H), 1.71 (sex, J=7.2 Hz, 2H), 0.96 (t, J=7.2 Hz, 3H). LCMS, [M+1]⁺: 466.

Compound 5-49

N-(5-(4-fluorophenoxy)-4-(4-propoxyphenyl)thiazol-2-yl)-5-nitrofuran-2-carboxamide

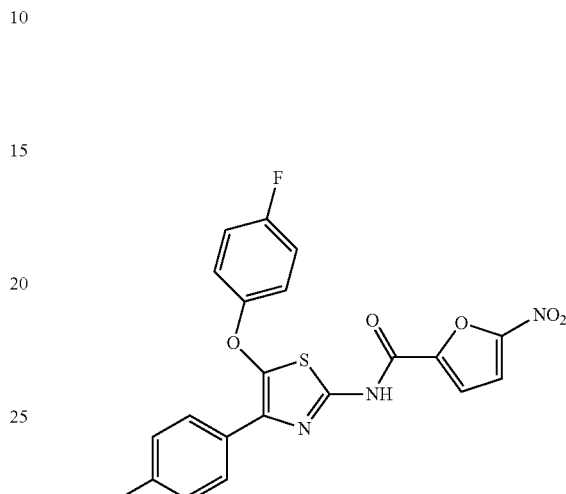

¹H NMR (400 MHz, CDCl₃): δ 10.83 (br, 1H), 7.73-7.69 (m, 2H), 7.31 (d, J=4.0 Hz, 1H), 7.26 (d, J=4.0 Hz, 1H), 7.12-7.07 (m, 2H), 7.04-6.98 (m, 2H), 6.84-6.80 (m, 2H), 3.88 (t, J=6.4 Hz, 2H), 1.77 (sex, J=7.2 Hz, 2H), 1.00 (t, J=7.2 Hz, 3H). LCMS, [M+1]⁺: 484.

Compound 5-50

N-(5-(3,5-difluorophenoxy)-4-(4-propoxyphenyl)thiazol-2-yl)-5-nitrothiophene-2-carboxamide

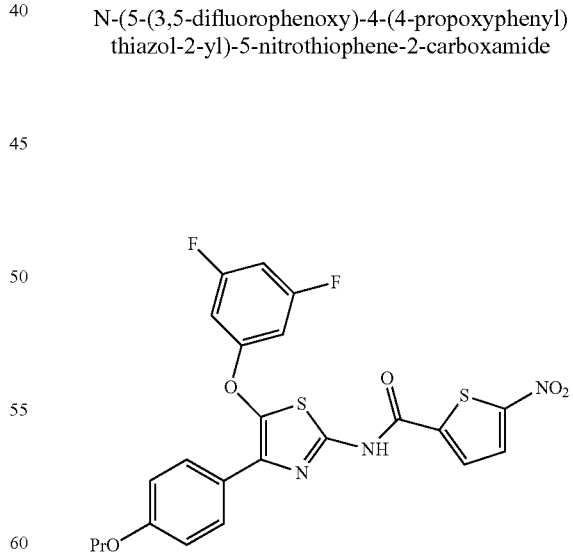

¹H NMR (400 MHz, CDCl₃): δ 10.51 (br, 1H), 7.74 (d, J=4.4 Hz, 1H), 7.64-7.61 (m, 2H), 7.44 (d, J=4.0 Hz, 1H), 6.84-6.80 (m, 2H), 6.65-6.58 (m, 2H), 6.58-6.52 (m, 1H), 3.87 (t, J=6.8 Hz, 2H), 1.77 (sex, J=7.2 Hz, 2H), 1.00 (t, J=7.2 Hz, 3H). MS (M+1): 518.

Compound 5-51

N-(4-(6-ethoxypyridin-3-yl)-5-phenoxythiazol-2-yl)-5-nitrothiophene-2-carboxamide

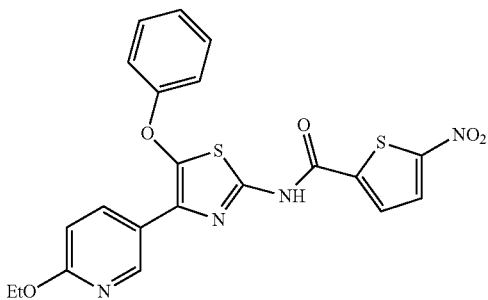 [SMILES: CCOc1ccc(-c2nc(NC(=O)c3ccc([N+](=O)[O-])s3)sc2Oc2ccccc2)cn1]

$^1$H NMR (400 MHz, CDCl$_3$): δ 8.68 (d, J=2.4 Hz, 1H), 8.04 (dd, J=8.8, 2.4 Hz, 1H), 7.88 (d, J=4.4 Hz, 1H), 7.61 (d, J=4.4 Hz, 1H), 7.35-7.30 (m, 2H), 7.14-7.08 (m, 3H), 6.70 (d, J=8.8 Hz, 1H), 4.33 (q, J=6.8 Hz, 2H), 1.36 (t, J=6.8 Hz, 3H). MS (M+1): 469.

Compound 5-52

5-nitro-N-(4-(4-propoxyphenyl)-5-(quinolin-8-yloxy)thiazol-2-yl)thiophene-2-carboxamide

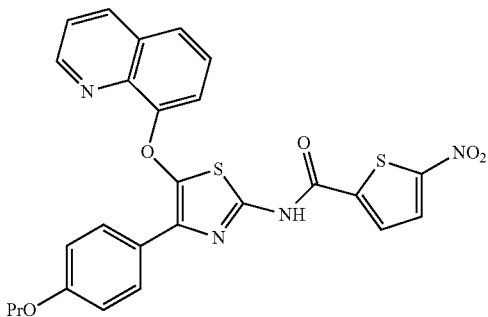

$^1$H NMR (400 MHz, DMSO-d$_6$): 13.27 (br, 1H), 8.99 (dd, J=4.4, 1.6 Hz, 1H), 8.46 (dd, J=8.4, 1.6 Hz, 1H), 8.21-8.17 (m, 2H), 7.94-7.90 (m, 2H), 7.80 (dd, J=8.4, 0.8 Hz, 1H), 7.66 (dd, J=8.4, 4.4 Hz, 1H), 7.55 (t, J=8.0 Hz, 1H), 7.39 (dd, J=8.0, 0.8 Hz, 1H), 6.95-6.91 (m, 2H), 3.90 (t, J=6.4 Hz, 2H), 1.68 (sex, J=6.8 Hz, 2H), 0.93 (t, J=7.2 Hz, 3H). MS (M+1): 533.

Compound 5-53

N-(4-(4-ethoxy-2-fluorophenyl)-5-phenoxythiazol-2-yl)-5-nitrothiophene-2-carboxamide

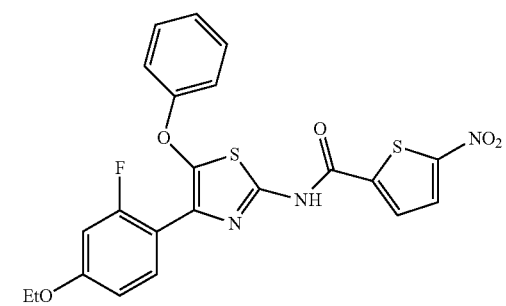 [SMILES: CCOc1ccc(-c2nc(NC(=O)c3ccc([N+](=O)[O-])s3)sc2Oc2ccccc2)c(F)c1]

$^1$H NMR (400 MHz, CDCl$_3$): δ 11.68 (br, 1H), 7.60 (d, J=4.0 Hz, 1H), 7.37 (t, J=8.8 Hz, 1H), 7.34-7.29 (m, 3H), 7.13-7.09 (m, 3H), 6.56 (dd, J=8.8, 2.4 Hz, 1H), 6.43 (dd, J=12.0, 2.4 Hz, 1H), 3.91 (q, J=7.2 Hz, 2H), 1.36 (t, J=7.2 Hz, 3H). MS (M+1): 486.

Compound 5-54

N-(4-(4-ethoxyphenyl)-5-(3-fluorophenoxy)thiazol-2-yl)-5-nitrothiophene-2-carboxamide

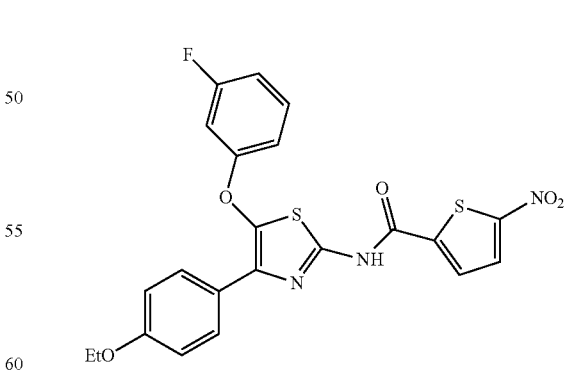

$^1$H NMR (400 MHz, CDCl$_3$): δ 11.06 (br, 1H), 7.63 (d, J=4.4 Hz, 1H), 7.62-7.59 (m, 2H), 7.32 (d, J=4.4 Hz, 1H), 7.30-7.25 (m, 1H), 6.89 (dd, J=8.8, 2.0 Hz, 1H), 6.84-6.79 (m, 2H), 6.79-6.75 (m, 2H), 3.95 (q, J=6.8 Hz, 2H), 1.37 (t, J=6.8 Hz, 3H). MS (M+1): 486.

Compound 5-55

N-(4-(4-ethoxyphenyl)-5-(4-fluorophenoxy)thiazol-2-yl)-5-nitrothiophene-2-carboxamide

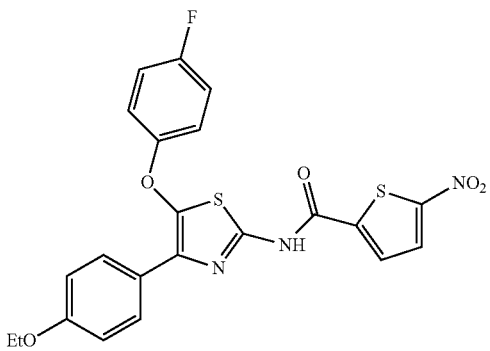 [SMILES: CCOc1ccc(-c2nc(NC(=O)c3ccc([N+](=O)[O-])s3)sc2Oc2ccc(F)cc2)cc1]

¹H NMR (400 MHz, CDCl₃): δ 10.33 (br, 1H), 7.75 (d, J=4.4 Hz, 1H), 7.71-7.67 (m, 2H), 7.44 (d, J=4.4 Hz, 1H), 7.08-7.04 (m, 2H), 7.03-6.98 (m, 2H), 6.84-6.81 (m, 2H), 6.84-6.80 (m, 2H), 3.99 (q, J=6.8 Hz, 2H), 1.38 (t, J=6.8 Hz, 3H). MS (M+1): 486.

Compound 5-56

N-(4-(4-butoxyphenyl)-5-phenoxythiazol-2-yl)-5-nitrothiophene-2-carboxamide

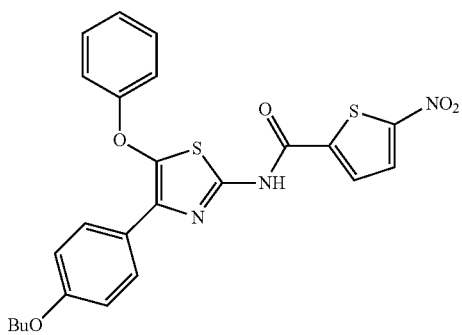

¹H NMR (400 MHz, CDCl₃): δ 7.73 (d, J=4.4 Hz, 1H), 7.64-7.71 (m, 2H), 7.43 (d, J=4.4 Hz, 1H), 7.28-7.37 (m, 2H), 7.07-7.16 (m, 3H), 6.78-6.86 (m, 2H), 3.91 (t, J=6.6 Hz, 2H), 1.68-1.78 (m, 2H), 1.39-1.51 (m, 3H), 0.95 (t, J=7.3 Hz, 3H). MS (M+1):496.

Compound 5-57

N-(4-(4-ethoxyphenyl)-5-(2-fluorophenoxy)thiazol-2-yl)-5-nitrothiophene-2-carboxamide

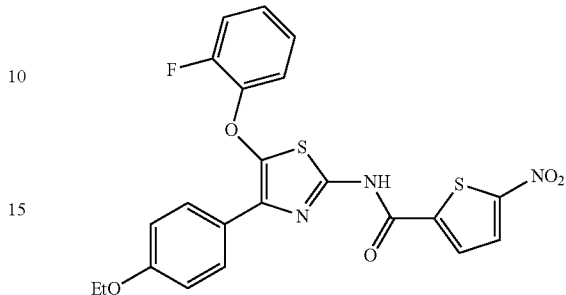

¹H NMR (400 MHz, DMSO-d₆): 13.36 (br, 1H), 8.16-8.28 (m, 2H), 7.79-7.85 (m, J=8.8 Hz, 2H), 7.38-7.47 (m, 1H), 7.16-7.25 (m, 3H), 6.97-7.02 (m, J=9.3 Hz, 2H), 4.04 (q, J=7.2 Hz, 2H), 1.32 (t, J=7.1 Hz, 3H). MS (M+1):486.

Compound 5-58

N-(5-(2-fluorophenoxy)-4-(4-propoxyphenyl)thiazol-2-yl)-5-nitrothiophene-2-carboxamide

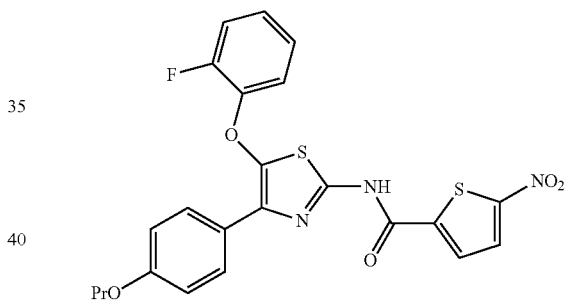

¹H NMR (400 MHz, DMSO-d₆): 13.35 (br, 1H), 8.15-8.29 (m, 2H), 7.75-7.87 (m, J=8.8 Hz, 2H), 7.42 (ddd, J=11.4, 8.2, 2.0 Hz, 1H), 7.15-7.25 (m, 3H), 6.96-7.03 (m, 2H), 3.94 (t, J=6.6 Hz, 2H), 1.66-1.77 (m, 2H), 0.97 (t, J=7.3 Hz, 3H). MS (M+1):500.

Compound 5-59

5-nitro-N-(4-(4-(tert-pentyl)phenyl)-5-phenoxythiazol-2-yl)thiophene-2-carboxamide

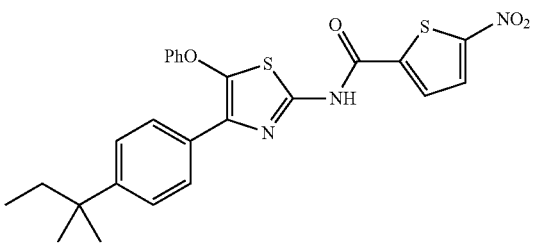 [SMILES: CCC(C)(C)c1ccc(-c2nc(NC(=O)c3ccc([N+](=O)[O-])s3)sc2Oc2ccccc2)cc1]

¹H NMR (400 MHz, CDCl₃): δ 7.64-7.68 (m, 2H), 7.59 (d, J=4.4 Hz, 1H), 7.32-7.38 (m, 2H), 7.27 (d, J=3.9 Hz, 1H), 7.20-7.24 (m, 2H), 7.11-7.17 (m, 3H), 1.55 (q, J=7.3 Hz, 2H), 1.19 (s, 6H), 0.56-0.62 (m, 3H). MS (M+1):494.

Compound 5-60

5-nitro-N-(4-(4-nitrophenyl)-5-phenoxythiazol-2-yl)thiophene-2-carboxamide

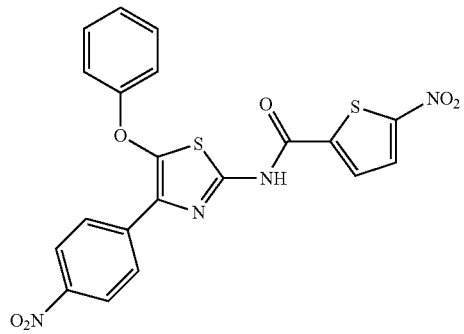 [SMILES: O=C(Nc1nc(-c2ccc([N+](=O)[O-])cc2)c(Oc2ccccc2)s1)c1ccc([N+](=O)[O-])s1]

¹H NMR (400 MHz, CDCl₃): δ 9.17 (br. s., 1H), 8.20-8.26 (m, 2H), 8.08-8.16 (m, 2H), 7.93 (d, J=4.4 Hz, 1H), 7.61 (d, J=3.9 Hz, 1H), 7.34-7.42 (m, 2H), 7.12-7.22 (m, 3H). MS (M+1):469.

Compound 5-61

5-nitro-N-(5-phenoxy-4-(3,4,5-trimethoxyphenyl)thiazol-2-yl)thiophene-2-carboxamide

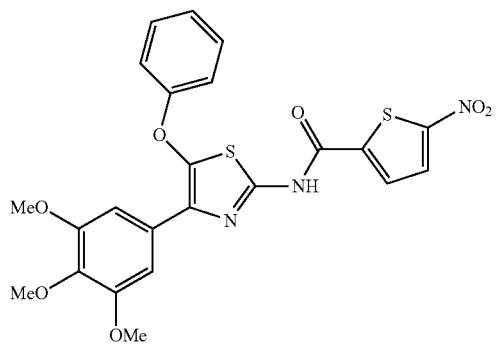 [SMILES: COc1cc(-c2nc(NC(=O)c3ccc([N+](=O)[O-])s3)sc2Oc2ccccc2)cc(OC)c1OC]

¹H NMR (400 MHz, CDCl₃): δ 10.31 (br. s., 1H), 7.80 (d, J=4.4 Hz, 1H), 7.50 (d, J=4.4 Hz, 1H), 7.30-7.40 (m, 2H), 7.06-7.16 (m, 3H), 7.05 (s, 2H), 3.80 (s, 3H), 3.68-3.77 (m, 8H), 1.23 (t, J=6.8 Hz, 3H). MS (M+1):514.

Compound 5-62

N-(4-(4-fluorophenyl)-5-(4-(tert-pentyl)phenoxy)thiazol-2-yl)-5-nitrothiophene-2-carboxamide

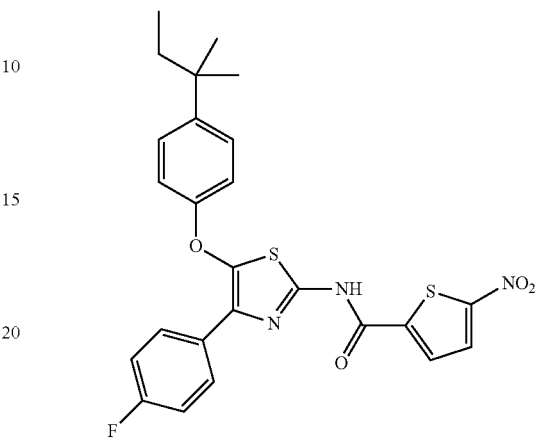

¹H NMR (400 MHz, CDCl₃): δ 10.12 (br. s., 1H), 7.81-7.87 (m, 2H), 7.76-7.81 (m, 1H), 7.46 (d, J=4.4 Hz, 1H), 7.25-7.32 (m, 2H), 6.96-7.09 (m, 4H), 1.61 (q, J=7.3 Hz, 2H), 1.25 (s, 6H), 0.67 (t, J=7.3 Hz, 3H). MS (M+1): 512.

Compound 5-63

N-(5-(4-fluorophenoxy)-4-(4-(tert-pentyl)phenyl)thiazol-2-yl)-5-nitrothiophene-2-carboxamide

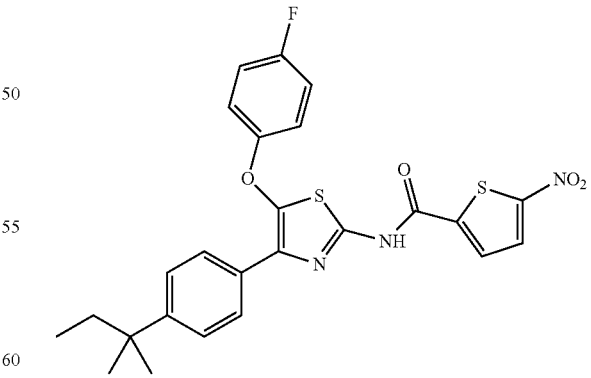

¹H NMR (400 MHz, CDCl₃): δ 11.14 (br. s., 1H), 7.60-7.73 (m, 3H), 7.35 (dd, J=4.4, 2.0 Hz, 1H), 7.14-7.29 (m, 2H), 7.06-7.14 (m, 2H), 6.95-7.06 (m, 2H), 1.57 (q, J=7.3 Hz, 2H), 1.21 (s, 6H), 0.61 (t, J=7.6 Hz, 3H). MS (M+1):512.

Compound 5-64

N-(5-(4-(tert-butyl)phenoxy)-4-(4-fluorophenyl)thiazol-2-yl)-5-nitrothiophene-2-carboxamide

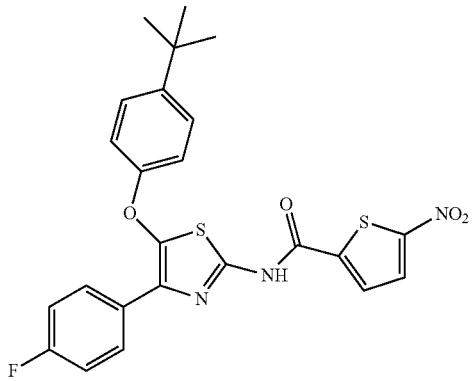 [SMILES: CC(C)(C)c1ccc(Oc2sc(NC(=O)c3ccc([N+](=O)[O-])s3)nc2-c2ccc(F)cc2)cc1]

¹H NMR (400 MHz, CDCl₃): δ 9.83 (br. s., 1H), 7.82-7.91 (m, 3H), 7.52 (d, J=4.4 Hz, 1H), 7.29-7.39 (m, 2H), 6.99-7.09 (m, 4H), 1.29 (s, 9H). MS (M+1):498.

Compound 5-65

N-(5-(4-butylphenoxy)-4-(4-fluorophenyl)thiazol-2-yl)-5-nitrothiophene-2-carboxamide

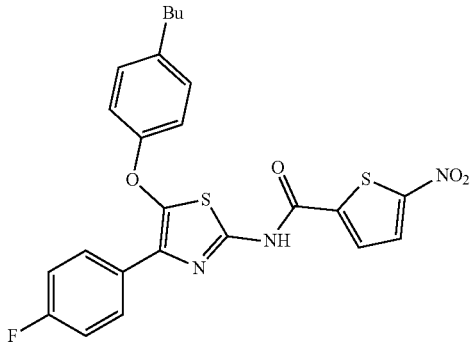

¹H NMR (400 MHz, CDCl₃): δ10.02 (br. s., 1H), 7.77-7.89 (m, 3H), 7.46 (d, J=4.4 Hz, 1H), 7.08-7.18 (m, 2H), 6.99-7.06 (m, 4H), 2.50-2.63 (m, 2H), 1.50-1.59 (m, 2H), 1.33 (dq, J=15.0, 7.2 Hz, 2H), 0.84-0.95 (m, 3H). MS (M+1):498.

Compound 5-66

N-(5-(4-butoxyphenoxy)-4-(4-fluorophenyl)thiazol-2-yl)-5-nitrothiophene-2-carboxamide

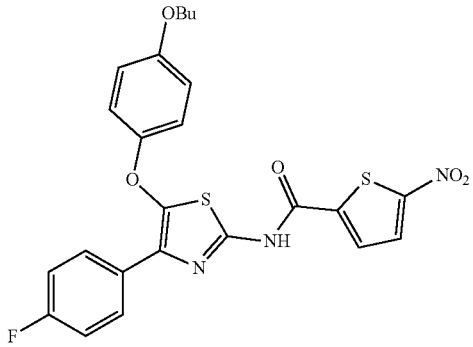

¹H NMR (400 MHz, CDCl₃): δ 7.79-7.90 (m, 3H), 7.52 (d, J=3.9 Hz, 1H), 6.98-7.09 (m, 4H), 6.80-6.88 (m, 2H), 3.92 (t, J=6.4 Hz, 2H), 1.69-1.79 (m, 3H), 1.42-1.53 (m, 3H), 0.96 (t, J=7.3 Hz, 3H). MS (M+1):514.

Compound 5-67

N-(4-(4-(hexyloxy)phenyl)-5-phenoxythiazol-2-yl)-5-nitrothiophene-2-carboxamide

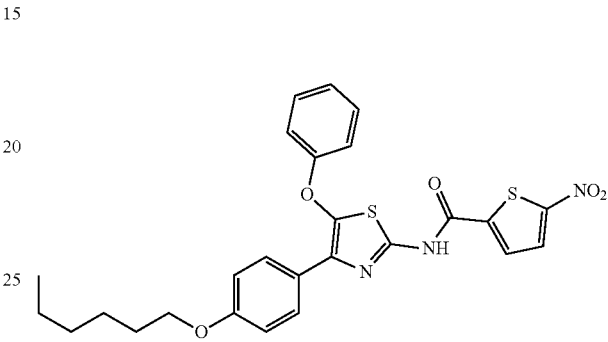

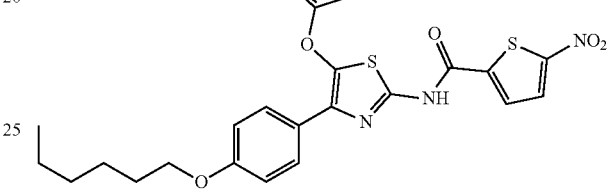

¹H NMR (400 MHz, CDCl₃): δ 10.73 (br. s., 1H), 7.61-7.72 (m, 3H), 7.28-7.40 (m, 3H), 7.07-7.16 (m, 3H), 6.79 (d, J=8.8 Hz, 2H), 3.88 (t, J=6.6 Hz, 2H), 1.67-1.79 (m, 2H), 1.38-1.49 (m, 2H), 1.25-1.38 (m, 4H), 0.84-0.94 (m, 3H). MS (M+1):524.

Compound 5-68

N-(5-(4-(tert-butyl)phenoxy)-4-(4-fluorophenyl)thiazol-2-yl)-5-nitrothiophene-2-carboxamide

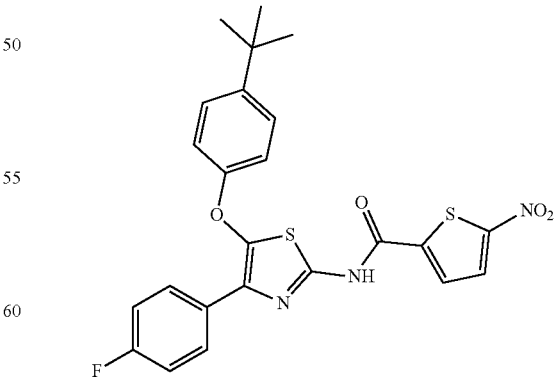

¹H NMR (400 MHz, CDCl₃): δ 9.83 (br. s., 1H), 7.82-7.91 (m, 3H), 7.52 (d, J=4.4 Hz, 1H), 7.29-7.39 (m, 2H), 6.99-7.09 (m, 4H), 1.29 (s, 9H). MS (M+1):498.

Compound 5-69

N-(5-(4-butylphenoxy)-4-(4-fluorophenyl)thiazol-2-yl)-5-nitrothiophene-2-carboxamide

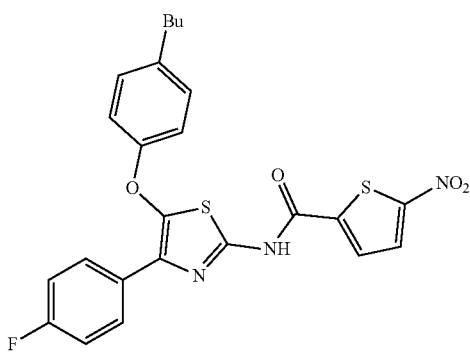

$^1$H NMR (400 MHz, CDCl$_3$): δ 10.02 (br. s., 1H), 7.77-7.89 (m, 3H), 7.46 (d, J=4.4 Hz, 1H), 7.08-7.18 (m, 2H), 6.99-7.06 (m, 4H), 2.50-2.63 (m, 2H), 1.50-1.59 (m, 2H), 1.33 (dq, J=15.0, 7.2 Hz, 2H), 0.84-0.95 (m, 3H). MS (M+1):498.

Compound 5-70

N-(5-(4-butoxyphenoxy)-4-(4-fluorophenyl)thiazol-2-yl)-5-nitrothiophene-2-carboxamide

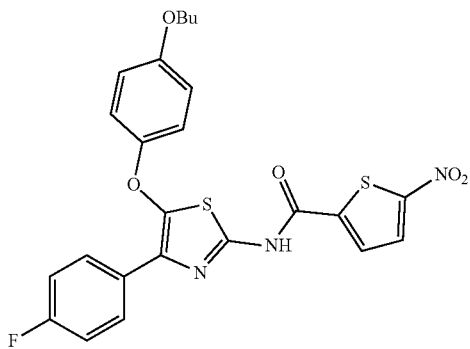

$^1$H NMR (400 MHz, CDCl$_3$): δ 7.79-7.90 (m, 3H), 7.52 (d, J=3.9 Hz, 1H), 6.98-7.09 (m, 4H), 6.80-6.88 (m, 2H), 3.92 (t, J=6.4 Hz, 2H), 1.69-1.79 (m, 3H), 1.42-1.53 (m, 3H), 0.96 (t, J=7.3 Hz, 3H). MS (M+1):514.

Compound 5-71

5-nitro-N-(5-(4-(tert-pentyl)phenoxy)-4-(4-(trifluoromethyl)phenyl)thiazol-2-yl)thiophene-2-carboxamide

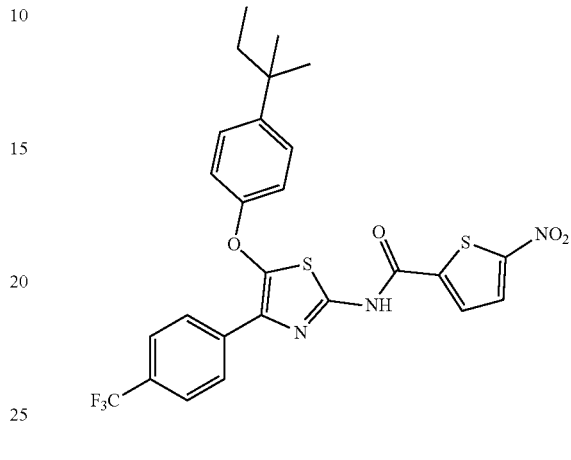

$^1$H NMR (400 MHz, DMSO-d$_6$): 13.42 (br. s., 1H), 8.23 (d, J=7.34 Hz, 2H), 8.14 (d, J=6.85 Hz, 2H), 7.82 (d, J=6.85 Hz, 2H), 7.38 (d, J=7.34 Hz, 2H), 7.17 (d, J=7.34 Hz, 2H), 1.52-1.64 (m, 2H), 1.23 (s, 6H), 0.62 (s, 3H). MS (M+1): 562.

Compound 5-72

N-(4-(4-butoxyphenyl)-5-(2-fluorophenoxy)thiazol-2-yl)-5-nitrothiophene-2-carboxamide

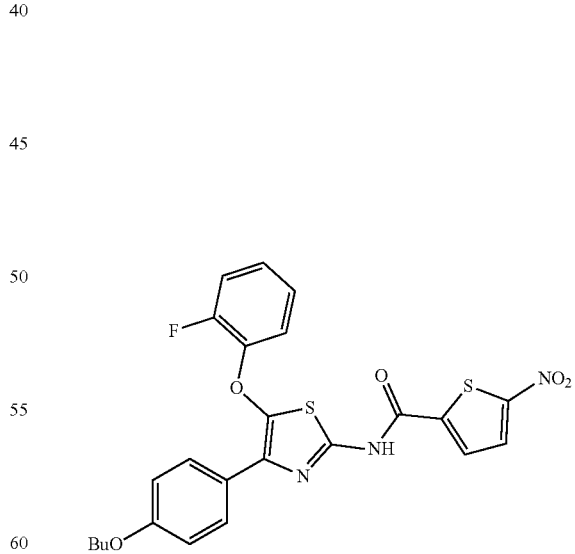

$^1$H NMR (400 MHz, CDCl$_3$): δ 10.88 (br. s., 1H), 7.61-7.73 (m, 3H), 7.31 (d, J=4.4 Hz, 1H), 7.12-7.21 (m, 1H), 7.00-7.12 (m, 3H), 6.77-6.84 (m, 2H), 3.89 (t, J=6.4 Hz, 2H), 1.68-1.76 (m, 2H), 1.40-1.50 (m, 2H), 0.95 (t, J=7.3 Hz, 3H). MS (M+1):514.

Compound 5-73

N-(4-(4-butoxyphenyl)-5-(4-fluorophenoxy)thiazol-2-yl)-5-nitrothiophene-2-carboxamide

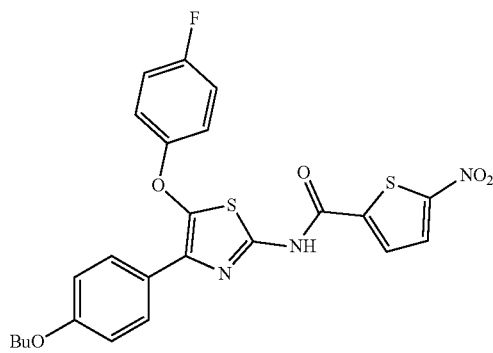

$^1$H NMR (400 MHz, CDCl$_3$): δ 7.57-7.65 (m, 3H), 7.31 (d, J=4.4 Hz, 1H), 6.98-7.09 (m, 4H), 6.73-6.81 (m, 2H), 3.88 (t, J=6.6 Hz, 2H), 1.67-1.76 (m, 2H), 1.39-1.51 (m, 2H), 0.95 (t, J=7.3 Hz, 3H). MS (M+1):514.

Compound 5-74

N-(4-(4-(tert-butyl)phenyl)-5-(4-(trifluoromethyl)phenoxy)thiazol-2-yl)-5-nitrothiophene-2-carboxamide

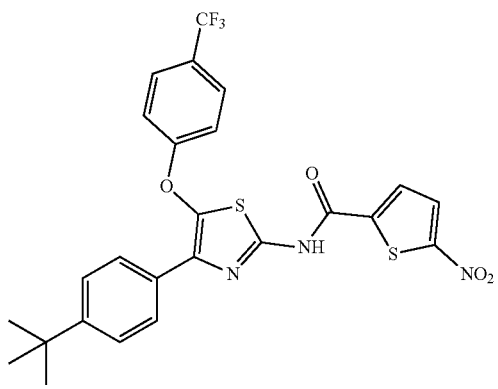 [SMILES: CC(C)(C)c1ccc(-c2nc(NC(=O)c3ccc([N+](=O)[O-])s3)sc2Oc2ccc(C(F)(F)F)cc2)cc1]

$^1$H NMR (400 MHz, DMSO-d$_6$): δ 13.46 (br. s., 1H), 8.18-8.27 (m, 2H), 7.78 (dd, J=8.8, 6.8 Hz, 4H), 7.44 (d, J=8.8 Hz, 2H), 7.36 (d, J=8.8 Hz, 2H), 1.26 (s, 9H). MS (M+1): 548.

Compound 5-75

N-(4-(4-(tert-butyl)phenyl)-5-(2-(trifluoromethyl)phenoxy)thiazol-2-yl)-5-nitrothiophene-2-carboxamide

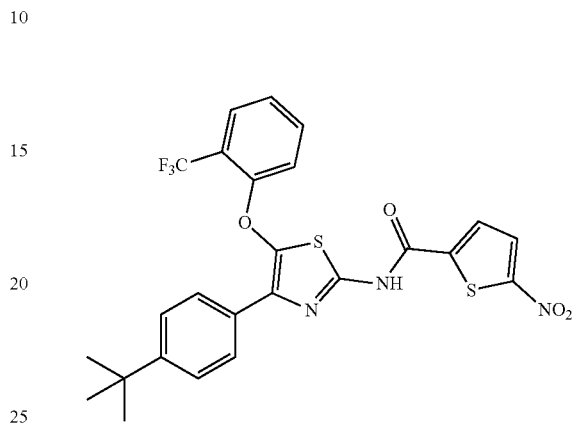

$^1$H NMR (400 MHz, DMSO-d$_6$): 13.48 (br. s., 1H), 8.18-8.29 (m, 2H), 7.79-7.87 (m, 3H), 7.62-7.70 (m, 1H), 7.42-7.48 (m, 2H), 7.36 (t, J=7.6 Hz, 1H), 7.24 (d, J=8.3 Hz, 1H), 1.27 (s, 9H) MS (M+1): 548.

Compound 5-76

5-nitro-N-(4-(4-(pentyloxy)phenyl)-5-phenoxythiazol-2-yl)thiophene-2-carboxamide

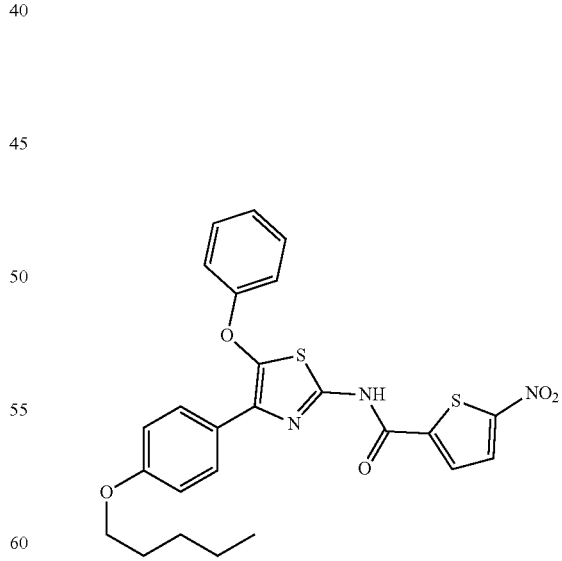

$^1$H NMR (400 MHz, CDCl$_3$): δ 10.69 (br. s., 1H), 7.63-7.73 (m, 3H), 7.29-7.39 (m, 3H), 7.06-7.16 (m, 3H), 6.79 (d, J=8.8 Hz, 2H), 3.88 (t, J=6.4 Hz, 2H), 1.74 (quin, J=7.0 Hz, 2H), 1.31-1.45 (m, 4H), 0.85-0.95 (m, 3H). MS (M+1):510.

Compound 5-77

5-nitro-N-(5-phenoxy-4-(4-propylphenyl)thiazol-2-yl)thiophene-2-carboxamide

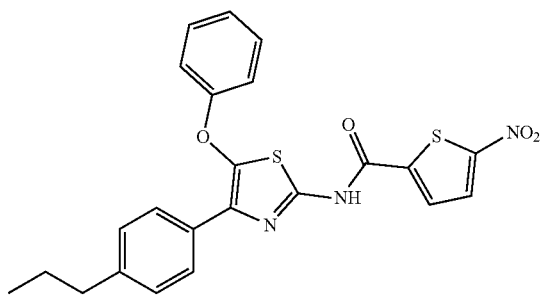 [SMILES: CCCc1ccc(-c2nc(NC(=O)c3ccc([N+](=O)[O-])s3)sc2Oc2ccccc2)cc1]

$^1$H NMR (400 MHz, CDCl$_3$): δ 11.04 (br. s., 1H), 7.61-7.70 (m, 3H), 7.31-7.39 (m, 3H), 7.11-7.16 (m, 3H), 7.08 (d, J=8.3 Hz, 2H), 2.42-2.57 (m, 2H), 1.48-1.58 (m, 2H), 0.81-0.96 (m, 3H) MS (M+1):466.

Compound 5-78

N-(5-(2-fluorophenoxy)-4-(4-propylphenyl)thiazol-2-yl)-5-nitrothiophene-2-carboxamide

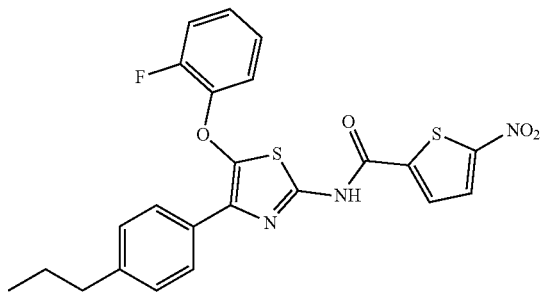 [SMILES: CCCc1ccc(-c2nc(NC(=O)c3ccc([N+](=O)[O-])s3)sc2Oc2ccccc2F)cc1]

$^1$H NMR (400 MHz, CDCl$_3$): δ 11.48 (br. s., 1H), 7.65 (d, J=8.3 Hz, 2H), 7.46-7.62 (m, 1H), 7.02-7.23 (m, 7H), 2.38-2.56 (m, 2H), 1.44-1.58 (m, 2H), 0.76-0.98 (m, 3H). MS (M+1):484.

Compound 5-79

N-(4-(4-butylphenyl)-5-phenoxythiazol-2-yl)-5-nitrothiophene-2-carboxamide

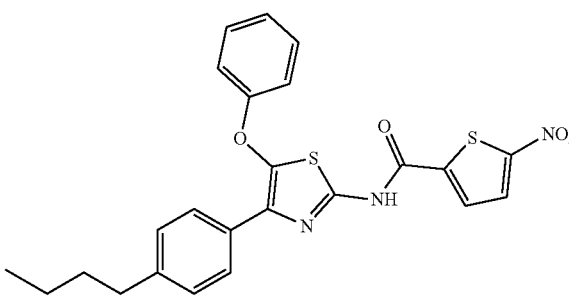

$^1$H NMR (400 MHz, CDCl$_3$): δ 7.58-7.66 (m, J=7.8 Hz, 2H), 7.57 (d, J=4.4 Hz, 1H), 7.29-7.38 (m, 2H), 7.26 (d, J=4.4 Hz, 1H), 7.09-7.16 (m, 3H), 7.02-7.09 (m, J=8.3 Hz, 2H), 2.41-2.61 (m, 2H), 1.41-1.52 (m, 2H), 1.28 (dq, J=15.0, 7.2 Hz, 2H), 0.81-0.95 (m, 3H). MS (M+1):480.

Compound 5-80

N-(4-(4-butylphenyl)-5-(2-fluorophenoxy)thiazol-2-yl)-5-nitrothiophene-2-carboxamide

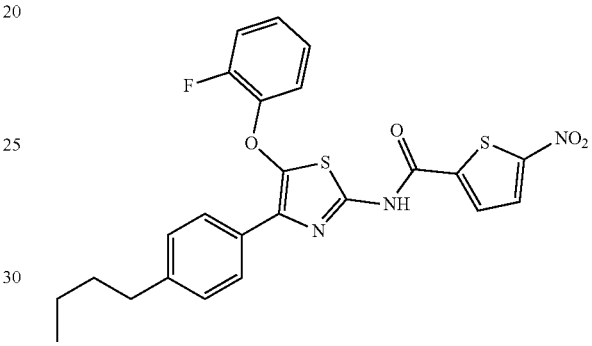

$^1$H NMR (400 MHz, CDCl$_3$): δ 7.68 (d, J=7.8 Hz, 2H), 7.63 (d, J=4.4 Hz, 1H), 7.30 (d, J=3.9 Hz, 1H), 7.16-7.24 (m, 1H), 7.03-7.16 (m, 5H), 2.47-2.59 (m, 2H), 1.45-1.54 (m, 2H), 1.24-1.35 (m, 2H), 0.85-0.93 (m, 3H). MS (M+1):498.

Compound 5-81

5-nitro-N-(5-phenoxy-4-(4-(trifluoromethyl)phenyl)thiazol-2-yl)thiophene-2-carboxamide

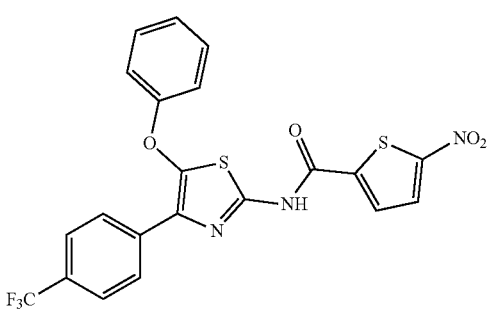 [SMILES: O=C(Nc1nc(-c2ccc(C(F)(F)F)cc2)c(Oc2ccccc2)s1)c1ccc([N+](=O)[O-])s1]

$^1$H NMR (400 MHz, CDCl$_3$): δ 10.00 (br. s., 1H), 7.92-8.03 (m, J=8.3 Hz, 2H), 7.82 (d, J=4.4 Hz, 1H), 7.55-7.62 (m, J=8.3 Hz, 2H), 7.51 (d, J=4.4 Hz, 1H), 7.29-7.42 (m, 2H), 7.09-7.20 (m, 3H). MS (M+1):492.

Compound 5-82

N-(4-(4-ethoxyphenyl)-5-phenoxythiazol-2-yl)-N-methyl-5-nitrothiophene-2-carboxamide

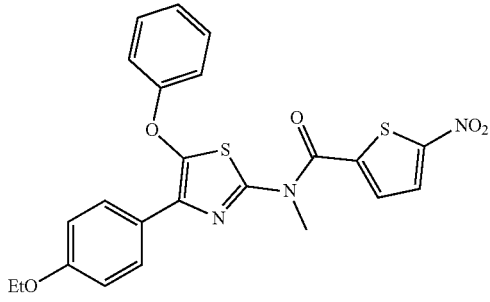 [SMILES: CCOc1ccc(-c2nc(N(C)C(=O)c3ccc([N+](=O)[O-])s3)sc2Oc2ccccc2)cc1]

¹H NMR (400 MHz, CDCl₃): 7.86 (d, J=4.0 Hz, 1H), 7.70 (d, J=4.4 Hz, 1H), 7.29-7.24 (m, 4H), 7.08 (t, J=8.0 Hz, 1H), 7.01-6.99 (m, 2H), 6.97-6.94 (m, 2H), 4.04 (q, J=6.8 Hz, 2H), 3.66 (s, 3H), 1.41 (t, J=6.8 Hz, 3H). MS (M+1): 482.

Compound 5-83

N-(5-(2-fluorophenoxy)-4-(4-(trifluoromethyl)phenyl)thiazol-2-yl)-5-nitrothiophene-2-carboxamide

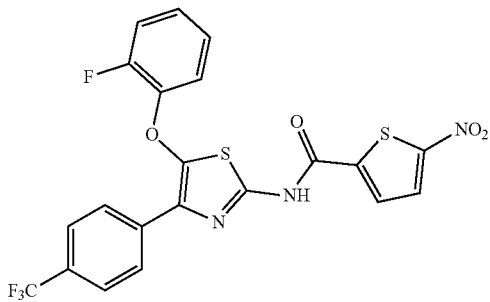 [SMILES: O=C(Nc1nc(-c2ccc(C(F)(F)F)cc2)c(Oc2ccccc2F)s1)c1ccc([N+](=O)[O-])s1]

¹H NMR (400 MHz, CDCl₃): δ 9.87 (br. s., 1H), 8.01-8.08 (m, J=8.3 Hz, 2H), 7.81-7.87 (m, 1H), 7.59-7.66 (m, J=8.3 Hz, 2H), 7.54 (d, J=3.9 Hz, 1H), 7.04-7.23 (m, 4H). MS (M+1):510.

Compound 5-84

5-nitro-N-(5-phenoxy-4-(4-(trifluoromethoxy)phenyl)thiazol-2-yl)thiophene-2-carboxamide

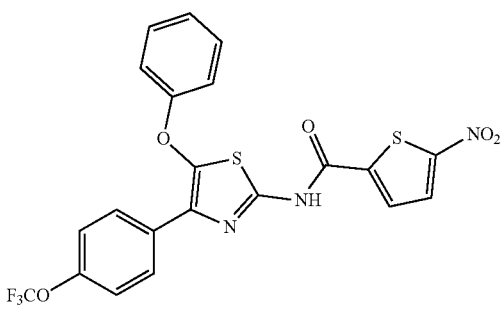 [SMILES: O=C(Nc1nc(-c2ccc(OC(F)(F)F)cc2)c(Oc2ccccc2)s1)c1ccc([N+](=O)[O-])s1]

¹H NMR (400 MHz, CDCl₃): δ 9.87 (br. s., 1H), 7.87-7.92 (m, 2H), 7.84 (d, J=4.4 Hz, 1H), 7.51-7.54 (m, 1H), 7.32-7.38 (m, 2H), 7.10-7.21 (m, 5H). MS (M+1):508.

Compound 5-85

N-(5-(2-fluorophenoxy)-4-(4-(trifluoromethoxy)phenyl)thiazol-2-yl)-5-nitrothiophene-2-carboxamide

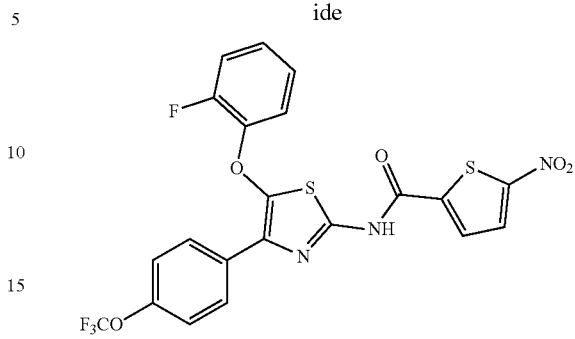

¹H NMR (400 MHz, CDCl₃): δ 10.58 (br. s., 1H), 7.88 (d, J=8.8 Hz, 2H), 7.74 (d, J=4.4 Hz, 1H), 7.42 (d, J=4.4 Hz, 1H), 7.04-7.23 (m, 6H). MS (M+1):526.

Compound 5-86

N-(5-(4-bromophenoxy)-4-(4-butoxyphenyl)thiazol-2-yl)-5-nitrothiophene-2-carboxamide

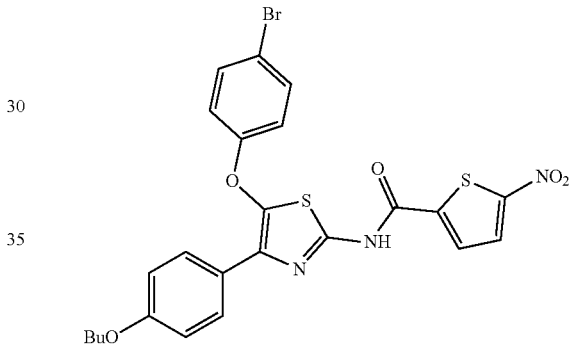

¹H NMR (400 MHz, CDCl₃): δ 9.94 (br. s., 1H), 7.82 (d, J=4.4 Hz, 1H), 7.63-7.73 (m, 2H), 7.47-7.54 (m, 1H), 7.35-7.45 (m, 2H), 6.93-7.02 (m, 2H), 6.79-6.89 (m, 2H), 3.93 (t, J=6.6 Hz, 2H), 1.69-1.79 (m, 2H), 1.40-1.50 (m, 2H), 0.95 (t, J=7.3 Hz, 3H). MS (M+1):574.

Compound 5-87

N-(5-(4-bromo-3,5-dimethylphenoxy)-4-(4-butoxyphenyl)thiazol-2-yl)-5-nitrothiophene-2-carboxamide

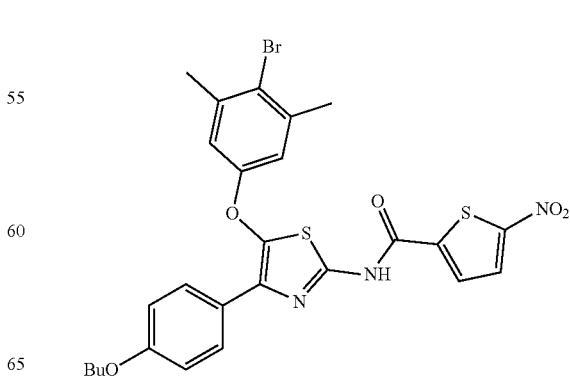

¹H NMR (400 MHz, CDCl₃): δ 7.75 (d, J=4.4 Hz, 1H), 7.65-7.70 (m, 2H), 7.45 (d, J=4.4 Hz, 1H), 6.80-6.85 (m, 4H), 3.92 (t, J=6.6 Hz, 2H), 2.36 (s, 6H), 1.69-1.77 (m, 2H), 1.41-1.49 (m, 2H), 0.95 (t, J=7.6 Hz, 3H). MS (M+1):602.

Compound 5-88

N-(4-(4-(tert-butyl)phenyl)-5-(4-propylphenoxy)thiazol-2-yl)-5-nitrothiophene-2-carboxamide

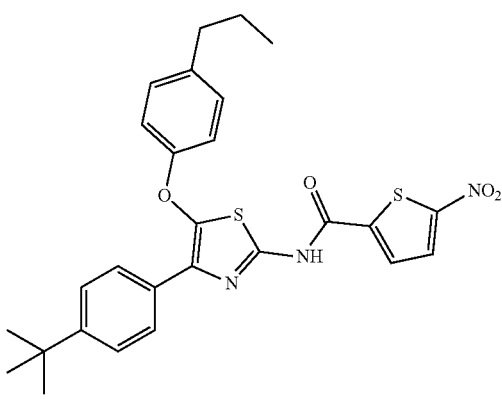 [SMILES: CCCc1ccc(Oc2sc(NC(=O)c3ccc([N+](=O)[O-])s3)nc2-c2ccc(C(C)(C)C)cc2)cc1]

¹H NMR (400 MHz, CDCl₃): δ 12.23 (br. s., 1H), 7.54-7.65 (m, J=8.3 Hz, 2H), 7.45 (d, J=4.4 Hz, 1H), 7.23 (d, J=8.3 Hz, 2H), 7.11-7.19 (m, 3H), 7.00-7.11 (m, 2H), 2.56 (t, J=7.6 Hz, 2H), 1.54-1.68 (m, 2H), 0.93 (t, J=7.3 Hz, 3H). MS (M+1):522.

Compound 5-89

N-(4-(4-(tert-butyl)phenyl)-5-(4-butylphenoxy)thiazol-2-yl)-5-nitrothiophene-2-carboxamide

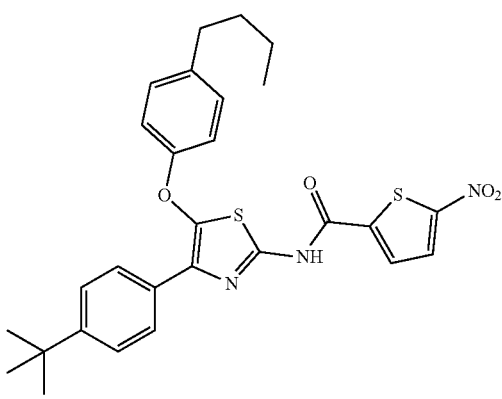 [SMILES: CCCCc1ccc(Oc2sc(NC(=O)c3ccc([N+](=O)[O-])s3)nc2-c2ccc(C(C)(C)C)cc2)cc1]

¹H NMR (400 MHz, CDCl₃): δ 11.66 (br. s., 1H), 7.59-7.69 (m, 2H), 7.55 (d, J=4.4 Hz, 1H), 7.23-7.29 (m, 3H), 7.11-7.18 (m, 2H), 6.99-7.08 (m, 2H), 2.52-2.64 (m, 2H), 1.50-1.60 (m, 2H), 1.30-1.42 (m, 2H), 1.20-1.26 (m, 9H), 0.92 (t, J=7.3 Hz, 3H). MS (M+1):536.

Compound 5-90

N-(4-(4-butoxyphenyl)-5-(4-(tert-butyl)phenoxy)thiazol-2-yl)-5-nitrothiophene-2-carboxamide

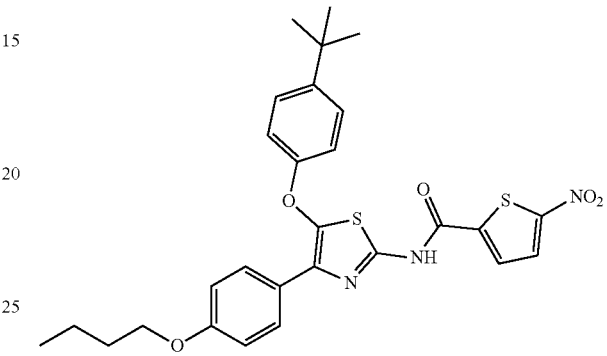

¹H NMR (400 MHz, CDCl₃): δ 7.58 (d, J=8.3 Hz, 2H), 7.47 (d, J=3.9 Hz, 1H), 7.27-7.42 (m, J=8.3 Hz, 2H), 7.17 (d, J=3.4 Hz, 1H), 6.95-7.12 (m, J=8.3 Hz, 2H), 6.71 (d, J=8.3 Hz, 2H), 3.84 (t, J=6.1 Hz, 2H), 1.60-1.85 (m, 2H), 1.37-1.60 (m, 2H), 1.30 (s, 9H), 0.95 (t, J=7.3 Hz, 3H). MS (M+1):552.

Compound 5-91

N-(4-(4-butoxyphenyl)-5-(4-cyanophenoxy)thiazol-2-yl)-5-nitrothiophene-2-carboxamide

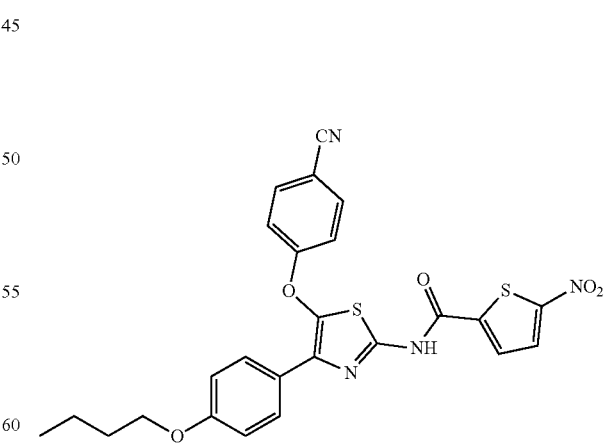

¹H NMR (400 MHz, CDCl₃): δ 7.82 (d, J=4.4 Hz, 1H), 7.57-7.66 (m, 4H), 7.55 (d, J=4.4 Hz, 1H), 7.10-7.18 (m, 2H), 6.77-6.87 (m, 2H), 3.91 (t, J=6.6 Hz, 2H), 1.68-1.77 (m, 2H), 1.40-1.51 (m, 2H), 0.94 (t, J=7.3 Hz, 3H). MS (M+1):521.

Compound 5-92

N-(4-(4-((5-aminopentyl)oxy)phenyl)-5-phenoxythiazol-2-yl)-5-nitrothiophene-2-carboxamide

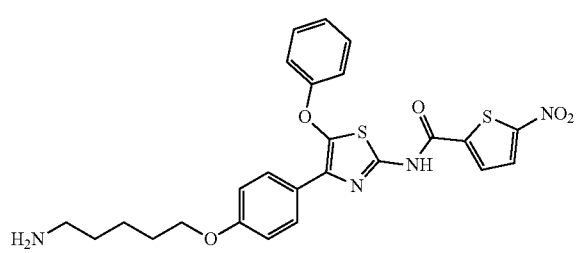 [SMILES: NCCCCCOc1ccc(-c2nc(NC(=O)c3ccc([N+](=O)[O-])s3)sc2Oc2ccccc2)cc1]

$^1$H NMR (400 MHz, DMSO-d$_6$): δ 13.32 (br. s., 1H), 8.21 (d, J=1.00 Hz, 1H), 7.81 (d, J=8.80 Hz, 2H), 7.73 (br. s., 2H), 7.37-7.45 (m, 2H), 7.13-7.20 (m, 2H), 6.96-7.00 (m, 2H), 3.98 (t, J=6.36 Hz, 2H), 2.79 (br. s, 2H), 2.51-2.54 (m, 2H), 1.67-1.78 (m, 2H), 1.54-1.64 (m, 2H), 1.40-1.50 (m, 2H). MS (M+1):525.

Compound 5-93

N-(4-(4-butoxyphenyl)-5-(4-propylphenoxy)thiazol-2-yl)-5-nitrothiophene-2-carboxamide

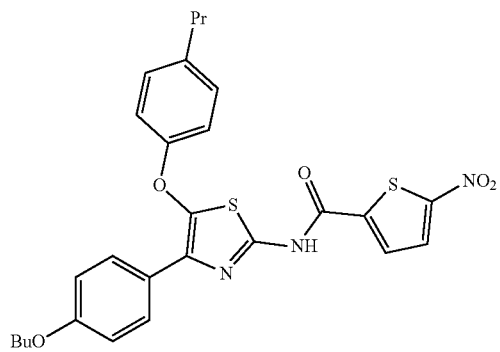

$^1$H NMR (400 MHz, CDCl$_3$): δ 12.28 (br. s., 1H), 7.48-7.66 (m, J=8.8 Hz, 2H), 7.42 (d, J=3.9 Hz, 1H), 7.08-7.21 (m, 3H), 6.97-7.08 (m, J=8.3 Hz, 2H), 6.69 (d, J=8.8 Hz, 2H), 3.83 (t, J=6.4 Hz, 2H), 2.55 (t, J=7.6 Hz, 2H), 1.66-1.84 (m, 2H), 1.50-1.66 (m, 2H), 1.44 (dq, J=14.7, 7.5 Hz, 2H), 0.94 (d, J=7.8 Hz, 3H), 0.82-1.05 (m, 3H). MS (M+1):538.

Compound 5-94

N-(4-(4-butylphenyl)-5-(4-fluorophenoxy)thiazol-2-yl)-5-nitrothiophene-2-carboxamide

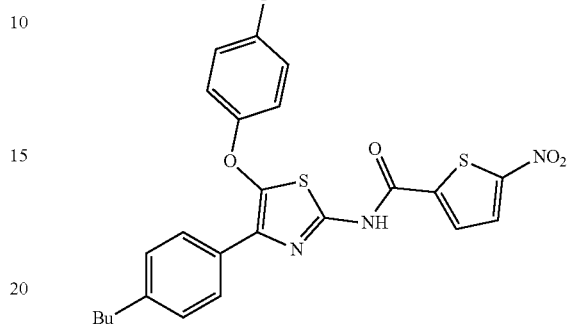

$^1$H NMR (400 MHz, CDCl$_3$): δ 10.99 (br. s., 1H), 7.58-7.68 (m, 3H), 7.35 (d, J=4.4 Hz, 1H), 7.05-7.17 (m, 4H), 6.95-7.05 (m, 2H), 2.45-2.58 (m, 2H), 1.47-1.57 (m, 2H), 1.25-1.36 (m, 2H), 0.85-0.95 (m, 3H). MS (M+1):498.

Compound 5-95

N-(4-(4-(tert-butyl)phenyl)-5-(4-propoxyphenoxy)thiazol-2-yl)-5-nitrothiophene-2-carboxamide

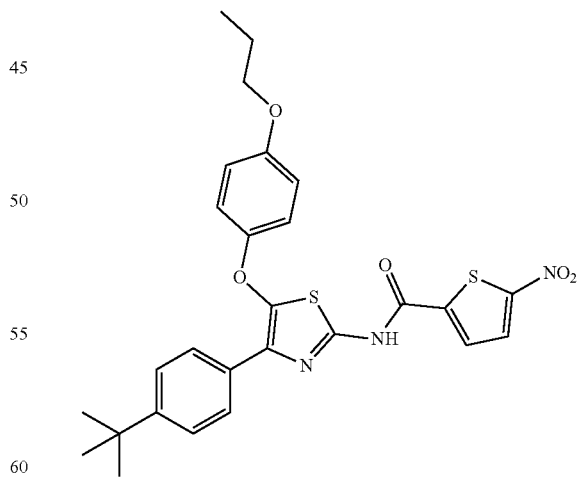

$^1$H NMR (400 MHz, CDCl$_3$): δ 10.80 (br. s., 1H), 7.69-7.75 (m, 2H), 7.68 (d, J=4.4 Hz, 1H), 7.36 (d, J=4.4 Hz, 1H), 7.29-7.35 (m, 2H), 7.02-7.10 (m, 2H), 6.79-6.90 (m, 2H), 3.88 (t, J=6.6 Hz, 2H), 1.73-1.84 (m, 2H), 1.26 (s, 9H), 1.02 (t, J=7.3 Hz, 3H). MS (M+1):538.

Compound 5-96

N-(5-(4-(tert-butyl)phenoxy)-4-(4-(tert-butyl)phenyl)thiazol-2-yl)-5-nitrothiophene-2-carboxamide

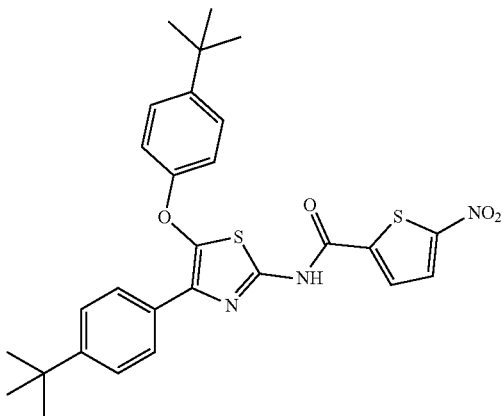 [SMILES: CC(C)(C)c1ccc(Oc2sc(NC(=O)c3ccc([N+](=O)[O-])s3)nc2-c2ccc(C(C)(C)C)cc2)cc1]

$^1$H NMR (400 MHz, CDCl$_3$): δ 11.18 (br. s., 1H), 7.66-7.71 (m, 2H), 7.62 (d, J=4.4 Hz, 1H), 7.33-7.38 (m, 2H), 7.27-7.32 (m, 3H), 7.04-7.10 (m, 2H), 1.30 (s, 9H), 1.24 (s, 9H). MS (M+1):536.

Compound 5-97

N-(4-(4-(tert-butyl)phenyl)-5-(4-(2,4,4-trimethylpentan-2-yl)phenoxy)thiazol-2-yl)-5-nitrothiophene-2-carboxamide $^1$H NMR (400 MHz, CDCl$_3$): δ 11.94 (br. s., 1H), 7.62 (d, J=8.3 Hz, 2H), 7.50 (d, J=3.9 Hz, 1H), 7.29-7.39 (m, J=8.8 Hz, 2H), 7.22-7.28 (m, 2H), 7.20 (d, J=4.4 Hz, 1H), 6.99-7.10 (m, J=8.8 Hz, 2H), 1.71 (s, 3H), 1.35 (s, 6H), 1.21 (s, 9H), 0.71 (s, 9H). MS (M+1):592.

Compound 5-98

N-(4-(4-butoxyphenyl)-5-(4-(tert-pentyl)phenoxy)thiazol-2-yl)-5-nitrothiophene-2-carboxamide

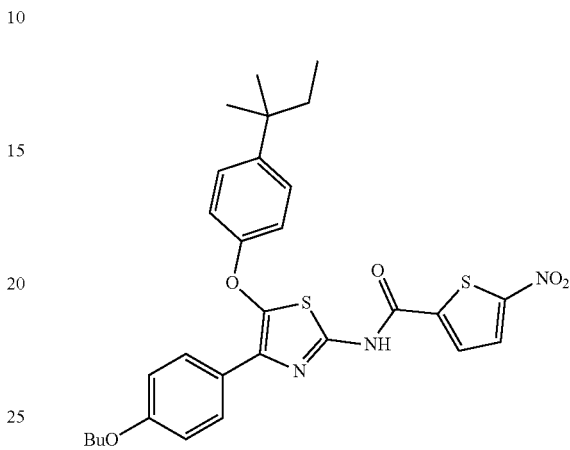

$^1$H NMR (400 MHz, CDCl$_3$): δ 11.07 (br. s., 1H), 7.64-7.70 (m, 2H), 7.63 (d, J=4.4 Hz, 1H), 7.32 (d, J=3.9 Hz, 1H), 7.25-7.29 (m, 2H), 7.01-7.08 (m, 2H), 6.74-6.81 (m, 2H), 3.89 (t, J=6.6 Hz, 2H), 1.67-1.79 (m, 2H), 1.57-1.64 (m, 2H), 1.39-1.51 (m, 2H), 1.25 (s, 6H), 0.95 (t, J=7.3 Hz, 3H), 0.67 (t, J=7.3 Hz, 3H) MS (M+1):566.

Compound 5-99

N-(5-(4-bromo-3,5-dimethylphenoxy)-4-(4-(tert-butyl)phenyl)thiazol-2-yl)-5-nitrothiophene-2-carboxamide

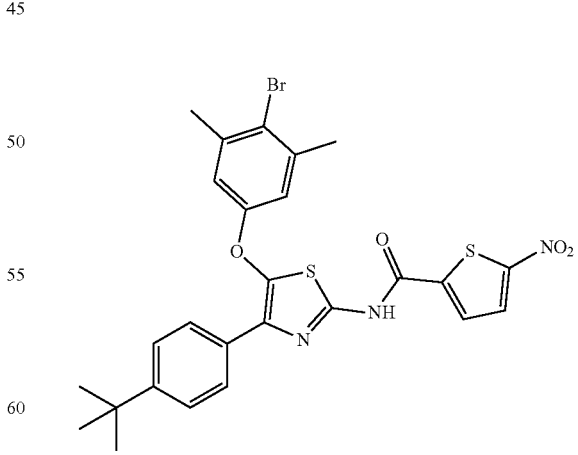

$^1$H NMR (400 MHz, CDCl$_3$): δ 11.16 (br. s., 1H), 7.64-7.69 (m, 1H), 7.59-7.64 (m, 2H), 7.33 (d, J=4.4 Hz, 1H), 7.26-7.31 (m, 2H), 6.86 (s, 2H), 2.38 (s, 6H), 1.24 (s, 9H). MS (M+1):586.

Compound 5-100

N-(5-(4-bromo-3,5-dimethylphenoxy)-4-(4-fluorophenyl)thiazol-2-yl)-5-nitrothiophene-2-carboxamide

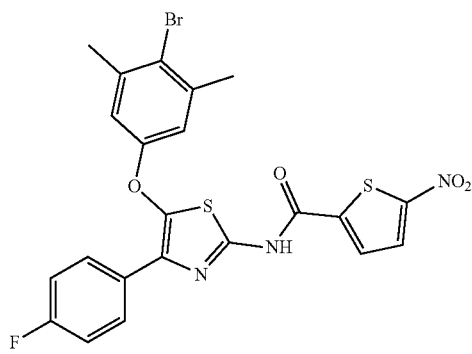 [SMILES: Cc1cc(Oc2sc(NC(=O)c3ccc([N+](=O)[O-])s3)nc2-c2ccc(F)cc2)cc(C)c1Br]

¹H NMR (400 MHz, CDCl₃): δ 7.90 (d, J=4.4 Hz, 1H), 7.79-7.87 (m, 2H), 7.59 (d, J=4.4 Hz, 1H), 7.02-7.10 (m, 2H), 6.83 (s, 2H), 2.37 (s, 6H). MS (M+1):548.

Compound 5-101

N-(4-(4-(tert-butyl)phenyl)-5-(4-(tert-pentyl)phenoxy)thiazol-2-yl)-5-nitrothiophene-2-carboxamide

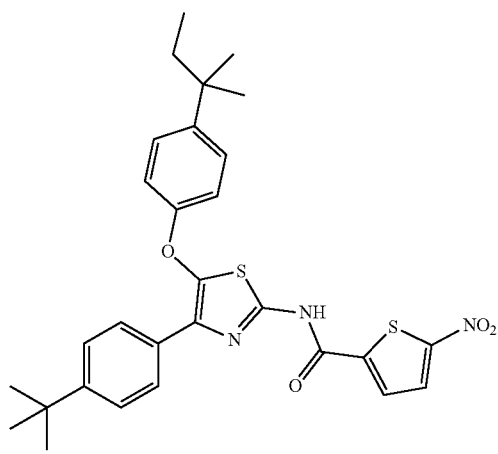 [SMILES: CCC(C)(C)c1ccc(Oc2sc(NC(=O)c3ccc([N+](=O)[O-])s3)nc2-c2ccc(C(C)(C)C)cc2)cc1]

¹H NMR (400 MHz, CDCl₃): δ 11.18 (br. s., 1H), 7.69 (d, J=8.3 Hz, 2H), 7.62 (d, J=4.4 Hz, 1H), 7.25-7.37 (m, 5H), 7.02-7.14 (m, 2H), 1.59-1.65 (m, 2H), 1.26 (s, 6H), 1.24 (s, 9H), 0.67 (t, J=7.3 Hz, 3H). MS (M+1):550.

Compound 5-102

N-(5-(4-(tert-butyl)phenoxy)-4-(4-ethylphenyl)thiazol-2-yl)-5-nitrothiophene-2-carboxamide

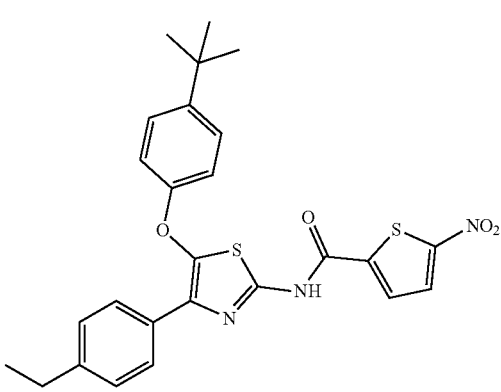 [SMILES: CCc1ccc(-c2nc(NC(=O)c3ccc([N+](=O)[O-])s3)sc2Oc2ccc(C(C)(C)C)cc2)cc1]

¹H NMR (400 MHz, CDCl₃): δ 11.47 (br. s., 1H), 7.64 (d, J=8.3 Hz, 2H), 7.57 (d, J=4.4 Hz, 1H), 7.31-7.38 (m, 2H), 7.26 (d, J=3.9 Hz, 1H), 7.03-7.10 (m, 4H), 2.54 (q, J=7.5 Hz, 2H), 1.30 (s, 9H), 1.15 (t, J=7.6 Hz, 3H). MS (M+1):508.

Compound 5-103

N-(4-(4-ethylphenyl)-5-(4-(tert-pentyl)phenoxy)thiazol-2-yl)-5-nitrothiophene-2-carboxamide

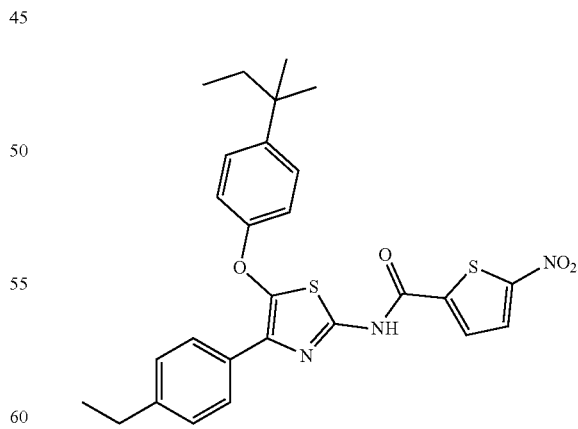

¹H NMR (400 MHz, CDCl₃): δ 11.64 (br. s., 1H), 7.62 (d, J=8.3 Hz, 2H), 7.53 (d, J=3.9 Hz, 1H), 7.25-7.33 (m, 2H), 7.21-7.25 (m, 1H), 7.03-7.11 (m, 4H), 2.53 (q, J=7.8 Hz, 2H), 1.56-1.64 (m, 2H), 1.26 (s, 6H), 1.14 (t, J=7.6 Hz, 3H), 0.67 (t, J=7.3 Hz, 3H). MS (M+1):522.

Compound 5-104

N-(4-(4-butylphenyl)-5-(4-(tert-pentyl)phenoxy)thiazol-2-yl)-5-nitrothiophene-2-carboxamide

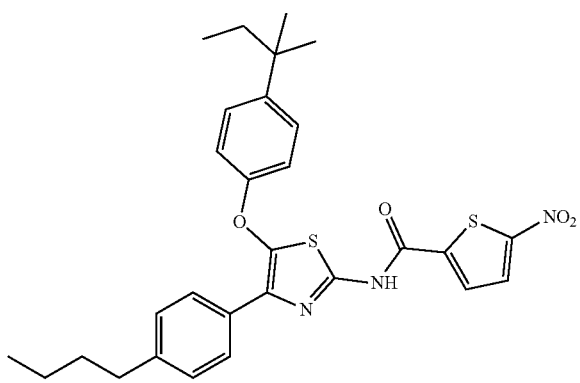 [SMILES: CCCCc1ccc(-c2nc(NC(=O)c3ccc([N+](=O)[O-])s3)sc2Oc2ccc(C(C)(C)CC)cc2)cc1]

$^1$H NMR (400 MHz, CDCl$_3$): δ 11.23 (br. s., 1H), 7.65 (d, J=7.8 Hz, 2H), 7.56-7.62 (m, 1H), 7.25-7.32 (m, 3H), 7.00-7.14 (m, 4H), 2.51 (t, J=7.8 Hz, 2H), 1.57-1.65 (m, 2H), 1.44-1.52 (m, 2H), 1.27-1.34 (m, 2H), 1.22-1.27 (m, 6H), 0.89 (t, J=7.3 Hz, 3H), 0.67 (t, J=7.6 Hz, 3H). MS (M+1):550.

Compound 5-105

N-(4-(4-(tert-butyl)phenyl)-5-(p-tolyloxy)thiazol-2-yl)-5-nitrothiophene-2-carboxamide

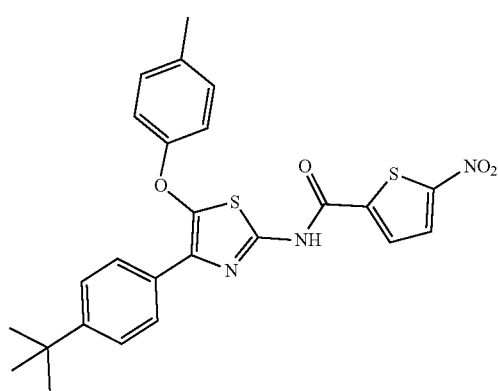 [SMILES: Cc1ccc(Oc2sc(NC(=O)c3ccc([N+](=O)[O-])s3)nc2-c2ccc(C(C)(C)C)cc2)cc1]

$^1$H NMR (400 MHz, CDCl$_3$): δ 11.29 (br. s., 1H), 7.66 (d, J=8.8 Hz, 2H), 7.60 (d, J=3.9 Hz, 1H), 7.26-7.36 (m, 3H), 7.09-7.17 (m, J=8.3 Hz, 2H), 6.97-7.08 (m, 2H), 2.32 (s, 3H), 1.24 (s, 9H) MS (M+1):494.

Compound 5-106

N-(4-(4-butoxyphenyl)-5-(3,5-dimethyl phenoxy)thiazol-2-yl)-5-nitrothiophene-2-carboxamide

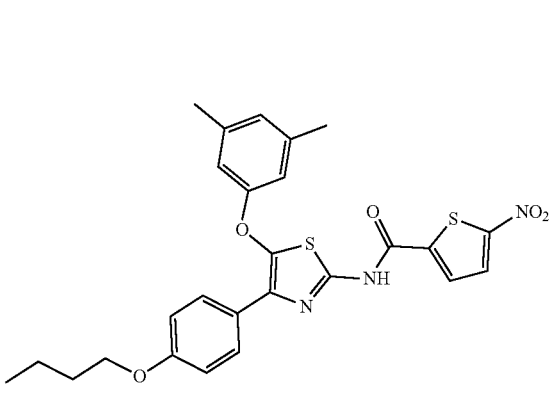 [SMILES: CCCCOc1ccc(-c2nc(NC(=O)c3ccc([N+](=O)[O-])s3)sc2Oc2cc(C)cc(C)c2)cc1]

$^1$H NMR (400 MHz, CDCl$_3$): δ 11.00 (br. s., 1H), 7.60-7.70 (m, 3H), 7.32 (dd, J=4.4, 1.0 Hz, 1H), 6.74-6.81 (m, 3H), 6.73 (s, 2H), 3.89 (t, J=6.6 Hz, 2H), 2.28 (s, 6H), 1.67-1.77 (m, 2H), 1.39-1.51 (m, 2H), 0.95 (t, J=7.3 Hz, 3H). MS (M+1):524.

Compound 5-107

N-(4-(4-(tert-butyl)phenyl)-5-(4-(dimethylamino)phenoxy)thiazol-2-yl)-5-nitrothiophene-2-carboxamide

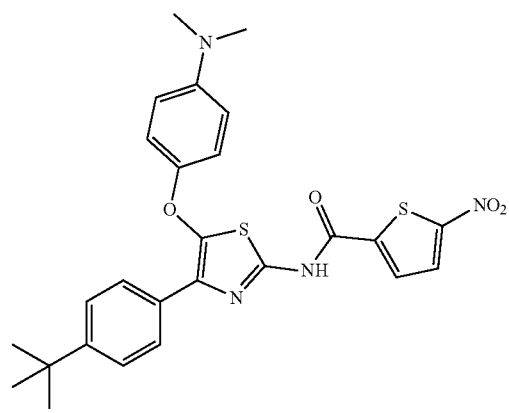 [SMILES: CN(C)c1ccc(Oc2sc(NC(=O)c3ccc([N+](=O)[O-])s3)nc2-c2ccc(C(C)(C)C)cc2)cc1]

$^1$H NMR (400 MHz, CDCl$_3$): δ 7.62-7.75 (m, 2H), 7.58 (d, J=4.4 Hz, 1H), 7.28-7.33 (m, 2H), 7.27 (d, J=4.4 Hz, 1H), 7.00-7.11 (m, 2H), 6.63-6.76 (m, 2H), 2.92 (s, 6H), 1.24 (s, 9H). MS (M+1):523.

Compound 5-108

N-(4-(4-(tert-butyl)phenyl)-5-(4-morpholinophenoxy)thiazol-2-yl)-5-nitrothiophene-2-carboxamide

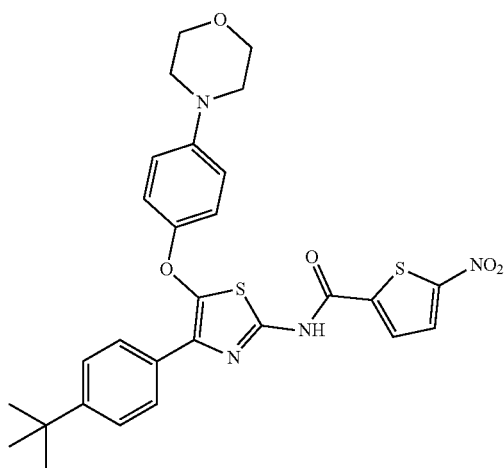 [SMILES: CC(C)(C)c1ccc(-c2nc(NC(=O)c3ccc([N+](=O)[O-])s3)sc2Oc2ccc(N3CCOCC3)cc2)cc1]

$^1$H NMR (400 MHz, CDCl$_3$): δ 11.13 (br. s., 1H), 7.66-7.74 (m, 2H), 7.62 (d, J=3.9 Hz, 1H), 7.26-7.35 (m, 3H), 7.05-7.12 (m, 2H), 6.83-6.92 (m, 2H), 3.85 (dd, J=5.6, 4.2 Hz, 4H), 3.04-3.15 (m, 4H), 1.25 (s, 9H). MS (M+1): 565.

Typical synthesis procedure of Compounds of EXAMPLE 6

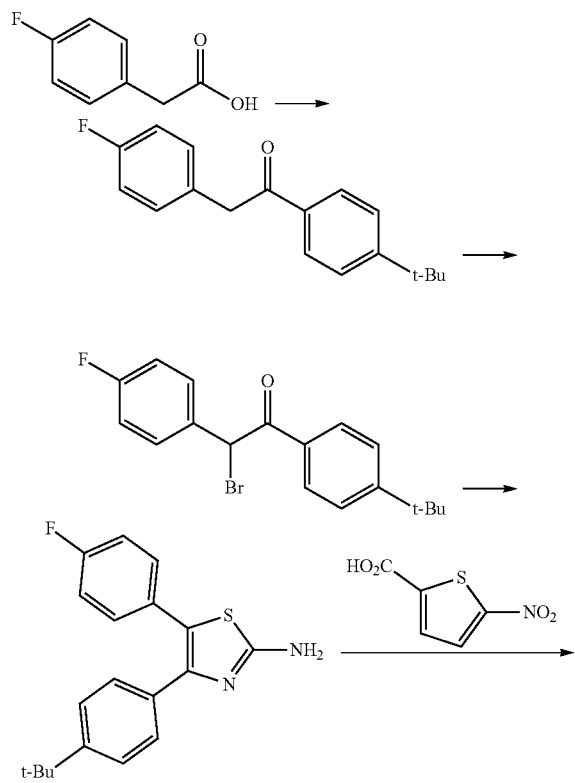

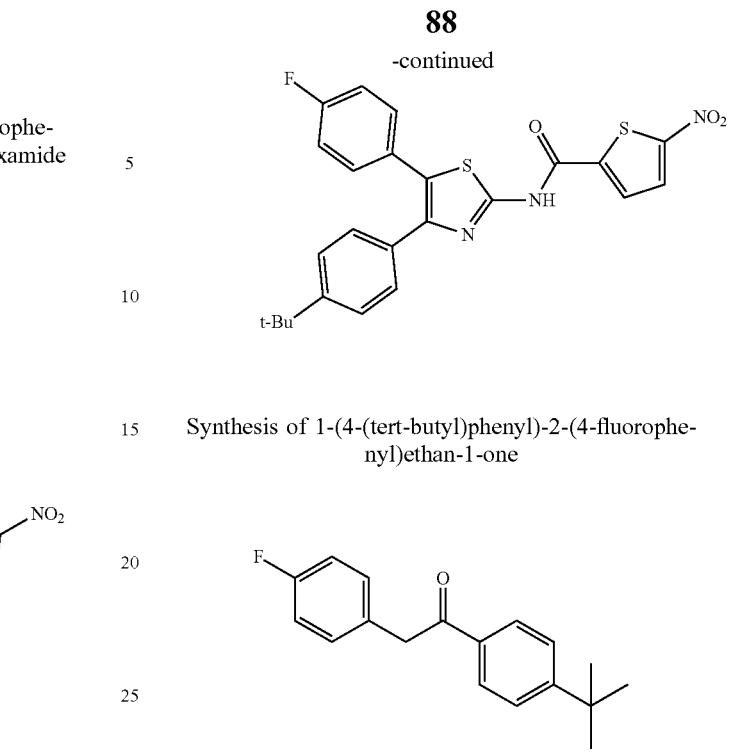

Synthesis of 1-(4-(tert-butyl)phenyl)-2-(4-fluorophenyl)ethan-1-one

AlCl$_3$ (9.3 g, 70 mmol) was added to a solution of tert-butylbenzene (9.33 g, 69.5 mmol) in 40 mL chloroform at 0° C. by ice bath after stirred for 20 min, then 2-(4-fluorophenyl)acetyl chloride (10.0 g, 58 mmol) in 20 mL CHCl$_3$ was added drop wise at 0° C. by ice bath. Remove ice bath and stirred at room temperature for 1 h. Then, quench with 250 mL cold water and extraction with DCM and remove solvent by rota vapor under vacuum.

The crude product was purified by flash chromatography (hexane:EA=1:0 to 9:1) to afford 1-(4-(tert-butyl)phenyl)-2-(4-fluorophenyl)ethan-1-one as red solid (12.9 g, 82% yield).

Synthesis of 2-Bromo-1-(4-ethoxyphenyl)ethanone formation

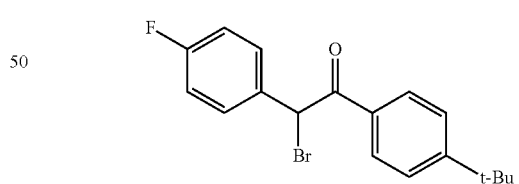

AlCl$_3$ (0.3 g, 2.22 mmol) was added to a solution of 1-(4-(tert-butyl)phenyl)-2-(4-fluorophenyl)ethan-1-one (12.0 g, 44 mmol) in CHCl$_3$ (55 mL) at 0° C. by ice bath and the resulting mixture were added Bromine (7.8 g, 49 mmol) in 55 mL CHCl$_3$ at 0° C. by ice bath and stirred at room temperature for 4 hours. And added Water (400 ml) and extracted with DCM (200 mL). The organic phase is washed with brine, dried (Na$_2$SO$_4$) and concentrated in vacuum. The crude product was purified by flash chromatography (hexane:EA=1:0 to 9:1) to afford 2-bromo-1-(4-(tert-butyl)phenyl)-2-(4-fluorophenyl)ethan-1-one (12.4 g, yield 80%).

Synthesis of 4-(4-(tert-butyl)phenyl)-5-(4-fluorophenyl)thiazol-2-amine

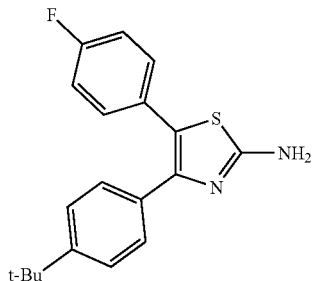 [SMILES: CC(C)(C)c1ccc(-c2nc(N)sc2-c2ccc(F)cc2)cc1]

To a mixture of thiourea (3.24 g, 42.6 mmol) and 2-bromo-1-(4-(tert-butyl)phenyl)-2-(4-fluorophenyl)ethan-1-one (12.4 g, 35.5 mmol) was added 62 mL ethanol. The reaction mixture was heated up to reflux for 16 hours. The reaction was cooled down to 40° C. and removed Ethanol and extraction with 200 ml EA and 150 ml saturated. The crude product was purified by flash chromatography (hexanes:EA=1:0 to 8:2) to afford the yellow powder 4-(4-(tert-butyl)phenyl)-5-(4-fluorophenyl)thiazol-2-amine 8.8 g, 75% yield.

Synthesis of N-(4-(4-(tert-butyl)phenyl)-5-(4-fluorophenyl)thiazol-2-yl)-5-nitrothiophene-2-carboxamide

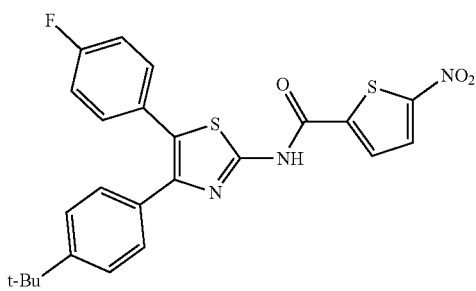 [SMILES: CC(C)(C)c1ccc(-c2nc(NC(=O)c3ccc([N+](=O)[O-])s3)sc2-c2ccc(F)cc2)cc1]

To a solution of 5-nitrothiophene-2-carboxylic acid (5.1 g, 29.4 mmol), 4-(4-(tert-butyl)phenyl)-5-(4-fluorophenyl)thiazol-2-amine (8.0 g, 24.5 mmol), EDCl (11.3 g, 58.8 mmol) and HOBt (7.95 g, 58.8 mmol) in DCM (600 mL) were stirred at room temperature for overnight. Extraction and remove solvent. The crude product was purified by flash chromatography (hexane:EtOAc=1:0 to 7:3) to afford the red solid powder 13.6 g, The crude product was slurry by 500 mL DCM at 40° C. (filtrate by 0.45 uM) and 450 mL EtOH 80° C. for 1 h to removed DCM and 200 ml EtOH by distilled and solution cooled to RT then suction to afford the solid powder N-(4-(4-(tert-butyl)phenyl)-5-(4-fluorophenyl)thiazol-2-yl)-5-nitrothiophene-2-carboxamide as red solid (8.8 g, 74%).

Example 6: Compounds 6-1 to 6-61

Compound 6-1

5-nitro-N-(4-(3-nitrophenyl)thiazol-2-yl)thiophene-2-carboxamide

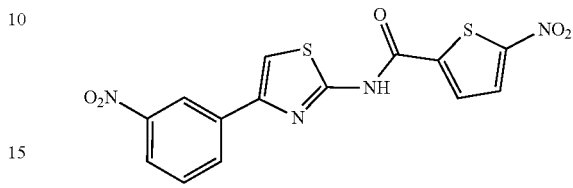

$^1$H NMR (400 MHz, DMSO-$d_6$): δ 13.41 (br. s., 1H), 8.81 (t, J=1.7 Hz, 1H), 8.40 (d, J=8.3 Hz, 1H), 8.28 (d, J=4.4 Hz, 1H), 8.22-8.24 (m, 1H), 8.20 (dd, J=8.1, 1.7 Hz, 1H), 8.09 (s, 1H), 7.76 (t, J=8.1 Hz, 1H). MS (M+1): 377.

Compound 6-2

N-(5-(4-bromophenyl)-4-(p-tolyl)thiazol-2-yl)-5-nitrothiophene-2-carboxamide

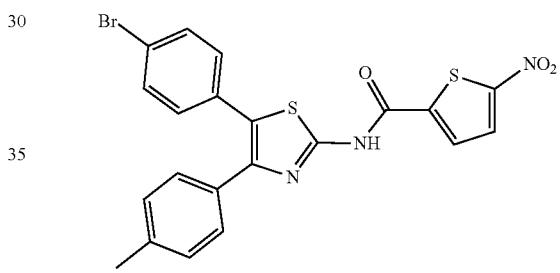

$^1$H NMR (400 MHz, CDCl$_3$): δ 11.75 (br. s., 1H), 7.55 (d, J=4.4 Hz, 1H), 7.46-7.42 (m, 2H), 7.23-7.15 (m, 5H), 6.96 (d, J=8.0 Hz, 2H), 2.23 (s, 3H). MS (M+1): 500.

Compound 6-3

5-nitro-N-(5-(3-nitrophenyl)-4-(p-tolyl)thiazol-2-yl)thiophene-2-carboxamide

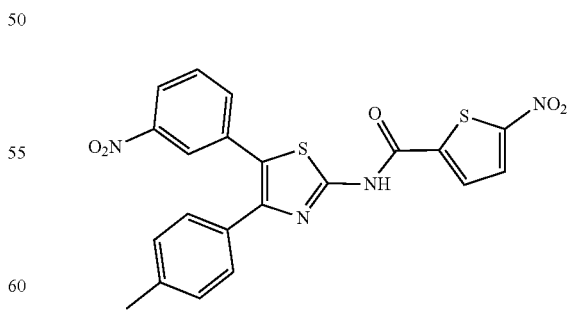

$^1$H NMR (400 MHz, CDCl$_3$): δ 11.26 (br, 1H), 8.21 (t, J=2.0 Hz, 1H), 8.16-8.14 (m, 1H), 7.69 (d, J=4.4 Hz, 1H), 7.64-7.62 (m, 1H), 7.48 (t, J=8.4 Hz, 1H), 7.40 (d, J=4.4 Hz, 1H), 7.20 (d, J=8.0 Hz, 1H), 7.03 (d, J=8.0 Hz, 1H), 2.28 (s, 3H). MS (M+1): 467.

Compound 6-4

N-(5-(3,4-dimethoxyphenyl)-4-(p-tolyl)thiazol-2-yl)-5-nitrothiophene-2-carboxamide

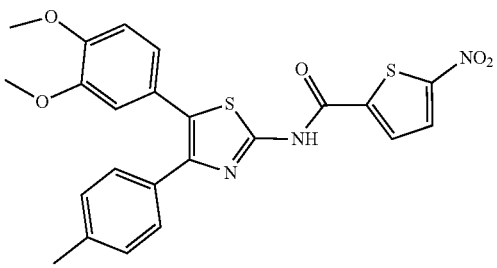 [SMILES: COc1ccc(-c2sc(NC(=O)c3ccc([N+](=O)[O-])s3)nc2-c2ccc(C)cc2)cc1OC]

$^1$H NMR (400 MHz, CDCl$_3$): δ 11.58 (br, 1H), 7.59 (d, J=4.0 Hz, 1H), 7.29 (d, J=4.4 Hz, 1H), 7.21 (d, J=7.6 Hz, 2H), 6.98 (d, J=7.6 Hz, 2H), 6.93 (dd, J=8.4, 2.0 Hz, 1H), 6.82 (d, J=8.4 Hz, 1H), 6.79 (d, J=2.0 Hz, 1H), 3.88 (s, 3H), 3.67 (s, 3H), 2.24 (s, 3H). MS (M+1): 482

Compound 6-5

N-(5-(3,5-bis(trifluoromethyl)phenyl)-4-(p-tolyl)thiazol-2-yl)-5-nitrothiophene-2-carboxamide

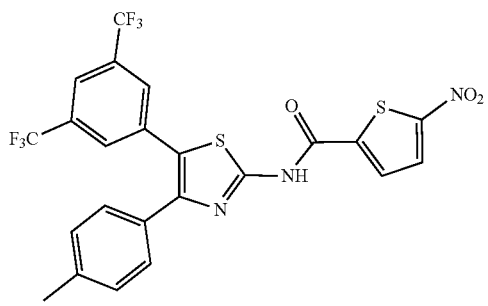 [SMILES: Cc1ccc(-c2nc(NC(=O)c3ccc([N+](=O)[O-])s3)sc2-c2cc(C(F)(F)F)cc(C(F)(F)F)c2)cc1]

$^1$H NMR (400 MHz, CDCl$_3$): δ 11.84 (br, 1H), 7.78 (s, 1H), 7.75 (s, 2H), 7.56 (d, J=4.4 Hz, 1H), 7.24 (d, J=4.0 Hz, 1H), 7.14 (d, J=8.4 Hz, 2H), 6.99 (d, J=8.4 Hz, 2H), 2.25 (s, 3H). MS (M+1): 558.

Compound 6-6

N-(5-(4-fluorophenyl)-4-(p-tolyl)thiazol-2-yl)-5-nitrothiophene-2-carboxamide

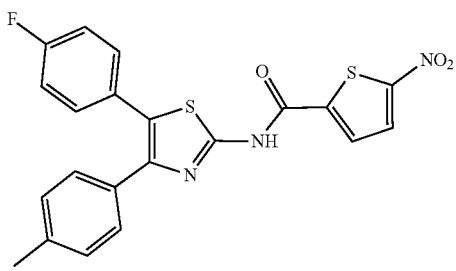 [SMILES: Cc1ccc(-c2nc(NC(=O)c3ccc([N+](=O)[O-])s3)sc2-c2ccc(F)cc2)cc1]

$^1$H NMR (400 MHz, CDCl$_3$): δ 12.09 (br, 1H), 7.49 (d, J=4.4 Hz, 1H), 7.33-7.28 (m, 2H), 7.18 (d, J=4.4 Hz, 1H), 7.14 (d, J=8.4 Hz, 2H), 7.05-6.99 (m, 2H), 6.93 (d, J=7.6 Hz, 2H), 2.21 (s, 3H). MS (M+1): 440.

Compound 6-7

N-(4-(4-bromophenyl)thiazol-2-yl)-5-nitrothiophene-2-carboxamide

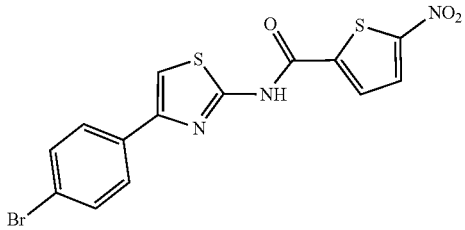 [SMILES: O=C(Nc1nc(-c2ccc(Br)cc2)cs1)c1ccc([N+](=O)[O-])s1]

$^1$H NMR (400 MHz, CDCl$_3$): δ 8.04 (s, 1H), 7.84 (d, J=3.6 Hz, 1H), 7.64-7.61 (m, 3H), 7.53-7.49 (m, 2H), 7.21 (s, 1H). MS (M+1): 410.

Compound 6-8

N-(4-(3-methoxyphenyl)thiazol-2-yl)-5-nitrothiophene-2-carboxamide

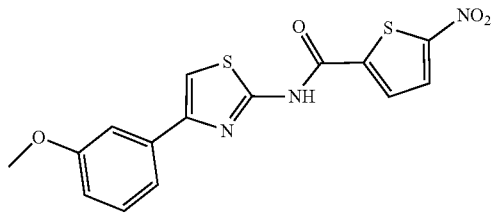 [SMILES: COc1cccc(-c2csc(NC(=O)c3ccc([N+](=O)[O-])s3)n2)c1]

$^1$H NMR (400 MHz, CDCl$_3$): δ 10.75 (br, 1H), 7.77 (d, J=4.0 Hz, 1H), 7.48 (d, J=4.4 Hz, 1H), 7.29-7.26 (m, 3H), 7.20 (s, 1H), 6.85-6.82 (m, 1H). MS (M+1): 362.

Compound 6-9

N-(4-(4-bromophenyl)-5-phenylthiazol-2-yl)-5-nitrothiophene-2-carboxamide

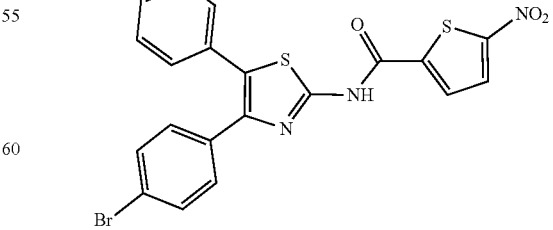

$^1$H NMR (400 MHz, CDCl$_3$): δ 7.79 (d, J=4.4 Hz, 1H), 7.65 (d, J=4.4 Hz, 1H), 7.40-7.36 (m, 2H), 7.35-7.29 (m, 5H), 7.24-7.21 (m, 2H). MS (M+1): 486.

Compound 6-10

N-(5-bromo-4-(4-bromophenyl)thiazol-2-yl)-5-nitro-thiophene-2-carboxamide

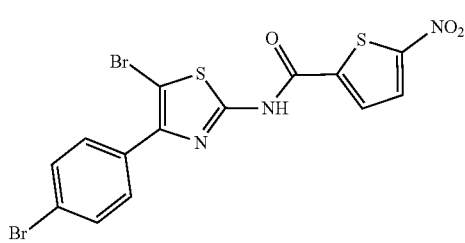 [SMILES: O=C(Nc1nc(-c2ccc(Br)cc2)c(Br)s1)c1ccc([N+](=O)[O-])s1]

$^1$H NMR (400 MHz, DMSO-d$_6$): δ 13.67 (br, 1H), 8.24-8.21 (m, 2H), 7.87-7.84 (m, 2H), 7.74-7.70 (m, 2H). MS (M+1): 485.

Compound 6-11

5-nitro-N-(4-(2-nitrophenyl)thiazol-2-yl)thiophene-2-carboxamide

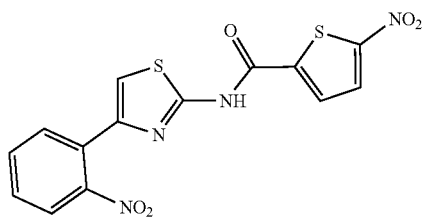 [SMILES: O=C(Nc1nc(-c2ccccc2[N+](=O)[O-])cs1)c1ccc([N+](=O)[O-])s1]

$^1$H NMR (400 MHz, DMSO-d$_6$): δ 13.28 (br, 1H), 8.25 (br, 1H), 8.20 (d, J=4.4 Hz, 1H), 7.95 (d, J=7.6 Hz, 1H), 7.81-7.75 (m, 2H), 7.67-7.64 (m, 2H). MS (M+1):377.

Compound 6-12

N-(5-bromo-4-(2-nitrophenyl)thiazol-2-yl)-5-nitro-thiophene-2-carboxamide

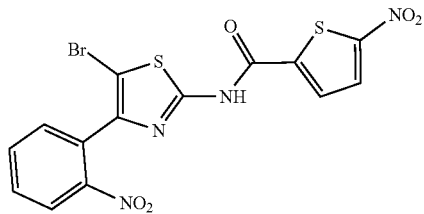 [SMILES: O=C(Nc1nc(-c2ccccc2[N+](=O)[O-])c(Br)s1)c1ccc([N+](=O)[O-])s1]

$^1$H NMR (400 MHz, DMSO-d$_6$): δ 13.61 (br, 1H), 8.22-8.20 (m, 2H), 8.14-8.11 (m, 1H), 7.89-7.85 (m, 1H), 7.78-7.73 (m, 2H). MS (M+1):455.

Compound 6-13

N-(5-bromo-4-(3-nitrophenyl)thiazol-2-yl)-5-nitro-thiophene-2-carboxamide

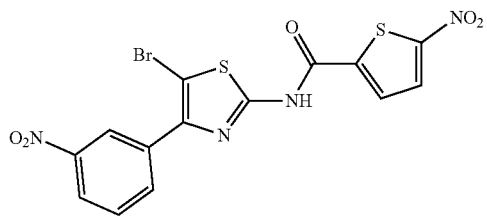 [SMILES: O=C(Nc1nc(-c2cccc([N+](=O)[O-])c2)c(Br)s1)c1ccc([N+](=O)[O-])s1]

$^1$H NMR (400 MHz, acetone-d$_6$): δ 12.19 (br, 1H), 8.12 (t, J=2.0 Hz, 1H), 8.51-8.48 (m, 1H), 8.32-8.29 (m, 1H), 8.28 (d, J=4.4 Hz, 1H), 8.14 (d, J=4.4 Hz, 1H), 7.83 (t, J=8.0 Hz, 1H). MS (M+1): 455.

Compound 6-14

N-(5-bromo-4-(3-methoxyphenyl)thiazol-2-yl)-5-nitrothiophene-2-carboxamide

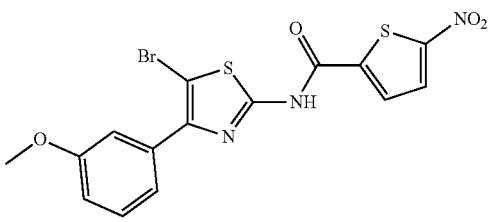 [SMILES: COc1cccc(-c2nc(NC(=O)c3ccc([N+](=O)[O-])s3)sc2Br)c1]

$^1$H NMR (400 MHz, acetone-d$_6$): δ 12.07 (br, 1H), 8.25 (d, J=4.4 Hz, 1H), 8.13 (d, J=4.4 Hz, 1H), 7.53-7.47 (m, 2H), 7.41 (t, J=8.0 Hz, 1H), 7.02-6.99 (m, 1H), 3.86 (s, 3H). MS (M+1): 440.

Compound 6-15

N-(4-(4-ethoxyphenyl)-5-(4-fluorophenyl)thiazol-2-yl)-5-nitrothiophene-2-carboxamide

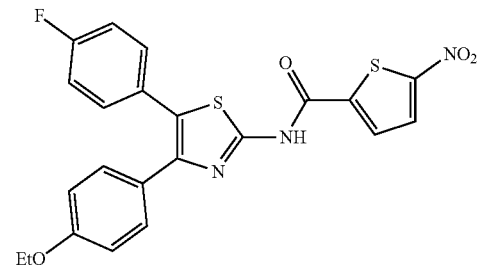 [SMILES: CCOc1ccc(-c2nc(NC(=O)c3ccc([N+](=O)[O-])s3)sc2-c2ccc(F)cc2)cc1]

$^1$H NMR (400 MHz, CDCl$_3$): δ 7.60 (d, J=4.0 Hz, 1H), 7.33-7.29 (m, 3H), 7.21-7.18 (m, 2H), 7.04-6.99 (m, 2H), 6.69-6.66 (m, 2H), 3.93 (q, J=6.8 Hz, 2H), 1.37 (t, J=6.8 Hz, 3H). MS (M+1): 470.

Compound 6-16

N-(5-(4-fluorophenyl)-4-(4-propoxyphenyl)thiazol-2-yl)-5-nitrothiophene-2-carboxamide

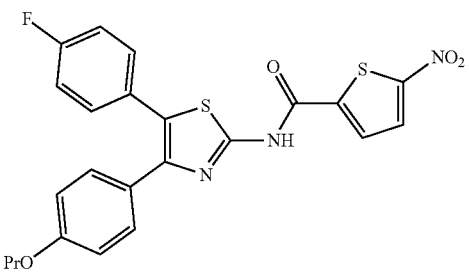

$^1$H NMR (400 MHz, CDCl$_3$): δ 12.08 (br, 1H), 7.55 (d, J=4.4 Hz, 1H), 7.32-7.27 (m, 3H), 7.19-7.16 (m, 2H), 7.04-6.98 (m, 2H), 6.67-6.64 (m, 2H), 3.80 (t, J=6.4 Hz, 2H), 1.76 (sex, J=7.2 Hz, 2H), 1.01 (t, J=7.2 Hz, 3H). MS (M+1): 484.

Compound 6-17

N-(5-bromo-4-(4-ethoxyphenyl)thiazol-2-yl)-5-nitro-thiophene-2-carboxamide

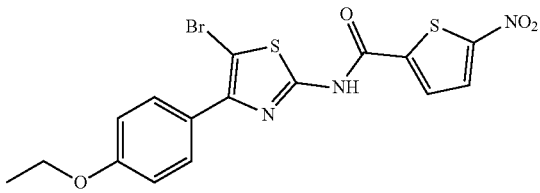 [SMILES: CCOc1ccc(-c2nc(NC(=O)c3ccc([N+](=O)[O-])s3)sc2Br)cc1]

$^1$H NMR (400 MHz, DMSO-d$_6$): δ 8.20 (d, J=3.9 Hz, 1H), 7.84 (s, 1H), 7.73 (d, J=8.3 Hz, 1H), 7.38 (d, J=8.8 Hz, 1H), 6.99 (d, J=8.8 Hz, 1H), 6.92 (d, J=8.3 Hz, 1H), 4.05 (dd, J=14.4, 7.1 Hz, 2H), 1.33 (q, J=7.3 Hz, 3H). MS (M+1):455

Compound 6-18

N-(4-(4-butoxyphenyl)-5-(4-fluorophenyl)thiazol-2-yl)-5-nitrothiophene-2-carboxamide

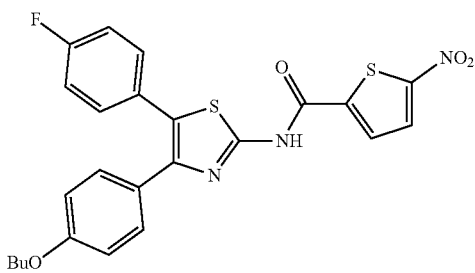

$^1$H NMR (400 MHz, CDCl$_3$): δ 12.29 (br. s, 1H), 7.47 (d, J=4.4 Hz, 1H), 7.34-7.29 (m, 2H), 7.16-7.13 (m, 3H), 7.04-6.99 (m, 2H), 6.63-6.59 (m, 2H), 3.81 (t, J=5.6 Hz, 2H), 1.74-1.67 (m, 2H), 1.45 (sex, J=7.2 Hz, 2H), 0.96 (t, J=7.2 Hz, 3H). MS (M+1): 498.

Compound 6-19

N-(4-(4-ethoxyphenyl)-5-(4-(trifluoromethyl)phenyl)thiazol-2-yl)-5-nitrothiophene-2-carboxamide

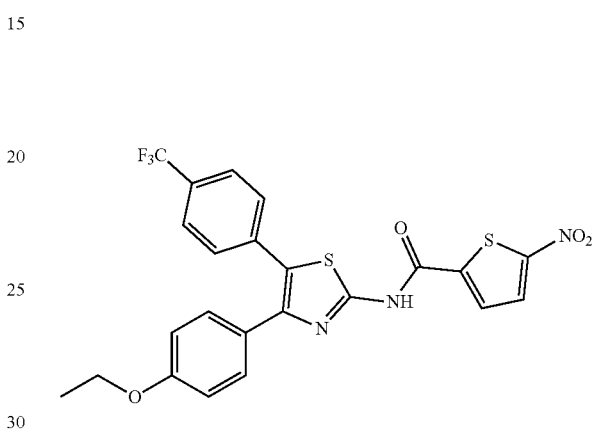

$^1$H NMR (400 MHz, DMSO-d$_6$): δ 8.26 (br. s., 1H), 8.20 (d, J=3.9 Hz, 1H), 7.85 (d, J=8.8 Hz, 1H), 7.73 (d, J=8.3 Hz, 1H), 7.50-7.61 (m, 1H), 7.38 (d, J=8.8 Hz, 1H), 6.99 (d, J=8.8 Hz, 1H), 6.92 (d, J=8.3 Hz, 1H), 4.05 (dq, J=14.3, 7.0 Hz, 2H), 1.33 (q, J=7.3 Hz, 3H). MS (M+1):520

Compound 6-20

N-(5-(4-bromo-3-ethoxyphenyl)-4-(p-tolyl)thiazol-2-yl)-5-nitrothiophene-2-carboxamide $^1$H NMR (400 MHz, CDCl$_3$): δ 11.87 (br, 1H), 7.57 (d, J=4.4 Hz, 1H), 7.52 (d, J=8.8 Hz, 1H), 7.29 (d, J=4.4 Hz, 1H), 7.16 (d, J=8.8 Hz, 2H), 6.93 (d, J=8.0 Hz, 2H), 6.86 (d, J=3.2 Hz, 1H), 6.81 (dd, J=8.8, 2.8 Hz, 1H), 4.10 (q, J=7.2 Hz, 2H), 2.20 (s, 3H), 1.34 (t, J=6.8 Hz, 3H). MS (M+1): 544.

Compound 6-21

N-(4-(4-(tert-butyl)phenyl)-5-phenylthiazol-2-yl)-5-nitrothiophene-2-carboxamide

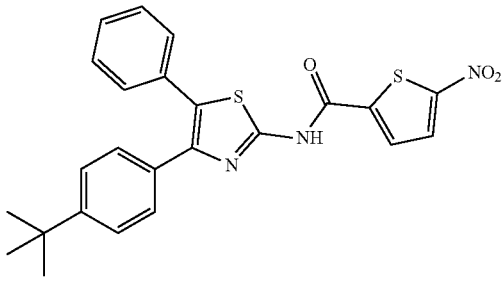 [SMILES: CC(C)(C)c1ccc(-c2nc(NC(=O)c3ccc([N+](=O)[O-])s3)sc2-c2ccccc2)cc1]

¹H NMR (400 MHz, CDCl₃): δ 11.87 (br. s, 1H), 7.59 (d, J=4.4 Hz, 1H), 7.38-7.31 (m, 6H), 7.28-7.25 (m, 2H), 7.19-7.17 (m, 2H), 1.22 (s, 9H). MS (M+1):464.

Compound 6-22

N-(5-(4-methylpiperazin-1-yl)-4-(4-propoxyphenyl)thiazol-2-yl)-5-nitrothiophene-2-carboxamide

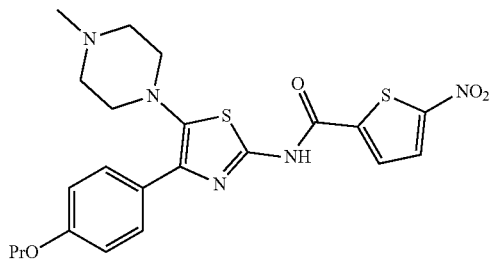

¹H NMR (400 MHz, DMSO-d₆): δ 12.85 (br, 1H), 8.18 (d, J=4.4 Hz, 1H), 8.15 (d, J=4.4 Hz, 1H), 8.05-8.01 (m, 2H), 7.01-6.97 (m, 2H), 3.96 (t, J=6.8 Hz, 2H), 2.90 (t, J=4.4 Hz, 4H), 2.55 (br, 4H), 2.29 (s, 3H), 1.74 (sex, J=7.2 Hz, 2H), 0.99 (t, J=7.2 Hz, 3H). MS (M+1):488.

Compound 6-23 ethyl 2-(5-nitrothiophene-2-carboxamido)-4-(4-propoxyphenyl)thiazole-5-carboxylate

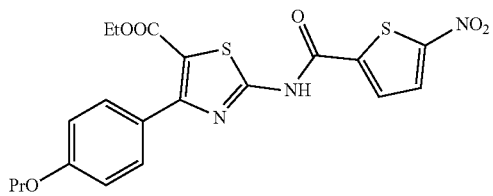

¹H NMR (400 MHz, DMSO-d₆): δ 13.70 (br, 1H), 8.23-8.20 (m, 2H), 7.72 (d, J=8.8 Hz, 2H), 7.01-6.97 (m, 2H), 4.22 (q, J=7.2 Hz, 2H), 3.99 (t, J=6.8 Hz, 2H), 1.76 (sex, J=7.2 Hz, 2H), 1.24 (t, J=7.2 Hz, 3H), 1.00 (t, J=7.2 Hz, 3H). MS (M+1): 462.

Compound 6-24

N-(4-(4-(tert-butyl)phenyl)-5-(4-fluorophenyl)thiazol-2-yl)-5-nitrothiophene-2-carboxamide

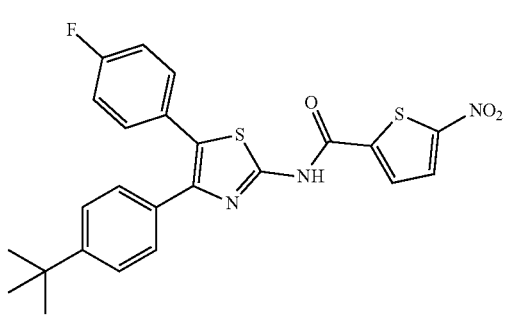 [SMILES: CC(C)(C)c1ccc(-c2nc(NC(=O)c3ccc([N+](=O)[O-])s3)sc2-c2ccc(F)cc2)cc1]

¹H NMR (400 MHz, CDCl₃): δ 7.59 (d, J=4.4 Hz, 1H), 7.36-7.31 (m, 2H), 7.29 (d, J=4.4 Hz, 1H), 7.26-7.23 (m, 2H), 7.19 (d, J=8.4 Hz, 2H), 7.06-7.01 (m, 2H), 1.22 (s, 9H). MS (M+1):482.

Compound 6-25

N-(4-(2,4-diethoxyphenyl)thiazol-2-yl)-5-nitrothiophene-2-carboxamide

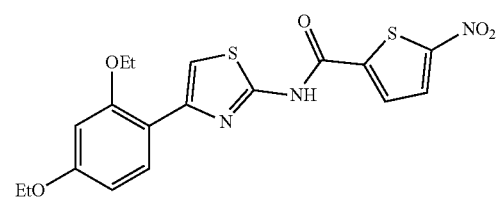 [SMILES: CCOc1ccc(-c2csc(NC(=O)c3ccc([N+](=O)[O-])s3)n2)c(OCC)c1]

¹H NMR (400 MHz, DMSO-d₆): δ 13.21 (s, 1H), 8.26-8.20 (m, 2H), 8.05 (br, 1H), 7.63 (br, 1H), 6.63-6.61 (m, 2H), 4.16 (q, J=6.8 Hz, 2H), 4.08 (q, J=6.8 Hz, 2H), 1.45 (t, J=6.8 Hz, 3H), 1.34 (t, J=6.8 Hz, 3H). MS (M+1):420.

Compound 6-26

N-(4-(4-(dimethylamino)phenyl)thiazol-2-yl)-5-nitrothiophene-2-carboxamide

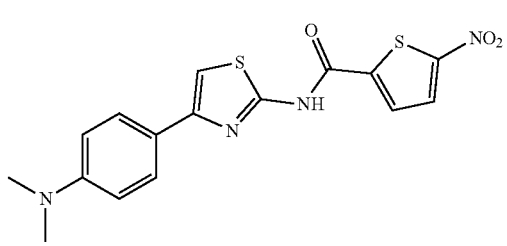 [SMILES: CN(C)c1ccc(-c2csc(NC(=O)c3ccc([N+](=O)[O-])s3)n2)cc1]

¹H NMR (400 MHz, DMSO-d₆): δ 13.27 (s, 1H), 8.25-8.20 (m, 2H), 7.75 (d, J=8.8 Hz, 2H), 7.42 (br, 1H), 6.79-6.75 (m, 2H), 2.94 (s, 6H). MS (M+1): 375.

Compound 6-27

N-(3,5-difluorophenyl)-4-(4-ethoxyphenyl)-2-(5-nitrothiophene-2-carboxamido)thiazole-5-carboxamide

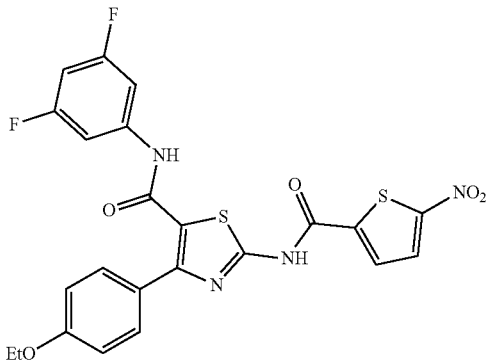 [SMILES: CCOc1ccc(-c2nc(NC(=O)c3ccc([N+](=O)[O-])s3)sc2C(=O)Nc2cc(F)cc(F)c2)cc1]

¹H NMR (400 MHz, DMSO-d₆): δ 13.66 (br, 1H), 10.62 (s, 1H), 8.25-8.22 (m, 2H), 7.66 (d, J=8.8 Hz, 2H), 7.34-7.29 (m, 2H), 6.99-6.94 (m, 3H), 4.06 (q, J=6.8 Hz, 2H), 1.33 (t, J=6.8 Hz, 3H). MS (M+1):531.

Compound 6-28

N-(4-(4-ethoxyphenyl)-5-(methyl (phenyl)amino) thiazol-2-yl)-5-nitrothiophene-2-carboxamide

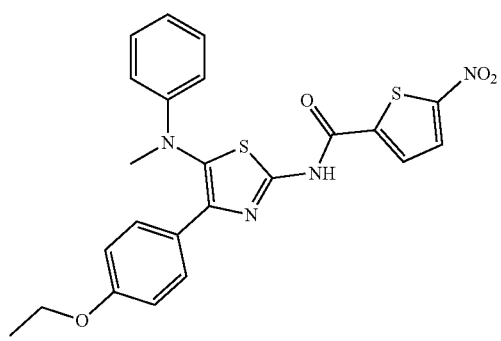 [SMILES: CCOc1ccc(-c2nc(NC(=O)c3ccc([N+](=O)[O-])s3)sc2N(C)c2ccccc2)cc1]

¹H NMR (400 MHz, DMSO-d₆): δ 13.28 (br. s., 1H), 8.21 (d, J=4.4 Hz, 2H), 7.74 (d, J=7.8 Hz, 2H), 7.23 (t, J=7.8 Hz, 2H), 6.93 (d, J=8.8 Hz, 2H), 6.76-6.85 (m, 3H), 4.02 (q, J=6.8 Hz, 2H), 3.19 (s, 3H), 1.31 (t, J=6.8 Hz, 3H). MS (M+1):481

Compound 6-29

N-(5-(morpholine-4-carbonyl)-4-(4-propoxyphenyl) thiazol-2-yl)-5-nitrothiophene-2-carboxamide

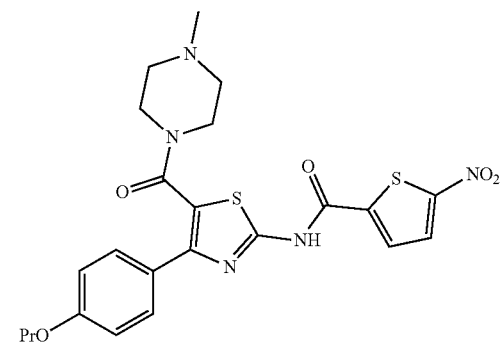

¹H NMR (400 MHz, DMSO-d₆): δ 8.19-8.16 (m, 2H), 7.53 (d, J=8.8 Hz, 2H), 7.04 (d, J=8.8 Hz, 2H), 3.96 (t, J=6.4 Hz, 2H), 3.16 (br, 8H), 1.73 (sex, J=6.8 Hz, 2H), 0.97 (t, J=7.2 Hz, 3H). MS (M+1): 503.

Compound 6-30

N-(5-(4-methylpiperazine-1-carbonyl)-4-(4-propoxyphenyl)thiazol-2-yl)-5-nitrothiophene-2-carboxamide ¹H NMR (400 MHz, DMSO-d₆): δ 8.16 (d, J=4.4 Hz, 1H), 8.07 (d, J=4.4 Hz, 1H), 7.53 (d, J=8.8 Hz, 2H), 7.02 (d, J=8.8 Hz, 2H), 3.97 (t, J=6.8 Hz, 2H), 2.19 (br, 10H), 1.74 (sex, J=6.8 Hz, 2H), 0.98 (t, J=7.2 Hz, 3H). MS (M+1): 516.

Compound 6-31

N-(2,4-difluorophenyl)-2-(5-nitrothiophene-2-carboxamido)-4-(4-propoxyphenyl)thiazole-5-carboxamide

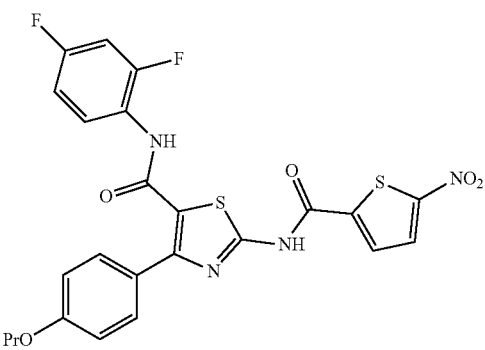

$^1$H NMR (400 MHz, CDCl$_3$): δ 10.12 (s, 1H), 8.30-8.24 (m, 1H), 7.85 (d, J=4.4 Hz, 1H), 7.71 (s, 1H), 7.53-7.50 (m, 3H), 7.02-6.98 (m, 2H), 6.86-6.82 (m, 1H), 6.76-6.71 (m, 1H), 3.96 (t, J=6.8 Hz, 2H), 1.84 (sex, J=6.8 Hz, 2H), 1.05 (t, J=7.2 Hz, 3H). MS (M+1): 545.

Compound 6-32

N-(5-(4-bromophenyl)-4-(p-tolyl)thiazol-2-yl)-5-nitrofuran-2-carboxamide

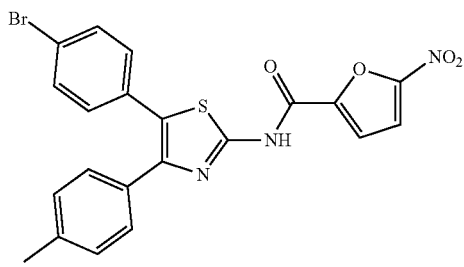 [SMILES: Cc1ccc(-c2nc(NC(=O)c3ccc([N+](=O)[O-])o3)sc2-c2ccc(Br)cc2)cc1]

$^1$H NMR (400 MHz, DMSO-d$_6$): δ 13.41 (br s, 1H), 7.91 (br s, 1H), 7.83 (d, J=4.0 Hz, 1H), 7.60-7.56 (m, 2H), 7.34 (d, J=7.6 Hz, 2H), 7.29 (d, J=7.2 Hz, 2H), 7.17 (d, J=8.0 Hz, 2H), 2.31 (s, 3H). LCMS, [M+1]$^+$: 484.

Compound 6-33

N-(5-benzyl-4-(4-ethoxyphenyl)thiazol-2-yl)-5-nitrofuran-2-carboxamide

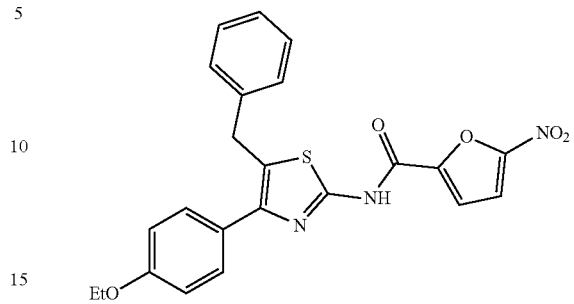

$^1$H NMR (400 MHz, CDCl$_3$): δ 7.39-7.46 (m, 2H), 7.26-7.35 (m, 4H), 7.20-7.26 (m, 6H), 6.84-6.90 (m, 2H), 4.21 (s, 2H), 4.03 (q, J=6.8 Hz, 2H), 1.41 (t, J=7.1 Hz, 3H) LCMS, [M+1]$^+$: 450.

Compound 6-34

N-(5-benzyl-4-(4-ethoxyphenyl)thiazol-2-yl)-5-nitrothiophene-2-carboxamide

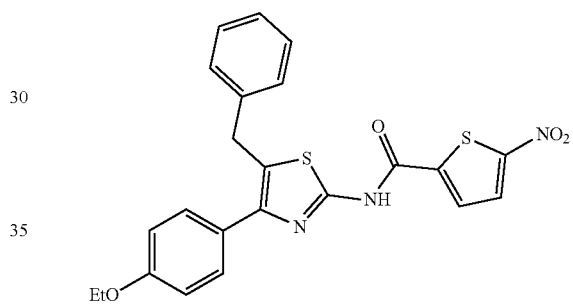

$^1$H NMR (400 MHz, CDCl$_3$): δ 7.55-7.62 (m, 1H), 7.25-7.34 (m, 6H), 7.17-7.23 (m, 2H), 6.79 (d, J=8.8 Hz, 2H), 4.16 (s, 2H), 3.97 (q, J=6.8 Hz, 2H), 1.39 (t, J=7.1 Hz, 3H). MS (M+1): 466

Compound 6-35

N-(4-(4-ethoxyphenyl)-5-(4-fluorobenzyl)thiazol-2-yl)-5-nitrothiophene-2-carboxamide

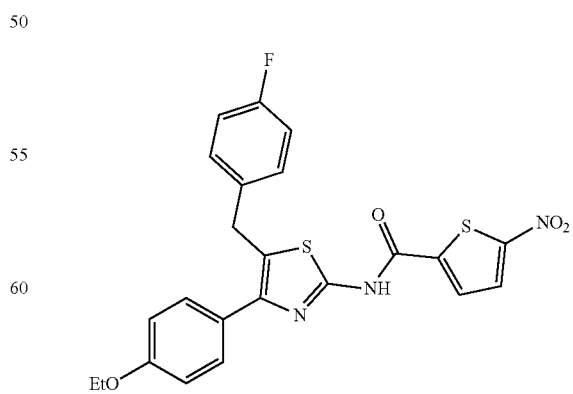

$^1$H NMR (400 MHz, CDCl$_3$): δ 7.51 (d, J=3.9 Hz, 1H), 7.20-7.29 (m, 2H), 7.11-7.20 (m, 3H), 6.99 (t, J=8.8 Hz, 2H), 6.71-6.78 (m, 2H), 4.13 (s, 2H), 3.95 (q, J=6.8 Hz, 2H), 1.39 (t, J=7.1 Hz, 3H). MS (M+1): 484.

Compound 6-36

N-(4-(4-ethoxyphenyl)-5-(3-fluorobenzyl)thiazol-2-yl)-5-nitrothiophene-2-carboxamide

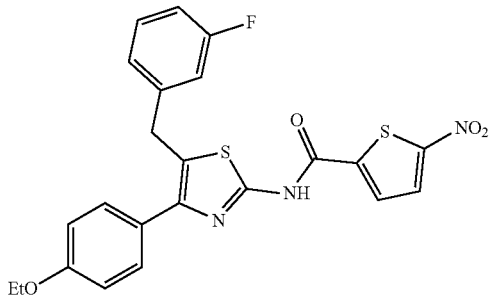 [SMILES: CCOc1ccc(-c2nc(NC(=O)c3ccc([N+](=O)[O-])s3)sc2Cc2cccc(F)c2)cc1]

¹H NMR (400 MHz, CDCl₃): δ 11.77 (br. s., 1H), 7.56 (d, J=4.4 Hz, 1H), 7.24-7.32 (m, 4H), 6.99 (d, J=8.3 Hz, 1H), 6.94 (td, J=8.3, 2.4 Hz, 1H), 6.85-6.90 (m, 1H), 6.73-6.81 (m, 2H), 4.16 (s, 2H), 3.96 (q, J=7.0 Hz, 2H), 1.39 (t, J=6.8 Hz, 3H). MS (M+1): 484.

Compound 6-37

N-(4-(4-(tert-butyl)phenyl)-5-(4-fluorobenzyl)thiazol-2-yl)-5-nitrothiophene-2-carboxamide

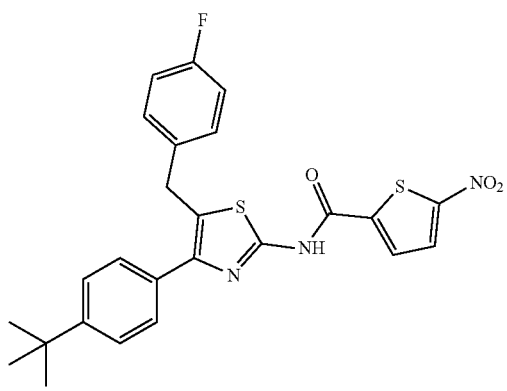 [SMILES: CC(C)(C)c1ccc(-c2nc(NC(=O)c3ccc([N+](=O)[O-])s3)sc2Cc2ccc(F)cc2)cc1]

¹H NMR (400 MHz, CDCl₃): δ 7.54 (d, J=3.9 Hz, 1H), 7.31 (d, J=2.4 Hz, 4H), 7.21-7.26 (m, 2H), 7.18 (dd, J=8.8, 5.4 Hz, 2H), 7.01 (t, J=8.8 Hz, 2H), 4.18 (s, 2H), 1.23-1.27 (m, 9H). MS (M+1):496.

Compound 6-38

N-(4-(4-(tert-butyl)phenyl)-5-(3,5-difluorophenyl)thiazol-2-yl)-5-nitrothiophene-2-carboxamide

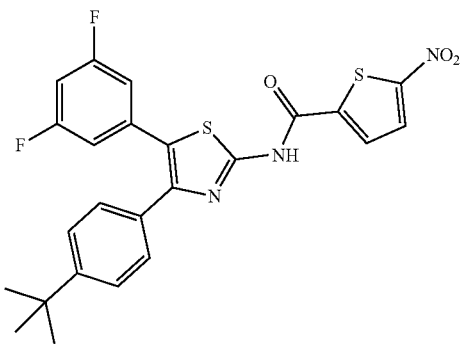 [SMILES: CC(C)(C)c1ccc(-c2nc(NC(=O)c3ccc([N+](=O)[O-])s3)sc2-c2cc(F)cc(F)c2)cc1]

¹H NMR (400 MHz, CDCl₃): δ 7.59 (d, J=4.4 Hz, 1H), 7.20-7.28 (m, 5H), 6.87 (dd, J=8.1, 2.2 Hz, 2H), 6.77 (s, 1H), 1.23 (s, 9H). MS (M+1):500.

Compound 6-39

N-(4-(4-(tert-butyl)phenyl)-5-(2,4-difluorophenyl)thiazol-2-yl)-5-nitrothiophene-2-carboxamide

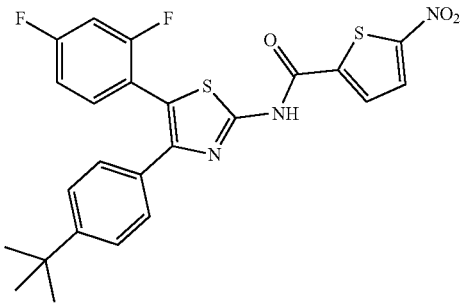 [SMILES: CC(C)(C)c1ccc(-c2nc(NC(=O)c3ccc([N+](=O)[O-])s3)sc2-c2ccc(F)cc2F)cc1]

¹H NMR (400 MHz, CDCl₃): δ 7.53 (d, J=4.4 Hz, 1H), 7.28 (d, J=6.4 Hz, 1H), 7.14-7.23 (m, 5H), 6.84-6.95 (m, 2H), 1.18-1.23 (m, 9H). MS (M+1):500.

Compound 6-40

N-(5-(4-fluorophenyl)-4-(4-(tert-pentyl)phenyl)thiazol-2-yl)-5-nitrothiophene-2-carboxamide

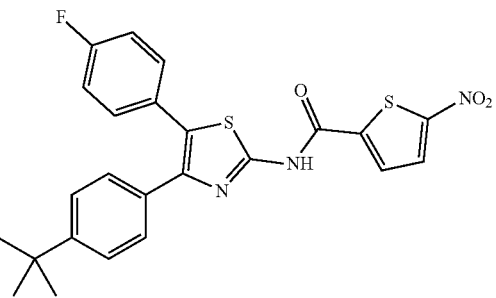

¹H NMR (400 MHz, DMSO-d₆): 8.06-8.13 (m, 2H), 7.29-7.37 (m, 5H), 7.21-7.27 (m, 2H), 7.13-7.21 (m, 2H), 1.54 (q, J=7.3 Hz, 2H), 1.19 (s, 6H), 0.57 (t, J=7.3 Hz, 3H). MS (M+1):496.

Compound 6-41

N-(4-(4-(tert-butyl)phenyl)-5-(3-fluorophenyl)thiazol-2-yl)-5-nitrothiophene-2-carboxamide

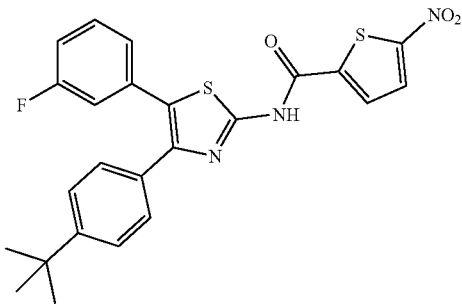 [SMILES: CC(C)(C)c1ccc(-c2nc(NC(=O)c3ccc([N+](=O)[O-])s3)sc2-c2cccc(F)c2)cc1]

¹H NMR (400 MHz, CDCl₃): δ 7.61 (d, J=4.4 Hz, 1H), 7.28-7.34 (m, 2H), 7.25-7.28 (m, 2H), 7.19-7.23 (m, 2H), 7.16 (dt, J=7.8, 1.2 Hz, 1H), 6.99-7.08 (m, 2H), 1.20-1.25 (m, 9H). MS (M+1):482.

Compound 6-42 ethyl 4-(4-(tert-butyl)phenyl)-2-(5-nitrothiophene-2-carboxamido)thiazole-5-carboxylate

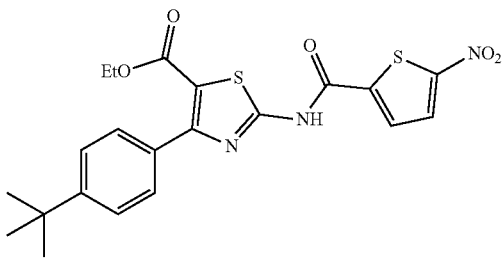 [SMILES: CCOC(=O)c1sc(NC(=O)c2ccc([N+](=O)[O-])s2)nc1-c1ccc(C(C)(C)C)cc1]

¹H NMR (400 MHz, CDCl₃): δ 11.32 (br. s., 1H), 7.67 (d, J=3.9 Hz, 1H), 7.52-7.60 (m, 2H), 7.30-7.38 (m, 2H), 7.25 (d, J=4.4 Hz, 1H), 4.30 (q, J=7.3 Hz, 2H), 1.31 (t, J=7.1 Hz, 3H), 1.27 (s, 9H). MS (M+1):460.

Compound 6-43

N-(4-(4-(tert-butyl)phenyl)-5-(4-methylpiperazine-1-carbonyl)thiazol-2-yl)-5-nitrothiophene-2-carboxamide

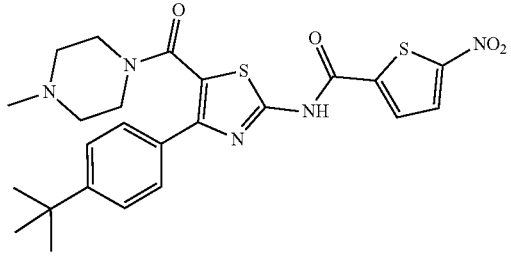 [SMILES: CN1CCN(C(=O)c2sc(NC(=O)c3ccc([N+](=O)[O-])s3)nc2-c2ccc(C(C)(C)C)cc2)CC1]

¹H NMR (400 MHz, DMSO-d₆): 8.19 (d, J=4.4 Hz, 2H), 8.12 (d, J=4.4 Hz, 2H), 7.56 (d, J=8.8 Hz, 2H), 7.49 (d, J=8.8 Hz, 2H), 3.30-3.38 (m, 8H), 2.14 (s, 3H), 1.32 (s, 9H). MS (M+1): 514

Compound 6-44

4-(4-(tert-butyl)phenyl)-N-cyclopropyl-2-(5-nitrothiophene-2-carboxamido)thiazole-5-carboxamide

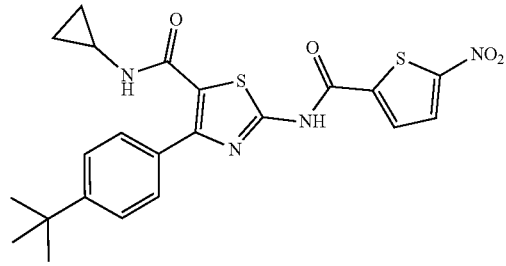 [SMILES: CC(C)(C)c1ccc(-c2nc(NC(=O)c3ccc([N+](=O)[O-])s3)sc2C(=O)NC2CC2)cc1]

¹H NMR (400 MHz, DMSO-d₆): 13.51 (br. s., 1H), 8.34 (d, J=4.4 Hz, 1H), 8.21 (d, J=4.4 Hz, 1H), 7.64 (d, J=8.3 Hz, 2H), 7.47 (d, J=8.3 Hz, 2H), 2.72-2.84 (m, 1H), 1.32 (s, 9H), 0.55-0.71 (m, 2H), 0.39-0.51 (m, 2H). MS (M+1): 471

Compound 6-45 ethyl 4-(4-ethoxyphenyl)-2-(5-nitrothiophene-2-carboxamido)thiazole-5-carboxylate

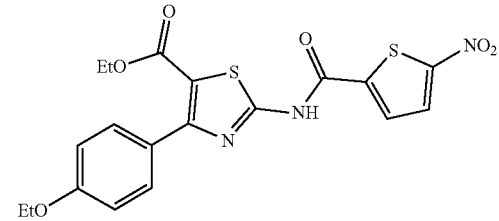 [SMILES: CCOC(=O)c1sc(NC(=O)c2ccc([N+](=O)[O-])s2)nc1-c1ccc(OCC)cc1]

¹H NMR (400 MHz, CDCl₃): δ 11.04 (br. s., 1H), 7.70 (d, J=3.9 Hz, 1H), 7.48-7.61 (m, J=8.8 Hz, 2H), 7.32 (d, J=4.4 Hz, 1H), 6.75-6.87 (m, J=8.8 Hz, 2H), 4.29 (q, J=7.3 Hz,

2H), 4.00 (q, J=7.0 Hz, 2H), 1.41 (t, J=7.1 Hz, 3H), 1.31 (t, J=7.1 Hz, 3H). MS (M+1):448.

Compound 6-46

N-(4-(4-(tert-butyl)phenyl)-5-(3,4-difluorophenyl)thiazol-2-yl)-5-nitrothiophene-2-carboxamide

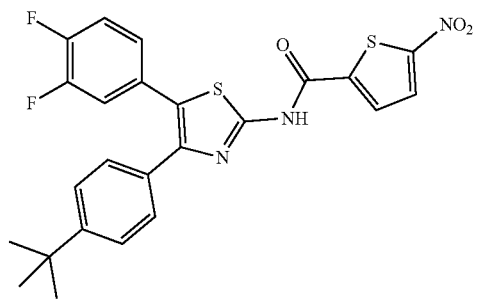 [SMILES: CC(C)(C)c1ccc(-c2nc(NC(=O)c3ccc([N+](=O)[O-])s3)sc2-c2ccc(F)c(F)c2)cc1]

$^1$H NMR (400 MHz, CDCl$_3$): δ 12.31 (br. s., 1H), 7.48 (d, J=3.9 Hz, 1H), 7.07-7.22 (m, 8H), 1.20 (s, 9H). MS (M+1): 500.

Compound 6-47

N-(5-(2,4-difluorophenyl)-4-(4-(tert-pentyl)phenyl)thiazol-2-yl)-5-nitrothiophene-2-carboxamide

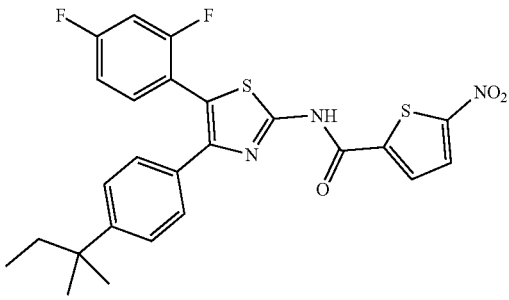 [SMILES: CCC(C)(C)c1ccc(-c2nc(NC(=O)c3ccc([N+](=O)[O-])s3)sc2-c2ccc(F)cc2F)cc1]

$^1$H NMR (400 MHz, CDCl$_3$): δ 12.13 (br. s., 1H), 7.52 (d, J=4.4 Hz, 1H), 7.27 (td, J=8.3, 6.4 Hz, 1H), 7.21 (d, J=8.3 Hz, 2H), 7.19 (d, J=4.4 Hz, 1H), 7.10 (d, J=8.3 Hz, 2H), 6.84-6.94 (m, 2H), 1.50 (q, J=7.5 Hz, 2H), 1.15 (s, 6H), 0.57 (t, J=7.3 Hz, 3H). MS (M+1):514.

Compound 6-48

N-(4-(4-(tert-butyl)phenyl)-5-(2-fluorophenyl)thiazol-2-yl)-5-nitrothiophene-2-carboxamide

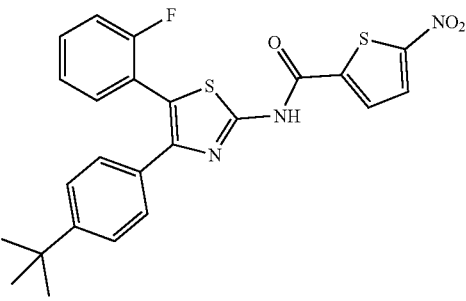 [SMILES: CC(C)(C)c1ccc(-c2nc(NC(=O)c3ccc([N+](=O)[O-])s3)sc2-c2ccccc2F)cc1]

$^1$H NMR (400 MHz, CDCl$_3$): δ 11.99 (s, 1H), 7.54 (d, J=4.4 Hz, 1H), 7.27-7.42 (m, 2H), 7.20-7.27 (m, 3H), 7.08-7.18 (m, 4H), 1.20 (s, 9H). MS (M+1):482.

Compound 6-49

N-(4-(4-(tert-butyl)phenyl)-5-(morpholine-4-carbonyl)thiazol-2-yl)-5-nitrothiophene-2-carboxamide

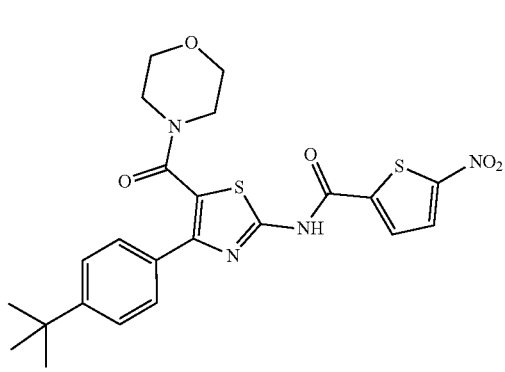 [SMILES: CC(C)(C)c1ccc(-c2nc(NC(=O)c3ccc([N+](=O)[O-])s3)sc2C(=O)N2CCOCC2)cc1]

$^1$H NMR (400 MHz, CDCl$_3$): δ 8.22 (s, 2H), 7.58 (d, J=8.31 Hz, 2H), 7.52 (d, J=8.80 Hz, 2H), 3.54 (br. s., 4H), 3.11 (br. s., 4H), 1.31 (s, 9H). MS (M+1):501.

Compound 6-50

N-(4-(4-(tert-butyl)phenyl)-5-cyanothiazol-2-yl)-5-nitrothiophene-2-carboxamide

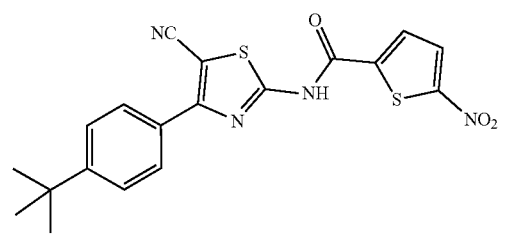 [SMILES: CC(C)(C)c1ccc(-c2nc(NC(=O)c3ccc([N+](=O)[O-])s3)sc2C#N)cc1]

¹H NMR (400 MHz, DMSO-d₆): 14.17 (br. s., 1H), 8.22 (s, 2H), 7.94-8.01 (m, J=8.8 Hz, 2H), 7.57-7.64 (m, J=8.3 Hz, 2H), 1.33 (s, 9H). MS (M+1):413.

Compound 6-51

N-(4-(4-(tert-butyl)phenyl)-5-(3,4,5-trifluorophenyl)thiazol-2-yl)-5-nitrothiophene-2-carboxamide

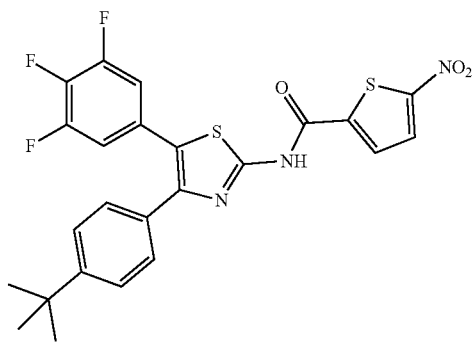 [SMILES: CC(C)(C)c1ccc(-c2nc(NC(=O)c3ccc([N+](=O)[O-])s3)sc2-c2cc(F)c(F)c(F)c2)cc1]

¹H NMR (400 MHz, CDCl₃): δ 7.63 (br. s., 1H), 7.29 (br. s., 1H), 7.12-7.24 (m, 4H), 6.84-7.02 (m, 3H). MS (M+1): 518.

Compound 6-52

N-(4-(4-(tert-butyl)phenyl)-5-(2,4,6-trifluorophenyl)thiazol-2-yl)-5-nitrothiophene-2-carboxamide

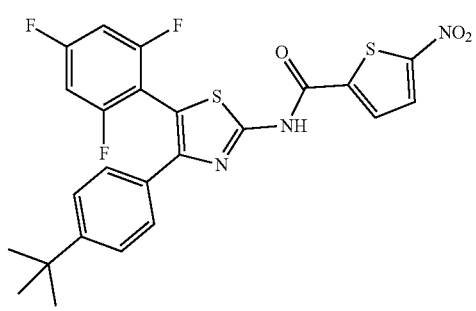 [SMILES: CC(C)(C)c1ccc(-c2nc(NC(=O)c3ccc([N+](=O)[O-])s3)sc2-c2c(F)cc(F)cc2F)cc1]

¹H NMR (400 MHz, CDCl₃): δ 7.62 (d, J=4.4 Hz, 1H), 7.29 (d, J=4.4 Hz, 1H), 7.22-7.27 (m, 6H), 7.17-7.22 (m, 2H), 6.75 (dd, J=8.6, 7.1 Hz, 2H), 1.22 (s, 9H). MS (M+1):518.

Compound 6-53

N-(5-(4-bromophenyl)-4-(4-(tert-butyl)phenyl)thiazol-2-yl)-5-nitrothiophene-2-carboxamide

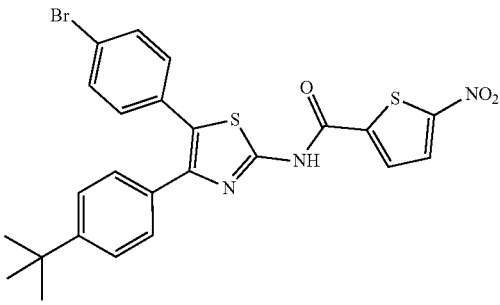 [SMILES: CC(C)(C)c1ccc(-c2nc(NC(=O)c3ccc([N+](=O)[O-])s3)sc2-c2ccc(Br)cc2)cc1]

¹H NMR (400 MHz, CDCl₃): δ 11.92 (br. s., 1H), 7.59 (d, J=4.4 Hz, 1H), 7.46-7.56 (m, 2H), 7.25-7.30 (m, 7H), 7.20-7.25 (m, 2H), 1.26 (s, 10H). MS (M+1):542.

Compound 6-54

N-(4-(4-(tert-butyl)phenyl)-5-(4-methoxyphenyl)thiazol-2-yl)-5-nitrothiophene-2-carboxamide

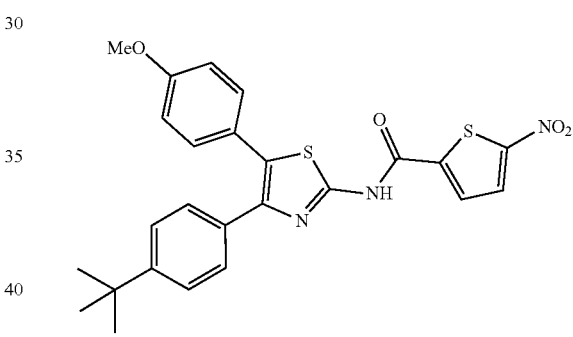

¹H NMR (400 MHz, CDCl₃): δ 7.46 (d, J=4.4 Hz, 1H), 7.26-7.32 (m, 2H), 7.21-7.25 (m, 3H), 7.10-7.16 (m, 3H), 6.84-6.91 (m, 2H), 3.83 (s, 3H), 1.16-1.21 (m, 9H). MS (M+1):494.

Compound 6-55

N-(4-(4-(tert-butyl)phenyl)-5-(2-chlorophenyl)thiazol-2-yl)-5-nitrothiophene-2-carboxamide

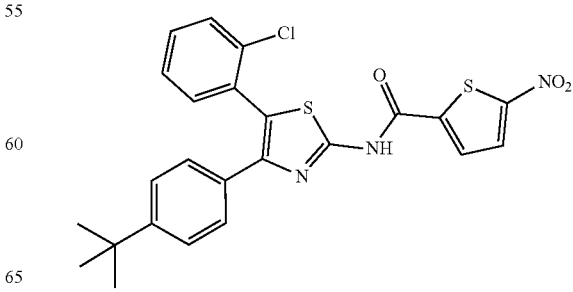

¹H NMR (400 MHz, CDCl₃): δ 7.60 (d, J=3.9 Hz, 1H), 7.51 (dd, J=8.1, 1.2 Hz, 1H), 7.32-7.40 (m, 2H), 7.25-7.32 (m, 2H), 7.18-7.23 (m, 2H), 7.12-7.18 (m, 2H), 1.20 (s, 9H). MS (M+1):498.

Compound 6-56

N-(4-(4-(tert-butyl)phenyl)-5-(3-chlorophenyl)thiazol-2-yl)-5-nitrothiophene-2-carboxamide

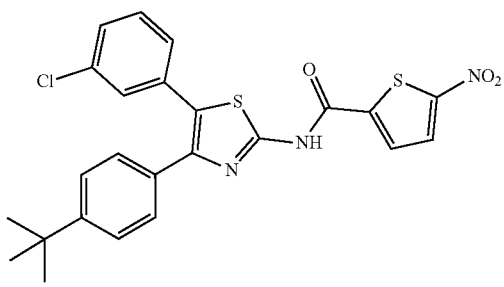 [SMILES: CC(C)(C)c1ccc(-c2nc(NC(=O)c3ccc([N+](=O)[O-])s3)sc2-c2cccc(Cl)c2)cc1]

¹H NMR (400 MHz, CDCl₃): δ 12.10 (br. s., 1H), 7.52 (d, J=3.9 Hz, 1H), 7.35 (t, J=1.7 Hz, 1H), 7.25-7.32 (m, 2H), 7.20-7.24 (m, 3H), 7.15-7.20 (m, 3H), 1.21 (s, 9H). MS (M+1):498.

Compound 6-57

N-(5-(2-bromophenyl)-4-(4-(tert-butyl)phenyl)thiazol-2-yl)-5-nitrothiophene-2-carboxamide

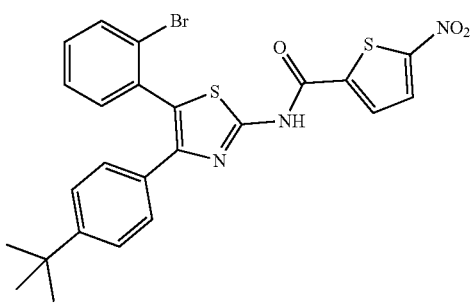 [SMILES: CC(C)(C)c1ccc(-c2nc(NC(=O)c3ccc([N+](=O)[O-])s3)sc2-c2ccccc2Br)cc1]

¹H NMR (400 MHz, CDCl₃): δ 7.57 (d, J=4.4 Hz, 1H), 7.50 (t, J=1.7 Hz, 1H), 7.45 (dt, J=7.8, 1.5 Hz, 1H), 7.24-7.31 (m, 3H), 7.16-7.24 (m, 4H), 1.22 (s, 10H). MS (M+1):542.

Compound 6-58

N-(5-(3-bromophenyl)-4-(4-(tert-butyl)phenyl)thiazol-2-yl)-5-nitrothiophene-2-carboxamide

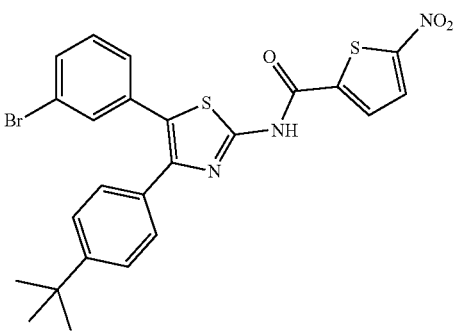 [SMILES: CC(C)(C)c1ccc(-c2nc(NC(=O)c3ccc([N+](=O)[O-])s3)sc2-c2cccc(Br)c2)cc1]

¹H NMR (400 MHz, CDCl₃): δ 12.21 (br. s., 1H), 7.69-7.74 (m, 1H), 7.53 (d, J=4.4 Hz, 1H), 7.26-7.37 (m, 3H), 7.21 (d, J=4.4 Hz, 1H), 7.15-7.20 (m, 2H), 7.08-7.14 (m, 2H), 1.18 (s, 9H). MS (M+1): 542.

Compound 6-59

N-(4-(4-(tert-butyl)phenyl)-5-(4-chlorophenyl)thiazol-2-yl)-5-nitrothiophene-2-carboxamide

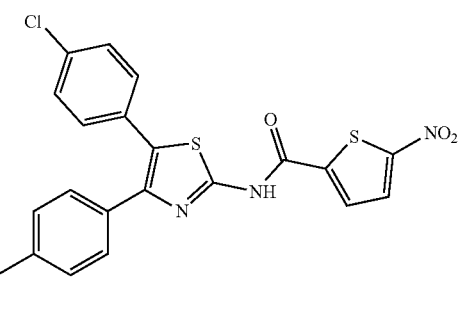

¹H NMR (400 MHz, CDCl₃): δ 11.47 (br. s., 1H), 7.62 (br. s., 1H), 7.24-7.33 (m, 7H), 7.17-7.23 (m, 2H), 1.23 (s, 10H). MS (M+1):498.

Compound 6-60

N-(5-bromo-4-(4-(tert-butyl)phenyl)thiazol-2-yl)-5-nitrothiophene-2-carboxamide

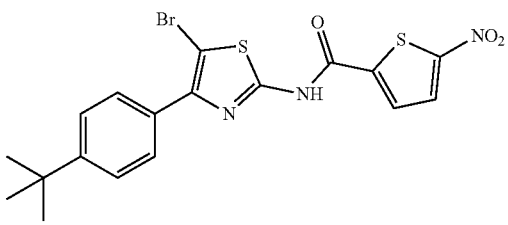 [SMILES: CC(C)(C)c1ccc(-c2nc(NC(=O)c3ccc([N+](=O)[O-])s3)sc2Br)cc1]

¹H NMR (400 MHz, CDCl₃): δ 11.44 (br. s., 1H), 7.59-7.70 (m, 3H), 7.29-7.41 (m, 2H), 7.24-7.29 (m, 1H), 1.27 (s, 9H). MS (M+1):466.

Compound 6-61

N-(3-(4-bromophenyl)-1H-pyrazol-5-yl)-5-nitrothiophene-2-carboxamide

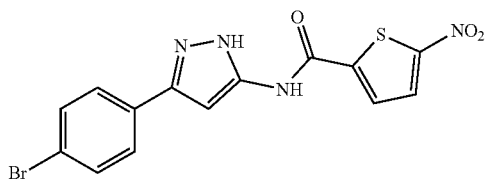 [SMILES: O=C(Nc1cc(-c2ccc(Br)cc2)n[nH]1)c1ccc([N+](=O)[O-])s1]

¹H NMR (400 MHz, DMSO-d₆): δ 13.19 (s, 1H), 11.55 (s, 1H), 8.18 (d, J=4.4 Hz, 1H), 8.15 (d, J=4.4 Hz, 1H), 7.72 (d, J=8.4 Hz, 2H), 7.67 (d, J=8.4 Hz, 2H), 7.06 (d, J=2.0 Hz, 1H). MS (M+1): 393.

In EXAMPLES 1-6, the detail synthesized procedures of some compounds are not repeated again if the synthesized procedures thereof are similar to those of the forgoing compounds.

Example 7: Evaluation of Compounds of Formula (I) in In Vitro Assays

The potency of selected compounds was defined by the growth inhibition ability to the hepatocellular carcinoma cell line Hep3B. The Hep3B cells were treated with selected compounds for 48 hr under 37° C., 5% CO₂, and 95% relative humidity.

The number of treated cells was determined by GE InCell 2200 system, and treated cells were stained with Hoechst 33342 which can reveal the remained nucleus in culture plate. The proportion of survival cells then were calculated with the ratio of treated/non-treated cells. The growth inhibition/cytotoxic effect of selected compounds were evaluated by the following protocol of NCI-60 screening platform. The human tumor cell lines are plating on a 96 well plate in a fixed density 24 hr prior compound treatment. Compounds with multiple concentrations are then added into each well for further 48 hr incubation. Cell viability is assessed by MTS method and the potency of compound is represented by GI₅₀ and LC₅₀ calculated by MTS result.

The compounds prepared in EXAMPLES 1-6 were tested in two in vitro assays, and the results are shown in Tables 1-6 shown below. Herein, the "Ratio in 10 μM (%)" in the following Tables 1-6 refers to the ratio of the number of tumor cells treated with 10 μM of selected compounds to the number of non-treated tumer cells.

TABLE 1

| Compound | R₁ | R₄ | Ratio in 10 μM (%) |
|---|---|---|---|
| 1-1 | 3-ethoxyphenyl | H | NA |
| 1-2 | 4-ethoxyphenyl | H | 61% |
| 1-3 | 2-hydroxyphenyl | H | NA |
| 1-4 | 2-nitrophenyl | H | NA |
| 1-5 | 4-(trifluoromethyl)phenyl | H | NA |
| 1-6 | 2-methoxyphenyl | H | NA |
| 1-7 | 4-bromophenyl | H | NA |
| 1-8 | 4-nitrophenyl | H | 76% |
| 1-9 | 4-(dimethylamino)phenyl | H | 60% |
| 1-10 | 2-propoxyphenyl | H | 61% |
| 1-11 | 2-(trifluoromethoxy)phenyl | H | 68% |
| 1-12 | 4-iodophenyl | H | 67% |
| 1-13 | 4-bromo-3-nitrophenyl | H | 60% |
| 1-14 | 4-isopropoxyphenyl | H | 71% |
| 1-15 | 2-isopropoxyphenyl | H | 56% |
| 1-16 | 4-(pentan-3-yloxy)phenyl | H | 84% |
| 1-17 | 4-propoxyphenyl | H | 82% |
| 1-18 | 2,4-diethoxyphenyl | H | 70% |
| 1-19 | 4-hydroxyphenyl | H | NA |
| 1-20 | 2-butoxyphenyl | H | 81% |
| 1-21 | 4-butoxyphenyl | H | 81% |
| 1-22 | 2-(pentan-3-yloxy)phenyl | H | 66% |
| 1-23 | 2-butoxy-4-ethoxyphenyl | H | 71% |
| 1-24 | 2,4,6-triethoxyphenyl | H | 88% |
| 1-25 | 3-ethoxypyridin-4-yl | H | 54% |
| 1-26 | 4-ethoxy-2-(ethoxymethoxy)phenyl | H | 59% |
| 1-27 | 4-ethoxy-2-(2-(4-methylpiperazin-1-yl)ethoxy)phenyl | H | NA |
| 1-28 | 2-(3-(dimethylamino)propoxy)-4-ethoxyphenyl | H | NA |
| 1-29 | 2-(2-(dimethylamino)ethoxy)-4-ethoxyphenyl | H | NA |
| 1-30 | 5-ethoxypyridin-2-yl | H | 37% |
| 1-31 | 3-(2-(dimethylamino)ethoxy)pyridin-4-yl | H | NA |
| 1-32 | 4-ethoxy-2-(2-methoxyethoxy)phenyl | H | NA |
| 1-33 | 4-propylphenyl | H | 44% |
| 1-34 | 4-ethoxypyridin-3-yl | H | 78% |
| 1-35 | 4,6-diethoxypyridin-3-yl | H | 42% |
| 1-36 | 2,4-diethoxyphenyl | Me | 53% |
| 1-37 | 4,6-diethoxypyridin-3-yl | Me | 47% |

TABLE 2

| Compound | R₁ | Ratio in 10 μM (%) |
|---|---|---|
| 2-1 | 4-ethoxyphenyl | NA |
| 2-2 | 2-ethoxyphenyl | NA |
| 2-3 | 2-propoxyphenyl | NA |
| 2-4 | 2-(trifluoromethoxy)phenyl | 88% |

TABLE 3

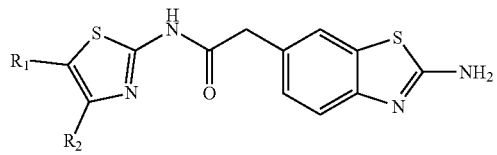

| Compound | R₁ | R₂ | Ratio in 10 μM (%) |
|---|---|---|---|
| 3-1 | 3-nitrophenyl | p-tolyl | NA |
| 3-2 | phenyl | 4-bromophenyl | NA |
| 3-3 | 4-bromophenyl | p-tolyl | 71% |
| 3-4 | 4-fluorophenyl | p-tolyl | NA |
| 3-5 | 3,4-dimethoxyphenyl | p-tolyl | 85% |
| 3-6 | 4-fluorophenyl | 4-propoxyphenyl | 83% |
| 3-7 | 3,5-bis(trifluoromethyl)phenyl | p-tolyl | 78% |
| 3-8 | Br | 3-methoxyphenyl | 84% |
| 3-9 | 4-fluorophenyl | 4-ethoxyphenyl | NA |
| 3-10 | 4-bromophenyl | 4-bromophenyl | 52% |
| 3-11 | 4-ethoxyphenyl | H | 60% |
| 3-12 | H | 2,4-diethoxyphenyl | 50% |
| 3-13 | phenoxy | 4-ethoxyphenyl | 58% |
| 3-14 | benzyl | 4-ethoxyphenyl | 76% |

TABLE 4

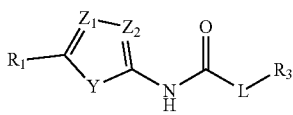

| Compound | $R_1$ | -L-$R_3$ | Y | $Z_1$ | $Z_2$ | Ratio in 10 μM (%) |
|---|---|---|---|---|---|---|
| 4-1 | 4-ethoxyphenyl | benzo[d]thiazole-2,6-diamine | S | N | N | NA |
| 4-2 | 4-ethoxyphenyl | 2-(2-aminobenzo[d]thiazol-6-yl) | S | C | C | 89% |
| 4-3 | 4-ethoxy-2-(2-methoxyethoxy)phenyl | 2-(2-aminobenzo[d]thiazol-6-yl) | N | C | N | 40% |
| 4-4 | 2,4-diethoxyphenyl | 2-(2-aminobenzo[d]thiazol-6-yl) | N | C | N | 40% |

TABLE 5

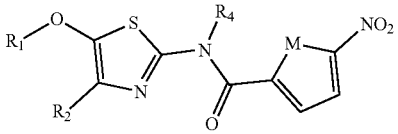

| Compound | $R_2$ | $R_1$ | M | $R_4$ | Ratio in 10 μM (%) |
|---|---|---|---|---|---|
| 5-1 | 4-bromophenyl | phenyl | S | H | 66% |
| 5-2 | 4-bromophenyl | 4-(trifluoromethoxy)phenyl | S | H | 60% |
| 5-3 | 3-nitrophenyl | phenyl | S | H | 82% |
| 5-4 | 3-methoxyphenyl | phenyl | S | H | 63% |
| 5-5 | 2-ethoxyphenyl | phenyl | S | H | 47% |
| 5-6 | 4-ethoxyphenyl | phenyl | S | H | 42% |
| 5-7 | 4-bromophenyl | 4-(trifluoromethyl)phenyl | S | H | 31% |
| 5-8 | 4-propoxyphenyl | 4-(trifluoromethoxy)phenyl | S | H | 24% |
| 5-9 | 4-propoxyphenyl | phenyl | S | H | 32% |
| 5-10 | 4-isopropoxyphenyl | phenyl | S | H | 29% |
| 5-11 | 4-bromophenyl | 3-(trifluoromethyl)phenyl | S | H | 21% |
| 5-12 | 2,4-diethoxyphenyl | phenyl | S | H | 46% |
| 5-13 | 4-propoxyphenyl | pyridin-3-yl | S | H | 53% |
| 5-14 | 4-(tert-butyl)phenyl | phenyl | S | H | 50% |
| 5-15 | 4-(2-methoxyethoxy)phenyl | pyridin-3-yl | S | H | 54% |
| 5-16 | 4-(2-methoxyethoxy)phenyl | phenyl | S | H | 59% |
| 5-17 | 4-propoxyphenyl | 3-(trifluoromethyl)phenyl | S | H | 37% |
| 5-18 | 4-bromophenyl | 4-(trifluoromethoxy)phenyl | S | H | 37% |
| 5-19 | 4-bromophenyl | 2-(trifluoromethyl)phenyl | S | H | 62% |
| 5-20 | 4-(tert-butyl)phenyl | 4-fluorophenyl | S | H | 62% |
| 5-21 | 4-propoxyphenyl | 2-ethoxyphenyl | S | H | 28% |
| 5-22 | 4-(tert-butyl)phenyl | 3-fluorophenyl | S | H | 30% |
| 5-23 | 4-ethoxyphenyl | 3-(trifluoromethyl)phenyl | S | H | 30% |

TABLE 5-continued

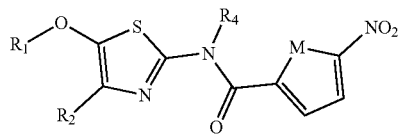

| Compound | R₂ | R₁ | M | R₄ | Ratio in 10 μM (%) |
|---|---|---|---|---|---|
| 5-24 | 4-propoxyphenyl | 3-fluorophenyl | S | H | 28% |
| 5-25 | 4-ethoxyphenyl | 4-(trifluoromethyl)phenyl | S | H | 32% |
| 5-26 | 4-propoxyphenyl | 4-(trifluoromethyl)phenyl | S | H | 24% |
| 5-27 | 4-propoxyphenyl | 4-bromophenyl | S | H | 31% |
| 5-28 | 4-propoxyphenyl | 4-bromo-3,5-dimethylphenyl | S | H | 32% |
| 5-29 | 4-ethoxyphenyl | 4-(tert-butyl) phenyl | S | H | 42% |
| 5-30 | 4-propoxyphenyl | 4-fluorophenyl | S | H | 40% |
| 5-31 | 4-fluorophenyl | 2-(trifluoromethyl)phenyl | S | H | 48% |
| 5-32 | 4-fluorophenyl | 2-(trifluoromethoxy)phenyl | S | H | 48% |
| 5-33 | 4-fluorophenyl | 4-(trifluoromethoxy)phenyl | S | H | 40% |
| 5-34 | 4-methoxyphenyl | phenyl | S | H | 54% |
| 5-35 | 4-(methylcarbamoyl)phenyl | 4-fluorophenyl | S | H | 68% |
| 5-36 | 3,5-diethoxyphenyl | phenyl | S | H | 39% |
| 5-37 | 4-propoxyphenyl | 2,4-difluorophenyl | S | H | 38% |
| 5-38 | 4-propoxyphenyl | 2-chloro-4-(trifluoromethyl)phenyl | S | H | 41% |
| 5-39 | 4-propoxyphenyl | 4-cyanophenyl | S | H | 56% |
| 5-40 | 4-propoxyphenyl | 4-cyano-2-methoxyphenyl | S | H | 46% |
| 5-41 | 3,3-dimethylbut-1-yn-1-yl)thiophen-2-yl | phenyl | S | H | 41% |
| 5-42 | 5-bromothiophen-2-yl | phenyl | S | H | 55% |
| 5-43 | 4-propoxyphenyl | pyridin-4-yl | S | H | NA |
| 5-44 | 4-propoxyphenyl | 3,4-dichlorophenyl | S | H | 41% |
| 5-45 | 4-propoxyphenyl | 2-chloro-4-fluorophenyl | S | H | 28% |
| 5-46 | 5-(3-(dimethylamino)prop-1-yn-1-yl)thiophen-2-yl | phenyl | S | H | 53% |
| 5-47 | 4-ethoxyphenyl | phenyl | O | H | NA |
| 5-48 | 4-propoxyphenyl | phenyl | O | H | 37% |
| 5-49 | 4-propoxyphenyl | 4-fluorophenyl | O | H | 41% |
| 5-50 | 4-propoxyphenyl | 3,5-difluorophenyl | S | H | 42% |
| 5-51 | 6-ethoxypyridin-3-yl | phenyl | S | H | 43% |
| 5-52 | 4-propoxyphenyl | quinolin-8-yl | S | H | 41% |
| 5-53 | 4-ethoxy-2-fluorophenyl | phenyl | S | H | 41% |
| 5-54 | 4-ethoxyphenyl | 3-fluorophenyl | S | H | 35% |
| 5-55 | 4-ethoxyphenyl | 4-fluorophenyl | S | H | 47% |
| 5-56 | 4-butoxyphenyl | phenyl | S | H | 40% |
| 5-57 | 4-ethoxyphenyl | 2-fluorophenyl | S | H | 43% |
| 5-58 | 4-propoxyphenyl | 2-fluorophenyl | S | H | 43% |
| 5-59 | 4-(tert-butyl)phenyl | phenyl | S | H | 38% |
| 5-60 | 4-nitrophenyl | phenyl | S | H | 38% |
| 5-61 | 3,4,5-trimethoxyphenyl | phenyl | S | H | 59% |
| 5-62 | 4-fluorophenyl | 4-(tert-pentyl)phenyl | S | H | 45% |
| 5-63 | 4-(tert-pentyl)phenyl | 4-fluorophenyl | S | H | 37% |
| 5-64 | 4-fluorophenyl | 4-(tert-pentyl)phenyl | S | H | 54% |
| 5-65 | 4-fluorophenyl | 4-butylphenyl | S | H | 43% |
| 5-66 | 4-fluorophenyl | 4-butoxyphenyl | S | H | 43% |
| 5-67 | 4-(hexyloxy)phenyl | phenyl | S | H | 46% |
| 5-68 | 4-fluorophenyl | 4-(tert-butyl)phenyl | S | H | 54% |
| 5-69 | 4-fluorophenyl | 4-butylphenyl | S | H | 43% |
| 5-70 | 4-fluorophenyl | 4-butoxyphenyl | S | H | 43% |
| 5-71 | 4-(trifluoromethyl)phenyl | 4-(tert-pentyl)phenyl | S | H | 49% |

TABLE 5-continued

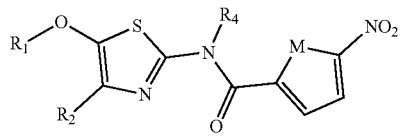

| Compound | R$_2$ | R$_1$ | M | R$_4$ | Ratio in 10 μM (%) |
|---|---|---|---|---|---|
| 5-72 | 4-butoxyphenyl | 2-fluorophenyl | S | H | 43% |
| 5-73 | 4-butoxyphenyl | 4-fluorophenyl | S | H | 49% |
| 5-74 | 4-(tert-butyl)phenyl | 4-(trifluoromethyl)phenyl | S | H | 33% |
| 5-75 | 4-(tert-butyl)phenyl | 4-(trifluoromethyl)phenyl | S | H | 34% |
| 5-76 | 4-(pentyloxy)phenyl | phenyl | S | H | 38% |
| 5-77 | 4-propylphenyl | phenyl | S | H | 33% |
| 5-78 | 4-propylphenyl | 2-fluorophenyl | S | H | 33% |
| 5-79 | 4-butylphenyl | phenyl | S | H | 31% |
| 5-80 | 4-butylphenyl | 2-fluorophenyl | S | H | 26% |
| 5-81 | 4-(trifluoromethyl)phenyl | phenyl | S | H | 30% |
| 5-82 | 4-ethoxyphenyl | phenyl | S | methyl | 59% |
| 5-83 | 4-(trifluoromethyl)phenyl | 2-fluorophenyl | S | H | 36% |
| 5-84 | 4-(trifluoromethoxy)phenyl | phenyl | S | H | 34% |
| 5-85 | 4-(trifluoromethoxy)phenyl | 2-fluorophenyl | S | H | 34% |
| 5-86 | 4-butoxyphenyl | 4-bromophenyl | S | H | 24% |
| 5-87 | 4-butoxyphenyl | 4-bromo-3,5-dimethylphenyl | S | H | 36% |
| 5-88 | 4-propylphenoxy | 4-propylphenyl | S | H | 36% |
| 5-89 | 4-(tert-butyl)phenyl | 4-butylphenyl | S | H | 36% |
| 5-90 | 4-butoxyphenyl | 4-(tert-butyl)phenyl | S | H | 48% |
| 5-91 | 4-butoxyphenyl | 4-cyanophenyl | S | H | 46% |
| 5-92 | 5-phenoxypentan-1-amine | phenyl | S | H | 46% |
| 5-93 | 4-butoxyphenyl | 4-propylphenyl | S | H | 45% |
| 5-94 | 4-butylphenyl | 4-fluorophenyl | S | H | 32% |
| 5-95 | 4-(tert-butyl)phenyl | 4-propoxyphenyl | S | H | 38% |
| 5-96 | 4-(tert-butyl)phenyl | 4-(tert-butyl) phenyl | S | H | 47% |
| 5-97 | 4-(tert-butyl)phenyl | 2,4,4-trimethylpentan-2-yl phenyl | S | H | NA |
| 5-98 | 4-butoxyphenyl | 4-(tert-pentyl) phenyl | S | H | 50% |
| 5-99 | 4-(tert-butyl)phenyl | 4-bromo-3,5-dimethyl phenyl | S | H | 40% |
| 5-100 | 4-fluorophenyl | 4-bromo-3,5-dimethyl phenyl | S | H | 30% |
| 5-101 | 4-(tert-butyl)phenyl | 4-(tert-pentyl) phenyl | S | H | 48% |
| 5-102 | 4-ethylphenyl | 4-(tert-butyl)phenyl | S | H | 40% |
| 5-103 | 4-ethylphenyl | 4-(tert-pentyl) phenyl | S | H | 33% |
| 5-104 | 4-butylphenyl | 4-(tert-pentyl) phenyl | S | H | 56% |
| 5-105 | 4-(tert-butyl)phenyl | 4-tolyl | S | H | 30% |
| 5-106 | 4-butoxyphenyl | 3,5-dimethyl phenyl | S | H | 29% |
| 5-107 | 4-(tert-butyl)phenyl | 4-(dimethylamino) phenyl | S | H | NA |
| 5-108 | 4-(tert-butyl)phenyl | 4-morpholino phenyl | S | H | NA |

TABLE 6

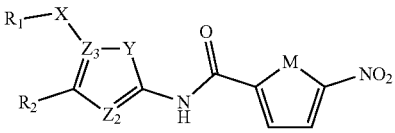

| Compound | R₂ | -X-R₁ | M | Y | Z₃ | Z₂ | Ratio in 10 µM (%) |
|---|---|---|---|---|---|---|---|
| 6-1 | 3-nitrophenyl | H | S | S | C | N | NA |
| 6-2 | p-tolyl | 4-bromophenyl | S | S | C | N | NA |
| 6-3 | p-tolyl | 3-nitrophenyl | S | S | C | N | 84% |
| 6-4 | p-tolyl | 3,4-dimethoxyphenyl | S | S | C | N | 64% |
| 6-5 | p-tolyl | 3,5-bis(trifluoromethyl)phenyl | S | S | C | N | 46% |
| 6-6 | p-tolyl | 4-fluorophenyl | S | S | C | N | 48% |
| 6-7 | 4-bromophenyl | H | S | S | C | N | 81% |
| 6-8 | 3-methoxyphenyl | H | S | S | C | N | NA |
| 6-9 | 4-bromophenyl | phenyl | S | S | C | N | 71% |
| 6-10 | 4-bromophenyl | Br | S | S | C | N | 50% |
| 6-11 | 2-nitrophenyl | H | S | S | C | N | 62% |
| 6-12 | 2-nitrophenyl | Br | S | S | C | N | 67% |
| 6-13 | 3-nitrophenyl | Br | S | S | C | N | 81% |
| 6-14 | 3-methoxyphenyl | Br | S | S | C | N | 83% |
| 6-15 | 4-ethoxyphenyl | 4-fluorophenyl | S | S | C | N | 64% |
| 6-16 | 4-propoxyphenyl | 4-fluorophenyl | S | S | C | N | 59% |
| 6-17 | 4-ethoxyphenyl | Br | S | S | C | N | 53% |
| 6-18 | 4-butoxyphenyl | 4-fluorophenyl | S | S | C | N | 26% |
| 6-19 | 4-ethoxyphenyl | 4-(trifluoromethyl)phenoxy | S | S | C | N | 26% |
| 6-20 | p-tolyl | 4-bromo-3-ethoxyphenyl | S | S | C | N | 45% |
| 6-21 | 4-(tert-butyl)phenyl | phenyl | S | S | C | N | 29% |
| 6-22 | 4-propoxyphenyl | 4-methylpiperazin-1-yl | S | S | C | N | 29% |
| 6-23 | 4-propoxyphenyl | Ethyl carboxylate | S | S | C | N | 33% |
| 6-24 | 4-(tert-butyl)phenyl | 4-fluorophenyl | S | S | C | N | 30% |
| 6-25 | 3,5-diethoxyphenyl | H | S | S | C | N | NA |
| 6-26 | 4-(dimethylamino)phenyl | H | S | S | C | N | NA |
| 6-27 | 4-ethoxyphenyl | N-(3,5-difluorophenyl)carboxamide | S | S | C | N | 36% |
| 6-28 | 4-ethoxyphenyl | methyl(phenyl)amino | S | S | C | N | 31% |
| 6-29 | 4-propoxyphenyl | morpholine-4-carbonyl | S | S | C | N | 58% |
| 6-30 | 4-propoxyphenyl | 4-methylpiperazine-1-carbonyl | S | S | C | N | 58% |
| 6-31 | 4-propoxyphenyl | N-(2,4-difluorophenyl)formamide | S | S | C | N | 61% |
| 6-32 | p-tolyl | 4-bromophenyl | O | S | C | N | 27% |
| 6-33 | 4-ethoxyphenyl | benzyl | O | S | C | N | 27% |
| 6-34 | 4-ethoxyphenyl | benzyl | S | S | C | N | 44% |
| 6-35 | 4-ethoxyphenyl | 4-fluorobenzyl | S | S | C | N | 47% |
| 6-36 | 4-ethoxyphenyl | 3-fluorobenzyl | S | S | C | N | 41% |
| 6-37 | 4-(tert-butyl)phenyl | 4-fluorobenzyl | S | S | C | N | 39% |
| 6-38 | 4-(tert-butyl)phenyl | 3,5-difluorophenyl | S | S | C | N | 30% |
| 6-39 | 4-(tert-butyl)phenyl | 2,4-difluorophenyl | S | S | C | N | 31% |
| 6-40 | 4-(tert-pentyl)phenyl | 4-fluorophenyl | S | S | C | N | 25% |
| 6-41 | 4-(tert-butyl)phenyl | 3-fluorophenyl | S | S | C | N | 36% |
| 6-42 | 4-(tert-butyl)phenyl | ethyl acetate | S | S | C | N | 49% |
| 6-43 | 4-(tert-butyl)phenyl | 4-methylpiperazine-1-carbonyl | S | S | C | N | 38% |
| 6-44 | 4-(tert-butyl)phenyl | N-cyclopropylacetamide | S | S | C | N | 81% |
| 6-45 | 4-ethoxyphenyl | ethyl acetate | S | S | C | N | NA |
| 6-46 | 4-(tert-butyl)phenyl | 3,4-difluorophenyl | S | S | C | N | 31% |
| 6-47 | 4-(tert-pentyl)phenyl | 2,4-difluorophenyl | S | S | C | N | 33% |
| 6-48 | 4-(tert-butyl)phenyl | 2-fluorophenyl | S | S | C | N | 45% |
| 6-49 | 4-(tert-butyl)phenyl | morpholine-4-carbonyl | S | S | C | N | 57% |
| 6-50 | 4-(tert-butyl)phenyl | cyano | S | S | C | N | 53% |
| 6-51 | 4-(tert-butyl)phenyl | 3,4,5-trifluorophenyl | S | S | C | N | 50% |
| 6-52 | 4-(tert-butyl)phenyl | 2,4,6-trifluorophenyl | S | S | C | N | 37% |
| 6-53 | 4-(tert-butyl)phenyl | 4-bromophenyl | S | S | C | N | 24% |
| 6-54 | 4-(tert-butyl)phenyl | 4-methoxyphenyl | S | S | C | N | 25% |
| 6-55 | 4-(tert-butyl)phenyl | 2-chlorophenyl | S | S | C | N | 30% |
| 6-56 | 4-(tert-butyl)phenyl | 3-chlorophenyl | S | S | C | N | 28% |
| 6-57 | 4-(tert-butyl)phenyl | 2-bromophenyl | S | S | C | N | 29% |
| 6-58 | 4-(tert-butyl)phenyl | 3-bromophenyl | S | S | C | N | 32% |
| 6-59 | 4-(tert-butyl)phenyl | 4-chlorophenyl | S | S | C | N | 27% |
| 6-60 | 4-(tert-butyl)phenyl | bromo | S | S | C | N | 45% |
| 6-61 | 4-bromophenyl | — | S | NH | N | C | NA |

Shown in Tables 1-6 are the structures and in vitro activities of exemplary compounds of formula (I). Most of the disclosed compounds were found to inhibit the growth of Hep3B cells.

Example 8: Evaluation of Compounds of Formula (I) in In Vitro MTS Assays

The cell viability measurement is based on the NCI-60 screening methodology (Nat. Rev. Cancer 6, 813-823, 2006). Briefly, cells are inoculated into 96-well plates at the optimal plating density. After 24 h, one of the two plates for each cell line is processed to determine a time zero cell viability (Tz) by MTS assay (Promega). Compounds are added over a 2-fold serial dilution to provide a total five drug concentrations plus DMSO control. Plates are incubated for a further 2 days, then measured cell viability by MTS assay [control growth (C) and test growth in the presence of drug at the five concentration levels (Ti)]. Growth inhibition of 50% ($GI_{50}$) is calculated from $[(Ti-Tz)/(C-Tz)] \times 100 = 50$, which is the drug concentration resulting in a 50% reduction of control cells during the drug incubation. The $LC_{50}$ is calculated from $[(Ti-Tz)/Tz] \times 100 = -50$, which is the drug concentration resulting in a 50% reduction at the end of the drug treatment as compared to that at the beginning.

The compounds prepared in EXAMPLES 1-6 were tested in two in vitro assays, and the results are shown in Tables 7-8 shown below. Herein, Hep3B refers to hepatocellular carcinoma cell line, SW480 refers to colon adenocarcinoma cell line, and NCI-H460 refers to human lung cancer cell line.

TABLE 7

| Compound | Hep3B GI$_{50}$ (µM) | SW480 GI$_{50}$ (µM) | NCI-H460 GI$_{50}$ (µM) |
| --- | --- | --- | --- |
| 1-2 | 0.16 | 3.55 | 0.86 |
| 1-7 | 3.17 | 7.70 | NA |
| 1-10 | 0.17 | 0.90 | NA |
| 1-15 | 0.17 | 0.62 | NA |
| 1-16 | 2.83 | 7.26 | NA |
| 1-17 | 0.60 | 1.81 | NA |
| 1-18 | 0.16 | 0.19 | 0.20 |
| 1-20 | 0.21 | 1.15 | NA |
| 1-22 | 0.09 | 1.23 | 2.67 |
| 1-23 | 0.48 | 0.52 | 0.58 |
| 1-25 | 0.17 | 0.35 | 0.32 |
| 1-26 | 0.16 | 0.21 | 0.20 |
| 1-29 | 0.20 | 3.34 | 5.20 |
| 1-32 | 0.17 | 0.23 | 0.14 |
| 1-35 | 0.55 | NA | 1.42 |
| 1-37 | 0.84 | 1.26 | 1.35 |
| 3-3 | 1.14 | 7.97 | NA |
| 3-4 | 2.07 | NA | 3.02 |
| 3-9 | 2.27 | 8.95 | 2.39 |
| 3-10 | 0.51 | 1.21 | 0.84 |
| 5-6 | 1.10 | 2.59 | 1.17 |
| 5-7 | 0.63 | 0.32 | 0.85 |
| 5-8 | 3.43 | NA | 3.01 |
| 5-9 | 2.43 | NA | 1.11 |
| 5-10 | 2.53 | NA | 0.88 |
| 5-11 | 6.54 | 7.04 | 0.63 |
| 5-14 | 0.34 | 1.51 | 1.72 |
| 5-17 | 0.30 | 1.26 | 1.16 |
| 5-18 | 3.09 | 2.52 | 6.40 |
| 5-19 | 1.79 | 1.51 | 2.88 |
| 5-20 | 0.79 | 0.88 | 2.76 |
| 5-22 | 1.43 | 2.50 | 2.09 |
| 5-23 | 1.22 | 6.42 | 2.49 |
| 5-24 | 0.95 | 1.14 | 1.57 |
| 5-26 | 0.83 | 1.05 | 1.15 |
| 5-27 | 0.82 | 1.23 | 1.96 |
| 5-29 | 1.84 | 3.34 | 3.24 |
| 5-30 | 0.92 | 0.53 | 0.70 |
| 5-32 | 0.46 | 0.40 | 0.69 |
| 5-38 | 0.37 | 0.77 | 0.57 |
| 5-39 | 0.89 | 1.49 | 0.23 |
| 5-48 | 5.22 | 1.81 | 1.40 |
| 5-56 | 0.55 | 1.54 | 0.70 |
| 5-62 | 0.45 | 0.76 | 0.59 |
| 5-63 | 0.43 | 0.88 | 0.68 |
| 5-66 | 0.52 | 0.95 | 0.39 |
| 5-67 | 0.62 | 1.03 | 0.79 |
| 5-71 | 0.63 | 0.81 | 1.53 |
| 5-74 | 1.16 | 0.69 | 0.72 |
| 5-75 | 0.80 | 0.73 | 0.67 |
| 5-76 | 0.56 | 1.27 | 0.74 |
| 5-80 | 0.68 | 1.46 | 0.84 |
| 5-81 | 0.98 | 2.47 | 0.81 |
| 5-85 | 0.87 | 1.66 | 0.75 |
| 6-2 | 1.27 | 0.97 | NA |
| 6-5 | 0.95 | 1.20 | 1.12 |
| 6-16 | 1.24 | 1.89 | 0.86 |
| 6-18 | 1.38 | 6.49 | 2.01 |
| 6-21 | 0.67 | 0.49 | 0.81 |
| 6-24 | 0.99 | 1.37 | 1.56 |
| 6-34 | 1.01 | 2.51 | 1.40 |
| 6-38 | 0.63 | 0.74 | 0.70 |
| 6-40 | 0.54 | 0.92 | 1.88 |
| 6-46 | 0.59 | 0.68 | 0.63 |
| 6-47 | 0.59 | 0.64 | 0.58 |
| 6-53 | 0.54 | 0.62 | 0.71 |
| 6-54 | 0.61 | 1.38 | 0.44 |
| 6-59 | 0.60 | 0.75 | 0.70 |

TABLE 8

| Compound | Hep3B LC$_{50}$ (µM) | SW480 LC$_{50}$ (µM) | NCI-H460 LC$_{50}$ (µM) |
| --- | --- | --- | --- |
| 1-2 | 0.48 | 8.93 | 1.24 |
| 1-7 | 9.4 | NA | NA |
| 1-10 | 0.55 | 5.17 | NA |
| 1-15 | 0.50 | NA | NA |
| 1-16 | 4.34 | NA | NA |
| 1-17 | 0.89 | NA | NA |
| 1-18 | 0.48 | 0.58 | 0.60 |
| 1-20 | 0.63 | NA | NA |
| 1-22 | 8.36 | NA | NA |
| 1-23 | 0.48 | 0.52 | 0.58 |
| 1-25 | 0.50 | 1.04 | NA |
| 1-26 | 0.49 | 0.63 | 0.59 |
| 1-29 | 1.10 | NA | NA |
| 1-32 | 0.54 | 0.69 | 0.60 |
| 1-35 | 3.68 | NA | NA |
| 1-37 | 1.24 | NA | NA |
| 3-10 | 1.29 | 7.08 | 6.62 |
| 5-6 | 4.35 | 5.52 | 3.99 |
| 5-7 | 1.23 | 2.80 | 1.85 |
| 5-8 | NA | NA | 4.66 |
| 5-9 | NA | NA | 2.86 |
| 5-10 | NA | NA | 5.31 |
| 5-11 | NA | NA | 3.98 |
| 5-14 | 7.35 | NA | NA |
| 5-17 | 1.60 | 2.41 | 2.29 |
| 5-18 | 4.77 | 4.75 | NA |
| 5-19 | 3.91 | 3.94 | NA |
| 5-20 | 2.63 | 3.73 | 8.34 |
| 5-22 | 4.03 | 4.27 | 4.53 |
| 5-23 | 3.96 | NA | 4.43 |
| 5-24 | 2.07 | 4.23 | 3.79 |
| 5-26 | 1.18 | 3.44 | 3.20 |
| 5-27 | 1.51 | 4.87 | 4.74 |
| 5-29 | 3.86 | 9.95 | 9.12 |
| 5-30 | 2.23 | 2.82 | 2.15 |
| 5-32 | 2.17 | 2.26 | 1.73 |
| 5-38 | 1.71 | 3.22 | 1.43 |
| 5-39 | 5.53 | 6.54 | 1.16 |
| 5-48 | 9.41 | NA | NA |
| 5-56 | 2.31 | 9.32 | 1.55 |
| 5-62 | 1.16 | 2.25 | 1.24 |
| 5-63 | 0.95 | 1.85 | 1.11 |
| 5-66 | 0.76 | 2.81 | 1.13 |
| 5-67 | 0.69 | 1.91 | 1.35 |
| 5-71 | 0.66 | 1.72 | 2.40 |
| 5-74 | 1.68 | 1.29 | 1.30 |
| 5-75 | 1.31 | 1.67 | 1.11 |
| 5-76 | 1.72 | 5.82 | 1.52 |
| 5-80 | 1.28 | 4.17 | 1.75 |
| 5-81 | 4.23 | 8.60 | 2.11 |
| 5-85 | 2.54 | 5.73 | 1.58 |
| 6-2 | 1.94 | 2.72 | NA |
| 6-5 | 1.08 | 1.41 | 1.63 |
| 6-16 | 1.83 | 2.79 | 1.75 |
| 6-18 | 2.17 | NA | 8.26 |
| 6-21 | 1.35 | 1.47 | 1.47 |
| 6-24 | 1.93 | 3.57 | 4.22 |
| 6-34 | 7.53 | NA | NA |
| 6-38 | 1.61 | 4.06 | 1.65 |
| 6-40 | 3.03 | 1.35 | 3.61 |
| 6-46 | 1.10 | 1.33 | 0.90 |
| 6-47 | 0.66 | 1.39 | 0.93 |
| 6-53 | 0.62 | 0.99 | 1.37 |
| 6-54 | 0.71 | 2.35 | 1.59 |
| 6-59 | 0.64 | 1.62 | 1.28 |

Shown in Tables 7-8 are in vitro activities of exemplary compounds of formula (I). The results indicate that the compounds of the present disclosure indeed have efficacy for inhibiting the growth of various tumor celles.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:
1. A compound of formula (I):

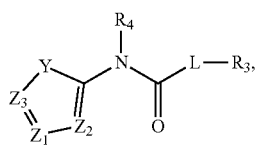

or a pharmaceutically acceptable salt thereof,
wherein
$Z_1$ is N or C—$R_2$;
$Z_2$ 1is C or N;
$Z_3$ is N or C—X—$R_1$, with the proviso that no more than two of $Z_1$, $Z_2$ and $Z_3$ are N;
X is a direct bond, —(CH$_2$)$_n$—, —O—, —NR$_a$—, —(C=O)NH— or —(C=O)—, in which n is 1, 2 or 3, and R$_a$ is hydrogen or alkyl;
Y is —CH—, —NR$_b$—, O or S, in which R$_b$ is hydrogen or alkyl;
L is a direct bond, —(CH$_2$)$_m$— or —NH—, in which m is 1, 2 or 3;
$R_1$ is hydrogen, halogen, cyano, alkyl, alkyloxy, cycloalkyl, heterocycloalkyl, aryl or heteroaryl, wherein each of alkyloxy, cycloalkyl, heterocycloalkyl, aryl and heteroaryl is optionally substituted with one to three moieties selected from the group consisting of halogen, hydroxyl, nitro, cyano, —NR$_c$R$_d$, lower alkyl carbamoyl, heterocycloalkyl, alkyl optionally substituted with one to three halo or aryl, and alkyloxy optionally substituted with one to three halo, alkyloxy, cycloalkyl, heterocycloalkyl, —NR$_e$R$_f$ or aryl, in which each of R$_c$, R$_d$, R$_e$ and R$_f$ independently is hydrogen or alkyl;
$R_2$ is hydrogen, halogen, alkyl, alkyloxy, cycloalkyl, heterocycloalkyl, aryl or heteroaryl, wherein each of alkyloxy, cycloalkyl, heterocycloalkyl, aryl and heteroaryl is optionally substituted with one to three moieties selected from the group consisting of halogen, hydroxyl, nitro, cyano, —NR$_g$R$_h$, lower alkyl carbamoyl, alkynyl, alkyl optionally substituted with one to three halo, and alkyloxy optionally substituted with one to three halo or alkyloxy, in which each of R$_g$ and R$_h$ independently is hydrogen or alkyl;

$R_3$ is

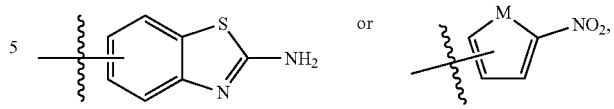

in which M is O or S; and
$R_4$ is H or alkyl,
wherein X is O when $R_3$ is

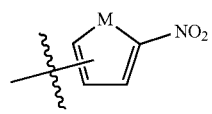

and M is O;
wherein —X—R, is not hydrogen when $R_3$ is

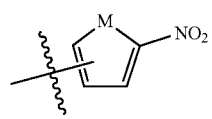

and M is S; and
wherein

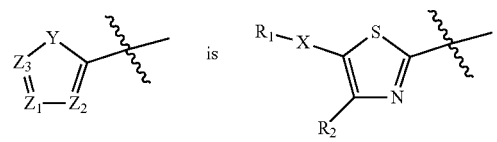

and —X—$R_1$ is not hydrogen when $R_3$ is

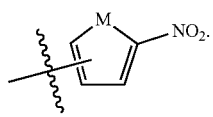

2. The compound or salt of claim 1, wherein

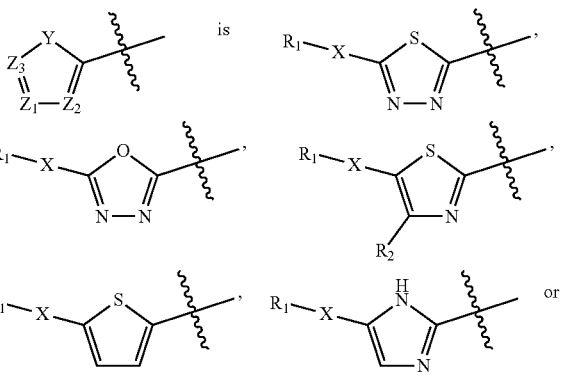

-continued

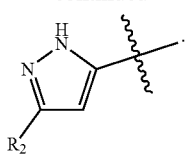

3. The compound or salt of claim 1, wherein

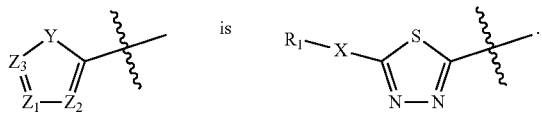

4. The compound or salt of claim 3, wherein X is a direct bond.

5. The compound or salt of claim 3, wherein L is a —CH₂—, and R₃ is

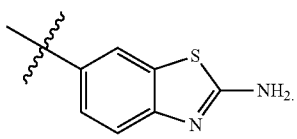 [SMILES: *c1ccc2nc(N)sc2c1]

6. The compound or salt of claim 3, wherein R₁ is aryl or heteroaryl, wherein each of aryl and heteroaryl is optionally substituted with one to three moieties selected from the group consisting of halogen, hydroxyl, nitro, cyano, —NR$_c$R$_d$, lower alkyl carbamoyl, heterocycloalkyl, alkyl optionally substituted with one to three halo or aryl, and alkyloxy optionally substituted with one to three halo, alkyloxy, cycloalkyl, heterocycloalkyl, —NR$_e$R$_f$ or aryl, in which each of R$_c$, R$_d$, R$_e$ and R$_f$ independently is hydrogen, methyl or ethyl.

7. The compound or salt of claim 6, wherein Ri is phenyl or pyridinyl, wherein each of phenyl or pyridinyl is optionally substituted with one to three alkyloxy optionally substituted with one to three halo, alkyloxy, cycloalkyl, heterocycloalkyl, —NR$_e$R$_f$ or aryl, in which each of R$_c$, R$_d$, R$_e$ and R$_f$ independently is hydrogen, methyl or ethyl.

8. The compound or salt of claim 3, wherein R₄ is H or methyl.

9. The compound or salt of claim 4, wherein L is a —CH₂—; R₃ is

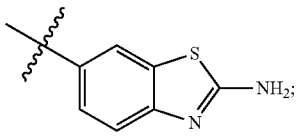 [SMILES: *c1ccc2nc(N)sc2c1]

R₄ is H or methyl; and R₁ is phenyl or pyridinyl, wherein each of phenyl or pyridinyl is optionally substituted with one or two ethoxy, butoxy, methoxy substituted with ethoxy, or ethoxy substituted with dimethylamino.

10. The compound or salt of claim 1, wherein

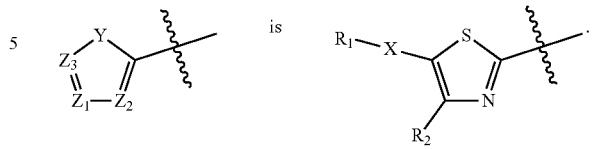

11. The compound or salt of claim 10, wherein X is a direct bond, —CH₂—, —O—, —N(CH₃)—, —(C=O)NH— or —(C=O)—.

12. The compound or salt of claim 10, wherein L is a direct bond, and R₃ is

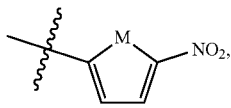

in which M is O or S.

13. The compound or salt of claim 10, wherein L is a —CH₂—, and R₃ is

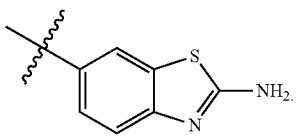 [SMILES: *c1ccc2nc(N)sc2c1]

14. The compound or salt of claim 10, wherein R₁ is hydrogen, halogen, cyano, alkoxy, aryl or heteroaryl, wherein each of aryl and heteroaryl is optionally substituted with one to three moieties selected from the group consisting of halogen, hydroxyl, nitro, cyano, —NR$_c$R$_d$, lower alkyl carbamoyl, heterocycloalkyl, alkyl optionally substituted with one to three halo or aryl, and alkyloxy optionally substituted with one to three halo, alkyloxy, cycloalkyl, heterocycloalkyl, —NR$_e$R$_f$ or aryl, in which each of R$_c$, R$_d$, R$_e$ and R$_f$ independently is hydrogen, methyl or ethyl.

15. The compound or salt of claim 14, wherein R₁ is phenyl, which is optionally substituted with one to three moieties selected from the group consisting of halogen and alkyl optionally substituted with one to three halo.

16. The compound or salt of claim 10, wherein R₂ is aryl or heteroaryl, wherein each of aryl and heteroaryl is optionally substituted with one to three moieties selected from the group consisting of halogen, nitro, cyano, lower alkyl carbamoyl, alkynyl, alkyl optionally substituted with one to three halo, and alkyloxy optionally substituted with one to three halo or alkyloxy.

17. The compound or salt of claim 16, wherein R₂ is phenyl, which is optionally substituted with one to three moieties selected from the group consisting of halogen, alkyl optionally substituted with one to three halo, and alkyloxy.

18. The compound or salt of claim 10, wherein R₄ is H or methyl.

19. The compound or salt of claim 10, wherein X is —O—; L is a direct bond; R₃ is

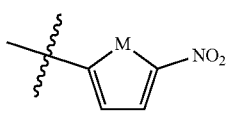

in which M is S; $R_4$ is H; $R_1$ is phenyl optionally substituted with fluoro, tert-pentyl or trifluoromethyl; and $R_2$ is phenyl substituted with ethoxy, butoxy, fluoro, tert-butyl, tert-pentyl or trifluoromethyl.

20. The compound or salt of claim 10, wherein X is a direct bond; L is a direct bond; $R_3$ is

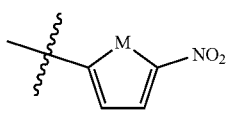

in which M is S; $R_4$ is H; $R_1$ is phenyl optionally substituted with one or two fluoro; and $R_2$ is phenyl substituted with tert-butyl or tert-pentyl.

21. The compound or salt of claim 1, which is any one selected from the group consisting of 2-(2-aminobenzo[d]thiazol-6-yl)-N-(5-(3-ethoxyphenyl)-1, 3,4-thiadiazol-2-yl)acetamide, 2-(2-aminobenzo[d]thiazol-6-yl)-N-(5-(4-ethoxyphenyl)-1, 3,4-thiadiazol-2-yl)acetamide, 2-(2-aminobenzo[d]thiazol-6-yl)-N-(5-(2-hydroxyphenyl)-1, 3,4-thiadiazol-2-yl)acetamide, 2-(2-aminobenzo[d]thiazol-6-yl)-N-(5-(2-nitrophenyl)-1, 3,4-thiadiazol-2-yl)acetamide, 2-(2-aminobenzo[d]thiazol-6-yl)-N-(5-(4-(trifluoromethyl)phenyl)-1,3,4-thiadiazol-2-yl)acetamide, 2-(2-aminobenzo[d]thiazol-6-yl)-N-(5-(2-methoxyphenyl)-1,3,4-thiadiazol-2-yl)acetamide, 2-(2-aminobenzo[d]thiazol-6-yl)-N-(5-(4-bromophenyl)-1,3,4-thiadiazol-2-yl)acetamide, 2-(2-aminobenzo[d]thiazol-6-yl)-N-(5-(4-nitrophenyl)-1,3,4-thiadiazol-2-yl)acetamide, 2-(2-aminobenzo[d]thiazol-6-yl)-N-(5-(4-(dimethylamino)phenyl)-1,3,4-thiadiazol-2-yl)acetamide, 2-(2-aminobenzo[d]thiazol-6-yl)-N-(5-(2-propoxyphenyl)-1,3,4-thiadiazol-2-yl)acetamide, 2-(2-aminobenzo[d]thiazol-6-yl)-N-(5-(2-(trifluoromethoxy)phenyl)-1, 3,4-thiadiazol-2-yl)acetamide, 2-(2-aminobenzo[d]thiazol-6-yl)-N-(5-(4-iodophenyl)-1, 3,4-thiadiazol-2-yl)acetamide, 2-(2-aminobenzo[d]thiazol-6-yl)-N-(5-(4-bromo-3-nitrophenyl)-1, 3,4-thiadiazol-2-yl)acetamide, 2-(2-aminobenzo[d]thiazol-6-yl)-N-(5-(4-isopropoxyphenyl)-1, 3,4-thiadiazol-2-yl)acetamide, 2-(2-aminobenzo[d]thiazol-6-yl)-N-(5-(2-isopropoxyphenyl)-1, 3,4-thiadiazol-2-yl)acetamide, 2-(2-aminobenzo[d]thiazol-6-yl)-N-(5-(4-(pentan-3-yl oxy)phenyl)-1,3,4-thiadiazol-2-yl)acetamide, 2-(2-aminobenzo[d]thiazol-6-yl)-N-(5-(4-propoxyphenyl)-1,3,4-thiadiazol-2-yl)acetamide, 2-(2-aminobenzo[d]thiazol-6-yl)-N-(5-(2,4-diethoxyphenyl)-1,3,4-thiadiazol-2-yl)acetamide, 2-(2-aminobenzo[d]thiazol-6-yl)-N-(5-(4-hydroxyphenyl)-1,3,4-thiadiazol-2-yl)acetamide, 2-(2-aminobenzo[d]thiazol-6-yl)-N-(5-(2-butoxyphenyl)-1, 3,4-thiadiazol-2-yl)acetamide, 2-(2-aminobenzo[d]thiazol-6-yl)-N-(5-(4-butoxyphenyl)-1, 3,4-thiadiazol-2-yl)acetamide, 2-(2-aminobenzo[d]thiazol-6-yl)-N-(5-(2-(pentan-3-yloxy)phenyl)-1,3,4-thiadiazol-2-yl)acetamide, 2-(2-aminobenzo[d]thiazol-6-yl)-N-(5-(2-butoxy-4-ethoxyphenyl)-1, 3,4-thiadiazol-2-yl)acetamide, 2-(2-aminobenzo[d]thiazol-6-yl)-N-(5-(2, 4,6-triethoxyphenyl)-1,3,4-thiadiazol-2-yl)acetamide, 2-(2-aminobenzo[d]thiazol-6-yl)-N-(5-(3-ethoxypyridin-4-yl)-1,3,4-thiadiazol-2-yl)acetamide, 2-(2-aminobenzo[d]thiazol-6-yl)-N-(5-(4-ethoxy-2-(ethoxymethoxy)phenyl)-1, 3,4-thiadiazol-2-yl)acetamide, 2-(2-aminobenzo[d]thiazol-6-yl)-N-(5-(4-ethoxy-2-(2-(4-methylpiperazin-1-yl)ethoxy)phenyl)-1,3,4-thiadiazol-2-yl)acetamide, 2-(2-aminobenzo[d]thiazol-6-yl)-N-(5-(2(3-(dimethylamino)propoxy)-4-ethoxyphenyl)-1,3,4-thiadiazol-2-yl)acetamide, 2-(2-aminobenzo[d]thiazol-6-yl)-N-(5-(2-(2-(dimethylamino)ethoxy)-4-ethoxyphenyl)-1, 3,4-thiadiazol-2-yl)acetamide, 2-(2-aminobenzo[d]thiazol-6-yl)-N-(5-(5-ethoxypyridin-2-yl)-1,3,4-thiadiazol-2-yl)acetamide, 2-(2-aminobenzo[d]thiazol-6-yl)-N-(5-(3-(2-(dimethylamino)ethoxy)pyridin-4-yl)-1, 3,4-thiadiazol-2-yl)acetamide, 2-(2-aminobenzo[d]thiazol-6-yl)-N-(5-(4-ethoxy-2-(2-methoxyethoxy)phenyl)-1,3,4-thiadiazol-2-yl)acetamide, 2-(2-aminobenzo[d]thiazol-6-yl)-N-(5-(4-propylphenyl)-1,3,4-thiadiazol-2-yl)acetamide, 2-(2-aminobenzo[d]thiazol-6-yl)-N-(5-(4-ethoxypyridin-3-yl)-1,3,4-thiadiazol-2-yl)acetamide, 2-(2-aminobenzo[d]thiazol-6-yl)-N-(5-(4, 6-diethoxypyridin-3-yl)-1,3,4-thiadiazol-2-yl)acetamide, 2-(2-aminobenzo[d]thiazol-6-yl)-N-(5-(2,4-diethoxyphenyl)-1,3,4-thiadiazol-2-yl)-N-methylacetamide, 2-(2-aminobenzo[d]thiazol-6-yl)-N-(5-(4,6-diethoxypyridin-3-yl)-1, 3,4-thiadiazol-2-yl)-N-methylacetamide, 2-(2-aminobenzo[d]thiazol-6-yl)-N-(5-(4-ethoxyphenyl)-1,3,4-oxadiazol-2-yl)acetamide, 2-(2-aminobenzo[d]thiazol-6-yl)-N-(5-(2-ethoxyphenyl)-1,3,4-oxadiazol-2-yl)acetamide, 2-(2-aminobenzo[d]thiazol-6-yl)-N-(5-(2-propoxyphenyl)-1,3,4-oxadiazol-2-yl)acetamide, 2-(2-aminobenzo[d]thiazol-6-yl)-N-(5-(2-(trifluoromethoxy)phenyl)-1,3,4-oxadiazol-2-yl)acetamide, 2-(2-aminobenzo[d]thiazol-6-yl)-N-(5-(3-nitrophenyl)-4-(p-tolyl)thiazol-2-yl)acetamide, 2-(2-aminobenzo[d]thiazol-6-yl)-N-(4-(4-bromophenyl)-5-phenylthiazol-2-yl)acetamide, 2-(2-aminobenzo[d]thiazol-6-yl)-N-(5-(4-bromophenyl)-4-(p-tolyl)thiazol-2-yl)acetamide, 2-(2-aminobenzo[d]thiazol-6-yl)-N-(5-(4-fluorophenyl)-4-(p-tolyl)thiazol-2-yl)acetamide, 2-(2-aminobenzo[d]thiazol-6-yl)-N-(5-(3,4-dimethoxyphenyl)-4-(p-tolyl)thiazol-2-yl)acetamide, 2-(2-aminobenzo[d]thiazol-6-yl)-N-(5-(4-fluorophenyl)-4-(4-propoxyphenyl)thiazol-2-yl)acetamide, 2-(2-aminobenzo[d]thiazol-6-yl)-N-(5-(3,5-bis(trifluoromethyl)phenyl)-4-(p-tolyl)thiazol-2-yl)acetamide, 2-(2-aminobenzo[d]thiazol-6-yl)-N-(5-bromo-4-(3-methoxyphenyl)thiazol-2-yl)acetamide, 2-(2-aminobenzo[d]thiazol-6-yl)-N-(4-(4-ethoxyphenyl)-5-(4-fluorophenyl)thiazol-2-yl)acetamide, 2-(2-aminobenzo[d]thiazol-6-yl)-N-(4,5-bis(4-bromophenyl)thiazol-2-yl)acetamide, 2-(2-aminobenzo[d]thiazol-6-yl)-N-(5-(4-ethoxyphenyl)thiazol-2-yl)acetamide, 2-(2-aminobenzo[d]thiazol-6-yl)-N-(4-(2,4-diethoxyphenyl)thiazol-2-yl)acetamide, 2-(2-aminobenzo[d]thiazol-6-yl)-N-(4-(4-ethoxyphenyl)-5-phenoxythiazol-2-yl)acetamide, 2-(2-aminobenzo[d]thiazol-6-yl)-N-(5-benzyl-4-(4-ethoxyphenyl)thiazol-2-yl)acetamide, 1-(2-aminobenzo[d]thiazol-6-yl)-3-(5-(4-ethoxyphenyl)-1, 3,4-thiadiazol-2-yl)acetamide, 2-(2-aminobenzo[d]thiazol-6-yl)-N-(5-(4-ethoxyphenyl)thiophen-2-yl)acetamide, 2-(2-aminobenzo[d]thiazol-6-yl)-N-(5-(4-ethoxy-2-(2-methoxyethoxy)phenyl)-1H-imidazol-2-yl)acetamide, 2-(2-aminobenzo[d]thiazol-6-yl)-N-(5-(2,4-diethoxyphenyl)-1H-imidazol-2-yl)acetamide, N-(4-(4-bromophenyl)-5-phenoxythiazol-2-yl)-5-nitrothiophene-2-carboxamide, N-(4-(4-bromophenyl)-5-(4-(trifluoromethoxy)phenoxy)thiazol-2-yl)-5-nitrothiophene-2-carboxamide, 5-nitro-N-(4-(3-nitrophenyl)-5-phenoxythiazol-2-yl)thiophene-2-carboxamide, N-(4-(3-methoxyphenyl)-5-phenoxythiazol-2-yl)-5-nitrothiophene-2-carboxamide, N-(4-(2-ethoxyphenyl)-5-phenoxythiazol-2-yl)-5-nitrothiophene-2-carboxamide, N-(4-(4-ethoxyphenyl)-5-phenoxythiazol-2-yl)-5-nitrothiophene-2- carboxamide, N-(4-(4-bromophenyl) -5-(4-(trifluoromethyl)phenoxy)thiazol-2-yl)-5-nitrothiophene-2-carboxamide, 5-nitro-N-(4-(4-propoxyphenyl)-5-(4-(trifluoromethoxy)phenoxy)thiazol-2-yl) thiophene-2-carboxamide, 5-nitro-N-(5-phenoxy-4-(4-propoxyphenyl)thiazol-2-yl) thiophene-2-carboxamide, N-(4-(4-isopropoxyphenyl)-5-phenoxythiazol-2-yl)-5-nitrothiophene -2-carboxamide, N-(4-(4-bromophenyl)-5-(3-(trifluoromethyl) phenoxy)thiazol-2-yl)-5-nitrothiophene-2-carboxamide, N-(4-(2,4-diethoxyphenyl) -5-phenoxythiazol-2-yl)-5-nitrothiophene-2-carboxamide, 5-nitro-N-(4-(4-propoxyphenyl) -5-(pyridin-3-yloxy)thiazol-2-yl)thiophene-2-carboxamide, N-(4-(4-(tert-butyl) phenyl)-5-phenoxythiazol-2-yl)-5-nitrothiophene-2-carboxamide, N-(4-(4-(2-methoxyethoxy)phenyl)-5-(pyridin-3-yloxy)thiazol-2-yl)-5-nitrothiophene-2-carboxamide, N-(4-(4-(2-methoxyethoxy)phenyl)-5-phenoxythiazol-2-yl)-5-nitrothiophene -2-carboxamide, 5-nitro-N-(4-(4-propoxyphenyl)-5-(3-(trifluoromethyl)phenoxy)thiazol-2-yl)thiophene-2-carboxamide, N-(4-(4-bromophenyl)-5-(2-(trifluoromethyl)phenoxy)thiazol-2-yl)-5-nitrothiophene-2-carboxamide, N-(4-(4-(tert-butyl) phenyl)-5-(4-fluorophenoxy)thiazol-2-yl)-5-nitrothiophene-2-carboxamide, N-(5-(2-ethoxyphenoxy)-4-(4-propoxyphenyl)thiazol-2-yl)-5-nitrothiophene-2-carboxamide, N-(4-(4-(tert-butyl)phenyl)-5-(3-fluorophenoxy)thiazol-2-yl) -5-nitrothiophene-2-carboxamide, N-(4-(4-ethoxyphenyl)-5-(3-(trifluoromethyl)phenoxy)thiazol-2-yl)-5-nitrothiophene-2-carboxamide, N-(5-(3-fluorophenoxy) -4-(4-propoxyphenyl)thiazol-2-yl)-5-nitrothiophene-2-carboxamide, N-(4-(4-ethoxyphenyl) -5-(4-(trifluoromethyl)phenoxy)thiazol-2-yl)-5-nitrothiophene-2-carboxamide, 5-nitro-N-(4-(4-propoxyphenyl)-5-(4-(trifluoromethyl)phenoxy)thiazol-2-yl) thiophene-2-carboxamide, N-(5-(4-bromophenoxy)-4-(4-propoxyphenyl)thiazol-2-yl)-5-nitrothiophene-2-carboxamide, N-(5-(4-bromo-3,5-dimethylphenoxy)-4-(4-propoxyphenyl) thiazol-2-yl)-5-nitrothiophene-2-carboxamide, N-(5-(4-(tert-butyl) phenoxy)-4-(4-ethoxyphenyl)thiazol-2-yl)-5-nitrothiophene-2-carboxamide, N-(5-(4-fluorophenoxy) -4-(4-propoxyphenyl)thiazol-2-yl)-5-nitrothiophene-2-carboxamide, N-(4-(4-fluorophenyl)-5-(2-(trifluoromethyl)phenoxy)thiazol-2-yl)-5-nitrothiophene-2-carboxamide, N-(4-(4-fluorophenyl)-5-(2-(trifluoromethoxy)phenoxy)thiazol-2-yl)-5-nitrothiophene-2-carboxamide, N-(4-(4-fluorophenyl)-5-(4-(trifluoromethoxy) phenoxy)thiazol-2-yl)-5-nitrothiophene-2-carboxamide, N-(4-(4-methoxyphenyl) -5-phenoxythiazol-2-yl)-5-nitrothiophene-2-carboxamide, N-(5-(4-fluorophenoxy)-4-(4-(methylcarbamoyl)phenyl) thiazol-2-yl)-5-nitrothiophene-2-carboxamide, N-(4-(3,5-diethoxyphenyl)-5-phenoxythiazol-2-yl)-5-nitrothiophene-2-carboxamide, N-(5-(2,4-difluorophenoxy)-4-(4-propoxyphenyl)thiazol-2-yl)-5-nitrothiophene-2-carboxamide, N-(5-(2-chloro-4-(trifluoromethyl)phenoxy)-4-(4-propoxyphenyl) thiazol-2-yl)-5-nitrothiophene-2-carboxamide, N-(5-(4-cyanophenoxy)-4-(4-propoxyphenyl)thiazol-2-yl)-5-nitrothiophene-2-carboxamide, N-(5-(4-cyano-2-methoxyphenoxy) -4-(4-propoxyphenyl)thiazol-2-yl)-5-nitrothiophene-2-carboxamide, N-(4-(5-(3,3-dimethylbut-l-yn-l-yl)thiophen-2-yl)-5-phenoxythiazol-2-yl)-5-nitrothiophene-2-carboxamide, N-(4-(5-bromothiophen-2-yl)-5-phenoxythiazol-2-yl)-5-nitrothiophene -2-carboxamide, 5-nitro-N-(4-(4-propoxyphenyl)-5-(pyridin-4-yloxy) thiazol-2-yl)thiophene-2-carboxamide, N-(5-(3,4-dichlorophenoxy)-4-(4-propoxyphenyl) thiazol-2-yl)-5-nitrothiophene-2-carboxamide, N-(5-(2-chloro-4-fluorophenoxy) -4-(4-propoxyphenyl)thiazol-2-yl)-5-nitrothiophene-2-carboxamide, N-(4-(5-(3-(dimethylamino)prop-1-yn-l-yl)thiophen-2-yl)-5-phenoxythiazol-2-yl)-5-nitrothiophene -2-carboxamide, N-(4-(4-ethoxyphenyl)-5-phenoxythiazol-2-yl)-5-nitrofuran -2-carboxamide, 5-nitro-N-(5-phenoxy-4-(4-propoxyphenyl)thiazol-2-yl)furan-2-carboxamide, N-(5-(4-fluorophenoxy)-4-(4-propoxyphenyl)thiazol-2-yl)-5-nitrofuran-2-carboxamide, N-(5-(3,5-difluorophenoxy)-4-(4-propoxyphenyl)thiazol-2-yl)-5-nitrothiophene-2-carboxamide, N-(4-(6-ethoxypyri din-3 -yl)-5-phenoxythiazol-2-yl)-5-nitrothiophene-2-carboxamide, 5-nitro-N-(4-(4-propoxyphenyl)-5-(quinolin-8-yloxy) thiazol-2-yl)thiophene-2-carboxamide, N-(4-(4-ethoxy-2-fluorophenyl)-5-phenoxythiazol-2-yl) -5-nitrothiophene-2-carboxamide, N-(4-(4-ethoxyphenyl)-5-(3-fluorophenoxy) thiazol-2-yl)-5-nitrothiophene-2-carboxamide, N-(4-(4-ethoxyphenyl)-5-(4-fluorophenoxy) thiazol-2-yl)-5-nitrothiophene-2-carboxamide, N-(4-(4-butoxyphenyl)-5-phenoxythiazol-2-yl)-5-nitrothiophene-2-carboxamide, N-(4-(4-ethoxyphenyl)-5-(2-fluorophenoxy) thiazol-2-yl)-5-nitrothiophene-2-carboxamide, N-(5-(2-fluorophenoxy)-4-(4-propoxyphenyl) thiazol-2-yl)-5-nitrothiophene-2-carboxamide, 5-nitro-N-(4-(4-(tert-pentyl)phenyl) -5-phenoxythiazol-2-yl)thiophene-2-carboxamide, 5-nitro-N-(4-(4-nitrophenyl) -5-phenoxythiazol-2-yl)thiophene-2-carboxamide, 5-nitro-N-(5 -phenoxy-4-(3, 4,5-trimethoxyphenyl)thiazol-2-yl)thiophene-2-carboxamide, N-(4-(4-fluorophenyl)-5-(4-(tert-pentyl)phenoxy)thiazol-2-yl)-5-nitrothiophene-2-carboxamide, N-(5-(4-fluorophenoxy) -4-(4-(tert-pentyl)phenyl)thiazol-2-yl)-5-nitrothiophene-2-carboxamide, N-(5-(4-(tert-butyl)phenoxy)-4-(4-fluorophenyl)thiazol-2-yl)-5-nitrothiophene-2-carboxamide, N-(5-(4-butylphenoxy)-4-(4-fluorophenyl) thiazol-2-yl)-5-nitrothiophene-2-carboxamide, N-(5-(4-butoxyphenoxy)-4-(4-fluorophenyl)thiazol-2-yl)-5-nitrothiophene-2-carboxamide, N-(4-(4-(hexyloxy)phenyl)-5-phenoxythiazol-2-yl)-5-nitrothiophene-2-carboxamide, 5-nitro-N-(5-(4-(tert-pentyl)phenoxy)-4-(4-(trifluoromethyl)phenyl)thiazol-2-yl) thiophene-2-carboxamide, N-(4-(4-butoxyphenyl)-5-(2-fluorophenoxy)thiazol-2-yl)-5-nitrothiophene-2-carboxamide, N-(4-(4-butoxyphenyl)-5-(4-fluorophenoxy)thiazol-2-yl) -5-nitrothiophene-2-carboxamide, N-(4-(4-(tert-butyl)phenyl)-5-(4-(trifluoromethyl) phenoxy)thiazol-2-yl)-5-nitrothiophene-2-carboxamide, N-(4-(4-(tert-butyl) phenyl)-5-(2-(trifluoromethyl)phenoxy)thiazol-2-yl)-5-nitrothiophene-2-carboxamide, 5-nitro-N-(4-(4-(pentyloxy)phenyl)-5-phenoxythiazol-2-yl)thiophene-2-carboxamide, 5-nitro-N-(5-phenoxy-4-(4-propylphenyl)thiazol-2-yl)thiophene-2-carboxamide, N-(5-(2-fluorophenoxy)-4-(4-propylphenyl) thiazol-2-yl)-5-nitrothiophene-2-carboxamide, N-(4-(4-butylphenyl)-5-phenoxythiazol-2-yl)-5-nitrothiophene-2-carboxamide, N-(4-(4-butylphenyl)-5-(2-fluorophenoxy) thiazol-2-yl)-5-nitrothiophene-2-carboxamide, 5-nitro-N-(5-phenoxy-4-(4-(trifluoromethyl)phenyl)thiazol-2-yl) thiophene-2-carboxamide, N-(4-(4-ethoxyphenyl)-5-phenoxythiazol-2-yl)-N-methyl-5-nitrothiophene-2-carboxamide, N-(5-(2-fluorophenoxy)-4-(4-(trifluoromethyl) phenyl)thiazol-2-yl)-5-nitrothiophene-2-carboxamide, 5-nitro-N-(5-phenoxy -4-(4-(trifluoromethoxy)phenyl)thiazol-2-yl)thiophene-2-carboxamide, N-(5-(2-fluorophenoxy)-4-(4-(trifluoromethoxy)phenyl)thiazol-2-yl)-5-nitrothiophene-2-carboxamide, N-(5-(4-bromophenoxy)-4-(4-butoxyphenyl) thiazol-2-yl)-5-nitrothiophene-2-carboxamide, N-(5-(4-bromo-3,5-dimethylphenoxy)-4-(4-butoxyphenyl)thiazol-2-yl)-5-nitrothiophene-2-carboxamide, N-(4-(4-(tert-butyl)

phenyl)-5-(4-propylphenoxy) thiazol-2-yl)-5-nitrothiophene-2-carboxamide, N-(4-(4-(tert-butyl) phenyl)-5-(4-butylphenoxy)thiazol-2-yl)-5-nitrothiophene-2-carboxamide, N-(4-(4-butoxyphenyl) -5-(4-(tert-butyl) phenoxy)thi azol-2-yl)-5-nitrothiophene-2-carboxamide, N-(4-(4-butoxyphenyl)-5-(4-cyanophenoxy)thiazol-2-yl)-5-nitrothiophene-2-carboxamide, N-(4-(4-((5-aminopentyl)oxy)phenyl)-5-phenoxythiazol-2-yl)-5-nitrothiophene-2-carboxamide, N-(4-(4-butoxyphenyl)-5-(4-propylphenoxy)thiazol-2-yl)-5-nitrothiophene-2-carboxamide, N-(4-(4-butylphenyl)-5-(4-fluorophenoxy)thiazol-2-yl)-5-nitrothiophene-2-carboxamide, N-(4-(4-(tert-butyl)phenyl)-5-(4-propoxyphenoxy) thiazol-2-yl)-5-nitrothiophene-2-carboxamide, N-(5-(4-(tert-butyl) phenoxy)-4-(4-(tert-butyl)phenyl)thiazol-2-yl)-5-nitrothiophene-2-carboxamide, N-(4-(4-(tert-butyl)phenyl)-5-(4-(2,4,4-trimethylpentan-2-yl)phenoxy)thiazol-2-yl)-5-nitrothiophene-2-carboxamide, N-(4-(4-butoxyphenyl)-5-(4-(tert-pentyl)phenoxy)thiazol-2-yl)-5-nitrothiophene-2-carboxamide, N-(5-(4-bromo-3,5-dimethylphenoxy)-4-(4-(tert-butyl)phenyl)thiazol-2-yl)-5-nitrothiophene-2-carboxamide, N-(5-(4-bromo-3,5-dimethylphenoxy)-4-(4-fluorophenyl)thiazol-2-yl)-5-nitrothiophene-2-carboxamide, N-(4-(4-(tert-butyl)phenyl)-5-(4-(tert-pentyl)phenoxy)thiazol-2-yl)-5-nitrothiophene-2-carboxamide, N-(5-(4-(tert-butyl)phenoxy)-4-(4-ethylphenyl)thiazol-2-yl)-5-nitrothiophene-2-carboxamide, N-(4-(4-ethylphenyl)-5-(4-(tert-pentyl)phenoxy)thiazol-2-yl)-5-nitrothiophene-2-carboxamide, N-(4-(4-butylphenyl)-5-(4-(tert-pentyl)phenoxy)thiazol-2-yl)-5-nitrothiophene-2-carboxamide, N-(4-(4-(tert-butyl)phenyl)-5-(p-tolyloxy)thiazol-2-yl)-5-nitrothiophene-2-carboxamide, N-(4-(4-butoxyphenyl)-5-(3,5-dimethylphenoxy)thiazol-2-yl)-5-nitrothiophene-2-carboxamide, N-(4-(4-(tert-butyl)phenyl)-5-(4-(dimethylamino)phenoxy)thiazol-2-yl)-5-nitrothiophene-2-carboxamide, N-(4-(4-(tert-butyl)phenyl)-5-(4-morpholinophenoxy)thiazol-2-yl)-5-nitrothiophene-2-carboxamide, N-(5-(4-bromophenyl)-4-(p-tolyl)thiazol-2-yl)-5-nitrothiophene-2-carboxamide, 5-nitro-N-(5-(3-nitrophenyl)-4-(p-tolyl)thiazol-2-yl)thiophene-2-carboxamide, N-(5-(3,4-dimethoxyphenyl)-4-(p-tolyl)thiazol-2-yl)-5-nitrothiophene-2-carboxamide, N-(5-(3,5-bis(trifluoromethyl)phenyl)-4-(p-tolyl)thiazol-2-yl)-5-nitrothiophene-2-carboxamide, N-(5-(4-fluorophenyl)-4-(p-tolypthiazol-2-yl)-5-nitrothiophene-2-carboxamide, N-(4-(4-bromophenyl)-5-phenylthiazol-2-yl)-5-nitrothiophene-2-carboxamide, N-(5-bromo-4-(4-bromophenyl)thiazol-2-yl)-5-nitrothiophene-2-carboxamide, N-(5-bromo-4-(2-nitrophenyl)thiazol-2-yl)-5-nitrothiophene-2-carboxamide, N-(5-bromo-4-(3-nitrophenyl)thiazol-2-yl)-5-nitrothiophene-2-carboxamide, N-(5-bromo-4-(3-methoxyphenyl)thiazol-2-yl)-5-nitrothiophene-2-carboxamide, N-(4-(4-ethoxyphenyl)-5-(4-fluorophenyl)thiazol-2-yl)-5-nitrothiophene-2-carboxamide, N-(5-(4-fluorophenyl)-4-(4-propoxyphenyl)thiazol-2-yl)-5-nitrothiophene-2-carboxamide, N-(5-bromo-4-(4-ethoxyphenyl)thiazol-2-yl)-5-nitrothiophene-2-carboxamide, N-(4-(4-butoxyphenyl)-5-(4-fluorophenyl)thiazol-2-yl)-5-nitrothiophene-2-carboxamide, N-(4-(4-ethoxyphenyl)-5-(4-(trifluoromethyl)phenyl)thiazol-2-yl)-5-nitrothiophene-2-carboxamide, N-(5-(4-bromo-3-ethoxyphenyl)-4-(p-tolypthiazol -2-yl)-5-nitrothiophene-2-carboxamide, N-(4-(4-tert-butyl)phenyl)-5-phenylthiazol-2-yl)-5-nitrothiophene-2-carboxamide, N-(5 -(4-methylpiperazin-1-yl)-4-(4-propoxyphenyl)thiazol-2-yl)-5-nitrothiophene-2-carboxamide, ethyl2-(5 -nitrothiophene-2-carboxamide)-4-(4-propoxyphenyl)thiazole-5-carboxylate, N-(4-(4-(tert-butyl)phenyl)-5-(4-fluorophenyl)thiazol-2-yl)-5-nitrothiophene-2-carboxamide, N-(3,5-difluorophenyl)-4-(4-ethoxyphenyl)-2-(5-nitrothiophene-2-carboxamido)thiazole-5-carboxamide, N-(4-(4-ethoxyphenyl)-5 -(methyl(phenyl)amino)thiazol-2-yl)-5-nitrothiophene-2-carboxamide, N-(5-(morpholine-4-carbonyl)-4-(4-propoxyphenyl)thiazol-2-yl)-5-nitrothiophene-2-carboxamide, N-(5-(4-methylpiperazine-1-carbonyl)4-(4-propoxyphenyl)thiazol-2-yl)-5-nitrothiophene-2-carboxamide, N-(2,4-difluorophenyl)-2-(5-nitrothiophene-2-carboxamido)-4-(4-propoxyphenyl)thiazole-5-carboxamide, N-(5-benzyl-4-(4-ethoxyphenyl)thiazol-2-yl)-5-nitrothiophene-2-carboxamide, N-(4-(4-ethoxyphenyl)-5-(4-fluorobenzypthiazol-2-yl)-5-nitrothiophene-2-carboxamide, N-(4-(4-ethoxyphenyl)-5-(3-fluorobenzypthiazol-2-yl)-5-nitrothiophene-2-carboxamide, N-(4-(4-(tert-butyl)phenyl)-5-(4-fluorobenzypthiazol-2-yl)-5-nitrothiophene-2-carboxamide, N-(4-(4-(tert-butyl)phenyl)-5-(3,5-difluorophenyl)thiazol-2-yl)-5-nitrothiophene-2-carboxamide, N-(4-(4-(tert-butyl)phenyl)-5 -(2,4-difluorophenyl)thiazol-2-yl)-5-nitrothiophene-2-carboxamide, N-(5-(4-fluorophenyl)-4-(4-(tert-pentyl)phenyl)thiazol-2-yl)-5-nitrothiophene-2-carboxamide, N-(4-(4-(tert-butyl)phenyl)-5-(3-fluorophenyl)thiazol-2-yl)-5-nitrothiophene-2-carboxamide, ethyl, 4-(4-(tert-butyl)phenyl)-2-(5-nitrothiophene-2-carboxamido)thiazole-5-carboxylate, N-(4-(4-(tert-butyl)phenyl)-5-(4-methylpiperazine-l-carbonyl)thiazol-2-yl) -5-nitrothiophene-2-carboxamide, 4-(4-(tert-butyl)phenyl)-N-cyclopropyl-2-(5-nitrothiophene-2-carboxamido)thiazole-5-carboxamide, ethyl 4-(4-ethoxyphenyl)-2-(5-nitrothiophene- 2-carboxamido)thiazole-5-carboxylate, N-(4-(4-(tert-butyl)phenyl)-5-(3,4-difluorophenyl) thiazol-2-yl)-5-nitrothiophene-2-carboxamide, N-(5-(2,4-difluorophenyl)-4-(4-(tert-pentyl)phenyl)thiazol-2-yl)5-nitrothiophene-2-carboxamide, N-(4-(4-(tert-butyl) phenyl)-5-(2-fluorophenyl)thiazol-2-yl)-5-nitrothiophene-2-carboxamide, N-(4-(4-(tert-butyl) phenyl)-5-(morpholine-4-carbonyl)thiazol-2-yl)-5-nitrothiophene-2-carboxamide, N-(4-(4-(tert-butyl)phenyl)-5-cyanothiazol-2-yl)-5-nitrothiophene-2-carboxamide, N-(4-(4-(tert-butyl)phenyl)-5-(3,4,5-trifluorophenyl)thiazol-2-yl)-5-nitrothiophene-2-carboxamide, N-(4-(4-(tert-butyl)phenyl)-5-(2,4,6-trifluorophenyl) thiazol-2-yl)-5-nitrothiophene-2-carboxamide, N-(5-(4-bromophenyl)-4-(4-(tert-butyl)phenyl)thiazol-2-yl)-5-nitrothiophene-2-carboxamide, N-(4-(4-(tert-butyl)phenyl)-5-(4-methoxyphenyl)thiazol-2-yl)-5-nitrothiophene-2-carboxamide, N-(4-(4-(tert-butyl)phenyl)-5-(2-chlorophenyl)thiazol-2-yl)-5-nitrothiophene-2-carboxamide, N-(4-(4-(tert-butyl)phenyl)-5-(3-chlorophenyl)thiazol-2-yl)-5-nitrothiophene-2-carboxamide, N-(5-(2-bromophenyl)-4-(4-(tert-butyl) phenyl)thiazol -2-yl)-5-nitrothiophene-2-carboxamide, N-(5 -(3 -bromophenyl)-4-(4-(tert-butyl)phenyl)thiazol -2-yl)-5-nitrothiophene-2-carboxamide, N-(4-(4-(tert-butyl)phenyl)-5-(4-chlorophenyl)thiazol-2-yl)-5-nitrothiophene-2-carboxamide, and N-(5-bromo-4-(4-(tert-butyl)phenyl)thiazol-2-yl)-5-nitrothiophene-2-carboxamide, N-(3 -(4-bromophenyl)-1H-pyrazol-5-yl)-5-nitrothiophene-2-carboxamide.

22. A pharmaceutical composition comprising a compound or salt of claim 1 and a pharmaceutically acceptable carrier.

23. A method for treating a cancer, comprising: administering to a subject in need thereof an effective amount of a compound or salt of claim 1, wherein the cancer is selected from the group consisting of pancreatic cancer, renal cell carcinoma, breast cancer, colon cancer, colorectal cancer, lung cancer and liver cancer.

* * * * *